US008354514B2

(12) United States Patent
Siezak et al.

(10) Patent No.: US 8,354,514 B2
(45) Date of Patent: Jan. 15, 2013

(54) MULTIPLEX DETECTION OF AGRICULTURAL PATHOGENS

(75) Inventors: Thomas R. Siezak, Livermore, CA (US); Shea Gardner, Oakland, CA (US); Clinton Torres, Pleasanton, CA (US); Elizabeth Vitalis, Livermore, CA (US); Raymond J. Lenhoff, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 180 days.

(21) Appl. No.: 12/842,952

(22) Filed: Jul. 23, 2010

(65) Prior Publication Data

US 2011/0070586 A1 Mar. 24, 2011

Related U.S. Application Data

(63) Continuation-in-part of application No. 11/652,841, filed on Jan. 12, 2007, now Pat. No. 7,794,938.

(51) Int. Cl.
*C07H 21/02* (2006.01)
*C12Q 1/68* (2006.01)

(52) U.S. Cl. ......................... 536/23.1; 435/6.1; 435/975

(58) Field of Classification Search ........................ None
See application file for complete search history.

(56) References Cited

OTHER PUBLICATIONS

Hindson, B.J. et al., "Diagnostic Evaluation of Multiplexed Reverse Transcription-PCR Microsphere Array Assay for Detection of Foot-and-Mouth and Look-Alike Disease Viruses," *Journal of Clinical Microbiology*, Mar. 2008, pp. 1081-1089, vol. 46, No. 3.
Jiang, C. et al., "A Functional Gene Array for Detection of Bacterial Virulence Elements," *PLoS ONE*, May 2008, e2I63, vol. 3, Issue 5, eleven pages.
Lenhoff, R.J. et al., "Multiplexed Molecular Assay for Rapid Exclusion of Foot-And-Mouth Disease," *Journal of Virol. Methods*, 2008, pp. 61-69, vol. 153, No. 1.
Perkins, J. et al. "Multiplexed Detection of Antibodies to Nonstructural Proteins of Foot-And-Mouth Disease Virus," *Analytical Chemistry*, Aug. 2006, pp. 5462-5468, vol. 78, No. 15.
Wilson, W.C. et al., "A Multiplex Real-Time Reverse Transcription Polymerase Chain Reaction Assay for Detection and Differentiation of *Bluetongue* Virus and *Epizootic* Hemorrhagic Disease Virus Serogroups," *Journal of Veterinary Diagnostic Investigation*, Nov. 2009, pp. 760-770, vol. 21, No. 6.
Alegre, M. et al., "Development of a Multiplex Polyymerase Chain Reaction for the Differentiation of Bovine Herpesvirus-1 and -5," *Journal of Veterinary Medicine Series B*, Oct. 2001, pp. 613-621, vol. 48, No. 8.
Callahan, J.D. et al., "Use of a Portable Real-time Reverse Transcriptase-polymerase Chain Reaction Assay for Rapid Detection for Foot-and-Mouth Disease Virus," *Journal of the American Veterinary Medical Association*, Jun. 1, 2002, vol. 220, No. 11, pp. 1636-1642.

Database EMBL [Online] Apr. 8, 1996, "Sequence 2 from Patent US 5462734," XP002515959, Retrieved from EBI Accession No. EMBL:I15275, Database Accession No. I15275 abstract and US 5,462,734 A (Letchworth III, Geoffrey J. [US] et al.) Oct. 31, 1995, 1 page.
Database EMBL [Online] Sep. 6, 2005, "Bovine Herpesvirus Type 1.1 Isolate T3 Glycoprotein C (gC) Gene, Partial Cds.," XP002515958, Retrieved from EBI Accession No. EMBL:DQ173736, Database Accession No. DQ173736 abstract, 2 pages.
Deka, D. et al., "Detection of Bovine Herpesvirus -1 Infection in Breeding Bull Semen by Virus Isolation and Polymerase Chain Reaction," *Revue Scientifique Et Technique, Office International Despizooties/Scientific and Technical Review, International Office of Epizootics*, Dec. 1, 2005, vol. 24, No. 3, Paris, France.
Deregt D. et al., "A Multiplex DNA Suspension Microarray for Simultaneous Detection and Differentiation of Classical Swine Fever Virus and Other Pestiviruses, " *Journal of Virological Methods*, Sep. 1, 2006, pp. 17-23, vol. 136, No. 1-2.
El-Kholy, A., "Molecular and Immunological Detection of Bovine Herpesvirus -1 in Clinical Specimens," *Egyptian Journal of Immunology*, Jan. 1, 2005, pp. 125-136, vol. 12, No. 2.
Harris, C., "Liquid Array Single-Handedly Detects Bounty of BW Agents," *Analytical Chemistry*, May 1, 2003, p. 202.
Heller, A., "Protecting the Nation's Livestock," *S&TR*, May 2006, pp. 11-17.
Hullinger, P. ,"Agricultural Security Domestic Deomonstration and Application Program (AgDDAP)," NIAA Annual Meeting Proceedings, [Online] 2006, Retrieved from the internet on Jul. 31, 2009: <http://animalagriculture.org/Proceedings/2006/Wednesday/AHEM/6%20Pam%20Hullinger%20speaker%20for%20AHEM.pdf>, 22 pages.
Mahlum, C. et al., "Detection of Bovine Viral Diarrhea Virus by TaqMan Reverse Transcription Polymerase Chain Reaction," *Journal of Veterinary Diagnostic Investigation: Official Publications of the American Association of Veterinary Laboratory Diagnosticians, Inc.*, Mar. 2002, pp. 120-125, vol. 14, No. 2.

McBride, M., et al., "Autonomous Detection of Aerosolized *Bacillus anthracis* and *Yersinia petsis," Analytical Chemistry*, Oct. 15, 2003, pp. 5293-5299, vol. 75, No. 20.

McBride, M., et al., "Multiplexed Liquid Arrays for Simultaneous Detection of Simulants of Biological Warfare Agents," *Analytical Chemistry*, Apr. 15, 2003, pp. 1924-1930, vol. 75, No. 8.

McBride, M., et al., "Tailored assays for the Detection of Foreign Disease Pathogens in Animals," *IVD Technology*, May 2005, pp. 49-52, vol. 11, No. 4.

PCT International Search Report and Written Opinion, PCT Application No. US2008/050304, May 14, 2009, 23 pages.

Reid, S.M. et al., "Detection of All Seven Serotypes of Foot-and-Mouth Disease Virus by Real-time, Fluorogenic Reverse Transcription Polymerase Chain Reaction Assay," *Journal of Virological Methods*, Aug. 1, 2002, pp. 67-80, vol. 105, No. 1.

Wilson, W., et al., "A multiplexed PCR-coupled liquid bead array for the simultaneous detection of four biothreat agents," *Molecular and Cellular Probes*, 2005, pp. 137-144, vol. 19.

*Primary Examiner* — Albert Navarro
(74) *Attorney, Agent, or Firm* — Fenwick & West LLP

(57) ABSTRACT

Described are kits and methods useful for detection of agricultural pathogens in a sample. Genomic sequence information from agricultural pathogens was analyzed to identify signature sequences, e.g., polynucleotide sequences useful for confirming the presence or absence of a pathogen in a sample. Primer and probe sets were designed and optimized for use in a PCR based, multiplexed Luminex assay and/or an array assay to successfully identify the presence or absence of pathogens in a sample.

18 Claims, 75 Drawing Sheets

Titration Curves for Endemic Diseases and FMD

- EHV-1
- EHV-3
- EPSV-1
- EPSV-2
- EPSV-4
- ETV-2
- ETV-3
- EVD-1a
- FMDV-1
- FMDV-2

FIG. 69A

MULTIPLEX DETECTION OF AGRICULTURAL PATHOGENS

CROSS REFERENCE TO RELATED APPLICATIONS

This application is a continuation-in-part of U.S. patent application Ser. No. 11/652,841, filed Jan. 12, 2007, the entire disclosure of which is hereby incorporated by reference in its entirety for all purposes.

LENGTHY TABLES

The patent contains a lengthy table section. A copy of the table is available in electronic form from the USPTO web site (http://seqdata.uspto.gov/?pageRequest=docDetail&DocID=US08354514B2). An electronic copy of the table will also be available from the USPTO upon request and payment of the fee set forth in 37 CFR 1.19(b)(3).

STATEMENT REGARDING FEDERALLY SPONSORED RESEARCH OR DEVELOPMENT

The United States Government has rights in this invention pursuant to Contract No. W-7405-ENG-48 between the U.S. Department of Energy and the University of California, for the operation of Lawrence Livermore National Laboratory.

REFERENCE TO TABLES 13-25

This application includes Tables 13-25 submitted electronically as text files named Table__13.txt (Table 13); Tables__14__15__16__17__18__19__20__21.txt (Tables 14-21); Tables__22__23.txt (Tables 22 and 23); and Tables__24__25.txt (Tables 24 and 25), all created on Jul. 19, 2010, with a size of 897 kilobytes; 574 kilobytes; 828 kilobytes; and 47.2 kilobytes, respectively. Table 13 describes probes for detecting FMDV. Table 14 describes probes for detecting PRRS. Table 15 describes probes for detecting SVD. Table 16 describes probes for detecting VESV. Table 17 describes probes for detecting VSV. Table 18 describes probes for detecting OvHV-2. Table 19 describes probes for detecting AHV 1. Table 20 describes probes for detecting BHV 1. Table 21 describes probes for detecting PPDX. Table 22 describes probes for detecting BVD. Table 23 describes probes for detecting BTV. Table 24 describes probes for detecting RPV. Table 25 describes probes for detecting BPSV. Tables 13-25 are herein incorporated by reference in their entirety, for all purposes.

SEQUENCE LISTING

The instant application contains a Sequence Listing which has been submitted via EFS-Web and is hereby incorporated by reference in its entirety. Said ASCII copy, created on Aug. 13, 2010, is named 13252US_CRF_sequencelisting.txt and is 5,347,740 bytes in size.

BACKGROUND OF THE INVENTION

1. Field of the Invention

The invention relates to nucleic acid based kits and methods for determining the presence or absence in a sample of agricultural pathogens.

2. Description of the Related Art

Agriculture is a major sector of the U.S. economy, accounting for more than 13% of the gross domestic product, and employing more than 15% of the U.S. population. Cattle and dairy farmers alone earn between $50 billion and $54 billion a year through meat and milk sales, and roughly $50 billion is raised every year through farm-related exports. Overall livestock sales in 2001 were in excess of $108 billion.

An agro-terrorism attack in the U.S. could cause devastating economic consequences, not only for the affected agribusinesses but also for allied industries and services, disrupting food supplies, trade, and tourism. Moreover, because of the structure of American agribusiness (e.g., highly concentrated herds with frequent movement, suboptimal animal tracking systems, minimal farm security/surveillance), agricultural and food industries are quite vulnerable to such an attack.

The agricultural community currently views an introduction of foot-and-mouth disease (FMD) into the United States as one of their greatest concerns. FMD is a severe, highly communicable viral disease of cattle, other ruminants, and swine, FMD is endemic to many countries in the world, and the virus is easy to obtain. Because FMD does not pose a direct threat to human health, there is no need for elaborate containment procedures or personal protective equipment while handling or preparing the virus. Recent estimates associated with the 2001 FMD outbreak in the United Kingdom place economic losses at greater than $30 billion (U.S.).

The Animal and Plant Health Inspection Service (APHIS), a branch of the U.S. Department of Agriculture (USDA), is charged with protecting the nation's livestock and poultry from the introduction of foreign animal diseases and for coordinating the response to an agricultural disease outbreak. The current system for detecting a foreign animal disease (FAD) such as FMD generally involves the following components: (1) observations by veterinary practitioners and livestock owners, who likely will be the first to suspect and report a FAD case; (2) investigation of suspect cases and submission of samples to USDA/APHIS at the Plum Island Animal Disease Center (PIADC); and (3) diagnostic work-up of tissues at the Plum Island Foreign Animal Diagnostic Disease Laboratory (FADDL). Currently, all testing for FMD is done (by law) at FADDL on Plum Island, which averages about 300 investigations per year. During a major outbreak, demand could rise to 100 investigations per week. The number of required diagnostic tests would far exceed current analysis capacity, and authorities would have to resort to subjective clinical observations to determine if herds must be destroyed.

A critical problem facing the USDA/APHIS and state agriculture departments in combating an outbreak of FMD is the lack of rapid, validated diagnostic assays for detection and identification of FMD. The need for improved diagnostics and surveillance programs to better enable the United Sates to detect and respond to foreign animal diseases (FADs) has been highlighted in several reports (e.g. National Association of State Departments of Agriculture and Research Foundation, the General Accounting Office, and the National Research Council) as well as Homeland Security Presidential Directive-9 (HSPD-9). Additionally, recent outbreaks of FMD in South America and the United Kingdom have heightened concerns about the ability of existing US surveillance systems to rapidly detect a FMD incursion early in the course of an outbreak and then provide the required diagnostic surge capacity needed for an outbreak response and the recovery of disease free status.

At PIADC, laboratory methods currently used to detect FADs include agar gel immunodiffusion assays, enzyme-linked immunosorbent assays (ELISA), serum neutralization assays, virus isolation in tissue culture, direct fluorescent antibody tests, electron microscopy, and animal inoculation. These methods are generally time-consuming and labor-intensive. Rapid polymerase chain reaction (PCR) assays have been used on a limited basis and a few rapid diagnostic tests are currently undergoing validation, but these tests are not yet available. (Callahan, J. D.; Brown, F.; Csorio, F. A.; Sur, J. H.; Kramer, E.; Long, G. W.; Lubroth, J.; Ellis. S. J.; Shoulars, K. S.; Gaffney, K. L.; Rock, D. L.; Nelson, W. M. "Use of a portable real-time reverse transcriptase-polymerase chain reaction assay for rapid detection of foot-and-mouth disease virus." J. Am. Vet. Med. Assn., 220 (11) 1636-1642, Jun. 1, 2002.)

APHIS also lacks rapid, validated diagnostic assays that can differentiate FMD from the many "look-alike" diseases indigenous to the animal agricultural industries (e.g., bovine viral diarrhea virus, contagious ecthyma, bluetongue virus). These domestic diseases induce signs that are similar to FMD: drooling, blisters, or lameness. In the absence of an FMD outbreak, these look-alike diseases can instill a sense of complacency on the part of practitioners and producers, who may have seen similar signs before and thus, believe these signs are the result of common enzootic diseases. When a practitioner notifies a regulatory agency of a suspicious disease, animal samples are sent to PIADC for FAD diagnosis only, not for diagnosis of look-alike domestic diseases. Consequently, without the ability to offer a timely diagnosis for the look-alike diseases that are indigenous, practitioners and producers might disregard important disease signs or develop a disinterest in becoming involved in an FAD investigation of their animals. In an actual FMD outbreak, however, the tendency is to err on the side of over-diagnosis. In the 2001 United Kingdom FMD outbreak, field diagnoses based on clinical observations resulted in a large number of false positive diagnoses (estimates are as high as 70-80%) and unnecessary slaughter of herds (4.3 million animals slaughtered), with only 2023 laboratory-confirmed cases of FMD.

Traditional approaches to DNA signature development started with the hypothesis that a particular gene was vital to the organism's virulence, host range, or other factors that might be considered "unique". Suitable primers and probe were designed for the detection system of choice, with or without computational screening (via BLAST or equivalent) for uniqueness. The resulting assay would then be tested with the available strain(s) and success declared if the targets were detected, but the assay didn't detect whatever near-neighbors were tested. This approach would sometimes yield good results, but failures occurred due to inadequate strain panel coverage and cross reactions with genetic near neighbors and complex environmental samples.

SUMMARY OF THE INVENTION

Disclosed herein are kits and methods for detection of bovine and/or porcine pathogens. The kits and methods can use, e.g., real-time PCR to detect pathogen nucleic acid signature sequences in a sample. The kits and methods can also use, e.g., oligonucleotide probes affixed to a solid support, e.g., an array for detection of pathogen nucleic acids in a sample.

One embodiment of the invention is a kit for determining the presence or absence of at least two porcine pathogens in a sample, the pathogens selected from the group consisting of FMDV, PRRS, SVD, VESV, and VSV, the kit including nucleic acid reagents for detection of at least one nucleic acid signature sequence from each of the at least two pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

In some embodiments, the kit is for determining the presence or absence of FMDV, PRRS, SVD, VESV, and VSV in a sample, the kit including nucleic acid reagents for detection of SEQ ID NO:129, SEQ ID NO:133, SEQ ID NO:137, SEQ ID NO:141, SEQ ID NO:145, SEQ ID NO:149, SEQ ID NO:153, SEQ ID NO:157, SEQ ID NO:161, SEQ ID NO:165, SEQ ID NO:169, SEQ ID NO:173, SEQ ID NO:177, SEQ ID NO:181, SEQ ID NO:185, SEQ ID NO:189, SEQ ID NO: 193, SEQ ID NO: 197, and SEQ ID NO: 201.

In some embodiments, the reagents include a set of oligonucleotides for each signature sequence to be detected, the set including PCR primers and hybridization probes for each signature sequence. In some embodiments, the reagents include at least two sets selected from the group consisting of PCR primers and hybridization probes disclosed in Table 11. In some embodiments, the reagents include all of the PCR primers and hybridization probes disclosed in Table 11. In some embodiments, the reagents include those for detection of control sequences disclosed in Table 11.

In some embodiments, the hybridization probes are affixed to a bead.

Also disclosed herein are methods for determining the presence or absence of at least two of the porcine pathogens FMDV, PRRS, SVD, VESV, and VSV in a sample, the method including the steps of using the kits disclosed herein. In some embodiments, the method includes PCR amplification of each signature sequence. Is some embodiments, the method includes reagents that include all of the PCR primers and hybridization probes disclosed in Table 11.

Also disclosed herein is a kit for determining the presence or absence of at least two bovine pathogens in a sample, the pathogens selected from the group consisting of OvHV-2/AHV1, BHV, PPDX, FMDV, BVD, BTV, VSV, and RPV, the kit including nucleic acid reagents for detection of at least one nucleic acid signature sequence from each of the at least two pathogens, wherein the following nucleic acid signature sequences are detected: for pathogen OvHV-2/AHV1, signature sequences consisting of SEQ ID NO:211 or SEQ ID NO:215 or SEQ ID NO:219; for pathogen BHV, signature sequences consisting of SEQ ID NO:223 or SEQ ID NO:227; for pathogen PPDX, signature sequences consisting of SEQ ID NO:231 or SEQ ID NO:235 or SEQ ID NO:239; for pathogen FMDV, signature sequences consisting of SEQ ID NO:243 or SEQ ID NO:247; for pathogen BVD, signature sequences consisting of SEQ ID NO:251 or SEQ ID NO:255 or SEQ ID NO:259 or SEQ ID NO:263 or SEQ ID NO:267 or SEQ ID NO:271; for pathogen VSV, signature sequences consisting of SEQ ID NO:275 or SEQ ID NO:279 or SEQ ID NO:283 or SEQ ID NO: 287, and for pathogen RPV, signature sequences consisting of SEQ ID NO:291 or SEQ ID NO:295 or SEQ ID NO:299.

In some embodiments, the kit is for determining the presence or absence of OvHV-2/AHV1, BHV, PPDX, FMDV, BVD, BTV, VSV, and RPV in a sample, the kit including nucleic acid reagents for detection of signature sequences SEQ ID NO:211, SEQ ID NO:215, SEQ ID NO:219, SEQ ID NO:223, SEQ ID NO:227, SEQ ID NO:231, SEQ ID NO:235, SEQ ID NO:239, SEQ ID NO:243, SEQ ID NO:247, SEQ ID NO:251, SEQ ID NO:255, SEQ ID NO:259, SEQ ID NO:263, SEQ ID NO:267, SEQ ID NO:271, SEQ ID NO: 275, SEQ ID NO: 279, SEQ ID NO: 283, SEQ ID NO: 287, SEQ ID NO: 291, SEQ ID NO: 295, and SEQ ID NO: 299.

In some embodiments, the reagents include a set of oligonucleotides for each signature sequence to be detected, the set including PCR primers and hybridization probes for each signature sequence. In some embodiments, the reagents include at least two sets selected from the group consisting of the PCR primers and hybridization probes disclosed in Table 12. In some embodiments, the reagents include all of the PCR primers and hybridization probes disclosed in Table 12. In some embodiments, the kit can further include the reagents for detection of control sequences disclosed in Table 12.

In some embodiments, the hybridization probes are affixed to a bead.

Also disclosed herein methods for determining the presence or absence of at least two bovine pathogens selected from the group consisting of OvHV-2/AHV1, BHV, PPDX, FMDV, BVD, BTV, VSV, and RPV in a sample, the method including the steps of using a kit disclosed herein. In some embodiments, the method includes a PCR amplification of each signature sequence.

In some embodiments, the method includes the steps of using a kit wherein the reagents comprise all of the PCR primers and hybridization probes disclosed in Table 12.

Also described herein is a kit for determining the presence or absence of at least two pathogens in a sample, the pathogens selected from the group consisting of FMDV, PRRS, SVD, VESV, VSV, OvHV-2, AHV1, BHV, PPDX, BVD, BTV, and RPV, the kit including oligonucleotide probes for detection of at least one nucleic acid sequence from each of the at least two pathogens, wherein the following oligonucleotide probes are used: for pathogen FMDV, oligonucleotide probes consisting of SEQ ID NO:306-8574; for pathogen PRRS, oligonucleotide probes consisting of SEQ ID NO:8575-9300; for pathogen SVD, oligonucleotide probes consisting of SEQ ID NO:9301-10720; for pathogen VESV, oligonucleotide probes consisting of SEQ ID NO:10721-11518; for pathogen VSV, oligonucleotide probes consisting of SEQ ID NO:11519-12572; for pathogen OvHV-2, oligonucleotide probes consisting of SEQ ID NO:12573-12701; for pathogen AHV1, oligonucleotide probes consisting of SEQ ID NO:12702-12775; for pathogen BHV, oligonucleotide probes consisting of SEQ ID NO:12776-13173; for pathogen PPDX, oligonucleotide probes consisting of SEQ ID NO:13174-14235; for pathogen BVD, oligonucleotide probes consisting of SEQ ID NO:14236-16339; for pathogen BTV, oligonucleotide probes consisting of SEQ ID NO:16340-22724; and for pathogen RPV, oligonucleotide probes consisting of SEQ ID NO:22725-23046.

In an embodiment, the kit is for determining the presence or absence of FMDV, PRRS, SVD, VESV, VSV, OvHV-2, AHV1, BHV, PPDX, BVD, BTV, and RPV in a sample, the kit including oligonucleotide probes consisting of SEQ ID NO:306-23046. In an embodiment, the kit includes reagents for detection of control sequences. In an embodiment, the oligonucleotides are affixed to a solid support, e.g., a glass slide.

Also described herein is a method for determining the presence or absence of at least two pathogens selected from the group consisting of FMDV, PRRS, SVD, VESV, VSV, OvHV-2, AHV1, BHV, PPDX, BVD, BTV, and RPV in a sample, the method including the steps of using a kit for determining the presence or absence of at least two pathogens in a sample, the pathogens selected from the group consisting of FMDV, PRRS, SVD, VESV, VSV, OvHV-2, AHV1, BHV, PPDX, BVD, BTV, and RPV, the kit including oligonucleotides for detection of at least one nucleic acid sequence from each of the at least two pathogens, wherein the following oligonucleotide probes are used: for pathogen FMDV, oligonucleotide probes consisting of SEQ ID NO:306-8574; for pathogen PRRS, oligonucleotide probes consisting of SEQ ID NO:8575-9300; for pathogen SVD, oligonucleotide probes consisting of SEQ ID NO:9301-10720; for pathogen VESV, oligonucleotide probes consisting of SEQ ID NO:10721-11518; for pathogen VSV, oligonucleotides consisting of SEQ ID NO:11519-12572; for pathogen OvHV-2, oligonucleotide probes consisting of SEQ ID NO:12573-12701; for pathogen AHV1, oligonucleotide probes consisting of SEQ ID NO:12702-12775; for pathogen BHV, oligonucleotide probes consisting of SEQ ID NO:12776-13173; for pathogen PPDX, oligonucleotide probes consisting of SEQ ID NO:13174-14235; for pathogen BVD, oligonucleotide probes consisting of SEQ ID NO:14236-16339; for pathogen BTV, oligonucleotide probes consisting of SEQ ID NO:16340-22724; and for pathogen RPV, oligonucleotide probes consisting of SEQ ID NO:22725-23046.

Also described herein is a method for determining the presence or absence of FMDV, PRRS, SVDV, VESV, VSV, OvHV-2, AHV1, BHV, PPDX, BVD, BTV, and RPV in a sample, the method including the steps of using a kit for determining the presence or absence of FMDV, PRRS, SVD, VESV, VSV, OvHV-2, AHV1, BHV, PPDX, BVD, BTV, and RPV in a sample, the kit including oligonucleotide probes consisting of SEQ ID NO:306-23046.

In an embodiment, the method includes hybridization of each oligonucleotide to a sample. In another embodiment of the method, the oligonucleotide probes are affixed to a solid support and the method includes processing the sample contacting the sample with the solid support under conditions to allow hybridization of nucleic acid to the oligonucleotide probes; and determining the presence or absence of the at least two pathogens in the sample.

Also described herein is a kit for determining the presence or absence of at least two pathogens in a sample, the pathogens selected from the group consisting of FMDV, PRRS, SVD, VESV, VSV, OvHV-2, AHV1, BHV, PPDX, BVD, BTV, and RPV, the kit including any combination of the kits described above.

Also described herein is a method for determining the presence or absence of at least two pathogens selected from the group consisting of FMDV, PRRS, SVD, VESV, VSV, OvHV-2, AHV1, BHV, PPDX, BVD, BTV, and RPV in a sample, the method including the steps of using any combination of the kits described above.

Also described herein is a kit for determining the presence or absence of agricultural pathogens FMDV and VSV in a sample, the kit including (a) nucleic acid reagents for detection of at least one nucleic acid signature sequence from each pathogen or (b) oligonucleotide probes for detection of each pathogen or both (a) and (b); and the nucleic acid reagents and oligonucleotide probes are selected from the following: nucleic acid reagents for detection of the following FMDV nucleic acid signature sequences: SEQ ID NO:129 or SEQ ID NO:133 or SEQ ID NO:243 or SEQ ID NO:247; nucleic acid reagents for detection of the following VSV nucleic acid signature sequences: SEQ ID NO:181 or SEQ ID NO:185 or SEQ ID NO:189 or SEQ ID NO: 193 or SEQ ID NO:197 or SEQ ID NO:201 or SEQ ID NO:275 or SEQ ID NO:279 or SEQ ID NO:283 or SEQ ID NO: 287; oligonucleotide probes for FMDV: SEQ ID NO:306-8574; and oligonucleotide probes for VSV: SEQ ID NO:11519-12572.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 3: Near-neighbor testing of BVD_1a and BVD-2 signatures against CSFV isolates in the bovine multiplex assay panel. Other parameters as described in FIG. 2.

FIG. 4: Near-neighbor testing of BVD_1a and BVD-2 signatures against CSFV isolates in the bovine multiplex assay panel. Other parameters as described in FIG. 2.

FIG. 6: The BVD_1a signature in the Version 1.0 detected lower concentrations of BVDV Type 1 strains compared to Type 2, with the exception of BVDV 1b TGAN. The LOD ($TCID_{50}$/mL) represents the lowest sample concentration tested that generated response above threshold. A threshold value of 40 MFI units was used.

FIG. 9: Near-neighbor testing of BTV signatures against BRV and three serotypes of EHDV in the bovine multiplex assay panel. Other parameters as described in FIG. 2.

FIG. 10: Near-neighbor testing of BTV signatures against AHSV in the bovine multiplex assay panel. Other parameters as described in FIG. 2.

FIG. 11: Multiplex screening of four BTV signatures against five US BTV strains (Types 2, 11, 10, 13 and 17) showing response over a wide range of virus concentrations. Samples were serial dilutions of total RNA Trizol extracted from titered virus-infected cell culture. Each point represents the mean response (n=2). Error bars indicate ±1σ of the mean.

FIG. 14: Near-neighbor testing of FMDV signatures against CVB5 and one SVDV isolate in the porcine multiplex assay panel. The response of the porcine multiplex assay to blanks (NTC) is included for reference. Testing was conducted at PIADC. Each sample was analyzed in triplicate. For each signature, the responses (MFI) from triplicate analyses were averaged. Error bars indicate ±1σ of the mean response.

FIG. 15: Near-neighbor testing of FMDV signatures against PTV in the porcine multiplex assay panel. Other parameters as described in FIG. 25.

FIG. 16: Near-neighbor testing of FMDV signatures against PTV and PEV-8 in the porcine multiplex assay panel. Other parameters as described in FIG. 25.

FIG. 17: Near-neighbor testing of FMDV signatures against BEV in the bovine multiplex assay panel. Other parameters as described in FIG. 3.

FIG. 18: Near-neighbor testing of FMDV signatures against CVB5 and SVDV in the bovine multiplex assay panel. FMDV A Arg 2001 is shown as a positive control. Other parameters as described in FIG. 3.

FIG. 19: Near-neighbor testing of FMDV signatures against SVDV in the bovine multiplex assay panel. Other parameters as described in FIG. 3.

FIG. 20: The FMD_TC signature in the Version 1.0 panel detected lower concentrations of virus than FMD_Pir for all seven serotypes. The LOD (pfu/ml) represents the lowest sample concentration tested that generated response above threshold. The threshold values for FMD_PIR and FMD_TC were 42 and 60 MFI units, respectively. Samples were A Argentina 2001, O1 South Korea, C4 Tierra Del Fuego, Asia1, SAT 1/6 SWA, SAT 2 Zim and SAT 3/3 Bech 1Nov05 (PIADC).

FIG. 24: Near-neighbor testing of the MCF signatures in the bovine multiplex assay panel against OHV-2. The response of the MCF signatures to targets (ALHV a US isolate from Minnesota and ALHV WC11, the laboratory reference strain) is shown for reference. BVDV cell culture contamination is evident in both ALHV strains tested. Other parameters as described in FIG. 3.

FIG. 29: Taqman screening of RPV signatures against nine RPV strains (PIADC). Samples were total RNA extracted (Qiagen RNeasy Mini kit) from virus-infected cell culture (Qiagen RNeasy Mini kit). Each reaction was spiked with 200 pg of template. Each point represents the mean (n=3) cycle threshold. If no cycle threshold was reached (i.e. infinite cycle threshold), a cycle threshold of 40 was assigned in this plot.

Figure 31:
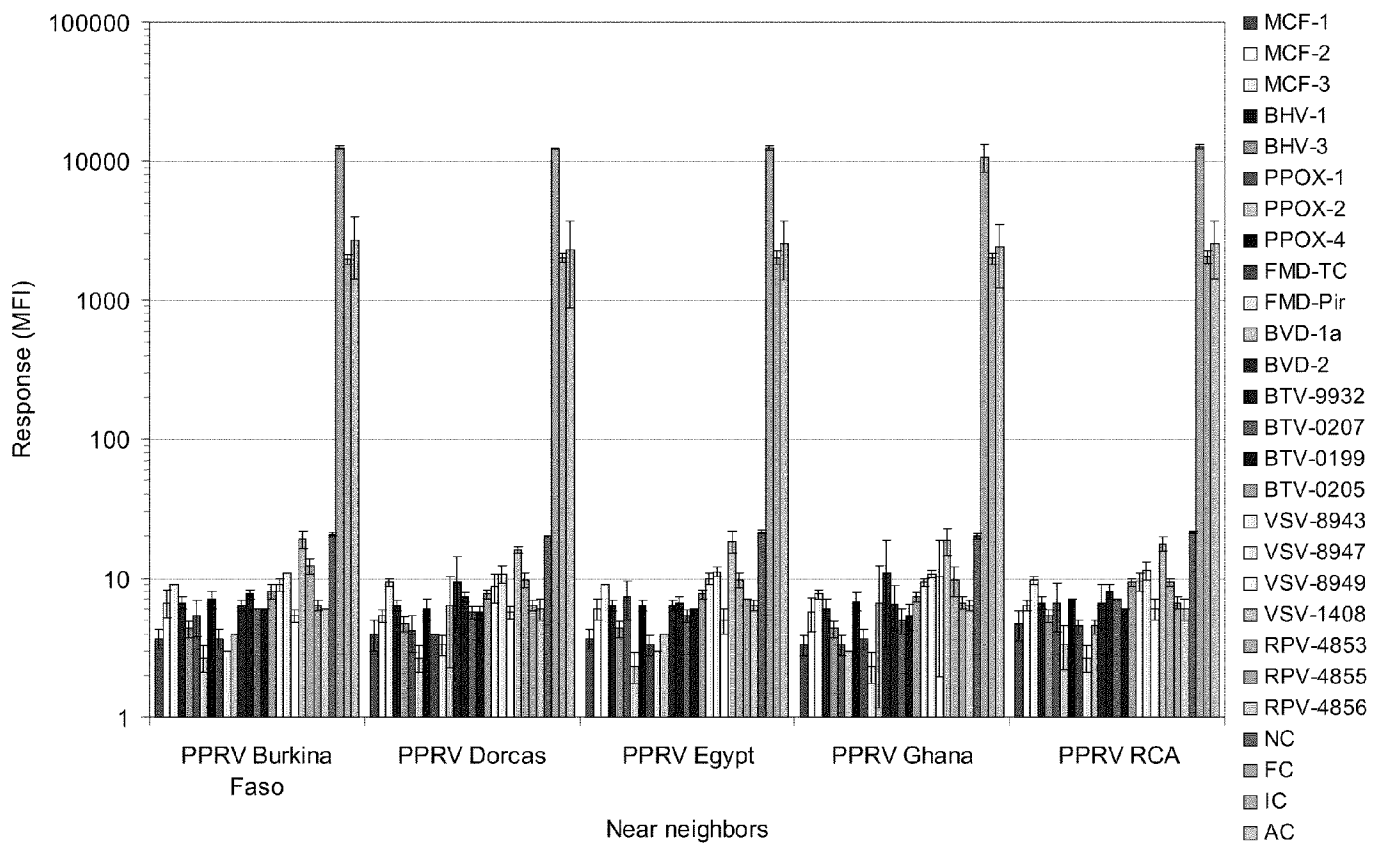

FIG. 31: Near-neighbor testing of the RPV signatures in the bovine multiplex assay panel against PPRV. Other parameters as described in FIG. 3.

FIG. 35: LOD comparison for SVD_1, SVD_2 and SVD_3 signatures in Version 1.0 showing the multi-loci detection of seven SVD isolates. Multiplex titrations were performed using serial dilution of total nucleic acid extracted from titered virus-infected cell culture (PIADC). Threshold values (MFI) were SVD-1=38, SVD-2=28, SVD-3=40.

Figure 39:
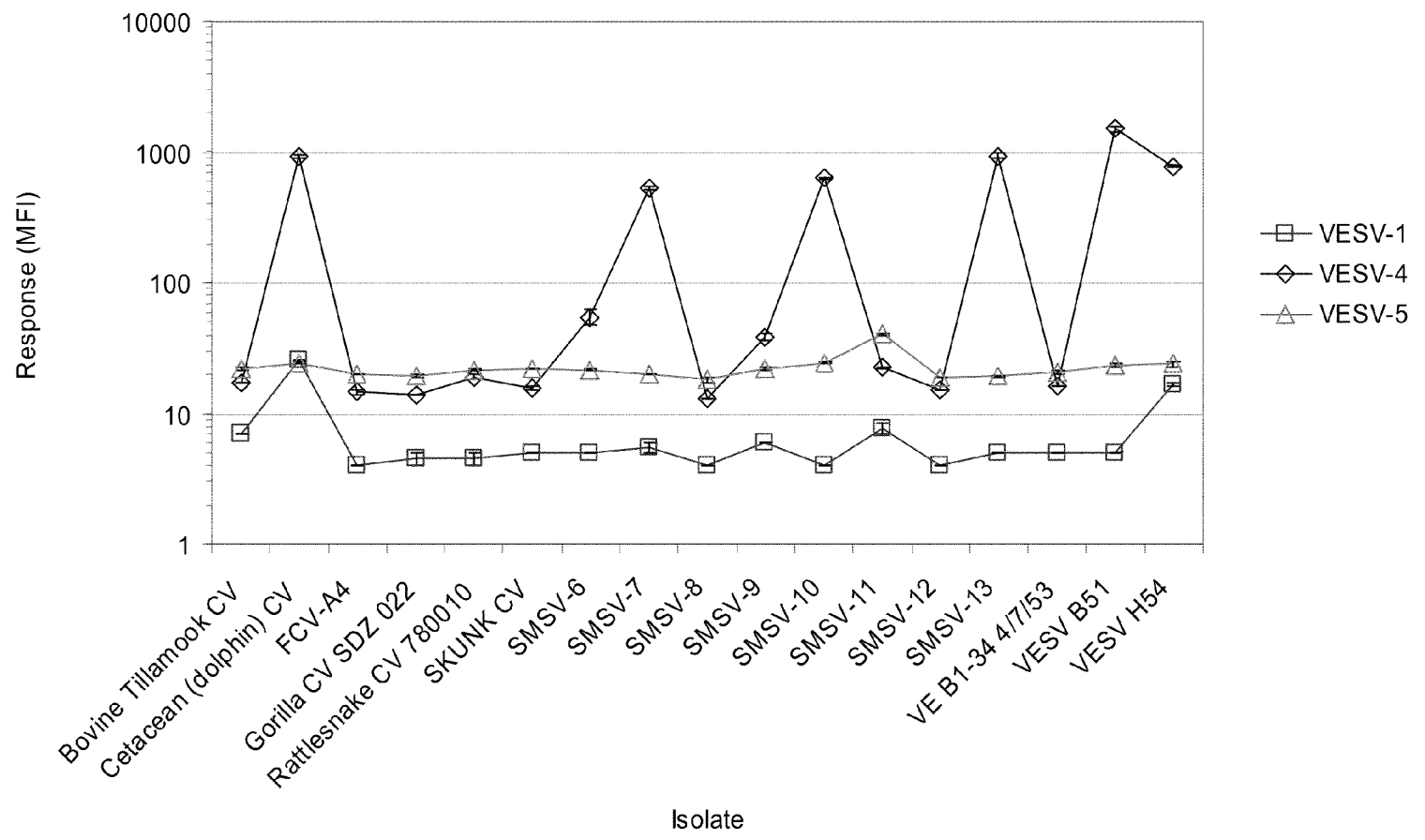

FIG. 39: Multiplex screening data for the three VESV signatures against extracted nucleic acids from caliciviruses.

FIG. 40: LOD comparison showing that VESV_4 signature in Version 1.0 panel afforded superior detection of the 9/11 VESV strains tested. Multiplex titrations were performed using serial dilution of total nucleic acid extracted from titered virus-infected cell culture (PIADC). Threshold values (MFI) were; VESV-1=24, VESV-4=105, VESV-5=56.

Figure 41:
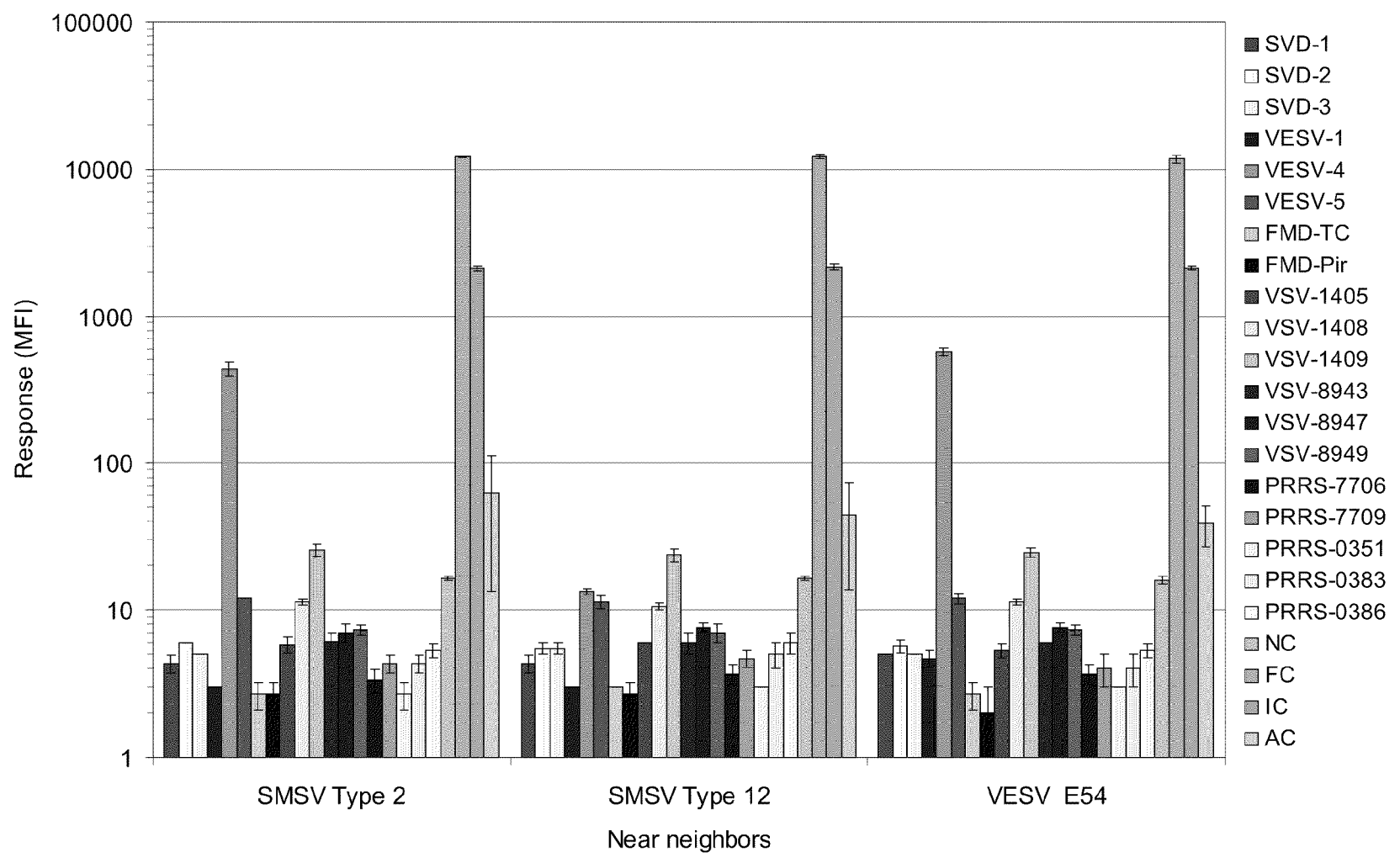

FIG. 41: Screening of VESV signatures against SMSV in the porcine multiplex assay panel. VESV E54 is shown as a positive control. Other parameters as described in FIG. 25.

FIG. 69 illustrates dose response curves for detection of the agricultural pathogens. FIG. 69A: The curves combined herewith represent common viral extraction units (pfu/mL) of representative strains for BHV, BPSV, BTV, BVDV and FMDV.

DETAILED DESCRIPTION OF THE INVENTION

Advantages and Utility

Figure 1:
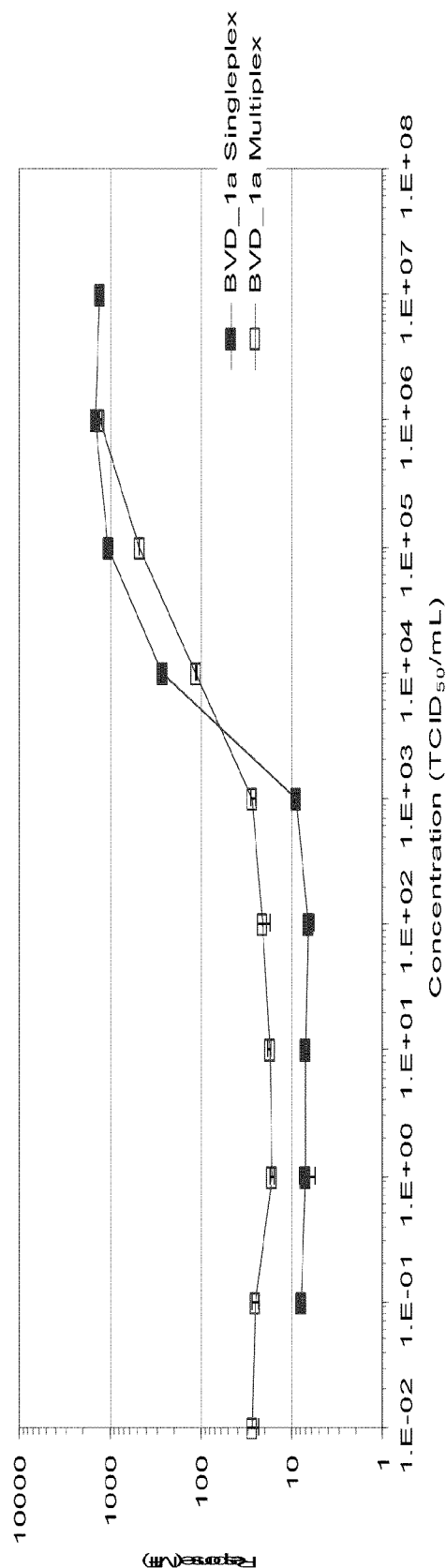
FIG. 1: BVDV signature screening in singleplex and multiplex Version 1.0 formats against a single BVD Type 1 strain (Singer). The sample was serially diluted from a stock sample of total RNA extracted from titered virus-infected cell culture. Each point represents the mean response (n=2). Error bars indicate ±1σ of the mean.

Briefly, and as described in more detail below, disclosed and claimed herein are kits and methods for determining the presence or absence of the agricultural pathogens in a sample. The kits and methods are based on detection of nucleic acid signature sequences using, e.g., multiplexed real time PCR and/or are based on hybridization to oligonucleotide probes, e.g., oligonucleotide probes affixed to a solid support in an array.

In one embodiment, the kits and methods utilize nucleic acid based methods for detection of at least one signature nucleic acid sequence for each of at least two agricultural pathogens of interest. In one embodiment, the presence or absence of all the agricultural pathogens is determined by detection of all disclosed signature sequences. In one embodiment, the signature sequences are amplified using exemplary primers disclosed herein, and the resulting amplicons are detected using hybridization probes (sequences disclosed herein) affixed to beads in a liquid array format; amplicons hybridized to probes affixed to beads are detected using a Luminex instrument.

Multiplexed detection capabilities provide many advantages over conventional detection methodologies. In the event of an outbreak of an agricultural pathogen, the use of multiplexed assay panels can provide rapid, sensitive, specific and cost-effective means of handling high volumes of samples. The assay panels can greatly improve response time and provide rapid results that can help reduce the impact of infectious disease outbreaks. The use of bead-based liquid arrays has proven to be a well adapted and versatile technology that can be custom tailored to rapidly screen for both DNA and RNA in a single tube, while also allowing for multi-loci detection.

The multiplexed assays are liquid arrays on a commercially available flow cytometer, e.g., a Luminex Bio-Plex. The liquid arrays utilize surface-functionalized polystyrene microbeads, embedded with precise ratios of red and infrared fluorescent dyes. There are 100 unique dye ratios, giving rise to 100 unique bead classes. When excited by a 635-nm laser, the two dyes emit light at different wavelengths, 658 and 712 nm and thus each bead class has a unique spectral address. Bead classes can be easily distinguished and therefore they can be combined and up to 100 different analytes can be measured simultaneously within the same sample. Although the liquid arrays have been demonstrated in a variety of applications, including detection of antigen, antibodies, small molecules, and peptides, in this application, beads are functionalized with a nucleic acid probe of approximately 30 oligonucleotides, where the probe sequence is complimentary to the desired target amplicon. Nucleic acid from the pathogen of interest is extracted, and amplified in an off-line PCR reaction. The PCR reaction is conducted using a mixture of all forward and reverse primers for each of the pathogen targets in the multiplexed panel. All forward and reverse primers are contained in the PCR reaction mixture and the amplified product is then introduced to the bead mixture, allowed to hybridize, and subsequently labeled with the fluorescent reporter, strepavidin-phycroerythrin. Each optically encoded and fluorescently-labeled microbead is then interrogated by the Luminex flow cytometer. A red laser excites the dye molecules inside the bead and classifies the bead to its unique bead set, and a green laser quantifies the assay at the bead surface. The flow cytometer is capable of reading several thousand beads each second; analysis can be completed in as little as 15 seconds.

In another embodiment, arrays of oligonucleotide probes that are complementary to target nucleic acid sequences from a pathogen can be used to identify a nucleic acid and detect the presence of the pathogen in a sample. Oligonucleotide arrays typically comprise a plurality of different oligonucleotide probes that are coupled to a surface of a substrate in different known locations.

The approach disclosed herein is more rapid than prior assays. Results on a clinical sample can be provided in about 4 hours, including sample preparation and processing, and data analysis.

Finally, the approach provides improved strain panel coverage and reduces cross-reactions with genetic near neighbors and complex environmental samples.

Definitions

Terms used in the claims and specification are defined as set forth below unless otherwise specified.

"Signature sequence" refers to a nucleic acid sequence specific and unique to an agricultural pathogen such that it can be used for detection of the pathogen in a sample.

"Amplicon" refers to the amplified product of a nucleic acid amplification reaction, e.g., the product of amplification of a signature sequence.

"Pathogen" means any disease-producing agent (especially a virus or bacterium or other microorganism). Pathogens include: Bovine Viral Diarrhea Virus (BVDV or BVD); Bluetongue Virus (BTV); Foot-and-Mouth Disease Virus (FMDV); Malignant Catarrhal Fever (MCF); ovine herpesvirus-2 (OvHV-2); alcelaphine herpesvirus-1 (AHV1); Porcine Respiratory Reproductive Syndrome Virus (PRRSV or PRRS); Rinderpest Virus (RPV); Swine Vesicular Disease Virus (SVDV or SVD); Vesicular Exanthema of Swine Virus (VESV); Vesicular Stomatitis Virus (VSV); Bovine Herpesvirus-1 (BHV-1 or BHV); Parapox (PPDX or PPox); and Bovine Papular Stomatitis Virus (BPSV).

"Agricultural pathogen" means a pathogen capable of infecting animals, e.g., bovine or porcine animals, or plants that are domesticated or propagated through human labor.

"Polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

"Oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

"Percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

It must be noted that, as used in the specification and the appended claims, the singular forms "a," "an" and "the" include plural referents unless the context clearly dictates otherwise.

Kits and Methods of the Invention

Disclosed herein is a rapid, multiplexed nucleic acid panel, e.g., a kit for the detection of agricultural pathogens including Foot and Mouth Disease Virus (FMDV) and its differentiation from a number of other viruses that cause clinical signs in animals that are indistinguishable from FMDV. The diagnostic assay panel detects signature sequences, e.g., unique nucleic acid sequences, for agricultural pathogens, including: Foot and Mouth Disease Virus (FMDV, 2 signatures), Bovine Herpes Virus-1 (BHV-1, 2 signatures), Bovine Papular Stomatitis Virus (BPSV, 3 signatures), Bovine Viral Diarrhea Virus (BVD, 1 signature), Bluetongue Virus (BTV (domestic) 2 signatures), Swine Vesicular Disease Virus (SVD or SVDV, 3 signatures) and Vesicular Exanthema of Swine Virus (VESV, 4 signatures). Signature sequences are presented in Tables 1, 11, and 12.

Accordingly one aspect of the invention is a kit for determining the presence or absence in a sample of at least one pathogen or at least two pathogens selected from the group consisting of FMDV, PRRS, SVDV, VESV, VSV, OvHV-2, AHV1, BHV, PPDX, BVD, BTV, and RPV, said kit having nucleic acid reagents for detection of at least one nucleic acid signature sequence from each pathogen.

In one embodiment, the kit further includes reagents for determining the presence or absence FMDV in a sample. The reagents detect at least one nucleic acid signature sequence for FMDV. Example signature sequences include those disclosed in Example 10, below. In other embodiment, FMDV signature sequences are those previously disclosed, e.g., SEQ ID NO:21 (JAVMA, Vol 220, No. 11, Jun. 1, 2002) and/or SEQ ID NO:25 (Journal of Virological Methods 105, (2002), 67-80).

In one aspect, the kit includes reagents for determining the presence or absence of all agricultural pathogens, e.g., FMDV, PRRS, SVDV, VESV, VSV, OvHV-2, AHV1, BHV, PPDX, BVD, BTV, and RPV in a sample. The kit includes nucleic acid reagents for detection of all signature sequences listed in Tables 1, 11, and 12.

In another aspect, the kits includes reagents for detection of less than all pathogens, e.g., for detection of at least 1, 2, 3, 4, 5, 6, 7, 8, 9, 10, or at least 11 of the pathogens.

In some embodiments, the kits include nucleic acid reagents that are sets of oligonucleotides for each signature sequence to be detected. Each set has PCR primers and hybridization probes for each signature sequence. Exemplary embodiments include the PCR primers and hybridization probes disclosed in Tables 1, 11, and 12. In one embodiment the kit includes each of the PCR primers and hybridization probes listed for the respective pathogen. In other embodiments, the kit includes a subset of the disclosed primer and probes, e.g., at least 1, 2, 3, 4, 5, 6, 7, 8, 9, 10, 11, 12 13, 14, 15, 16, 17, 18, 19, 20, 21, 22, 23, 24, 25, 26, 27, 28, 29, 30, 40, or at least 50 of the primer probe sets disclosed in Tables 1, 11, and 12.

Accordingly, in a preferred embodiment the invention provides the use of all PCR primers and hybridization probes in Tables 1, 11, and 12. Alternatively, the invention provides the use of all PCR primers and hybridization probes for a particular pathogen. In yet another embodiment the invention provides the use of all of the probes in Tables 1, and 11-25. Alternatively, the invention provides the use of all probes in Tables 13-25.

In one aspect the kits include control nucleic acid reagents. Exemplary control nucleic acid reagents are disclosed in Tables 1, 11, and 12.

Also disclosed herein is an oligonucleotide array for the detection of agricultural pathogens. The array includes oligonucleotide probes for agricultural pathogens, including: FMDV, PRRS, SVD, VESV, VSV, OvHV-2, AHV1, BHV, PPDX, BVD, BTV, and RPV. Exemplary probes are disclosed in Tables 13-25.

In one variation of the invention, the kit includes hybridization probes that are affixed to a solid substrate, e.g., a microsphere or a slide, e.g., a glass slide. Exemplary probes are disclosed in Tables 13-25. In one embodiment the kit includes each of the probes listed for the all of the respective pathogens in Tables 13-25. In other embodiments, the kit includes a subset of the disclosed probes, e.g., at least 1, 2, 3, 4, 5, 6, 7, 8, 9, 10, 11, 12 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900 or at least 1000 of the probes disclosed in Tables 13-25.

Also disclosed are methods using the kits disclosed herein. In some embodiments, the method includes a PCR based amplification step. In some embodiments, the method includes an array hybridization step.

Samples

The invention provides kits and methods for detection of agricultural pathogens in a sample. As will be appreciated by those in the art, the sample may comprise any number of things, including, but not limited to, bodily fluids (including, but not limited to, blood, nasopharyngeal secretions, urine, serum, lymph, saliva, milk, anal and vaginal secretions, and semen) of virtually any organism, with mammalian samples, including livestock, (e.g. sheep, cow, horse, pig, goat, lama, emu, ostrich or donkey), poultry (e.g. chicken, turkey, goose, duck, or game bird), fish (e.g. salmon or sturgeon), laboratory animal (e.g. rabbit, guinea pig, rat or mouse) companion animal (e.g. dog or cat) or a wild animal in captive or free state, being preferred, environmental samples (including, but not limited to, air, agricultural, water and soil samples); biological warfare agent samples; research samples; purified samples, such as purified genomic DNA, RNA, proteins, etc.; and raw samples (bacteria, virus, genomic DNA, etc.). As will be appreciated by those in the art, any experimental manipulation can have been performed on the sample before analysis.

In one embodiment, the sample type for diagnosis of vesicular diseases is vesicular epithelium/fluid. The vesicular diseases include FMD, VESV, SVD, and BVD (if oral lesions are present), parapox (BPSV), and BHV-1 (IBR). In other embodiments, the methods of the invention are performed using sample types including oral/nasal swabs and probang samples, for detection of, e.g., FMD, BVD, and BVH. For detection of BTV (vector-borne), the sample can be is EDTA whole blood. For BVD where no lesions are present, sample types include, e.g., tonsils (scrapings), lymph nodes and spleen.

Additional tissue samples include brain (brain stem, cerebellum, brain stem), spinal cord tissues or fluids, bone marrow, and ear notches.

The sample is generally processed before use. In some embodiments, processing entails simple isolation from the subject. If required, nucleic acid from the sample is isolated using known techniques. For example, the sample may be treated to lyse the cells, using known lysis buffers, sonication, electroporation, etc., with purification occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents that may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

In an embodiment, nucleic acid from the sample is isolated using Trizol reagent. After Trizol reagent treatment, RNA from cells can be precipitated with isopropanol and washed with 70% ethanol. The RNA pellet can be dried and reconstituted with RNase free water. 1 µg of RNA can be transcribed into double-strand cDNA with random hexamers using Superscript™ double-stranded cDNA synthesis kit from Invitrogen (Carlsbad, Calif.). The DNA or cDNA can be labeled using Cy-3 labeled nonamers from Trilink Biotechnologies for later detection.

Signature Sequences

Using the kits and methods of the invention, the presence or absence of an agricultural pathogen in a sample is determined using reagents for detection of a signature nucleic acid sequence. The term "signature sequence" or "signature nucleic acid" or grammatical equivalents herein means a nucleic acid sequence on a single strand of nucleic acid or its complement. The signature sequence may be a portion of a gene, a regulatory sequence, genomic DNA, cDNA, RNA including mRNA and rRNA, and the like.

The signature sequences detected are presented in Tables 1, 11, and 12.

As will be appreciated by those in the art, the signature sequence can take many forms. For example, it may be contained within a larger nucleic acid sequence, i.e. all or part of a gene or mRNA, a restriction fragment of a plasmid or genomic DNA, among others.

Amplification Methods

In one embodiment and as describe more fully herein, a signature sequence from a sample is amplified to produce a secondary target, e.g. an amplicon that is detected, as outlined herein.

Amplification involves the amplification (replication) of the signature sequence to be detected, such that the number of copies of the signature sequence is increased. Suitable amplification techniques include, but are not limited to, the polymerase chain reaction (PCR), strand displacement amplification (SDA), transcription mediated amplification (TMA) and nucleic acid sequence based amplification (NASBA).

In one embodiment, the amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", "allele-specific PCR", among others.

In another embodiment, the amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In another embodiment, the amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In another embodiment, the amplification technique is signal amplification. Signal amplification involves the use of limited number of target molecules as templates to either generate multiple signaling probes or allow the use of multiple signaling probes. Signal amplification strategies include LCR, CPT, QβR, invasive cleavage technology, and the use of amplification probes in sandwich assays.

In another embodiment, single base extension (SBE; sometimes referred to as "minisequencing") is used for amplification. Briefly, SBE is a technique that utilizes an extension primer that hybridizes to the target nucleic acid. A polymerase (generally a DNA polymerase) is used to extend the 3' end of the primer with a nucleotide analog labeled a detection label as described herein. Based on the fidelity of the enzyme, a nucleotide is only incorporated into the extension primer if it is complementary to the adjacent base in the target strand. Generally, the nucleotide is derivatized such that no further extensions can occur, so only a single nucleotide is added. However, for amplification reactions, this may not be necessary. Once the labeled nucleotide is added, detection of the label proceeds as outlined herein. See generally Sylvanen et al., Genomics 8:684-692 (1990); U.S. Pat. Nos. 5,846,710 and 5,888,819; Pastinen et al., Genomics Res. 7(6):606-614 (1997); all of which are expressly incorporated herein by reference.

In another embodiment, the signal amplification technique is OLA (oligonucleotide ligation amplification). OLA, which is referred to as the ligation chain reaction (LCR) when two-stranded substrates are used, involves the ligation of two smaller probes into a single long probe, using the target sequence as the template. In LCR, the ligated probe product becomes the predominant template as the reaction progresses. The method can be run in two different ways; in a first embodiment, only one strand of a target sequence is used as a template for ligation; alternatively, both strands may be used. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; WO 97/31256; and WO 89/09835, and U.S. Ser. Nos. 60/078,102 and 60/073,011, all of which are incorporated by reference.

In another embodiment the signal amplification technique is RCA. Rolling-circle amplification is generally described in Baner et al. (1998) Nuc. Acids Res. 26:5073-5078; Barany, F. (1991) Proc. Natl. Acad. Sci. USA 88:189-193; and Lizardi et al. (1998) Nat. Genet. 19:225-232, all of which are incorporated by reference in their entirety.

A second alternative approach involves OLA followed by RCA. In this embodiment, an immobilized primer is contacted with a target nucleic acid. Complementary sequences will hybridize with each other resulting in an immobilized duplex. A second primer is contacted with the target nucleic acid. The second primer hybridizes to the target nucleic acid adjacent to the first primer. An OLA assay is performed as described above. Ligation only occurs if the primers are complementary to the target nucleic acid. When a mismatch occurs, particularly at one of the nucleotides to be ligated, ligation will not occur. Following ligation of the oligonucleotides, the ligated, immobilized, oligonucleotide is then hybridized with an RCA probe. This is a circular probe that is designed to specifically hybridize with the ligated oligonucleotide and will only hybridize with an oligonucleotide that has undergone ligation. RCA is then performed as is outlined in more detail below.

Nucleic Acid Reagents: Primers and Probes

The kits and method disclosed herein use nucleic acid reagents, e.g., oligonucleotides, e.g., amplification primers and hybridization probes, for detection of the signature sequences. Exemplary primers and probes are disclosed herein, e.g., in Tables 1 and 11-25, and in one embodiment, the claimed kits and methods include the primers and probes disclosed in Tables 1 and/or 11-25. The invention also include kits and methods using variant versions of the primers and probes disclosed herein, e.g., oligonucleotides that are shorter or longer or have at least 95%, 96%, 97%, 98%, or at least 99% sequence identity, as long as the oligonucleotide accomplishes that same function, e.g., functions in the assay for the detection of the signature sequences.

In addition, one of skill can readily design additional primers and hybridization probes that can function as nucleic acid reagents for the detection of signature sequences. Generally the nucleic acid reagents include signature sequence, or complementary sequence, sufficient to confer specific amplification or hybridization to the target nucleic acid, e.g., agricultural pathogen nucleic acid.

The length of a nucleic acid reagent, e.g., a primer or hybridization probe, will vary depending on the application. In general, the total length can be from about 8 to 80 nucleobases in length. The primers and hybridization probes used in accordance with this invention preferably comprise from about 8 to about 80 nucleobases (i.e. from about 8 to about 80 linked nucleosides). One of ordinary skill in the art will appreciate that the invention embodies oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

Nucleic Acid Reagents: Adapters

In a preferred embodiment, a hybridization probe further comprises an adapter sequence. Adapters facilitate immobilization of probes to solid supports. That is, arrays (either solid phase or liquid phase arrays) are generated that contain capture probes that are not target specific, but rather specific to individual (preferably) artificial adapter sequences. The adapter sequences of the probes are preferably from 15-25 nucleotides in length, with 20 being especially preferred. The target specific portion of the probe is preferably from 15-50 nucleotides in length.

Thus, an adapter sequence is a nucleic acid that is generally not identical to or complementary to the signature sequence, i.e. is exogenous, but is added or attached to a hybridization probe. It should be noted that in this context, the signature sequence can include the primary signature sequence, or can be a derivative target such as a reactant or product of the reactions outlined herein; thus for example, the target sequence can be a PCR product, a first ligation probe or a ligated probe in an OLA reaction, etc.

The terms "barcodes", "adapters", "addresses", "tags" and "zip codes" have all been used to describe artificial sequences that are added to amplicons to allow separation of nucleic acid fragment pools. One preferred form of adapters is hybridization adapters. In this embodiment adapters are chosen so as to allow hybridization to the complementary capture probes on a surface of an array. In general, sets of adapters and the corresponding capture probes on arrays are developed to minimize cross-hybridization with both each other and other components of the reaction mixtures, including the signature sequences and sequences on the larger nucleic acid sequences outside of the target sequences (e.g. to sequences within genomic nucleic acid of the agricultural pathogen).

As will be appreciated by those in the art, the attachment, or joining, of the adapter sequence to the target sequence can be done in a variety of ways. In a preferred embodiment, the adapter sequences are added to the primers of the reaction (extension primers, amplification primers, readout probes, genotyping primers, Rolling Circle primers, etc.) during the chemical synthesis of the primers. The adapter then gets added to the reaction product during the reaction; for example, the primer gets extended using a polymerase to form the new target sequence that now contains an adapter sequence. Alternatively, the adapter sequences can be added enzymatically. Furthermore, the adapter can be attached to the target after synthesis; this post-synthesis attachment can be either covalent or non-covalent. In a preferred embodiment the adapter is added to the target sequence or associated with a particular allele during an enzymatic step.

In addition, as will be appreciated by those in the art, the adapter can be attached either on the 3' or 5' ends, or in an internal position, depending on the configuration of the system.

In one embodiment the use of adapter sequences allow the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In a preferred embodiment, an array of different and usually artificial capture probes are made; that is, the capture probes do not have complementarity to known target sequences. The adapter sequences can then be incorporated in the target probes.

As will be appreciated by those in the art, the length of the adapter sequences will vary, depending on the desired "strength" of binding and the number of different adapters desired. In a preferred embodiment, adapter sequences range from about 5 to about 25 basepairs in length, with 20 being especially preferred.

In a preferred embodiment, the adapter sequence uniquely positions the target analyte, e.g. agricultural organism nucleic acid, to which the target probe binds. That is, while the adapter sequence need not bind itself to the target analyte, the system allows for identification of the target analyte by detecting the presence of the adapter. Accordingly, following a binding or hybridization assay and washing, the probes including the adapters are amplified. Detection of the adapter then serves as an indication of the presence of the target analyte.

Detection of Nucleic Acids

As described herein, the kits and method described herein utilize detection of the signature sequences by detection of amplicons. In general, either direct or indirect detection of amplicon can be performed. Direct detection generally involves the incorporation of a label into the amplicon via, e.g., a labeled primer. Indirect detection involves incorporation of a label into, e.g., a hybridization probe.

For direct detection, the label(s) may be incorporated in four ways: (1) the primers comprise the label(s), for example attached to the base, a ribose, a phosphate, or to analogous structures in a nucleic acid analog; (2) modified nucleosides that are modified at either the base or the ribose (or to analogous structures in a nucleic acid analog) with the label(s); these label-modified nucleosides are then converted to the triphosphate form and are incorporated into the newly synthesized strand by a polymerase; (3) modified nucleotides are used that comprise a functional group that can be used to add a detectable label; or (4) modified primers are used that comprise a functional group that can be used to add a detectable label. Any of these methods result in a newly synthesized strand that comprises labels that can be directly detected as outlined below.

For indirect detection, the label is incorporated into the hybridization probe using methods well known to one of skill in the art. For example, the label can be incorporated by attaching the label to a base, ribose, phosphate, or to analogous structures in a nucleic acid analog, or by synthesizing the hybridization probe using a modified nucleoside.

Thus, a modified strands of the amplicon or the hybridization probe can include a detection label. By "detection label" or "detectable label" herein is meant a moiety that allows detection. This may be a primary label or a secondary label.

In one embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, alexa dyes, phycoerythrin, bodipy, and others described in the 6th Edition of the Molecular Probes Handbook by Richard P. Haugland, hereby expressly incorporated by reference.

In another embodiment, a secondary detectable label is used. Accordingly, detection labels may be primary labels (i.e. directly detectable) or secondary labels (indirectly detectable). A secondary label is one that is indirectly detected; for example, a secondary label can bind or react with a primary label for detection, or may allow the separation of the compound comprising the secondary label from unlabeled materials, etc. Secondary labels find particular use in systems requiring separation of labeled and unlabeled probes, such as SBE reactions. Secondary labels include, but are not limited to, one of a binding partner pair; chemically modifiable moieties; nuclease inhibitors, etc.

In another embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smallest of the pair is attached to the NTP for incorporation into the extension primer.

In another embodiment, the binding partner pair comprises biotin or imino-biotin and streptavidin Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In another embodiment, the binding partner pair comprises a primary detection label (for example, attached to the NTP and therefore to the extended primer) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about 10-4-10-6 M-1, with less than about 10-5 to 10-9 M-1 being preferred and less than about 10-7-10-9 M-1 being particularly preferred.

Formats

Detection of the amplified products described above preferably employs arrays, as described herein. In one embodiment, the arrays comprise hybridization probes affixed to a solid support.

By "substrate" or "solid support" or other grammatical equivalents herein is meant any material to which a hybridization probe can be immobilized. Possible substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, and a variety of other polymers. In general, the substrates allow optical detection and do not themselves appreciably fluoresce.

Generally the substrate is flat (planar), although as will be appreciated by those in the art, other configurations of substrates may be used as well.

In a preferred embodiment the array is a liquid array. In this embodiment, a species of hybridization probes is immobilized to a first set of microspheres. Likewise, a second species of hybridization probes is immobilized to a second set of microspheres. Similarly additional species of hybridization probes are attached to discrete populations of microspheres. There is no upward limit to the number of populations of microspheres or capture probes when populations are analyzed individually.

When multiple sets of microspheres are mixed and analyzed the number of sets is limited only by the number of encoding moieties applied to the microspheres. That is, microspheres are encoded so that the identity of each set of microspheres can be determined. Encoding moieties can be any distinguishable characteristic, e.g. size, shape, texture etc., of the microsphere. In preferred embodiments, encoding moieties are attributes that are not inherent in the bead or microsphere itself. Rather, the encoding moiety is a feature that is added to a bead. Preferred encoding moieties include, but are not limited to nucleic acids, proteins, and detectable labels or fluors. In addition, materials such as nanocrystals can be used as encoding moieties.

Also, in some embodiments, a plurality of different types of encoding moieties can be used to develop numerous different codes.

In a preferred embodiment, the beads and encoding system are those used in the Luminex flow cytometer. This system is described in more detail in U.S. Pat. No. 5,981,180, which is expressly incorporated herein by reference.

Briefly, the flow cytometer comprises a Luminex LX100 Flow Cytometer instrument with a sheath source and a waste reservoir. The hybridized bead array is introduced into the Luminex Flow Cytometer instrument where the beads are interrogated by two lasers, a red laser for the internal discriminator and a green laser for the external discriminator dyes respectively.

With the liquid arrays it is possible to simultaneously multiplex 100 or more different organisms or targets. The discrimination of the polystyrene Luminex bead array is dependent on the precise ratio of two internal discriminator dyes, a red and an infrared dye. The signal intensity on the surface of the bead is dependent on the concentration of the analyte in solution, in our case the amplified DNA of a suspect agent or an antigen or a toxin, whichever the case may be.

A 100-plex Luminex liquid array is generated by intercalating varying ratios of red and orange infrared dyes into polystyrene latex microspheres or beads. The process of producing varying ratios of red and orange infrared dyes in the beads is accomplished by increasing the amount of red dye and increasing the amount of orange dye. This gives each optically encoded bead a unique spectral address.

The beads are coated with capture probes complementary to adapter sequences, e.g., hybridization probes, as described herein. Each bead has an attachment site specific for a unique bioagent, e.g., hybridization probe.

The beads are analyzed in the flow cytometer, one at a time. A red laser classifies the bead, identifying the bead type. Subsequently a green laser quantifies the assay on the bead surface—only those beads with a complete sandwich will produce a fluoresce in the green, and the signal is a function of label concentration, which is indicative of the amount of target, e.g., amplicon.

Solid Support Arrays

In another aspect, arrays of oligonucleotide probes that are complementary to target nucleic acid sequences from a pathogen can be used to identify a nucleic acid and detect the presence of the pathogen in a sample. Oligonucleotide arrays typically comprise a plurality of different oligonucleotide probes that are coupled to a surface of a substrate in different known locations. Oligonucleotide arrays have been generally described in the art, for example, U.S. Pat. No. 5,143,854 and PCT patent publication Nos. WO 90/15070 and 92/10092. These arrays can generally be produced using mechanical synthesis methods or light directed synthesis methods that incorporate a combination of photolithographic methods and solid phase oligonucleotide synthesis methods. See Fodor et al., Science 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, the entire teachings are incorporated by reference herein. Techniques for the synthesis of these arrays using mechanical synthesis methods are described in, e.g., U.S. Pat. No. 5,384,261; the entire teachings are incorporated by reference herein. In another example, linear arrays can be utilized.

Once an oligonucleotide array is prepared, a sample potentially having the nucleic acid of interest is hybridized with the array and scanned. Hybridization and scanning are generally carried out by methods described herein and also in, e.g., published PCT Application Nos. WO 92/10092 and WO 95/11995, and U.S. Pat. No. 5,424,186, the entire teachings are incorporated by reference herein. In some aspects, a target nucleic acid sequence is not amplified prior to application to an array. In some aspects, a target nucleic acid sequence is amplified prior to application to an array. In brief, a target nucleic acid sequence is amplified by well-known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although primarily described in terms of a single detection block, e.g., for detecting a single nucleic acid of interest, arrays can include multiple detection blocks, and thus be capable of analyzing multiple, specific nucleic acids, e.g., a single array can be used for detection of multiple nucleic acids from multiple pathogens. In alternative aspects, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

Additional uses of oligonucleotide arrays for nucleic acid detection can be found, for example, in U.S. Pat. Nos. 5,858,659 and 5,837,832, the entire teachings of which are incorporated by reference herein.

In some aspects, array detection is used in tandem with RT-PCR for orthogonal detection of a nucleic acid or set of nucleic acids. For example, RT-PCR is used to obtain a rapid detection of target nucleic acids and then an array is used to obtain more detailed information about the sample from which the target nucleic acids were obtained.

Multi-platform Testing

Described herein are kits and methods for detection of agricultural pathogens using 2 assay platforms (multiplexed PCR and oligonucleotide arrays) that can be used independently from or in conjunction with each other. The two detection platforms are distinct and complementary. Jointly, they offer alternatives for users as well as orthogonal detection.

Real-time PCR has been the gold standard for detection, and the machines necessary are readily available in most labs including field labs. It is known to be rapid and sensitive.

Microarray technology enables deep detection and in general, a very large number of loci may be detected. This gives much greater assurance that the target organism will be detected. Since microarrays can accommodate thousands of probe sequences, the probes we provided may be added to existing microarrays to increase the range of pathogens detected.

In some embodiments, the two detection platforms are used in tandem for orthogonal detection. For example, a rapid answer can be first obtained using Real-time PCR, followed by more detailed information about the sample from microarray analysis.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B (1992); "Oligonucleotide Synthesis" (M. J. Gait, ed., 1984); "Animal Cell Culture" (R. I. Freshney, ed., 1987); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Summary of Assay Development

Figure 65:
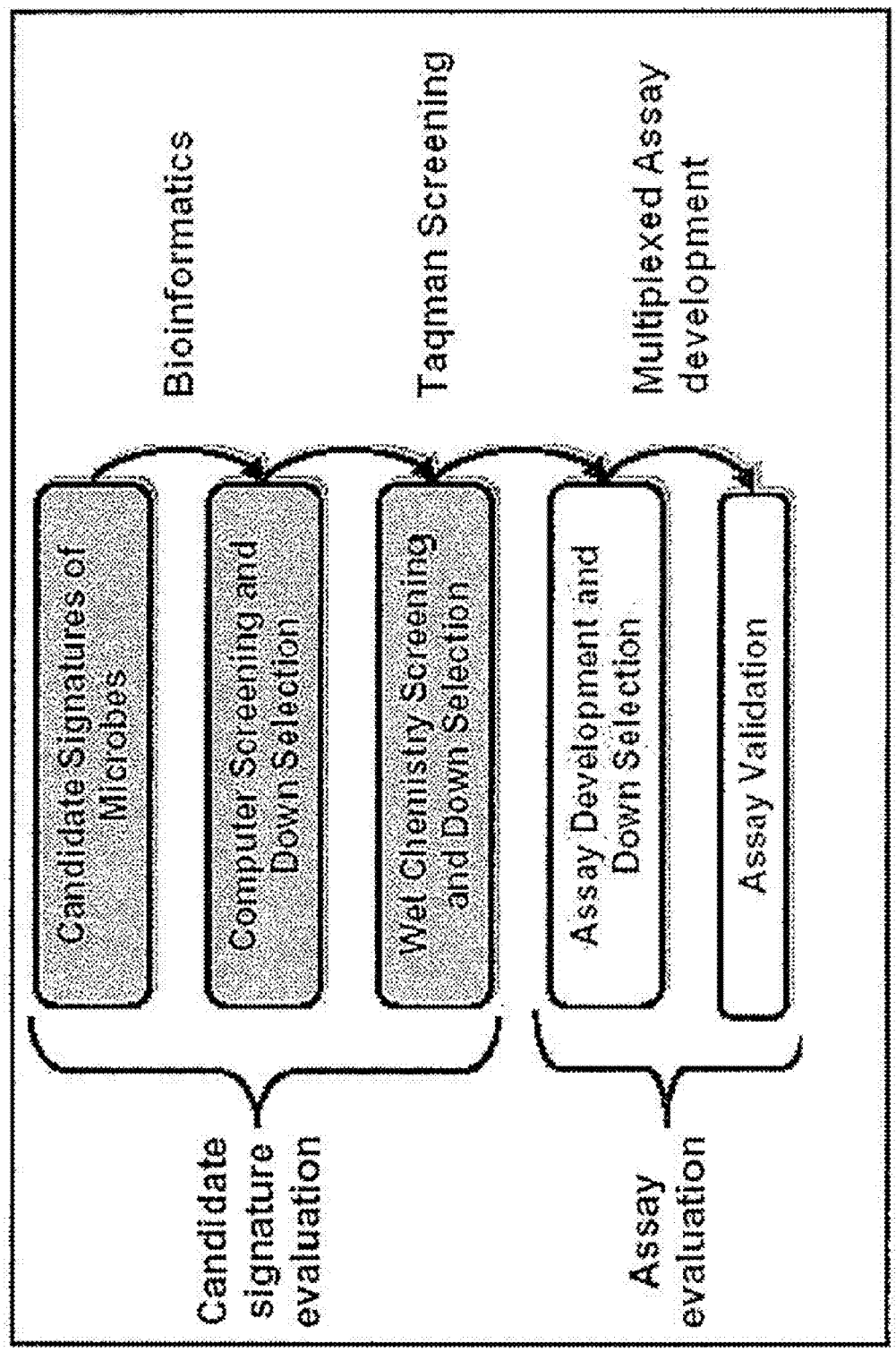

The Bioassays and Signatures Program (BSP) at Lawrence Livermore National Laboratory (LLNL) have constructed a robust technical architecture for the rapid development of highest-quality nucleic acid assays, tailored to end-user specifications. A summary of this process is shown in FIG. 65.

The pipeline process begins with an analysis of all available genomic sequence information, which forms the basis for the development of signatures. A signature is a region or set of regions on a chromosome that is unique to that organism. Candidate signatures can be selected based on performance criteria for specific detection technologies. Our nucleic acid assays employ PCR with primer pairs to generate the signature fragment(s) of interest. Once candidate signatures have been identified, they are subjected to a computational screening and down-selection process. This "in silico" screening method tests the candidate regions for uniqueness when compared to all the sequence data available. The computational screening also ensures that the signature primer pairs are amenable to assay chemistry requirements and provides rapid, low-cost initial screening of signatures.

The primers that emerge from the computational screening and down-selection are then tested against an extensive panel of DNAs and cDNAs. The bench screening consists of a panel of 2,000 to 3,000 samples, representing a wide range of organisms and backgrounds. This bench screening ensures that the primers will detect the strain diversity of the pathogen but will not react with the nucleic acids of other organisms that could be present in a sample.

Primer pairs that successfully pass the wet chemistry screening criteria are advanced to the assay development stage. Assay development includes the optimization of detection protocols, so that the assays perform consistently to required specifications on the prototype equipment selected. At the assay development stage, assays are fully characterized by assessing performance against a specified, standardized panel of targets (nucleic acid from various strains of the organism of interest, for which the assay was designed) and near-neighbors (genetically-related organisms), which yields rich data about the sensitivity and specificity of an assay. The results of all this work (from informatics through characterization) is captured in an extensive "certificate of analysis" that provides an assay pedigree. The pedigree comprises the entire history of the assay, including results of screening, metrics of performance such as sensitivity, specificity, and known cross-reactions (if any); all available at a glance, captured in a single data file.

Table 2 provides a summary of the number of signatures that were initially identified, screened in-silico, bench screened, and then screened in a mutiplex format.

TABLE 2

Summary of narrowing the search for signature sequences

| Agent | Initial # of candidate signatures | # of signatures forwarded to Taqman | # of signatures released to multiplex | # of signatures in Mux frozen panel |
|---|---|---|---|---|
| BPSV | 8 | 7 | 4 | 3 |
| BHV | 177 | 101 | 4 | 2 |
| BVD | 1 | 1 | 1 | 1 |
| FMDV | 4 | 4 | 4 | 1 |
| BTV | 8 | 8 | 4 | 2 |
| SVD | 4 | 4 | 4 | 3 |
| VESV | 44 | 20 | 6 | 4 |

Example 1

In-silico Identification of Candidate Signature Sequences

The LLNL Bioinformatics team developed "KPATH", a whole-genome comparative analysis software system. The general approach is the following: All available complete genomes of different strains of the target species are compared using multiple genome alignment programs. A consensus gestalt is formed from the alignments that contain the sequence conserved among all target inputs. This step is bypassed if only one target sequence is available. To establish that the organism-conserved sequence does not occur in any other sequenced microbial organism, the consensus gestalt is compared against the LLNL updated database of microbial organisms. A customized algorithm accomplishes this electronic subtraction, and the result is a uniqueness gestalt that is mined for potential signature candidates. A final computational screening is done to verify that cross-reactions are not detected.

KPATH allows the genome to define potential signature candidates. However, rather than selecting candidate signatures randomly (often there are more candidates than is economically feasible to screen in the wet lab), they can be prioritized based on annotation. Annotation allows signatures to be scrutinized in a biological context. Identifying genes responsible for rendering a pathogen virulent is one component of a good diagnostic signature set. We manually select candidates associated with genes of interest, and include a random selection of candidates within intergenic regions, for wet lab screening. The random unique intergenic regions are selected as a guard against gene deletion or substitution engineering to evade DNA-based detection. We note that there are few tools focused on viral gene finding, and none known to us that can adequately predict genes in certain RNA virus families Because signature candidates are generated using exact matches in the Vmatch step described above, additional electronic screening on the signature candidates is performed to catch potential non-exact matches that might result in false positives in the wet lab. We have seen cases where this would predict cross-reactions with near-neighbor species that had not been caught by the exact-matching step (due to as few as 1 or 2 fortuitously-placed mis-matched bases.)

Table 3 summarizes the genomes used to generate candidate signatures for the seven agricultural pathogens.

TABLE 3

Genomes screened via K-path to generate candidate signature sequences for 7 agricultural pathogens

| Pathogen | Genome Description | GI Number | Sequence Length (bp) |
|---|---|---|---|
| BHV | Bovine Herpesvirus 1 | 9629818 | 135301 |
| BPSV | Sequence 1 from Patent WO03006654 | 32167392 | 137560 |
| BPSV | raw sequence of Orf virus OV-IA82 from Dan Rock on Oct. 21, 2003 | 40019122 | 137241 |
| BPSV | raw sequence of Orf virus OV-SA00 from Dan Rock on Oct. 21, 2003 | 40019123 | 139962 |
| BPSV | raw sequence of Orf virus OV-SA00 from Dan Rock on Oct. 21, 2003 | 40019124 | 134431 |

TABLE 3-continued

Genomes screened via K-path to generate candidate signature sequences for 7 agricultural pathogens

| Pathogen | Genome Description | GI Number | Sequence Length (bp) |
|---|---|---|---|
| BVD | mature peptide N-Pro, proteinase, cleaves itself from the nascent polyprotein | 9626649|NC_001461.1 | 12573 |
| FMDV | Foot-and-mouth disease virus polyprotein, isolate C3Arg85 | 4007041/AJ007347.1 | 8161 |
| FMDV | Foot-and-mouth disease virus, derived from C3Arg85, clone 15 | 4007043/AJ007572.1 | 8161 |
| FMDV | Foot-and-mouth disease virus (FMDV) strain C, isolate c-s8c1 | 6318187/AJ133357.1 | 8115 |
| FMDV | Foot-and-mouth disease virus (FMDV) strain C, isolate rp99 | 6318189/AJ133358.1 | 8115 |
| FMDV | Foot-and-mouth disease virus (FMDV) strain C, isolate rp146 | 6318191/AJ133359.1 | 8115 |
| FMDV | Foot-and-mouth disease virus C strain C-S8 clone MARLS, | 10334811/AF274010.1 | 8115 |
| FMDV | FMDV RNA of primary translation product | 61063/X00429.1 | 7107 |
| FMDV | Foot & mouth disease virus A12; L, P2, and P3 polypeptide coding region | 210306/M10975.1 | 7712 |
| FMDV | Foot and Mouth Disease Virus A L-fragment of RNA genome | 397965/X74812.1 | 7820 |
| FMDV | Foot and mouth disease virus (FMDV-O1K) RNA for polyprotein precursor | 61076/X00871.1 | 7804 |
| FMDV | Foot-and-mouth disease virus (strain O1) polyprotein gene | 6456593/AF189157.1 | 6996 |
| FMDV | Foot-and-mouth disease virus polyprotein precursor | 5031481/AF154271.1 | 7739 |
| FMDV | Foot-and-mouth disease virus O strain Chu-Pei complete genome | 5921457/AF026168.2 | 7733 |
| FMDV | Foot-and-mouth disease virus, complete genome | 12018088/AF308157.1 | 8134 |
| FMDV | Foot-and-mouth disease virus C, complete genome | 10445391/NC_002554.1 | 8115 |
| BTV | Bluetongue virus (serotype 17/isolate USA) segment 1 from LLNL on Feb. 14, 2005 1:58PM | Segment 1 reference genome: 50253391/NC006023.1 | 3862 |
| BTV | Bluetongue virus (serotype 10 American isolate) segment 1 from LLNL on Feb. 14, 2005 1:51PM | Segment 1 reference genome: 50253391/NC006023.1 | 3703 |
| BTV | Bluetongue virus (serotype 2/isolate USA) segment 1 from LLNL on Feb. 14, 2005 2:01PM | Segment 1 reference genome: 50253391/NC006023.1 Segment 1 | 3857 |
| BTV | Bluetongue virus (serotype 11/isolate USA) segment 1 from LLNL on Feb. 14, 2005 1:53PM | Segment 1 reference genome: 50253391/NC006023.1 | 3755 |
| BTV | Bluetongue virus (serotype 13/isolate USA) segment 1 from LLNL on Feb. 14, 2005 1:56PM | Segment 1 reference genome: 50253391/NC006023.1 | 3830 |
| BTV | Bluetongue virus (serotype 17/isolate USA) segment 8 from LLNL on Feb. 14, 2005 2:00PM | Segment 8 reference genome: 50253377/NC_006007. | 1074 |
| BTV | Bluetongue virus (serotype 10/American isolate) segment 8 from LLNL on Feb. 14, 2005 1:51PM | Segment 8 reference genome: 50253377/NC_006007. | 1085 |
| BTV | Bluetongue virus (serotype 11/isolate USA) segment 8 from LLNL on Feb. 14, 2005 1:54PM | Segment 8 reference genome: 50253377/NC_006007. | 977 |
| BTV | Bluetongue virus (serotype 13/isolate USA) segment 8 from LLNL on Feb. 14, 2005 1:57PM | Segment 8 reference genome: 50253377/NC_006007. | 1090 |
| BTV | Bluetongue virus (serotype 17/isolate USA) segment 9 from LLNL on Feb. 14, 2005 2:00PM | Segment 9 reference genome: 50253379/NC_006008.1 | 997 |
| BTV | Bluetongue virus (serotype 10/American isolate) segment 9 from LLNL on Feb. 14, 2005 1:52PM | Segment 9 reference genome: 50253379/NC_006008.1 | 897 |
| BTV | Bluetongue virus (serotype 2/isolate USA) segment 9 from LLNL on Feb. 14, 2005 2:03PM | Segment 9 reference genome: 50253379/NC_006008.1 | 1029 |
| BTV | Bluetongue virus (serotype 11/isolate USA) segment 9 from LLNL on Feb. 14, 2005 1:54PM | Segment 9 reference genome: 50253379/NC_006008.1 | 808 |
| SVD | Swine vesicular disease virus strain NET/1/92, complete genome | 8896132 | 7406 |
| SVD | PISVDV Swine vesicular disease virus complete genomic RNA | 61167 | 7400 |
| SVD | SVDMPS Swine vesicular disease virus gene for polyprotein, complete cds | 37993797 | 7401 |
| SVD | Swine vesicular disease virus strain HK'70, complete genome | 402536 | 7401 |
| SVD | Swine vesicular disease virus (STRAIN H/3 '76) genomic RNA, complete genome | 1228947 | 7401 |
| VESV | Vesicular exanthema of swine virus, complete genome | 10314005/NC_002551.1 | 8284 |

Example 2

Use of Taqsim to Further Screen Candidate Signature Sequences

A computational TaqMan simulator program, "Taqsim", was used to identify all potential targets for each candidate signature from all sequences available in Genbank. Taqsim is a BLAST-based comparison of each signature as a triplet against all sequences in Genbank to identify the targets that are predicted to produce a TaqMan reaction at 57 degrees primer annealing and 67 degrees for probe annealing (these temperatures are according to Primer 3 oligo Tm calculations). Input parameters allow for standardized signature informatics that allows for universal protocol development and assay compatibility.

TABLE 4

Taqsim settings used for generation of candidate signatures
Primer3 Parameters

| Parameters | Standard Settings |
| --- | --- |
| PRIMER_OPT_SIZE | 20 |
| PRIMER_MIN_SIZE | 18 |
| PRIMER_MAX_SIZE | 27 |
| PRIMER_PRODUCT_OPT_SIZE | 100 |
| PRIMER_PRODUCT_SIZE_RANGE | 71-600 |
| PRIMER_OPT_TM | 62 |
| PRIMER_MIN_TM | 61 |
| PRIMER_MAX_TM | 63 |
| PRIMER_MIN_GC | 20 |
| PRIMER_MAX_GC | 80 |
| PRIMER_PICK_INTERNAL_OLIGO | 1 |
| PRIMER_INTERNAL_OLIGO_OPT_SIZE | 31 |
| PRIMER_INTERNAL_OLIGO_MIN_SIZE | 18 |
| PRIMER_INTERNAL_OLIGO_MAX_SIZE | 36 |
| PRIMER_INTERNAL_OLIGO_OPT_TM | 72 |
| PRIMER_INTERNAL_OLIGO_MIN_TM | 71 |
| PRIMER_INTERNAL_OLIGO_MAX_TM | 73 |
| Number of Primers/Probe Set generated: | 101 |

Example 3

Wet Chemistry Screening Process

To ensure extremely high selectivity and sensitivity, a rigorous wet-chemistry screening was performed to further down-select candidate nucleic acid signatures before taking those signatures that pass this screening on to assay development. This step ensures that the primers will detect the strain diversity of the pathogen, but will not react with the nucleic acids of other organisms that could be present in a sample. At this stage, only the primers are tested and many unsuitable primers (e.g., those that form primer-dimers, those that do not produce amplicons of the correct size, etc.) can be eliminated in this first step.

An initial screening of the PCR signatures was performed in duplicate using end-point PCR and gel electrophoresis as described herein. The signatures are initially screened against nucleic acid extractions from 5 soils, 5 eukaryotic nucleic acids, and 5 microbes, each picked at random, and selected near neighbors. The soils represent a diverse geographical and temporal distribution and contain complex mixtures of organisms. The eukaryotic nucleic acids are those that may potentially carry over from sample collection processes. The microbial nucleic acids were selected to span the range of microbial diversity. Near neighbors are organisms that are closely related at the genetic level and have the greatest likelihood of causing confounding results in the assays.

Signatures that produce amplicons with various soils, microbe, eukaryotic or near neighbor nucleic acids were eliminated. Furthermore, signatures were eliminated due to their inability to produce correct size PCR product when crossed with targets. The down-selected signatures are then put through intensive background screening in real-time (TaqMan) PCR format.

Reagents: Invitrogen Platinum Taq polymerase, Catalog #10966-083 (Carlsbad, Calif.); Invitrogen 10 PCR Buffer, Catalog #10966-083 (Carlsbad, Calif.); Invitrogen 50 mM MgC12, Catalogue #10966-083 (Carlsbad, Calif.); Sigma Chemical BSA, Catalogue #B8687 (St Louis, Mo.); Amersham dNTPs, Catalogue #27-2035-02 (Piscataway, N.J.); Biosearch Technologies oligonucleotides (Novato, Calif.); Nuclease-Free water; Cambrex 4% agarose gel, Catalogue #57225; Cambrex Simplyload 20 by ladder, catalogue #50331; Teknova 10× TBE, Catalogue #T0210; Teknova 10× Loading Dye, Catalogue #F3062; Clonetech Powerscript one step qRT-PCR kit, Catalogue #630051.

Sample preparation. Pathogen nucleic acids were isolated from virus grown in cell culture as described herein.

PCR assays for DNA templates: Background templates are added to each 25 ul reaction in the following amounts: 5 ng of total soil extract, 1 ng of total Eukaryotic extracted DNA and 200 pg of total extracted Prokaryotic DNA. Control on each plate consists of 2 *Bacillus thuringiensis* reactions (1 ng DNA per 25 ul reaction), and an NTC (No Template Control=5 ul PCR water in place of the template), for each primer used on the plate. Each reaction includes the following: 10× PCR Buffer (2.5 ul); 10 mM dNTPs (2.0 ul); 50 mM MgSO4 (2.25 ul); BSA (2 ug/ul) (1.0 ul); F/R Primers (2.5 uM) (1.0 ul); PlatinumTaq (0.125.0 ul); PCR water (11.125 ul); Template (in 5.0 ul). Thermalcycler Parameters are as follows: Cycle 1: (1×): Step 1: 94.0° C. for 01:00; Cycle 2: (39×) Step 1: 94.0° C. for 00:20; Step 2: 55.0° C. for 00:10; Step 3: 72.0° C. for 00:30; Cycle 3: (1×) Step 1: 15.0° C., HOLD.

PCR assays for RNA templates: Primer set assays are performed in triplicate against available RNA extractions of targets and near neighbors using 200 pg of extracted RNA to each 25 ul reaction. Each reaction includes the following: 2× One-step RT-PCR Buffer (12.5 ul); 50× Q Taq Polymerase Mix, 1.5 U/ul (0.5 ul); 60×Q PowerScript (0.42 ul); PCR water (5.53 ul); F/R Primers (10 uM) (1.05 ul); Template in 5 ul. Thermalcycler Parameters are as follows: Cycle 1: (1×) Step 1: 48.0° C. for 20:00; Step 2: 95.0° C. for 03:00; Cycle 2: (39×): Step 1: 95.0° C. for 00:15; Step 2: 60.0° C. for 01:00; Step 3: 72.0° C. for 00:15; Cycle 3: (1×): Step 1: 15.0° C. HOLD.

Gel electrophoresis. Product size was determined by running 15 ul of PCR product with 5 ul 10× loading dye (Teknova; Hollister, Calif.) on 4% agarose gels (Cambrex Rockland, IN) in Tris-borate-EDTA buffer (Teknova). Band size was determined using Cambrex's Simpleload 20 base pair ladder. The Epi Chemi II Darkroom Bioimaging system (UVP Bioimaging Systems Upland, Calif.) was used for visualization of the DNA.

Example 4

Taqman Format Screening

Following the wet screening process, signature sequences were screened in a real-time PCR format in triplicate against nucleic acid samples that include nucleic acid extracts from all targets and near neighbors, 16 eukaryotes, 55 soils, 45 prokaryotes, and a total of 2256 samples collected from aerosol collectors and pooled for background testing purposes. Primer pairs that successfully pass the wet chemistry screening criteria are advanced to the assay development stage.

Taqman assay development includes the bioinformatics selection and evaluation processes, and optimization and characterization. Optimization is conducted for every relevant parameter that impacts assay performance. For example, in a standard RT-PCR assay, parameters to be optimized include: primer/probe length, GC content, Tm, concentration(s), thermocycling parameters (2-step or 3-step, times, temperatures for each step) reaction conditions (MgC12 concentration), Taq polymerase (type and concentration), reaction buffers, extraction protocols, etc.

Taqman probes: Probes for Real-time PCR Taqman reactions were obtained from Biosearch Technologies using the Tamara fluorophore and Black Hole quencher. In some instances the Taqman probes had the same sequence as the probes used in the multiplex Luminex assay and described in Table 1, e.g., the Taqman probes were forward complement probes (FCP). In other instances, the Taqman probes were the reverse complement of probes disclosed in Table 1 and used in the Luminex assay. For example, for the BHV-1 assay, the sequence of the real-time probes was the reverse complement of the Luminex probe, e.g., the sequence was CTCCATGT-TAGCGCTCTGGAACCTGGA (SEQ ID NO: 69). The Taqman probes were as follows:

V/V (to 15 ml add 75 ul Triton). Add 0.5M EDTA to a final concentration of 20 mM (15 ml add 600 ul 0.5M EDTA. Mix vigorously and vortex, let sit 5 mM at room temp. Spin tube at <1000 rpm for 10 minutes. Discard pellet and to the supernatant add 10% (W/V) Sodium Dodecyl Sulfate (SDS) solution to a final concentration of 1% (to 15 ml add 1.5 ml of 10% SDS). Add proteinase K to a final concentration of 0.4 Upper ml (to 15 ml add 2.4 mg of 2.5 U/mg Roche or 60 ul of a 0.1 mg/ul solution of proteinase K in water). Incubate the tubes at 55° C. for one hour mixing every 10 minutes. Cool tubes to room temperature. Add 5 M NaCl to a final concentration of 150 mM (to 16.5 ml add 510 ul 5 M NaCl). Add an equal volume of room temperature phenol/chloroform/isoamyl alcohol (approx. 15 ml). Mix by inversion and swirling till phases are completely mixed. Let sit 5 mM then spin at 3,000 rpm for 10 mM Remove the upper aqueous layer and distribute 500 ul into 1.5 ml microcentrifuge tubes (for 15 mls need 30 tubes). Discard the lower layer in phenol/chloroform waste. Add two volumes (1 ml) of 100% ethanol to each microcentrifuge tube and leave at −20° C. one hour. Spin in microfuge at top speed refrigerated for 10 minutes. Discard supernatant and wash pellet once with 70% ethanol 150 mM NaCl. Remove all ethanol and dissolve the pellet in TE. For 15 ml extraction dissolve each pellet in each tube in 50 ul of liquid. Each tube should contain 50 fg/ul of puc 18.

Sample preparation, RNA: RNA was extracted from virus infected tissue culture samples as follows. Add 3× the volume

TABLE 5

Probes for Taqman assays

| SEQ ID NO: | Pathogen-assay | Real-time probe orientation | Sequence (5' => 3') |
|---|---|---|---|
| 69 | BHV-1 | Plus, RCP | CTCCATGTTAGCGCTCTGGAACCTGGA |
| 70 | BHV-3 | Plus, RCP | CGCGAATCTTATTTAAGTGCACACCGTGTTATTT |
| 71 | BPSV-1 | Plus, RCP | CACGTTCTCCACGTCGGAGTCGG |
| 72 | BPSV-2 | Plus, RCP | CGGAAGCCCATGAGCCCGTACA |
| 73 | BPSV-4 | Plus, RCP | CGCTTGTTGTCCGCCTCGAAGTC |
| 74 | BTV-2 | Plus, RCP | ACAGAAGATGATGATTGGCCCACGAGTTAG |
| 75 | BTV-3 | Minus, FCP | CTAACTCGTGGGCCAATCATCATCTTCTGT |
| 76 | BVD-1a(mod) | Plus, RCP | CTCGAGATGCCACGTGGACGAGG |
| 77 | FMDV.Pir | Minus, FCP | CCTCGGGGTACCTGAAGGGCATCC |
| 78 | FMDV.TC | Minus, FCP | GTCCCACGGCGTGCAAAGGA |
| 79 | SVD_1 | Plus, RCP | CGTCACAAGTTGTACCATCAGACACAATGCA |
| 80 | SVD_2 | Minus, FCP | TGACCGTAATGAGGTCATCGTGATTTCTCAC |
| 81 | SVD_3 | Minus, FCP | CTGGCGTCATAGCCTGAATAGTCAAACGCTA |
| 82 | VESV_1 | Plus, RCP | CCAAATTGCACATCTAAGGTTATCAACGATGATG |
| 83 | VESV_3 | Plus, RCP | CGACTCATCTGACAAGGTTGATTATGCCAATTT |
| 84 | VESV_4 | Plus, RCP | CTTCCTCCAACTCAGGCACCGAGC |
| 85 | VESV_5 | Plus, RCP | TGGTGACAAATGCCCGTCCCG |

Sample preparation, DNA: Total DNA was extracted from virus infected cell culture as follows. Add $5 \times 10^{-2}$ nanograms of Puc18 per ml of virus cell culture (to 15 ml add 0.75 ng Puc19). Add Triton X-100 to a final concentration of 0.5% Trizol (TRIZOL LS Invitrogen Cat. No. 10296-010) to the volume of sample. (Upon completion of this step, sample can be stored at −80, or continue with extraction.) Lyse cells in the sample suspension by passing the suspension several times through a pipette, or by shaking vigorously. Incubate for 15 minutes at room temperature. (Typically, LLNL uses 2× the volume Trizol to water (e.g., 15 ml sample and 30 mls TRIZOL.) Add 200 ul chloroform per 1 ml solution in the fume hood, cap and shake vigorously for 15 seconds. Incubate at room temperature for 5-15 minutes. Centrifuge at 3000 g for 15 minutes, at 4° C. Remove aqueous layer. Add 1 ml isopropyl alcohol per 500 ml aqueous layer. Gently mix by inverting several times. Incubate samples on the bench top for 10 minutes. Centrifuge at 12,000 g for 10 minutes at 4 C. Carefully, pour off liquid. Wash pellet with 70% EtOH. Vortex sample and re-centrifuge at 7,500 g for 5 minutes at 4° C. Pour off the EtOH, cap, re-spin at 7,500 g for 5 minutes and pipette off remaining liquid. Air dry briefly at 55° C., caution not to over-dry. Resuspend RNA in RNAse-free water and store at −80° C.

Reverse transcriptase. RNA samples were subjected to reverse transcription using the BD Clonetech kit, 48 degrees C. for 30 minutes.

Real-time PCR for DNA samples. Primer/probe set assays were performed in triplicate against 54 extracted soil samples, 16 Eukaryotic backgrounds and 45 Prokaryotic backgrounds and against 3 distinct aerosol extraction plates, adding 5 ul template to each 25 ul reaction. Background templates, with the exception of aerosols, were added to each 25 ul reaction in the following amounts: 5 ng of total soil extract, 1 ng of total Eukaryotic extracted DNA and 200 pg of total extracted Prokaryotic DNA. (The backgrounds are premade up in plates that are diluted to the proper concentrations so that 5 ul of each background is added to each 25 ul reaction.) Controls on each plate consist of 2 *Bacillus thuringiensis* reactions (1 ng DNA per 25 ul reaction), and an NTC (No Template Control=5 ul PCR water in place of a template), reaction for each primer/probe on the plate.

| Component | 1x (ul) |
|---|---|
| 10x PCR Buffer | 2.5 |
| 10 mM dNTPs | 0.5 |
| 50 mM MgSO4 | 3.0 |
| BSA (2 ug/ul) | 1.0 |
| F/R Primers (10 uM) | 0.5 |
| Probe (10 uM) | 1.0 |
| PlatinumTaq | 0.25 |
| PCR Water | 11.25 |
| Template (**/ul) | 5.0 |

| iCYCLER Parameters | | |
|---|---|---|
| Cycle 1: (1X) | 95.0° C. for 01:00 | |
| Cycle 2: (39X) | 95.0° C. for 00:20 | Data collection and real-time analysis enabled |
| | 55.0° C. for 00:10 | |
| | 72.0° C. for 00:30 | |
| Cycle 3: (1X) | 4.0° C. HOLD | |

PCR for RNA samples. Reverse transcriptase Real-Time Procedure. Follow steps 1 and 2 of the Real-Time DNA procedure for background screening on each signature. Perform primer set assays in triplicate against RNA extractions of targets and near neighbors using the Clonetech RT-PCR kit. Controls on each plate consist of 2 *Bacillus thuringiensis* (Bt) reactions (1 ng DNA per 25 ul reaction), and an NTC (No Template Control=5 ul PCR water in place of a template), reaction for each primer/probe on the plate. Be sure to use the Clonetech RT-KIT for Bt controls on RNA plates.

Clontech RT-PCR Reagent Mix Preparation:

| Component | 1x (ul) |
|---|---|
| 2x One-step RT-PCR Buffer | 12.5 |
| 50x Q Taq Polymerase Mix, 1.5 U/ul | 0.5 |
| 60x Q PowerScript | 0.42 |
| PCR water | 5.33 |
| F/R Primers (10 uM) | 1.05 |
| Probe (10 uM) | 0.20 |
| Template, concentration varies | 5.0 |

| iCYCLER Parameters | | |
|---|---|---|
| Cycle 1: (1X) | 48.0° C. for 20:00 | |
| Cycle 2: (39X) | 95.0° C. for 00:10 | Data collection and real-time analysis enabled |
| | 60.0° C. for 01:00 | |
| | 72.0° C. for 00:15 | |
| Cycle 3: (1X) | 15.0° C. HOLD | |

PCR efficiency. The efficiency, of the PCR assay was determined by testing dilutions from 3000 pg to 10 pg in triplicate. The average ct value was graphed against the template concentration, the equation of the resulting line yielded the R2 value that represents the PCR efficiency.

Signature sequences that performed well in the Taqman format are presented in Table 1.

TABLE 1

Signature sequences, PCR primers, and probes for detection of 7 agricultural pathogens in a sample.

| SEQ ID NO: | Pathogen_Assay | description | Sequence 5' => 3' |
|---|---|---|---|
| 1 | BVH_1 | SIGNATURE SEQUENCE 140 bp | GTGCCAGCCGCGTAAAAGCGGCGCTCCATGTTAGCGCTCTGGAACCAGGA GACGTCGCAGCGCAGGTTGGGCGGGTGGGCGGTTGGCGTCGCGTCCTCGA GCGTAAGGACGGACGTGCGCGAAAAGAGCCCGGAGTCGTC |
| 2 | BVH_1 | FORWARD PRIMER | GTGCCAGCCGCGTAAAAG |
| 3 | BVH_1 | REVERSE PRIMER | GACGACTCCGGGCTCTTTT |
| 4 | BVH_1 | PROBE | TCCTGGTTCCAGAGCGCTAACATGGAG |

TABLE 1-continued

Signature sequences, PCR primers, and probes for detection of 7 agricultural pathogens in a sample.

| SEQ ID NO: | Pathogen_Assay | description | Sequence 5' => 3' |
|---|---|---|---|
| 5 | BVH_3 | SIGNATURE SEQUENCE 114 bp | GTCCCCACGGGCGTAGTAGCACCGGGCGTGCTGTCCTCTGGCGTAGCGTC GGGGCTGTTGGGCGTGGGGGGCGTTGCGCCGGTGGTCCCAGCGGAGCTTT CCGTCTCGGTTGGG |
| 6 | BVH_3 | FORWARD PRIMER | TGAGGCCTATGTATGGGCAGTT |
| 7 | BVH_3 | REVERSE PRIMER | GCGCGCCAAACATAAGTAAA |
| 8 | BVH_3 | PROBE | AAATAACACGGTGTGCACTTAAATAAGATTCGCG |
| 9 | BPSV-1 | SIGNATURE SEQUENCE 178 bp | GCAGATGCGCTCCTGGTTCTGGCAGAACACCGAGTCTTCGATGATCAACA CCCTCCTGGTCCCGGCCGACCGCATGATGGCCATGGCCCGGATGAGCCTC TTCTTCGATCCGCGTATGGACATGGACCGGAGCACGTTCTCCACGTCGGA GTCGGAGACGTTGCAGCAGCAGAGGTGC |
| 10 | BPSV-1 | FORWARD PRIMER | GCAGATGCGCTCCTGGTT |
| 11 | BPSV-1 | REVERSE PRIMER | GCACCTCTGCTGCTGCAA |
| 12 | BPSV-1 | PROBE | CCGACTCCGACGTGGAGAACGTG |
| 13 | BPSV_2 | SIGNATURE SEQUENCE 95 bp | GATGGCCGTGCAGCTCTTGGCCGAGGCGTACGAGAAGAGCGCGCTGTTGC GGAAGCCCATGAGCCCGTACACGGAGTTGGCCGTGATCTTGTACG |
| 14 | BPSV_2 | FORWARD PRIMER | GATGGCCGTGCAGCTCTT |
| 15 | BPSV_2 | REVERSE PRIMER | CGTACAAGATCACGGCCAACT |
| 16 | BPSV_2 | PROBE | TGTACGGGCTCATGGGCTTCCG |
| 17 | BPSV_4 | SIGNATURE SEQUENCE 167 bp | GCAGCAGTGCACCACGTAGTACCCGGCGGTGGCGCGCAGGCGCTTGTTGT CCGCCTCGAAGTCCGCCTCCAACCCCTCGTTGAAGTACTTGTCGAATATG ATGGGCAGGAAGGATAGTTTTGACTCGGTGACCACCTTCCCGAAGTTGAG GATGTACGGGTTCAGCG |
| 18 | BPSV_4 | FORWARD PRIMER | GCAGCAGTGCACCACGTAGT |
| 19 | BPSV_4 | REVERSE PRIMER | CGCTGAACCCGTACATCCT |
| 20 | BPSV_4 | PROBE | GACTTCGAGGCGGACAACAAGCG |
| 21 | FMDV-TC | SIGNATURE SEQUENCE 280 bp | ACTGGGTTTTACAAACCTGTGATGGCCTCGAAGACCCTCGAGGCCATCCT CTCCTTTGCACGCCGTGGGACCATACAGGAGAAGTTGATCTCCGTGGCAG GACTCGC |
| 22 | FMDV-TC | FORWARD PRIMER | ACTGGGTTTTACAAACCTGTGA |
| 23 | FMDV-TC | REVERSE PRIMER | GCGAGTCCTGCCACGGA |
| 24 | FMDV-TC | PROBE | GTCCCACGGCGTGCAAAGGA |
| 25 | FMDV-pir | SIGNATURE SEQUENCE 280 bp | CACTTTAAAGTGACACTGAAACTGGTACCCAATCACTGGTGACAGGCTAA GGATGCCCTCCAGGTACCCCGAGGTAACACGAGACAC-TCGGGATCTG |
| 26 | FMDV-pir | FORWARD PRIMER | CACYTYAAGRTGACAYTGRTACTGGTAC |
| 27 | FMDV-pir | REVERSE PRIMER | CAGATYCCRAGTGWCICITGTTA |
| 28 | FMDV-pir | PROBE | CCTCGGGGTACCTGAAGGGCATCC |
| 29 | BVD_1a | SIGNATURE SEQUENCE 202 bp | GGTAGTCGTCAGTGGTTCGACACCTCGGAAAGAAGGTCTCGAGATGCCAC GTGGACGAGGGCATGCCCAAAGCACATCTTAACCTGGACGGGGGTCGCCC AGGTAAAAGCAGTTTTGACCAACTGTTATGGACACAGCCTGATAGGGTGC TGCAGAGGCCCACTGAATTGCTACTAAAAATCTCTGCTGTACATGGCACA TG |
| 30 | BVD_1a | FORWARD PRIMER | GGTAGTCGTCAGTGGTTCGAC |
| 31 | BVD_1a | REVERSE PRIMER | CATGTGCCATGTACAGCAGAGAT |
| 32 | BVD_1a | PROBE | CCTCGTCCACGTGGCATCTCGAG |
| 33 | BTV_2 | SIGNATURE SEQUENCE 271bp | TCAAGACGAATGAATGAGGAGAAGATCTTAGAGGCGGTGAAGTATTCGCA AAATTTAGGCTCGCACGATCGTAGGCTACCTCTTTTTGAAAAAATGTTAA AGATGGTTTATACTACACCATTCTACCCGCATAAGAGCTCGAACATGATA TTAGCATCTTTCCTATTAAGCATTCAAACCATTACTGGATATGGCAGGGC |

TABLE 1-continued

Signature sequences, PCR primers, and probes for detection of 7 agricultural pathogens in a sample.

| SEQ ID NO: | Pathogen_Assay | description | Sequence 5' => 3' |
|---|---|---|---|
| | | | GTGGGTGAAGAACGTGAGCACCGAGTTCGATAAACAGCTGAAACCGAACC CAAGC |
| 34 | BTV_2 | FORWARD PRIMER | GCACCCTATATGTTTCCAGACCA |
| 35 | BTV_2 | REVERSE PRIMER | CAGCTAACTCTTCAGCCACACG |
| 36 | BTV_2 | PROBE | CTAACTCGTGGGCCAATCATCATCTTCTGT |
| 37 | BTV_3 | SIGNATURE SEQUENCE 187 bp | GGATTTGCGATATGAAGGTTATACGTTAGAACAGATCATAGATTTTGGAT ATGGAGAGGGGAGGGTAGCGAATACGTTGTGGAACGGAAAGCGAAGACTG TTTAAGACTACATTTGACGCGTATATACGATTAGATGAGAGCGAGCGAGA CAAAGGTGGTTTCAAGGTCCCCAAGGGAGTGCTTCCAGTATCGAGTGTTG ACGTTGCGAATCGAATCGCGGTGGACAAGGGATTCGACACGCTTATCGCG GCA |
| 38 | BTV_3 | FORWARD PRIMER | GCACCCTATATGTTTCCAGACCA |
| 39 | BTV_3 | REVERSE PRIMER | CAGCTAACTCTTCAGCCACACG |
| 40 | BTV_3 | PROBE | CTAACTCGTGGGCCAATCATCATCTTCTGT |
| 41 | SVD_1 | SIGNATURE SEQUENCE 349 bp | CAGGATAATTTCTTCCAAGGGCCCCCAGGAGAGGTGATGGGAAGAGCCAT TTCCAGCCCTAACCGCCGCAGAGACAGGGCACACGTCACAAGTTGTACCA TCAGACACAATGCAAACTAGACACGTGAAGAATTACCATTCAAGATCAGA GTCGACAGTGGAGAACTTCCTGTGCAGATCTGCATGCGTCTTCTACACCA CATACAAGAACCATGACTCCGATGGCGACAACTTCGCCTACTGGGTGATC AACACACGGCAAGTTGCTCAACTGCGTCGGAAGCTCGAAATGTTCACGT |
| 42 | SVD_1 | FORWARD PRIMER | CAGGATAATTTCTTCCAAGGGC |
| 43 | SVD_1 | REVERSE PRIMER | ACGTGAACATTTCGAGCTTCC |
| 44 | SVD_1 | PROBE | TGCATTGTGTCTGATGGTACAACTTGTGACG |
| 45 | SVD_2 | SIGNATURE SEQUENCE 281 bp | GACTTGTTGTGGCTGGAGGACGACGCCATGGAGCAAGGAGTTAGGGATTA TGTGGAACAACTCGGCAACTGCTTCGGCTCAGGATTCACCAATCAAATTT GCGAACAGGTTACCCTTCTAAAAGAGTCGTTAATTGGACAGGATTCTATC CTTGAGAAGTCTCTCAAGGCCCTCGTCAAGATAGTATCAGCACTCGTGAT CGTGGTGAGAAATCACGATGACCTCATTACGGTCACCGCCACACTGGCGT TAATAGGATGCACTACCTCACCATGGCGCTG |
| 46 | SVD_2 | FORWARD PRIMER | GACTTGTTGTGGCTGGAGGA |
| 47 | SVD_2 | REVERSE PRIMER | CAGCGCCATGGTGAGGTAG |
| 48 | SVD_2 | PROBE | TGACCGTAATGAGGTCATCGTGATTTCTCAC |
| 49 | SVD_3 | SIGNATURE SEQUENCE 248 bp | GACAAAGTGGCCAAGGGAAAGTCCAGGCTCATCGAGGCTTCTAGCCTCAA CGACTCAGTAGCAATGAGGCAGACATTTGGAAACCTATATAAGACTTTCC ACCTCAACCCGGGCATCGTTACGGGTAGCGCCGTTGGGTGTGACCCAGAT GTCTTTTGGAGCAAGATTCCCGTCATGCTCGATGGACATCTCATAGCGTT TGACTATTCAGGCTATGACGCCAGCCTCAGCCCAGTGTGGTTTACGTG |
| 50 | SVD_3 | FORWARD PRIMER | GACAAAGTGGCCAAGGGAAA |
| 51 | SVD_3 | REVERSE PRIMER | CACGTAAACCACACTGGGCT |
| 52 | SVD_3 | PROBE | CTGGCGTCATAGCCTGAATAGTCAAACGCTA |
| 53 | VESV_1 | SIGNATURE SEQUENCE 153 bp | GCCTTCTCCCTTCCCAAAACGGACGGACCCACCGGAAACGAACCCGAATT CATCGCTGAGGCTTGCCCTAGCTGCGCTCTTTACGACACGTGTCCAAATT GCACATCTAAGGTTATCAACGATGATGGCTCAACTGACGGAACCATTCCT TCA |
| 54 | VESV_1 | FORWARD PRIMER | GCCTTCTCCCTTCCCAAAA |
| 55 | VESV_1 | REVERSE PRIMER | TGAAGGAATGGTTCCGTCAGT |
| 56 | VESV_1 | PROBE | CATCATCGTTGATAACCTTAGATGTGCAATTTGG |
| 57 | VESV_3 | SIGNATURE SEQUENCE 199 bp | GGGAATGAGGTGTGCATCATTGATGAATTCGACTCATCTGACAAGGTTGA TTATGCCAATTTTGTAGTCAACATGGTTAACACCAACCCCATGGTCTTAA ATTGTGATCTAATTGAAAACAAAGGCAAGACATTCACCTCAAAATACGTC ATCATGACGTCCAACACGGAAACACCAGTCAAGCCAACATCAAGACGTG |
| 58 | VESV_3 | FORWARD PRIMER | GGGAATGAGGTGTGCATCATT |

TABLE 1-continued

Signature sequences, PCR primers, and probes for detection of 7 agricultural pathogens in a sample.

| SEQ ID NO: | Pathogen_Assay | description | Sequence 5' => 3' |
|---|---|---|---|
| 59 | VESV_3 | REVERSE PRIMER | CACGTCTTGATGTTGGCTTGAC |
| 60 | VESV_3 | PROBE | AAATTGGCATAATCAACCTTGTCAGATGAGTCG |
| 61 | VESV_4 | SIGNATURE SEQUENCE 124 bp | GGTCGCTCTCACTGATGATGAGTACAATGATTGGAAACAGTCCAAAGCTG AAAAAAACCTCGACCTCACGGTCAAGGACTTCCTCCAACTCAGGCACCGA GCTGCAATGGGTGCTGATAACACC |
| 62 | VESV_4 | FORWARD PRIMER | GGTCGCTCTCACTGATGATGAGTA |
| 63 | VESV_4 | REVERSE PRIMER | GGTGTTATCAGCACCCATTGC |
| 64 | VESV_4 | PROBE | GCTCGGTGCCTGAGTTGGAGGAAG |
| 65 | VESV_5 | SIGNATURE SEQUENCE 200 bp | ACCACCTCTGGAAACATCTATGGAGCCTGCGGCTCATCGTGTTCACTGAC GAGACAGGGTGACTGCGGTCTCCCCTACGTCGACGATCACGGTGTTGTCG TTGGACTCCATGCTGGGTCTGGTGGTGACAAATGCCCGTCCCGAAAACTC ATTGTTCCCTACGTCAAGGTGGATATGAGAATTCGTGACACGTGCACAAA |
| 66 | VESV_5 | FORWARD PRIMER | ACCACCTCTGGAAACATCTATGG |
| 67 | VESV_5 | REVERSE PRIMER | TTTGTGCACGTGTCACGAAT |
| 68 | VESV_5 | PROBE | CGGGACGGGCATTTGTCACCA |

Example 5

Development of Multiplexed Liquid Array Format

Figure 66:
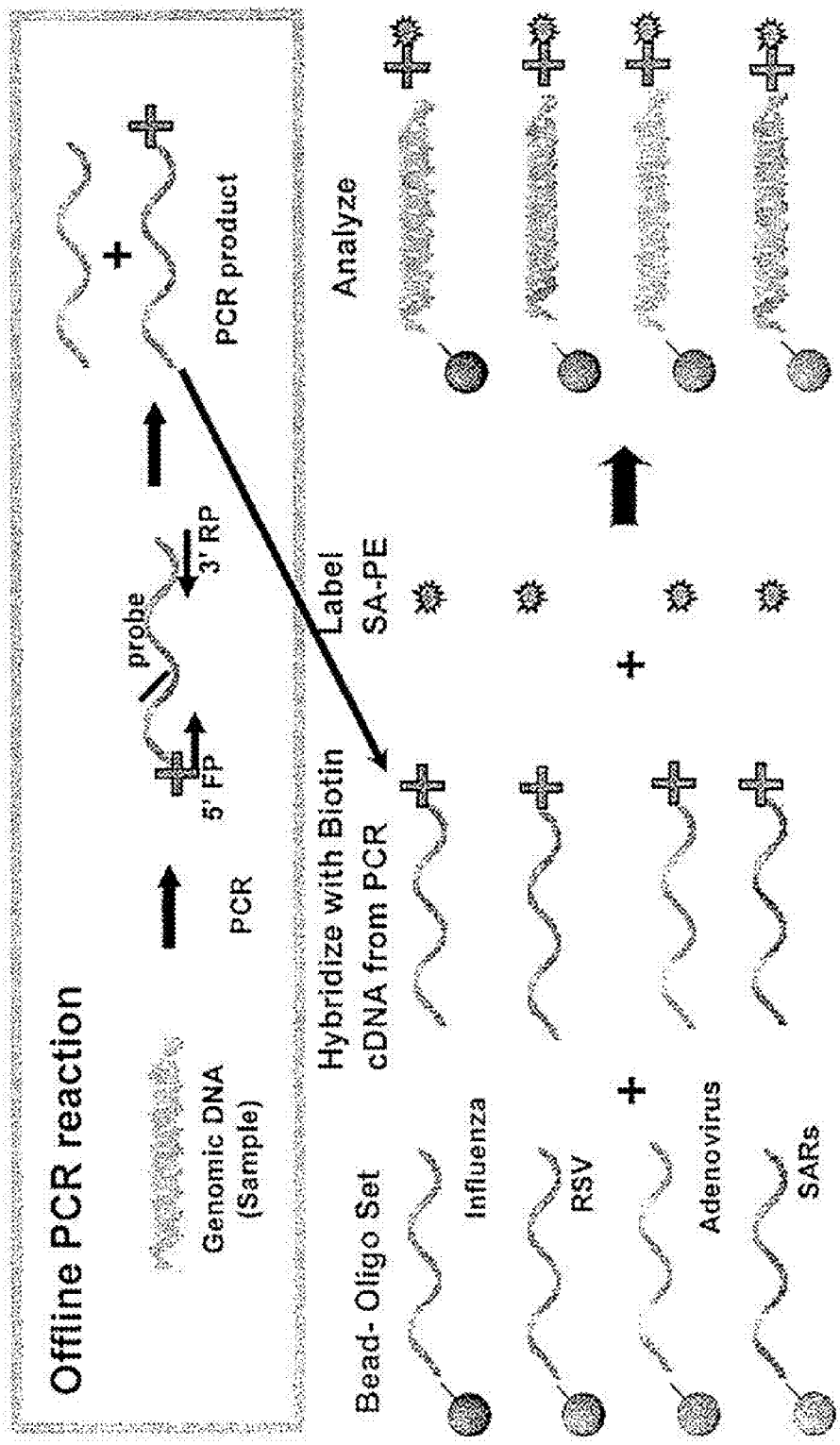
Figure 67:
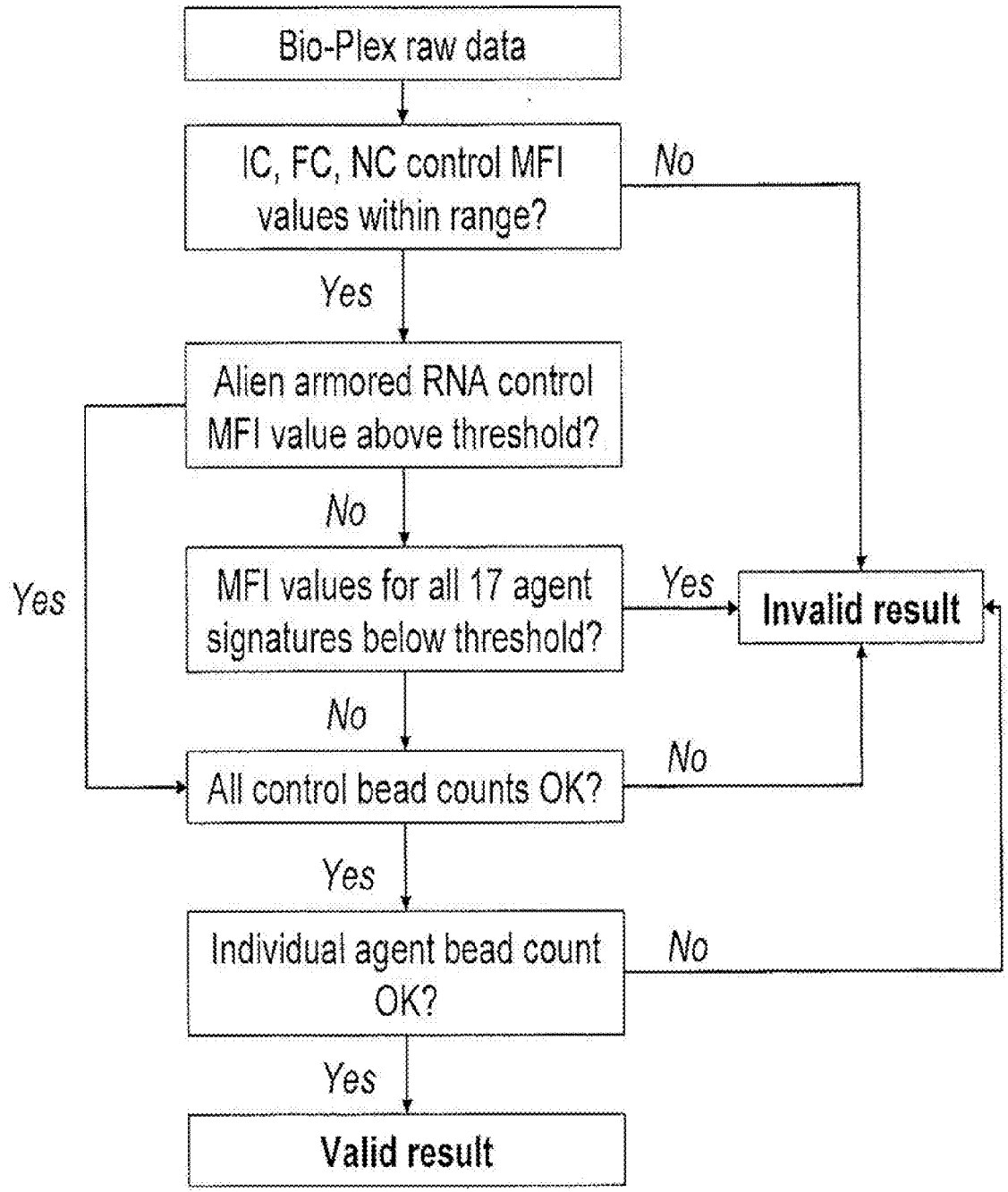
FIG. 67 is a flow diagram illustrating the process used to determine whether or not any individual assay result is valid based on results of the control data.

After ascertaining that signatures perform well in the Taqman format, they are then transitioned to the multiplexed liquid array format. The multiplexes liquid array format is summarized in FIG. 66.

This phase is divided into two steps. The first step, called 'Singlepex' testing, is a step in which each individual signature is tested against target virus. In this format, only two sets of primers are present in the PCR mix: the primers for the Alien RNA positive control (to ensure the PCR reaction proceeds well), and the primers for the signature being tested. The target virus is then spiked at various concentrations in order to generate a titration curve. All titrations are run in triplicate. In the cases in which various strains of the same virus are available, a titration is run for each one.

The second step, called 'Multiplexed' testing, is a step in which the individual signatures are added to the multiplexed panel. In this format, the primers of the signature being tested are added to the multiplexed PCR mix, with the other primers present in the panel. Titrations are then run in triplicate for each signature present in the panel in order to determine the limit of detection of the assay against each target in the multiplexed format, and also to control for signature cross-reactivity.

A summary of the multiplex PCR assay procedure is as follows. The sample, e.g., an oral swab placed in virus transport media, undergoes a magnetic bead extraction to purify target nucleic acids from impurities in the sample matrix. Target DNA or RNA is amplified by real-time-PCR. The forward primer is biotinylated. The reverse primer is unmodified. The double stranded PCR product is mixed with a suspension of probe-bead conjugates then melted at 95° C. to form single strand product. Extended forward primer is hybridized to the complementary probe-bead conjugate at 95° C. The hybridized product is then labeled with the fluorescent probe SA-PE. The bead suspension is analyzed using the flow cytometer.

For this application, oligonucleotide probes with sequences that are complementary to the target nucleic acid sequences were covalently coupled to beads. Nucleic acids from pathogens (targets) were amplified using standard PCR techniques. After target amplification, the amplicons, half of which contain the biotinylated forward (5'-3') primer were introduced to the beads and allowed to hybridize to their complementary probes on the appropriate bead. A fluorescent reporter molecule (strepavidin-phycoerythrin) was added, and binds the biotin functional groups within the forward primer. Therefore, the completed assay product comprises a bead+probe+biotinylated (and fluorescently tagged) amplicon. Each optically encoded and fluorescently-labeled microbead was then interrogated by the flow cytometer. The 635-nm red diode laser excites the dyes inside the bead and classifies each bead to its unique bead class, and a green "reporter" laser (532 nm) quantifies the assay at the bead surface. The flow cytometer is capable of reading several hundred beads each second; analysis can be completed in as little as 15 seconds. Conducting the assay requires multiple steps and significant thermocycling times; the process currently takes about 2 hours.

Extraction of Target Nucleic Acid from a Sample

Extractions of nucleic acid from the samples were conducted with an MagMax (catalog #1839, Ambion, Austin, Tex.) extraction kit using the standard protocol. The kit is specifically designed for the simultaneous extraction of both DNA and RNA using a single procedure. Nucleic acid was extracted from deactivated antigens to use as positives when testing the various signatures.

Primer and Probe Synthesis

Oligonucleotides for Luminex bead-based assays were purchased from Integrated DNA technologies (IDT DNA, Coralville, Iowa). Each forward primer has a 5 prime biotin and 2 internal biotins. Since the biotin molecules are proportionately larger than the bases, it is preferred that the biotins be separated by about 5-10 bases and it is important that there is not a biotin too near the 3 prime terminus of the forward primer, as this could interfere with amplification efficiencies. The reverse primer was unmodified.

The probe was modified with a 5' amine and a space amine modification for coupling the microbeads, e.g., if the real-time PCR probe sequence is 5' FAM-ATCCGCGCATAG-TAM3' (SEQ ID NO: 23,189), the Luminex probe sequence becomes 5'/5AmMC12//iSp18//ATCCGCGCATAG-3'. (SEQ ID NO: 23,189)

A number of oligonucleotide synthesis parameter were optimized for the multiplex, Luminex based assays. First, all oligonucleotides were HPLC purified. A small percentage of probes produced were contaminated by free biotin molecules that are residuals from the primer production. This contamination can cause undesirable interference with the assay. To minimize this occurrence and improve quality control, we have requested that IDT includes a SA (streptavidin agarose) purification followed by sephadex filtration to remove any contamination. We have also found that impurities in the oligonucleotides (synthesis "artifacts"; buffer crystals, truncated products, etc) can also weaken assay performance. As a result we require purity to be a minimum of 85% to pass quality standards with less than 15% impurities. Quality control documentation; signed ESI Mass Spectrometry Trace and Capillary Electrophoresis Trace was required. Oligonucleotides were shipped as lyophilosized pellets and are then resuspended to their desired concentrations; primers in TE [Tris EDTA, pH 8] buffer and probes in 0.1M MES [ (2-{N-morpholino } ethanesulfonic acid)] buffer, pH 4.5. All oligonucleotides are stored in small aliquots at −20° C.

Covalent Coupling of Oligonucleotide Probes to COOH-microbeads:

Different sets of carboxylated fluorescent microbeads were obtained from Luminex Corp (Austin, Tex.), and probes for each assay were assigned to a unique bead set. Oligonucleotide probes, with sequences representing the reverse complement to target region of the forward strand (5'-3') were obtained from Integrated DNA Technologies (Coralville, Iowa). Each probe contained a C-18 spacer between the amine reactive group and the 5' end of the oligo to enable optimum hybridization. Probes for each of the pathogen targets were coupled according to the manufacturer recommended coupling protocol. Briefly, a homogenized 1 ml aliquot (1.25×10$^7$) of beads was centrifuged for 5 min at 13,000 rpm, and re-suspended in 50 ul of 100 mM 2[N-morpholino] ethanesulfonic acid (MES) buffer, pH 4.5. To this suspension, 10 ul of probe at a concentration of 50 μM was added followed by addition of 50 μg of 1-ethyl-3-[3-dimethylaminopropyl]-carbodiimide hydrochloride (EDC) (Pierce Biotechnology [CU1], Rockford, Ill.). This solution was incubated in the dark at room temperature for 30 minutes. A second aliquot of EDC (25 μg) was added and incubated as before. The beads were rinsed in 1 ml phosphate buffered saline (PBS) containing 0.02% Tween-20 (Sigma), centrifuged at 13,000 rpm for 5 min, rinsed using 1 ml of 0.1% (w/v) sodium dodecyl sulfate (SDS) in water, and centrifuged as before. The supernatant was aspirated and the conjugated beads were washed in 100 ul of TE (10 mM Tris, 1 mM EDTA, Ph 8.0 [Sigma]) and then re-suspended in 250 ul TE and stored in the dark at 4° C. Each probe/bead conjugate was stored separately, and a fresh bead set containing all conjugates was prepared for each liquid bead array assay.

TABLE 6

Modified forward primers for Luminex assay

| Pathogen-assay | SEQ ID NO: | Sequence |
| --- | --- | --- |
| BHV-1 | 23,190 | 5'-/5Bio/G/iBiodT/GCCAGCCGCG/iBiodT/AAAAG-3' |
| BHV-3 | 86 | 5'-/5Bio/TGAGGCC/iBiodT/ATGTATGGGCAG/iBiodT/T-3' |
| BPSV-1 | 87 | 5'-/5Bio/GCAGA/iBiodT/GCGCTCC/iBiodT/GGTT-3' |
| BPSV-2 | 88 | 5'-/5Bio/GATGGCCG/iBiodT/GCAGC/iBiodT/CTT-3' |
| BPSV-4 | 89 | 5'-/5Bio/GCAGCAG/iBiodT/GCACCACG/iBiodT/AGT-3' |
| BTV-2 | 90 | 5'-/5Bio/GCACCC/iBiodT/ATATGTT/iBiodT/CCAGACCA-3' |
| BTV-3 | 91 | 5'-/5Bio/AGAAT/iBiodT/CAGGA/iBiodT/GGGCAGGA-3' |
| BVD-1a(mod) | 92 | 5'-/5Bio/GGTAGTCG/iBiodT/CAGTGGT/iBiodT/CGAC-3' |
| FMDV.Pir | 93 | 5'-/5Bio/CAC YTY AAG R/iBiodT/G ACA YTG RTA C/iBiodT/G GTA C |
| FMDV.TC | 94 | 5'-/5Bio/ACTGGG/iBiodT/TTTACAAACC/iBiodT/GTGA-3' |
| SVD_1 | 95 | 5'-/5Bio/CAGGA/iBiodT/AATTTCT/iBiodT/CCAAGGGC-3' |
| SVD_2 | 96 | 5'-/5Bio/GACTTG/iBiodT/TGTGGC/iBiodT/GGAGGA-3' |
| SVD_3 | 97 | 5'-/5Bio/GACAAAG/iBiodT/GGCCAAGGGAAA-3' |
| VESV_1 | 98 | 5'-/5Bio/GCCT/iBiodT/CTCCCT/iBiodT/CCCAAAA-3' |
| VESV_3 | 99 | 5'-/5Bio/GGGAA/iBiodT/GAGGTGTGCA/iBiodT/CATT-3' |
| VESV_4 | 100 | 5'-/5Bio/GGTCGC/iBiodT/CTCACTGATGA/iBiodT/GAGTA-3' |
| VESV_5 | 101 | 5'-/5Bio/ACCACC/iBiodT/CTGGAAACATC/iBiodT/ATGG-3' |

Multiplexed PCR Amplification:

Each amplification reaction was performed in a total volume of 25 µl. The reaction mix consisted of 12.5 µl of 2× Superscript III RT-PCR reaction Mix (Invitrogen, Carlsbad, Calif.), 0.1 µl each of forward and reverse primers (each at a concentration of 100 µl), 1 µl per reaction of Superscript III/Platinum Taq Enzyme Mix, 0.95 µl of 50 mM MgSO$_4$ (Invitrogen, Carlsbad, Calif.), 1 µl of 100 copies/µl "Alien RNA" internal control template (Ambion, Austin, Tex.), 5 µl of template, and enough RNase-free water to bring final volume to 25 µl. The "Superscript III RT-PCR System" kit 2× reaction mix contains 0.4 mM of each dNTP and 3.2 mM MgSO$_4$ plus "proprietary stabilizers". With the addition of 0.95 ul of 50 mM MgSO$_4$, the final component concentrations in the 1× reaction mix were as follows: 0.2 mM each dNTP, 3.5 mM MgSO4, 1× Superscript III RT-PCR buffer, 0.4 µM of each primer, and 300 copies of Tobacco Mosaic Virus internal control template. The Platinum Taq polymerase used is a "Hot Start" Taq that is robust and is held by binding a thermolabile inhibitor containing monoclonal antibodies to Taq polymerase.

Thermocycling conditions were as follows: 30 min at 55° C., 2 min at 95° C., followed by 35 cycles of 15 sec at 94° C., 30 sec at 60° C., 15 sec at 72° C., and concluding with one cycle at 72° C. for 2 min followed by 4° C. soak.

Hybridization of Amplified Sample to the Bead:

A bead set was prepared, consisting of a mixture of 3 µl of beads each covalently coupled to a probe listed in Table 1 into a volume equal to 1 ml of Tris-NaCl buffer (100 mM Tris, 0.05% Triton X100, 200 mM NaCl pH 8.0). Amplified PCR reaction product, e.g., amplicon (1 µl) was added to 22 µl of the bead mix. PCR products and bead mix were denatured at 95° C. for 2 min and allowed to hybridize at 55° C. for 5 min. The mix was transferred to a 96 well filter plate (Millipore, Bedford, Mass.). The beads were washed twice in 100 µl Tris-NaCl and incubated with 60 µl of 3 ng/µl Streptavidin-phycoerythrin (SAPE) (Caltag Laboratories, Burlingame, Calif.) for 5 min The hybridized beads were washed again with 100 µl Tris-NaCl buffer and re-suspended in a final volume of 100 µl Tris-NaCl buffer. The completed sample was then introduced to the Luminex flow analyzer for analysis.

Example 6

Controls for the Multiplexed Liquid Format Assay

Controls that convey important diagnostic information regarding reagent addition, quality and concentration, assay operator performance, and instrument stability can be easily added without compromising or limiting the screening capabilities of an assay. The disclosed assays employ a unique set of four rationally-designed internal controls built into every sample that monitors and reports every step of the assay.

IC: Instrument Control: The purpose of this control is to inform the user of the reporter laser's integrity and utility. It is a bead coupled to BSA conjugated to tetramethylrhodamine (TAMRA), a heat stable fluorophore; it automatically fluoresces and generates a signal in the presence of the reporter laser. If one notices a decline in the signal, it is due to decline in the laser's integrity. Under those circumstances, one must contact BioRad (or Luminex Customer Support) for a service request. The laser's output is important to monitor because it has a finite lifespan. This control is generally the most robust.

FC: Fluorescence Control/SAPE Addition Control: As a fluorescent control, or SAPE addition control, biotinylated BSA (b-BSA) is coupled to one of the beads. The biotin molecule has a very high binding affinity for streptavidin (biotin-avidin binding) and the Phycoerythrin (PE) component of SAPE is what is detected by the reporter laser (same as the fluorophore bound directly to the bead for the IC). If one does not detect a signal on the FC, then it is likely that SAPE was not added.

NC: Negative Binding Control: The NC is a bead bound to a DNA sequence specific to a random sequence from the genome of an organism found at the bottom of the ocean (*Maritima maritensis*, Mt7). MT-7 is a conserved DNA sequence from a maritima organism (a thermal vent microbe) that does not match those of published genomes of terrestrial organisms, and serves as a non-specific binding control in the multiplex PCR assay. In the absence of non-specific binding, the MFI values for the NC MT-7 bead should remain consistently low.

PCR/RT-PCR PC: RNA Amplification Control/Inhibition Control: Alien armored RNA (arRNA Alien) is a synthetic RNA sequence, ~1000 nucleotides in length, packaged in an MS2 phage (protein capsid). The sequence is termed "alien" as it has no homology to currently annotated GenBank sequences. Packaging increases the stability of the RNA in clinical sample matrices and more closely mimics the behavior of target virus particles during processing. An internal control assay for alien armored RNA was incorporated into the multiplex PCR assay using specific primers and probe. Alien armored RNA is used as an end-to-end internal control for reverse transcription, PCR amplification, Luminex microsphere array hybridization and Bio-Plex detection.

The alien RNA concentration used is typically 200 copies per well, which consistently yields a median fluorescent intensity (MFI) value above the assay detection limit for both clean and clinical sample matrixes. A low number copy number for the internal control was selected to minimize competition within the PCR reaction with the agent signatures. A low copy number can also better reflect detrimental changes in assay performance that could potentially result in a false negative. MFI values below threshold may indicate failed reverse transcription and PCR amplification, or a failed hybridization reaction.

The controls used in the multiplexed liquid format assay are shown in the following table.

TABLE 7

Controls for multiplexed liquid format assay

| Control | Description | Sequence (5' => 3') | SEQ ID NO | Organism |
|---|---|---|---|---|
| Instrument Control | Luminex probe | 5'-/5AmMC6//iSp18/CAAAGTGGGAGACGTCGTTG-3'Cy3 | 102 | Maritima 7-Cy3 |

TABLE 7-continued

Controls for multiplexed liquid format assay

| Control | Description | Sequence (5' => 3') | SEQ ID NO | Organism |
|---|---|---|---|---|
| Fluorescence Control | Luminex probe | 5'-/5AmMC6//iSp18/CAAAG/iBiodT/GGGAGACGTCG/iBiodT/TG-3' | 103 | Maritima 7-biotin |
| Negative Control | Luminex probe | 5'-/5AmMC6//iSp18/CAAAGGGGAGACGTCGTTG-3' | 104 | Maritima 7 |
| PCR Amplification/ Inhibition Control | Forward primer | 5' GACATCAAGGCTCAAACTAATTTTACC 3' | 105 | n/a |
| PCR Amplification/ Inhibition Control | Reverse primer | 5' CAAAGGCTGCCAACATAAAATG 3' | 106 | n/a |
| PCR Amplification/ Inhibition Control | Luminex probe | 5'-/5AmMC6//iSp18/CAAGCGTAAATGCAGCGTCCA-3' | 107 | n/a |

The controls are used to verify the integrity of the assay. Control results are used to determine whether the results for a given sample are valid or not. Assay integrity is determined using the following processes:

First, for each sample, MFI values for the 4 control bead classes are checked against a corresponding threshold. The thresholds used for the panel are still being determined and cannot be established until the multiplexed assay panel development is complete (i.e., no additional signatures are added). In general, if MFI values for the IC, NC or FC controls are out of range then the results from that sample are deemed invalid and excluded from further analysis.

Second, if the MFI value of the alien armored RNA control is out of range AND none of the MFI values for the 17 agent channels exceed threshold, then the results from that sample are deemed invalid and excluded from further analysis. If the MFI for the alien armored RNA control is out of range AND one or more of the MFI values for the 17 agent channels exceeds threshold, then the results from that sample are deemed valid and included in further analysis. We have observed that agent spikes above certain concentrations can cause a decrease in the alien armored RNA MFI, probably due to competition in the PCR reaction. When the alien armored RNA MFI drops below threshold on a sample considered negative for all signatures, the analysis would be discarded and would need to be repeated. This control reduces the probability of false negatives.

Third, if the MFI values for all four controls are within range, bead counts are checked. First, the bead counts for each of the 4 controls are checked. If the bead count minimum (40 beads) for any of the 4 controls was not reached, then the control MFI values are deemed invalid, and all assay results for that sample are excluded from further analysis.

The final step is to check the individual bead count for each of the 17 signatures for a given sample (non-control beads). If an individual agent bead class (signature) does not reach the bead count minimum (40 beads), that individual assay result is deemed invalid and only that individual result for that signature is removed from the analysis. If the bead counts for any of the agent channels exceeded the minimum, they are considered valid and included in the analysis.

Figure 68:
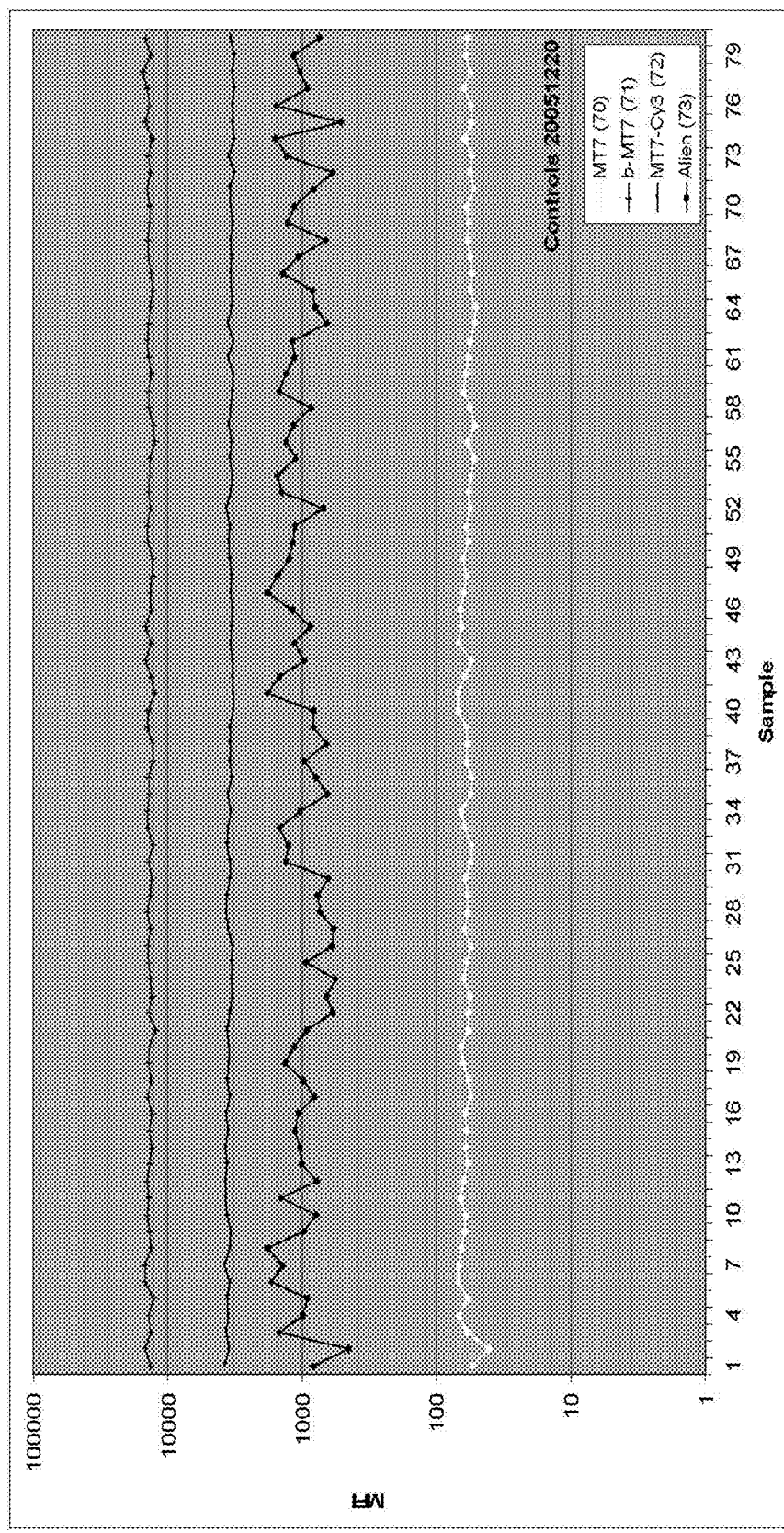
FIG. 68 a typical plot showing the MFI of four controls recorded in a multiplexed assay PCR assay across a microtiter plate (96-wells, 80 samples tested) and analyzed using a Luminex detector. The log of the median fluorescence intensity (MFI) is plotted on the Y-axis versus sample number shown on the X-axis. Each sample contains 4 internal controls. Controls should produce data that is constant form one sample to the next; therefore data in plots like this one should exhibit 4 straight lines. Fluctuations in MFI values for any of the 4 controls can indicate a problem with the assay. Additionally, each control is characterized by its inherent variation. Some controls produce data that is much less variable than others. The high deviation from point to point shown on this plot from the positive control Alien RNA is expected and normal.

A flow diagram of the process used to determine whether or not any individual assay result is valid or not is shown in FIG. 68.

Example 7

Limits of Detection

The panel of selected signature sequences was tested for the limit of detection (LOD) in both the single plex and multiplex format. The results are presented below.

TABLE 8

Limits of Detection (LOD)

| Assay ID | Target DNA | Reference Test Strain | Singleplex LOD | Multiplex LOD | LOD shift (logs) | Bkgrd SP | Bkgd Mux | Threshold (MFI) | Cross-reactivities with panel constituents |
|---|---|---|---|---|---|---|---|---|---|
| BVH_1 | Bovine Herpes Virus | BHV_N/A | 100 viral particles/uL | 100 viral particles/uL | 0 | 9 | 60 | 120 | None Noted |
| BVH_3 | Bovine Herpes Virus | BHV_N/A | 100 viral particles/uL | 100 viral particles/uL | 0 | 10 | 40 | 980 | None Noted |
| BPSV_1 | Bovine Papular Stomatitis Virus | BPSV_N/A | 1000 viral particles/uL | 100 viral particles/uL | −1 | 10 | 30 | 125 | None Noted |

TABLE 8-continued

Limits of Detection (LOD)

| Assay ID | Target DNA | Reference Test Strain | Singleplex LOD | Multiplex LOD | LOD shift (logs) | Bkgrd SP | Bkgd Mux | Threshold (MFI) | Cross-reactivities with panel constituents |
|---|---|---|---|---|---|---|---|---|---|
| BPSV_2 | Bovine Papular Stomatitis Virus | BPSV_N/A | 10 viral particles/uL | 10 viral particles/uL | 0 | 10 | 65 | 140 | Background cross-reactivity, not well defined |
| BPSV_4 | Bovine Papular Stomatitis Virus | BPSV_N/A | 100 viral particles/uL | 100 viral particles/uL | 0 | 10 | 35 | 600 | None Noted |
| FMDV.TC | Foot and Mouth Virus | 01 Manisa | $1 \times 10^{-8}$ pfu/ul | $1 \times 10^{-6}$ pfu/ul | 2 | 10 | 10 | 150 | None Noted |
| FMDV.Pir | Foot and Mouth Virus | 01 Manisa | $1 \times 10^{-4}$ pfu/ul | $1 \times 10^{-4}$ pfu/ul | 0 | 10 | 10 | 200 | None Noted |
| BVD_1a | Bovine Viral Diarrhea | BVD_N/A | 10 viral particles/uL | 10 viral particles/uL | 0 | 7 | 30 | 110 | None Noted |
| BTV_2 | Bluetongue Virus | BTV-13 | 1 viral particles/uL | 1 viral particles/uL | 0 | 11 | 30 | 90 | None Noted |
| BTV_3 | Bluetongue Virus | BTV-13 | 1 viral particles/uL | 10 viral particles/uL | 1 | 9 | 20 | 1000 | None Noted |
| SVD_1 | Swine Vesicular Disease | ITL/1/66 | $1 \times 10^{-6}$ pfu/ul | $1 \times 10^{-5}$ pfu/ul | 1 | 5 | 8 | 135 | None Noted |
| SVD_2 | Swine Vesicular Disease | ITL/1/66 | $1 \times 10^{-6}$ pfu/ul | $1 \times 10^{-4}$ pfu/ul | 2 | 10 | 10 | 150 | None Noted |
| SVD_3 | Swine Vesicular Disease | ITL/1/66 | $1 \times 10^{-5}$ pfu/ul | $1 \times 10^{-5}$ pfu/ul | 0 | 16 | 16 | 200 | None Noted |
| VESV_1 | Vesicular Exanthema of Swine Virus | E54[1]/A48[2] | $1 \times 10^{-6}$ pfu/ul | $1 \times 10^{-3}$ pfu/ul | N/A | 5 | 5 | 80 | None Noted |
| VESV_3 | Vesicular Exanthema of Swine Virus | A48[1]/A48[2] | $1 \times 10^{-6}$ pfu/ul | $1 \times 10^{-6}$ pfu/ul | N/A | 22 | 18 | 500 | None Noted |
| VESV_4 | Vesicular Exanthema of Swine Virus | E54[1]/A48[2] | $1 \times 10^{-6}$ pfu/ul | $1 \times 10^{-5}$ pfu/ul | N/A | 25 | 17 | 700 | None Noted |
| VESV_5 | Vesicular Exanthema of Swine Virus | A48[1]/A48[2] | $1 \times 10^{-6}$ pfu/ul | $1 \times 10^{-6}$ pfu/ul | N/A | 23 | 20 | 100 | None Noted |

Example 8

Disease Signature Thresholds

Thresholds were initially determined using all available data from known negative samples (blanks) by plotting a histogram that showed the probability of a given sample generating a particular MFI. In the absence of cross reactivity, each signature in the multiplex assay could be treated as an individual assay result. For example, for a sample spiked with BPSV virus, data for other disease signatures could contribute towards negative data, providing that cross reaction between disease signature sets was not observed. This is a way to increase the number of samples that can be used to establish thresholds.

To determine the degree of cross reactivity for each assay, the probability of obtaining a given MFI was plotted versus MFI for both true blank samples and spiked samples. Signatures intended to detect a virus-spiked sample were excluded from this analysis. Histograms generated from virus positive samples and true blank samples were not significantly different; the distributions indicated negligible cross reactivity. Using all negative sample data, a receiver operator characteristic (ROC) function describing the relationship between threshold values and the rate at which false positives occur was plotted. The threshold was determined from the ROC function by finding the MFI values that would yield a false positive at a given rate. A false positive rate of 0.002 was selected, which corresponds to 1 false positive every 500 samples. The resolution in false positive rate is determined by the number of samples that are present. For example to establish a false positive rate of 0.0001, or 1 false positive per 10,000 samples, a minimum of 10,000 samples are required.

The threshold values that were established for the assay controls and each signature in the multiplex assay panel are shown below. The BPSV-2 threshold was set at 400. The MFI value for a false positive rate of 0.002 was 730. This resulted in a sensitivity which was too low for the samples virus concentrations used.

TABLE 9

Threshold values for signature sequences

| Signature | Threshold (MFI) |
|---|---|
| BHV-1 | >49 |
| BHV-3 | >43 |
| BPSV-1 | >35 |
| BPSV-2* | >400 |
| BPSV-4 | >41 |
| FMDV-1 | >42 |
| FMDV-2 | >60 |
| BVD-1a | >40 |
| BTV-2 | >55 |
| BTV-3 | >31 |
| SVD-1 | >38 |
| SVD-2 | >28 |
| SVD-3 | >40 |
| VESV-1 | >24 |
| VESV-3 | >39 |
| VESV-4 | >105 |
| VESV-5 | >56 |

Example 9

Data from Multiplexed Luminex Assay

Figure 69B:
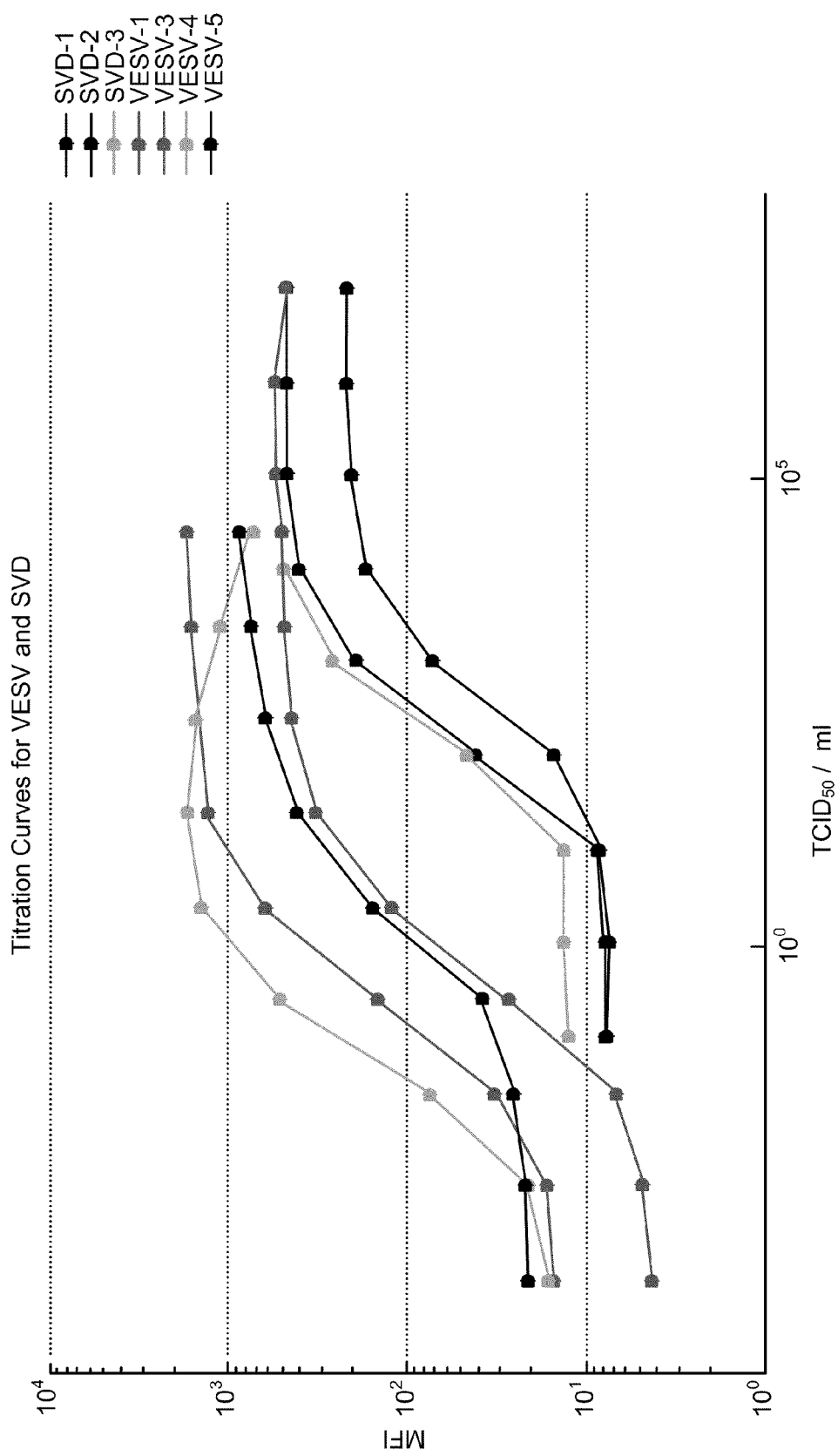
FIG. 69B: The curves combined herewith represent common viral extraction units (TCID50/mL) of representative strains for SVD and VESV.

FIG. 69 is plot of dose-response curves for select domestic and foreign animal diseases that constitute the FMDV rule-out panel as described in Table 1. The curves combined herewith represent common viral extraction units (pfu/mL) of representative strains for BHV, BPSV, BTV, BVDV and FMDV. The results demonstrate that the signature sequences described in Table 1 effectively detect and differentiate between multiple pathogens in a sample.

Example 10

Multiplexed Detection of Agricultural Pathogens Using a Microarray Approach

In another embodiment, the signature sequences used herein are used for detection of pathogens in a sample using a microarray, e.g., a microarray manufactured by Nimblegen Systems. Nimblegen builds its arrays based on photodeprotection chemistry using its proprietary Maskless Array Synthesizer (MAS) system. The Digital Micromirror Device, at the heart of the system, creates digital masks whose design can be easily changed. Up to 390,000 custom oligos can be synthesized onto glass slides within a few hours. To detect the agricultural pathogens, oligonucleotide probes of up to 70 bases long that are complementary to the signature sequences disclosed herein are designed using a set of probe design parameters. Due to the ultra high density, multiple probes from the same sequence can be included on the same chip with on-chip replicates, which increases the confidence in probe calls. A variety of techniques for probe design can be employed, ranging from non-overlapping (sampling) to overlapping (tiling) to the detection of Single Nucleotide Polymorphisms (resequencing, using short oligos.) The pathogen nucleic acid sample is amplified with fluorescently labeled random primers and the labeled DNA is hybridized to the chip. The chip is washed to get rid of non-specifically bound samples and scanned using a laser scanner at high resolution. The raw data and images are analyzed using statistical tools and presence/absence calls are made. Though not as sensitive as Taqman assays and bead assays, microarray allows the detection of presence or absence of multiple viruses simultaneously, and shortens the optimization time for multiplexing assays.

Example 11

Additional FMDV Signature Sequences

Using the in-silico identification techniques described herein, additional signature sequences for determining the presence or absence of FMDV in sample were determined as follows.

TABLE 10

Additional FMDV signature sequences

| SEQ ID NO: | Assay reference | SEQUENCE DESCRIPTION | SEQUENCE (5'->3') |
|---|---|---|---|
| 108 | FMDV-1261 | Signature sequence | CAAACCTGTGATGGCTTCGAAGACCCTCGAAGCTATCCTCTCCTTTGCACGCCGTGGGACCATTCAGGAGAAGTTGATCTNNNNNNNNNNNNNNNNNNNTCCACTCCGGACAAGACGAGTACCGGCGTCTCT |
| 109 | FMDV-1261 | Forward primer | CAAACCTGTGATGGCTTCGA |
| 110 | FMDV-1261 | Reverse primer | AGAGACGCCGGTACTCGTCTT |
| 111 | FMDV-1261 | Probe | TGCACGCCGTGGGACCATTC |
| 112 | FMDV-1261R | Signature sequence | AGAGACGCCGGTACTCGTCTTGTCCGGAGTGGANNNNNNNNNNNNNNNNNNNAGATCAACTTCTCCTGAATGGTCCCACGGCGTGCAAAGGAGAGGATAGCTTCGAGGGTCTTCGAAGCCATCACAGGTTTG |
| 113 | FMDV-1261R | Forward primer | AGAGACGCCGGTACTCGTCTT |
| 114 | FMDV-1261R | Reverse primer | CAAACCTGTGATGGCTTCGA |
| 115 | FMDV-1261R | Probe | TCCTGAATGGTCCCACGGCGT |
| 116 | FMDV-1674 | Signature sequence | CCAACGCAGGTAAAGTGATCTGTAGCTTGGAATCTCGAACGTCCNNNNNNNNNNNNNNNNNNNGACGCCGGTACTCGTCTTGTCCGG |

TABLE 10-continued

Additional FMDV signature sequences

| SEQ ID NO: | Assay reference | SEQUENCE DESCRIPTION | SEQUENCE (5'->3') |
|---|---|---|---|
| 117 | FMDV-1674 | Forward primer | AGTGGANNNNNNNNNNNNNNNNNNNNAGATCAACTTCTCCTGAAT GGTCCCACGGCGTGCAAAGGAGAGGATAGCTTCGAGG CCAACGCAGGTAAAGTGATCTG |
| 118 | FMDV-1674 | Reverse primer | AACCTGTGATGGCTTCGAAGAC |
| 119 | FMDV-1674 | Probe | TCCTGAATGGTCCCACGGCGT |
| 120 | FMDV-3238 | Signature sequence | AGCATCATCAACACAATTCTGAACAACATCTACGTGCTCTACG CGCTGCGTAGGCACTACGAGGGAGTTGAGCTGGACACTTACAC CATGATCTCCTACGGGGACGACATCGTGGTTGCAAGTGATTAC GATCTNNNNNNNNNNNNNNNNNNNNNNNNNNNNNNNNNNNNNNNN NNNNNNNNNNNNNNNNNNNNNNNNNNNNNNNNNNNNNNNNNNNN NNNNNGTCACTCCATTACCGATGTCACTTTCCTCAAAAGACAC TTCCACATGGATTATGGAACTGGGTTTTACAAACCTGTGATGG CTTCGAAGACCCTCGAAGCCATCCTCTCCTTTGCACGCCGTG |
| 121 | FMDV-3238 | Forward primer | AGCATCATCAACACAATTCTGAACA |
| 122 | FMDV-3238 | Reverse primer | CATCACAGGTTTGTAAAACCCAGTT |
| 123 | FMDV-3238 | Probe | CACTTTCCTCAAAAGACACTTCCACATGGATTATG |

The signature sequences disclosed in Table 9 are used, either individually or in combination with each other, in kits and methods disclosed herein for determining the presence or absence of FMDV in a sample by detection of the signature sequences. The kits and methods use the signature sequences disclosed in Table 9 alone or in combination with one or more additional signature sequences from FMDV and other agricultural pathogens, e.g., those disclosed in Table 1.

For detection of the signature sequences via amplification, primers suitable for PCR were designed and are disclosed in Table 9. The forward and reverse primers in Table 9 are used for PCR based detection of FMDV in a sample via detection of the signature sequences disclosed in Table 9 in the sample. Detection of the amplicon, e.g., the amplified signature sequence, is performed using an agarose gel.

For detection of signature sequences using real-time PCR, probes suitable for Taqman PCR were designed and are disclosed in Table 9. The primers and probes in Table 9 are used for Taqman PCR based detection of FMDV in a sample via detection of the signature sequences disclosed in Table 9 in a sample. Detection of the amplicon, e.g., the amplified signature sequence, is performed using an iCycler.

The primers and probes are also used for Luminex based detection of the signature sequences in Table 9. Probes are covalently attached to fluorescent microbeads and hybridized to samples subjected to PCR using the disclosed primers.

Example 12

Additional Bovine and Porcine Signature Sequences

Using the in-silico identification techniques described herein, additional signature sequences for determining the presence or absence of FMDV, PRRS, SVD, VESV, VSV, OvHV-2/AHV1, BHV, PPDX, FMDV, BVD, BTV, and/or RPV in a sample were determined using the methods and techniques described above and as follows.

The signature sequences disclosed in Tables 11 and 12 are used, either individually or in combination with each other, in kits and methods disclosed herein for determining the presence or absence of FMDV, PRRS, SVD, VESV, VSV, OvHV-2/AHV1, BHV, PPDX, FMDV, BVD, BTV, and/or RPV in a sample by detection of the signature sequences. The kits and methods use the signature sequences disclosed in Tables 11 and 12 alone or in combination with one or more additional signature sequences from other agricultural pathogens, e.g., those disclosed in Tables 1, 10, and others as described herein.

For detection of the signature sequences via amplification, primers suitable for PCR were designed and are disclosed in Tables 11 and 12. The forward and reverse primers in Tables 11 and 12 are used for PCR based detection of FMDV, PRRS, SVD, VESV, VSV, OvHV-2/AHV1, BHV, PPDX, FMDV, BVD, BTV, and/or RPV in a sample via detection of the signature sequences disclosed in Tables 11 and 12 in the sample. Detection of the amplicon, e.g., the amplified signature sequence, is performed using an agarose gel.

For detection of signature sequences using real-time PCR, probes suitable for Taqman PCR were designed and are disclosed in Tables 11 and 12. The primers and probes in Tables 11 and 12 are used for Taqman PCR based detection of FMDV, PRRS, SVD, VESV, VSV, OvHV-2/AHV1, BHV, PPDX, FMDV, BVD, BTV, and/or RPV in a sample via detection of the signature sequences disclosed in Tables 11 and 12 in a sample. Detection of the amplicon, e.g., the amplified signature sequence, is performed using an iCycler.

The primers and probes are also used for Luminex based detection of the signature sequences in Tables 11 and 12. Probes are covalently attached to fluorescent microbeads and hybridized to samples subjected to PCR using the disclosed primers.

TABLE 11

Porcine Panel

| organism Assay ID | Forward Primer Reverse Primer Luminex Probe | Amplicon sequence Reference genome Amplicon size |
|---|---|---|
| FMDV FMDV.TC | ACTGGGTTTTACAAACCTGTGA (SEQ ID NO: 126) | ACTGGGTTTTACAAACCTGTG ATGGCCTCAAAGACCCTTGAG GCTATCCTCTCCTTTGCACGCC GTGGGACCATACAGGAGAAGT TGATCTCCGTGGCAGGACTCGC (SEQ ID NO: 129) |
| | GCGAGTCCTGCCACGGA (SEQ ID NO: 127) | ref\|NC_004915.1\|gnl\|NCBI_GENOMES\| 17191\|gi\|32188257\|Foot-and-mouth disease virus Asia 1, complete genome\|kpath_id\|1129999 |
| | GTCCCACGGCGTGCAAAGGA (SEQ ID NO: 128) | 107 |
| FMDV FMDV.Pir | CACYTYAAGRTGACAYTGRTACT GGTAC (SEQ ID NO: 130) | CACTTTAAGGTGACACTGATA CTGGTACTCAAACACTGGTGA CAGGCTAAGGATGCCCTTCAG GTACCCCGAGGTAACACGCGA CACTCGGGATCTG (SEQ ID NO: 133) |
| | CAGATYCCRAGTGWCICITGTTA (SEQ ID NO: 131) | ref\|NC_011450.1\|gnl\|NCBI_GENOMES\| 17687\|gi\|48429536\|Foot-and-mouth disease virus A, complete genome\|kpath_id\|1130015 |
| | CCTCGGGGTACCTGAAGGGCATCC (SEQ ID NO: 132) | 97 |
| PRRS PRRS_1807709 | GAGCGGCAATTGTGTCTGTC (SEQ ID NO: 134) | GAGCGGCAATTGTGTCTGTCG TCAATCCAGACCGCCTTTAAT CAAGGCGCTGGGACTTGCACC CTGTCAGATTCAGGGAGGATA AGTTACACTGTGGAGTTTAGT TTGCCTACGCATCATACTGTG CGCCTGATCCGCGTCACAGCA TCACCCTCAGC (SEQ ID NO: 137) |
| | GCTGAGGGTGATGCTGTGAC (SEQ ID NO: 135) | ref\|NC_001961.1\|gi\|9630807\|gnl\|NCBI_GENOMES\| 14001\|Porcine respiratory and reproductive syndrome virus, complete genome\|kpath_id\|1150959 |
| | CGCACAGTATGATGCGTAGGCAAA CTAAACTC (SEQ ID NO: 136) | 158 |
| PRRS PRRS_1810351 | TTCTTGTGACCACGATTCGC (SEQ ID NO: 138) | TTCTTGTGACCACGATTCGCC GGAATGTCATGCTGAGCTTTT GGCTCTTGAGCAGCGCCAACT TTGGGAACCTGTGCGCGGCCT TGTGGTTGGCCCCTCAGGTCT CTTATGTGTCATCCTTGGCAA GTTACTCGGTGGGTC (SEQ ID NO: 141) |
| | GACCCACCGAGTAACTTGCC (SEQ ID NO: 139) | gb\|DQ489311.1\|gi\|99082872\|Porcine reproductive and respiratory syndrome virus strain SD01-08, complete genome\|kpath_id\|889562 |
| | GCTCAAGAGCCAAAAGCTCAGCA TGACA (SEQ ID NO: 140) | 141 |
| PRRS PRRS_1807706 | ATTGGTTTGCTCCGCGATAC (SEQ ID NO: 142) | ATTGGTTTGCTCCGCGATACTC CGTACGCGCCCTGCCATTCAC TCTGAGCAATTACAGAAGATC TTATGAGGCCTTTCTTTCCCAG TGCCAAGTGGACATTCCCACC TGGGGAACTAAACATCCTTTG GGGATGCTTTGGCACCATAAG GTGTCAACCTTGATAGATGAA ATGGTGTCGCGTCGAATGTAC CGCATCATGGAAAAATCAGGG CAGGCTGCCTGGAAACAGGTG GTGAGCGAGGCTACACTGTCT |

TABLE 11-continued

Porcine Panel

| organism Assay ID | Forward Primer Reverse Primer Luminex Probe | Amplicon sequence Reference genome Amplicon size |
|---|---|---|
| | AAATGAGCCACCACATCCAA (SEQ ID NO: 143) CGGTACATTCGACGCGACACCATT TC (SEQ ID NO: 144) | CGCATTAGTAGTTTGGATGTG GTGGCTCATTT (SEQ ID NO: 145) ref\|NC_001961.1\|gi\|9630807\|gnl\|NCBI_GENOMES\| 14001\|Porcine respiratory and reproductive syndrome virus, complete genome\|kpath_id\|1150959 286 |
| PRRS PRRS_1810383 | CAGTGTGCACGCTTCCATTT (SEQ ID NO: 146) CTCGAATGATGTGTTGCCGT (SEQ ID NO: 147) AAACATAGCGTAGAGCTGGAATT CGAAGCCA (SEQ ID NO: 148) | CAGTGTGCATGCTTCCATTTTT TCCTCTGTGGCTTCATCTGTTA CCTTGTTCATAGTGCTTTGGCT GCGAATTCCAGCTCTACGCTA TGTTTTTGGTTTCCATTGGCCC ACGGCAACACATCATTCGAG (SEQ ID NO: 149) gb\|DQ489311.1\|gi\|99082872\|Porcine reproductive and respiratory syndrome virus strain SD01-08, complete genome\|kpath_id\|889562 129 |
| PRRS PRRS_1810386 | GCTTTCTGCGTGCCTTTTCT (SEQ ID NO: 150) ACAACGCCAGAGACATTCCC (SEQ ID NO: 151) TGACTTTGAAGCCTTTCTCGCTCA TTTCTGA (SEQ ID NO: 152) | GCTTTCTGCGTGCCTTTTCCAC GCCTCAGAAATGAGCGAGAA AGGCTTCAAAGTTATCTTTGG GAATGTCTCTGGCGTTGT (SEQ ID NO: 153) gi\|112821997\|gb\|DQ864705.1\| Porcine respiratory and reproductive syndrome virus strain 01CB1, complete genome\|kpath_id\|788611 81 |
| SVD SVD_1727049 | CAGGATAATTTCTTCCAAGGGC (SEQ ID NO: 154) ACGTGAACATTTCGAGCTTCC (SEQ ID NO: 155) TGCATTGTGTCTGATGGTACAACT TGTGACG (SEQ ID NO: 156) | CAGGATAATTTCTTCCAAGGG CCCCCAGGAGAGGTGATGGAA AGAGCCATTGCCCGCGTCGCT GATACTACTGGGAGCGGACCA GTTAACTCGGAATCCATTCCA GCTCTAACCGCCGCAGAGACA GGGCACACGTCACAAGTTGTA CCATCAGACACAATGCAAACT AGGCACGTGAAGAATTACCAT TCAAGGTCAGAGTCGACAGTG GAGAACTTCCTGTGCAGATCT GCATGCGTTTTCTACACCACA TACAAGAACCATGACTCTGAT GGCGACAACTTCGCCTACTGG GTGATCAACACACGGCAAGTT GCTCAACTGCGTCGGAAGCTC GAAATGTTCACGT (SEQ ID NO: 157) gi\|402536\|dbj\|D16364.1\|SVDMPS Swine vesicular disease virus gene for polyprotein, complete cds\|kpath_id\|62762 349 |
| SVD SVD_1727050 | GACTTGTTGTGGCTGGAGGA (SEQ ID NO: 158) | GACTTGTTGTGGCTGGAGGAC GATGCCATGGAGCAAGGAGTT AGGGATTATGTGGAACAACTC GGCAATGCCTTCGGCTCAGGA TTCACCAATCAAATTTGCGAA CAGGTTACCCTTCTAAAAGAG TCGTTAATTGGACAGGATTCT GTCCTTGAGAAGTCTCTCAAG |

TABLE 11-continued

| Porcine Panel | | |
|---|---|---|
| organism<br>Assay ID | Forward Primer<br>Reverse Primer<br>Luminex Probe | Amplicon sequence<br>Reference genome<br>Amplicon size |
| | | GCCCTCGTCAAGATAGTATCA<br>GCACTCGTGATCGTGGTGAGA<br>AATCACGATGACCTCATTACG<br>GTCACCGCCACACTGGCGTTA<br>ATAGGATGTACTACCTCACCA<br>TGGCGCTG<br>(SEQ ID NO: 161) |
| | CAGCGCCATGGTGAGGTAG<br>(SEQ ID NO: 159) | gi\|402536\|dbj\|D16364.1\|SVDMPS<br>Swine vesicular disease virus gene for polyprotein, complete cds\|kpath_id\|62762 |
| | TGACCGTAATGAGGTCATCGTGATTTCTCAC<br>(SEQ ID NO: 160) | 281 |
| SVD<br>SVD_1727051 | GACAAAGTGGCCAAGGGAAA<br>(SEQ ID NO: 162) | GACAAAGTGGCCAAGGGAAA<br>GTCCAGGCTCATCGAGGCTTC<br>TAGCCTCAACGACTCAGTGGC<br>AATGAGGCAGACATTTGGAAA<br>CCTATATAAGACTTTCCACCTC<br>AACCCGGGCATCGTTACGGGT<br>AGCGCCGTTGGGTGTGACCCA<br>GATGTCTTTTGGAGCAAGATC<br>CCCGTCATGCTCGATGGACAT<br>CTCATAGCGTTTGACTATTCA<br>GGCTATGACGCCAGCCTCAGC<br>CCAGTGTGGTTTACGTG<br>(SEQ ID NO: 165) |
| | CACGTAAACCACACTGGGCT<br>(SEQ ID NO: 163) | gi\|402536\|dbj\|D16364.1\|SVDMPS<br>Swine vesicular disease virus gene for polyprotein, complete cds\|kpath_id\|62762 |
| | CTGGCGTCATAGCCTGAATAGTCAAACGCTA<br>(SEQ ID NO: 164) | 248 |
| VESV<br>VESV_95653.F,<br>VESV_95654.R,<br>VESV_95655.P | GCCTTCTCCCTTCCCAAAA<br>(SEQ ID NO: 166) | GCCTTCTCCCTTCCCAAAACG<br>GACGGACCCACCGGAAACGA<br>ACCCGAATTCATCGCTGAGGC<br>TTGCCCTAGCTGCGCTCTTTAC<br>GACACGTGTCCAAATTGCACA<br>TCTAAGGTTATCAACGATGAT<br>GGCTCAACTGACGGAACCATT<br>CCTTCA<br>(SEQ ID NO: 169) |
| | TGAAGGAATGGTTCCGTCAGT<br>(SEQ ID NO: 167) | ref\|NC_002551.1\|gnl\|NCBI_GENOMES\|15509\|gi\|10314005\|Vesicular exanthema of swine virus, complete genome\|kpath_id\|888158 |
| | CATCATCGTTGATAACCTTAGATGTGCAATTTGG<br>(SEQ ID NO: 168) | 153 |
| VESV<br>VESV_95686.F,<br>VESV_95687.R,<br>VESV_95688.P | GGTCGCTCTCACTGATGATGAGTA<br>(SEQ ID NO: 170) | GGTCGCTCTCACTGATGATGA<br>GTACAATGATTGGAAACAGTC<br>CAAAGCTGAAAAAAACCTCGA<br>CCTCACGGTCAAGGACTTCCT<br>CCAACTCAGGCACCGAGCTGC<br>AATGGGTGCTGATAACACC<br>(SEQ ID NO: 173) |
| | GGTGTTATCAGCACCCATTGC<br>(SEQ ID NO: 171) | ref\|NC_002551.1\|gnl\|NCBI_GENOMES\|15509\|gi\|10314005\|Vesicular exanthema of swine virus, complete genome\|kpath_id\|888158 |
| | GCTCGGTGCCTGAGTTGGAGGAAG<br>(SEQ ID NO: 172) | 124 |
| VESV<br>VESV_95692.F,<br>VESV_95693.R,<br>VESV_95694.P | ACCACCTCTGGAAACATCTATGG<br>(SEQ ID NO: 174) | ACCACCTCTGGAAACATCTAT<br>GGAGCCTGCGGCTCATCGTGT<br>TCACTGACGAGACAGGGTGAC<br>TGCGGTCTCCCCTACGTCGAC<br>GATCACGGTGTTGTCGTTGGA<br>CTCCATGCTGGGTCTGGTGGT<br>GACAAATGCCCGTCCCGAAAA |

TABLE 11-continued

| | | Porcine Panel | |
|---|---|---|---|
| organism Assay ID | Forward Primer Reverse Primer Luminex Probe | Amplicon sequence Reference genome Amplicon size | |

| organism Assay ID | Forward Primer / Reverse Primer / Luminex Probe | Amplicon sequence / Reference genome / Amplicon size |
|---|---|---|
| | | CTCATTGTTCCCTACGTCAAG GTGGATATGAGAATTCGTGAC ACGTGCACAAA (SEQ ID NO: 177) |
| | TTTGTGCACGTGTCACGAAT (SEQ ID NO: 175) | ref\|NC_002551.1\|gnl\|NCBI_GENOMES\| 15509\|gi\|10314005\|Vesicular exanthema of swine virus, complete |
| | CGGGACGGGCAT

TABLE 11-continued

Porcine Panel

| organism Assay ID | Forward Primer Reverse Primer Luminex Probe | Amplicon sequence Reference genome Amplicon size |
|---|---|---|
| VSV VSV_1811405 | AAGAGATGGTCACGAGTGAC (SEQ ID NO: 194) | AAGAGATGGTCACGAGTGACT TGTGTCACCAATGACCAAATA CCCACTTGTGCTAATATAATG AGCTCAGTTTCCACAAATGCTC (SEQ ID NO: 197) |
| | GAGCATTTGTGGAAACCGAGC (SEQ ID NO: 195) | ref\|NC_001560.1\|gnl\|NCBI_GENOMES\| 10405\|gi\|9627229\|Vesicular stomatitis Indiana virus, complete genome\|kpath_id\|1100794 |
| | TGGGTATTTGGTCATTGGTGACACA (SEQ ID NO: 196) | 85 |
| VSV VSV_1811408 | CTCACAACATGGGTCCTGAA (SEQ ID NO: 198) | CTCACAACATGGGTCCTGAAT AGGGAAGTTGCAGACGAGCTA TGCCAGATGATGTATCCGGGT CAAGAA (SEQ ID NO: 201) |
| | TTCTTGACCTGGATACATCAT (SEQ ID NO: 199) | ref\|NC_001560.1\|gnl\|NCBI_GENOMES\| 10405\|gi\|9627229\|Vesicular stomatitis Indiana virus, complete genome\|kpath_id\|1100794 |
| | GGCATAGYTCGTCTGCRACTTCCCT (SEQ ID NO: 200) | 69 |
| Maritima N/A | NT NT CAAAGTGGGAGACGTCGTTG (SEQ ID NO: 202) | Probe only |
| Maritima N/A | NT NT CAAAGTGGGAGACGTCGTTG (SEQ ID NO: 203) | Probe only |
| N/A N/A | NT NT CAAAGTGGGAGACGTCGTTG (SEQ ID NO: 204) | Probe only |
| None Alien RNA | GACATCAAGGCTCAAACTAATTTT ACC (SEQ ID NO: 205) CAAAGGCTGCCAACATAAAATG (SEQ ID NO: 206) CAAGCGTAAATGCAGCGTCCA (SEQ ID NO: 207) | Proprietary |

TABLE 12

Bovine Panel

| organism Assay ID | Forward Primer Reverse Primer Luminex Proble | Amplicon sequence Reference genome Amplicon size |
|---|---|---|
| MCF emcf_94975.F, emcf_94976.R, emcf_94977.P | ATGCCAGTCACTGGCTCTCA (SEQ ID NO: 208) | ATGCCAGTCACTGGCTCTCAAG AGGGGTACCAGGGTGCCACCG TGATCAACCCCATTTCAGGATT CTACAACACCC (SEQ ID NO: 211) |
| | GGGTGTTGTAGAATCCTGAAATGG (SEQ ID NO: 209) | ref\|NC_002531.1\|gnl\|NCBI_GENOMES\| 15497\|gi\|10140926\|Alcelaphine herpesvirus 1, complete genome\|kpath_id\|881213 |
| | GTTGATCACGGTGGCACCCTGG (SEQ ID NO: 210) | 76 |

TABLE 12-continued

Bovine Panel

| organism Assay ID | Forward Primer Reverse Primer Luminex Proble | Amplicon sequence Reference genome Amplicon size |
|---|---|---|
| MCF emcf_95059.F, emcf_95060.R, | GTTCTGGAAACTGACCAAACAGT GT (SEQ ID NO: 212) | GTTCTGGAAACTGACCAAACAG TGTTCTTATGTGCACTTATTTTGT ATTTCCCTTATGCCTGCCAGAGT GCTCAATAAAAGTTACACTCAA GTGCCACT (SEQ ID NO: 215) |
| emcf_95061.P | AGTGGCACTTGAGTGTAACTTTT ATTG (SEQ ID NO: 213) GCACTCTGGCAGGCATAAGGGAA ATACA (SEQ ID NO: 214) | ref\|NC_002531.1\|gnl\|NCBI_GENOMES\| 15497\|gi\|10140926\|Alcelaphine herpesvirus 1, complete genome\|kpath_id\|881213 99 |
| MCF emcf_95155.F, emcf_95156R, emcf_95157.P | CCCTGGAAGCTGTCATACAAAA (SEQ ID NO: 216) | CCCTGGAAGCTGTCATACAAA AAGCTTTCCTGCCAGGAGACCC AGCTGAGGCTCTAAACAGTAG CCAGTTTTGTGAGACAACTGCA GCCCTGGACTCTACTGCACCTT GCAAGATATGCCAATGTTT (SEQ ID NO: 219) |
| | AAACATTGGCATATCTTGCAAGGT (SEQ ID NO: 217) CAGTAGAGTCCAGGGCTGCAGTT GTCTCA (SEQ ID NO: 218) | ref\|NC_002531.1\|gnl\|NCBI_GENOMES\| 15497\|gi\|10140926\|Alcelaphine herpesvirus 1, complete genome\|kpath_id\|881213 127 |
| BHV BVH_94666.F, BVH_94667.R, BVH_94668.P | GTGCCAGCCGCGTAAAAG (SEQ ID NO: 220) | GTGCCAGCCGCGTAAAAGCGG CGCTCCATGTTAGCGCTCTGGA ACCAGGAGACGTCGCAGCGCA GGTTGGGCGGGTGGGCGGTTG GCGTCGCGTCCTCGAGCGTAAG GACGGACGTGCGCGAAAAGAG CCCGGAGTCGTC) (SEQ ID NO: 223) |
| | GACGACTCCGGGCTCTTTT (SEQ ID NO: 221) TCCTGGTTCCAGAGCGCTAACAT GGAG (SEQ ID NO: 222) | ref\|NC_001847.1\|gnl\|NCBI_GENOMES\| 12918\|gi\|9629818\|Bovine herpesvirus 1, complete genome\|kpath_id\|1109875 140 |
| BHV BVH_94738.F, BVH_94739.R, BVH94740.P | TGAGGCCTATGTATGGGCAGTT (SEQ ID NO: 224) | TGAGGCCTATGTATGGGCAGTT CGGGTGCCAATAATAAATTTTG CGCGAATCTTATTTAAGTGCAC ACCGTGTTATTTGCGGCTGTTT GTTTTTCTTGGAGGCGGGACGT GCGCGCGAGCTCGGCCGGATT AGGGTTCGGCGCCACCCGGGC ACGGCAGGGCGCCCTTTACTTA TGTTTGGCGCGC (SEQ ID NO: 227) |
| | GCGCGCCAAACATAAGTAAA (SEQ ID NO: 225) AAATAACACGGTGTGCACTTAAA TAAGATTCGCG (SEQ ID NO: 226) | ref\|NC_001847.1\|gnl\|NCBI_GENOMES\| 12918\|gi\|9629818\|Bovine herpesvirus 1, complete genome\|kpath_id\|1109875 186 |
| BPSV BPSV_95719.F, BPSV_95720.R, BPSV_95721.P | GCAGATGCGCTCCTGGTT (SEQ ID NO: 228) | GCAGATGCGCTCCTGGTTCTGG CAGAACACCGAGTCTTCGATG ATCAACACTCTCCTGCTCCCGG CCGACCGCATGATGGCCATGG CCCGGATGAGCCTCTTCTTCGA GCCCCGGATGGACATGGACCG GAGCACGTTCTCCACGTCGGAG |

TABLE 12-continued

Bovine Panel

| organism Assay ID | Forward Primer Reverse Primer Luminex Proble | Amplicon sequence Reference genome Amplicon size |
|---|---|---|
| | GCACCTCTGCTGCTGCAA (SEQ ID NO: 229) CCGACTCCGACGTGGAGAACGTG (SEQ ID NO: 230) | TCGGACACGTTGCAGCAGCAG AGGTGC (SEQ ID NO: 231) ref\|NC_005337.1\|gnl\|NCBI_GENOMES\| 17541\|gi\|41057437\|Bovine papular stomatitis virus, complete genome\|kpath_id\|879465 178 |
| BPSV BPSV_95722.F, BPSV_95723.R, BPSV_95724.P | GATGGCCGTGCAGCTCTT (SEQ ID NO: 232) CGTACAAGATCACGGCCAACT (SEQ ID NO: 233) TGTACGGGCTCATGGGCTTCCG (SEQ ID NO: 234) | GATGGCCGTGCAGCTCTTGGCG GAGGCGTACGAGAAGAGCGCG CTGTTCCGGAAGCCCATGAGCC CGTACACGGAGTTGGCCGTGAT CTTGTACG (SEQ ID NO: 235) ref\|NC_005337.1\|gnl\|NCBI_GENOMES\| 17541\|gi\|41057437\|Bovine papular stomatitis virus, complete genome\|kpath_id\|879465 95 |
| BPSV BPSV_95731.F, BPSV_95732.R, BPSV_95733.P | GCAGCAGTGCACCACGTAGT (SEQ ID NO: 236) CGCTGAACCCGTACATCCT (SEQ ID NO: 237) GACTTCGAGGCGGACAACAAGCG (SEQ ID NO: 238) | GCAGCAGTGCACCACGTAGTA CCCGGCGGTGGCGCGCAGACG CTTGTTGTCCGCCTCGAAGTCG GCCTCCAGGCCCTCGTTGAAGT ACTTGTCGAAGATGATGGGCA GGAAGGAGAGCTTGGACTCGG TGACCACCTTCCCGAAGTTGAG GATGTACGGGTTCAGCG (SEQ ID NO: 239) ref\|NC_005337.1\|gnl\|NCBI_GENOMES\| 17541\|gi\|41057437\|Bovine papular stomatitis virus, complete genome\|kpath_id\|879465 167 |
| FMDV FMDV.TC | ACTGGGTTTTACAAACCTGTGA (SEQ ID NO: 240) GCGAGTCCTGCCACGGA (SEQ ID NO: 241) GTCCCACGGCGTGCAAAGGA (SEQ ID NO: 242) | ACTGGGTTTTACAAACCTGTGA TGGCCTCAAAGACCCTTGAGGC TATCCTCTCCTTTGCACGCCGT GGGACCATACAGGAGAAGTTG ATCTCCGTGGCAGGACTCGC (SEQ ID NO: 243) ref\|NC_011450.1\|gnl\|NCBI_GENOMES\| 17687\|gi\|48429536\|Foot-and- mouth disease virus A, complete genome\|kpath_id\|1130015 107 |
| FMDV FMDV.Pir | CACYTYAAGRTGACAYTGRTACT GGTAC (SEQ ID NO: 244) CAGATYCCRAGTGWCICITGTTA (SEQ ID NO: 245) CCTCGGGGTACCTGAAGGGCATCC (SEQ ID NO: 246) | CACTTTAAGGTGACACTGATAC TGGTACTCAAACACTGGTGACA GGCTAAGGATGCCCTTCAGGTA CCCCGAGGTAACACGCGACACT CGGGATCTG (SEQ ID NO: 247) ref\|NC_004915.1\|gnl\|NCBI_GENOMES\| 17191\|gi\|32188257\|Foot-and- mouth disease virus Asia 1, complete genome\|kpath_id\|1129999 97 |
| BVD BVD_1a | GGTAGTCGTCAGTG)GTTCGAC (SEQ ID NO: 248) | GGTAGTCGTCAGTGGTTCGACG CCTTGGAATAAAGGTCTCGAG ATGCCACGTGGACGAGGGCAT GCCCAAAGCACATCTTAACCTG AGCGGGGGTCGCCCAGGTAAA AGCAGTTTTAACCGACTGTTAC GAATACAGCCTGATAGGGTGC TGCAGAGGCCCACTGTATTGCT |

TABLE 12-continued

Bovine Panel

| organism Assay ID | Forward Primer Reverse Primer Luminex Proble | Amplicon sequence Reference genome Amplicon size |
|---|---|---|
| | CATGTGCCATGTACAGCAGAGAT (SEQ ID NO: 249) CCTCGTCCACGTGGCATCTCGAG (SEQ ID NO: 250) | ACTAAAAATCTCTGCTGTACAT GGCACATG (SEQ ID NO: 251) ref\|NC_001461.1\|gnl\|NCBI_GENOMES\| 10192\|gi\|9626649\|Bovine viral diarrhea virus 1, complete genome\|kpath_id\|963464 202 |
| BVD BVD_1821165.F, BVD_1821164.R, BVD_1821166.P | GGGAGTCGTCAATGGTTCGAC (SEQ ID NO: 252) TCCATGTGCCATGTACAGCAGAG (SEQ ID NO: 253) CCTCGTCCACITGGCATCTCGAG (SEQ ID NO: 254) | GGGAGTCGTCAATGGTTCGAC ACTCCATTAGTCGAGGAGTCTC GAGATGCCATGTGGACGAGGG CATGCCCACGGCACATCTTAAC CCACGCGGGGGTTGCATGGGT GAAAGCGCTATTCGTGGCGTTA TGGACACAGCCTGATAGGGTG TAGCAGAGACCTGCTATTCCGC TAGTAAAAACTCTGCTGTACAT GGCACATGGA (SEQ ID NO: 255) ref\|NC_002032.1\|gnl\|NCBI_GENOMES\| 12254\|gi\|9629506\|Bovine viral diarrhea virus genotype 2, complete genome\|kpath_id\|885447 204 |
| BTV BTV10_1810207 | GCACCCTATATGTTTCCAGACCA (SEQ ID NO: 256) CAGCTAACTCTTCAGCCACACG (SEQ ID NO: 257) CTAACTCGTGGGCCAATCATCAT CTTCTGT (SEQ ID NO: 258) | GCACCCTATATGTTTCCAGACC AAAATTTGTCTCCGCAGTTCTA TATACAGAAGATGATGATTGG CCCACGAGTTAGCTCACGAGTG CGGAATTCTTATGTTGATCGAA TTGATGTGATATTAAGAAAGG ATGTCGTAATGCGAGGTTTTAT TACTGCCAATACGATTCTGAAC GTAATTGAAAAATTAGGGACT AATCACTCAGTGGGAGATCTG GTTACGGTCTTCACGCTTATGA ATATCGAAACACGTGTGGCTG AAGAGTTAGCTG (SEQ ID NO: 259) ref\|NC_006023.1\|gnl\|NCBI_GENOMES\| 17828\|gi\|50253391\|Bluetongue virus segment 1, complete sequence\|kpath_id\|1106954 271 |
| BTV BTV10_1810207 | CAAACACAAAAGGCGGAGAAG (SEQ ID NO: 260) GGCGTTTAATCTGTCTTAGTCTTA CGT (SEQ ID NO: 261) GAAACGCTTCTGCGTACGATGCGA (SEQ ID NO: 262) | CAAACACAAAAGGCGGAGAAG GCTGCATTCGCATCGTACGCAG AAGCGTTTCGTGATGACGTAAG ACTAAGACAGATTAAACGCC (SEQ ID NO: 263) ref\|NC_006015.1\|gnl\|NCBI_GENOMES\| 17820\|gi\|50253387\|Bluetongue virus segment 10, complete sequence\|kpath_id\|1106952 85 |
| BTV BTV10_1810199 | CACATGTCGCTTAATTTGTCTTAA CC (SEQ ID NO: 264) | GCGGAGAAGGCTGCATTCGCA TCGTACGCGGAAGCGTTTCGTG ATGATGTGAGGTTGAGACAAA TTAAACGACATGTG (SEQ ID NO: 267) |

TABLE 12-continued

Bovine Panel

| organism<br>Assay ID | Forward Primer<br>Reverse Primer<br>Luminex Proble | Amplicon sequence<br>Reference genome<br>Amplicon size |
|---|---|---|
| | GCGGAGAAGGCTGCATT<br>(SEQ ID NO: 265) | gb\|AY426602.1\|gi\|37723339\|Bluetongue virus isolate BT4-2227 segment S10, complete sequence\|kpath_id\|1136623 |
| | ACGAAACGCTTCCGCGTACGATG<br>(SEQ ID NO: 266) | 78 |
| BTV<br>BTV10_1810205 | TCAATTTTGGTAGAATTTGTTCATTCA<br>(SEQ ID NO: 268) | GCGGAGAAGGCTGCATTCGCATCGTACGCAGAAGCGTTTCGTGATGATGTGAGATTGAGACAGATTAAACGACATGTGAATGAACAAATTCTACCAAAGTTGA<br>(SEQ ID NO: 271) |
| | GCGGAGAAGGCTGCATTC<br>(SEQ ID NO: 269) | gb\|AY426602.1\|gi\|37723339\|Bluetongue virus isolate BT4-2227 segment S10, complete sequence\|kpath_id\|1136623 |
| | ACGAAACGCTTCCGCGTACGATG<br>(SEQ ID NO: 270) | 103 |
| VSV<br>VSV_1798943 | CGCCACAAGGCAGAGATGT<br>(SEQ ID NO: 272) | CGCCACAAGGCAGAGATGTGGTCGAATGGCTCGGATGGTTTGAAGATCAAAACAGAAAACCGACTCCTGATATGATGCAGTATGCGAAAAGAGCAGTCATGTCACTGCAAGGCCTAAGAGAGAAGACAATTGGCAAGTATGCTAAGTCAGAATTTGACA<br>(SEQ ID NO: 275) |
| | TGTCAAATTCTGACTTAGCATACTTGC<br>(SEQ ID NO: 273) | ref\|NC_001560.1\|gnl\|NCBI_GENOMES\|10405\|gi\|9627229\|Vesicular stomatitis Indiana virus, complete genome\|kpath_id\|1100794 |
| | GCATACTGCATCATATCAGGAGTCGGTTTTCTG<br>(SEQ ID NO: 274) | 159 |
| VSV<br>VSV_1798947 | CCCAATCAATGCCATGATACA<br>(SEQ ID NO: 276) | CCCAATCAATGCCATGATACAGTACAATTATTTTGGGACATTTGCTAGACTCTTGTTGATGATGCATGATCCTGCTCTTCGTCAATCATTGTATGAAGTTCAAGATAAGATACCGGGCTTGCACAGTTCTACTTTCAAATACGCCATGTTGTATTTGGACCCTTCCATTGGAG<br>(SEQ ID NO: 279) |
| | CTCCAATGGAAGGGTCCAAA<br>(SEQ ID NO: 277) | ref\|NC_001560.1\|gnl\|NCBI_GENOMES\|10405\|gi\|9627229\|Vesicular stomatitis Indiana virus, complete genome\|kpath_id\|1100794 |
| | TTTGAAAGTAGAACTGTGCAAGCCCGGTATC<br>(SEQ ID NO: 278) | 173 |
| VSV<br>VSV_1798949 | GGCGCTCATTATAAAATTCGGA<br>(SEQ ID NO: 280) | GGCGCTCATTATAAAATTCGGAGTATATTACATGGAATGGGAATCCATTACAGGGACTTCTTGAGTTGTGGAGACGGCTCCGGAGGGATGACTGCTGCATTACTACGAGAAAATGT<br>(SEQ ID NO: 283) |
| | ACATTTTCTCGTAGTAATGCAGCAG<br>(SEQ ID NO: 281) | ref\|NC_001560.1\|gnl\|NCBI_GENOMES\|10405\|gi\|9627229\|Vesicular stomatitis Indiana virus, complete genome\|kpath_id\|1100794 |
| | GAAGTCCCTGTAATGGATTCCCATTCCATGT<br>(SEQ ID NO: 282) | 116 |
| VSV<br>VSV_1811408 | CTCACAACATGGGTCCTGAA<br>(SEQ ID NO: 284) | CTCACAACATGGGTCCTGAATAGGGAAGTTGCAGACGAGCTATGCCAGATGATGTATCCGGGTCAAGAA<br>(SEQ ID NO: 287) |

TABLE 12-continued

Bovine Panel

| organism Assay ID | Forward Primer Reverse Primer Luminex Proble | Amplicon sequence Reference genome Amplicon size |
|---|---|---|
| | TTCTTGACCTGGATACATCAT (SEQ ID NO: 285) | ref\|NC_001560.1\|gnl\|NCBI_GENOMES\| 10405\|gi\|9627229\|Vesicular stomatitis Indiana virus, complete genome\|kpath_id\|1100794 |
| | GGCATAGYTCGTCTGCRACTTCC CT (SEQ ID NO: 286) | 69 |
| RPV RPV_1814853 | GGATCGCTGAAATGATCTGTGA (SEQ ID NO: 288) | GGATCGCTGAAATGATCTGTGA CATTGATACCTACATAGTGGAG GCAGGGTTGGCCAGTTTTATAC TCACTATCAAATTTGGTATAGA AACGATGTACCCAGCACTGGG CCTGCATGAATTCGCCGGAGA GCTCTCCACAATCGAGTCTCTT ATGAATCTGTACCAGCAAATG GGTGAACTGGCTCC (SEQ ID NO: 291) |
| | GGAGCCAGTTCACCCATTTG (SEQ ID NO: 289) | ref\|NC_006296.2\|gnl\|NCBI_GENOMES\| 17932\|gi\|56410431\|Rinderpest virus (strain Kabete O), complete genome\|kpath_id\|882961 |
| | CTGGCCAACCCTGCCTCCACTAT GTA (SEQ ID NO: 290) | 187 |
| RPV RPV_1814855 | TGCATCTTATGTGACTTTGGTTCA (SEQ ID NO: 292) | TGCATCTTATGTGACTTTGGTT CAGCCAATTATGGTTGGTTTTT TGTACCATCGAACTGTCAGTTG GATGACATAGATAGAGAGACG TCAGCACTCAGGGTCCCCTACA TCGGATCGACAACAGATGAGA GGACTGATATGAAGCTCGCATT TGTTAAGTCACCCAGTCGAACC CTGCGGTCAGCTGTGCGGATAG CC (SEQ ID NO: 295) |
| | GGCTATCCGCACAGCTGAC (SEQ ID NO: 293) | ref\|NC_006296.2\|gnl\|NCBI_GENOMES\| 17932\|gi\|56410431\|Rinderpest virus (strain Kabete O), complete genome\|kpath_id\|882961 |
| | CAGTCCTCTCATCTGTTGTCGATC CGATGTA (SEQ ID NO: 294) | 198 |
| RPV RPV_1814856 | AACTCCTGACCTCATTCCTTGC (SEQ ID NO: 296) | AACTCCTGACCTCATTCCTTGC AAGGATGAGTAAGAGCGTATT CAAGGTCTTTGTGAATGCACTG AGCCACCCCAAGATTTACAGG AAGTTCTGGCATAGTGGGATTA TAGAGCC (SEQ ID NO: 299) |
| | GGCTCTATAATCCCACTATGCCA (SEQ ID NO: 297) | ref\|NC_006296.2\|gnl\|NCBI_GENOMES\| 17932\|gi\|56410431\|Rinderpest virus (strain Kabete O), complete genome\|kpath_id\|882961 |
| | TGGCTCAGTGCATTCACAAAGAC CTTGAATA (SEQ ID NO: 298) | 115 |
| Maritima N/A | NT NT CAAAGTGGGAGACGTCGTTG (SEQ ID NO: 300) | Probe only |
| N/A N/A | NT NT CAAAGTGGGAGACGTCGTTG (SEQ ID NO: 301) | Probe only |
| N/A N/A | NT NT CAAAGTGGGAGACGTCGTTG (SEQ ID NO: 302) | Probe only |

TABLE 12-continued

Bovine Panel

| organism<br>Assay ID | Forward Primer<br>Reverse Primer<br>Luminex Proble | Amplicon sequence<br>Reference genome<br>Amplicon size |
|---|---|---|
| None<br>Alien RNA | GACATCAAGGCTCAAACTAATTT<br>TACC<br>(SEQ ID NO: 303)<br>CAAAGGCTGCCAACATAAAATG<br>(SEQ ID NO: 304)<br>CAAGCGTAAATGCAGCGTCCA<br>(SEQ ID NO: 305) | Proprietary |

Example 13

Testing of the Additional Bovine and Porcine Signature Sequences

1. Bovine Viral Diarrhea Virus (BVDV)—Bovine Panel

Signature candidates: Two signatures, BVD_1a and BVD_2, are available for consideration. BVD_1a was adopted from the Version 1.0 panel without change. BVD_2 is a redesigned version of BVD_1a. The BVD_2 forward primer includes 2 nucleotide substitutions, the reverse primer was shifted 2 nucleotides, and the probe uses the same sequence except for 1 inosine substitution.

Signature origin: BVD primers designed by Ridpath et al. were adapted to Taqman format by Faaberg et al., and subsequently modified by scientists at the California Animal Health and Food Safety Laboratories. The CAHFS version of the Taqman signature was adapted to the Luminex multiplex format.

The BVD_1A signature was tested in singleplex format using a dilution series of BVDV RNA (Singer strain, NVSL) from titered virus-infected cell culture. The results in FIG. 1 are plotted together with data acquired using Version 1.0. The qualitative limit of detection was similar for both singleplex and multiplex Version 1.0.

Near-neighbor screening: In the Version 1.0 panel, BVD_1a signature responded to Border Disease Virus (BDV) Aveyron and Frijters strains but not 137-7. Also in the Version 1.0 panel, BVD_1a signature responded to Classical Swine Fever Virus (CSFV) Brescia ($\geq$550 TCID$_{50}$/mL) and Paderborn ($\geq$6550 TCID50/mL) but not Kanagawa.

Figure 2:
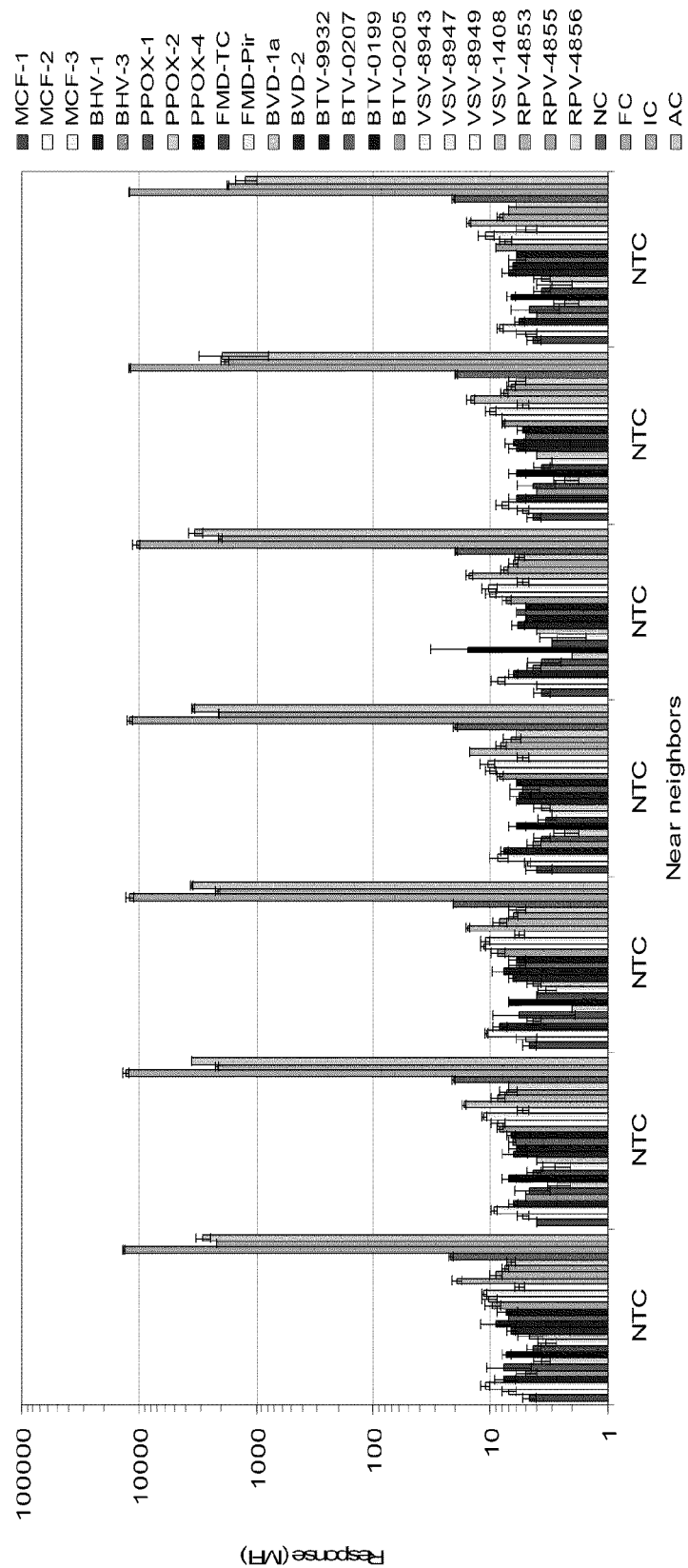
FIG. 2: Response of the bovine panel to no template control (NTC, water) showing that the signature response for detection channels is typically less than 20 MFI units. The response of the four control channels should remain constant and are included for reference. Testing was conducted at PIADC. Each sample was analyzed in triplicate. For each signature, the responses (MFI) from triplicate analyses were averaged. Error bars indicate ±1σ of the mean response.

All near-neighbor and target screening conducted at PIADC for the bovine multiplex assay was conducted using a total of three 96-well plates. The responses of the bovine panel to no template control (NTC, water) are shown in FIG. 2. The response of each signature used for viral detection was typically less than 20 MFI units. Each signature requires a distinct cutoff. To determine cutoffs for PIADC target and near-neighbor screening the results from blank samples (no template control, NTC) from all plates analyzed were pooled. To establish cutoffs in the later stages of analytical and diagnostic characterization requires more rigorous experimentation and data analysis. Generally, this would require a finalized panel, analysis of many blank samples of the desired sample matrix, application of non-parametric statistics to determine cutoff for a given false positive rate, and determination of limit of detection at a given probability of detection.

Figure 3:
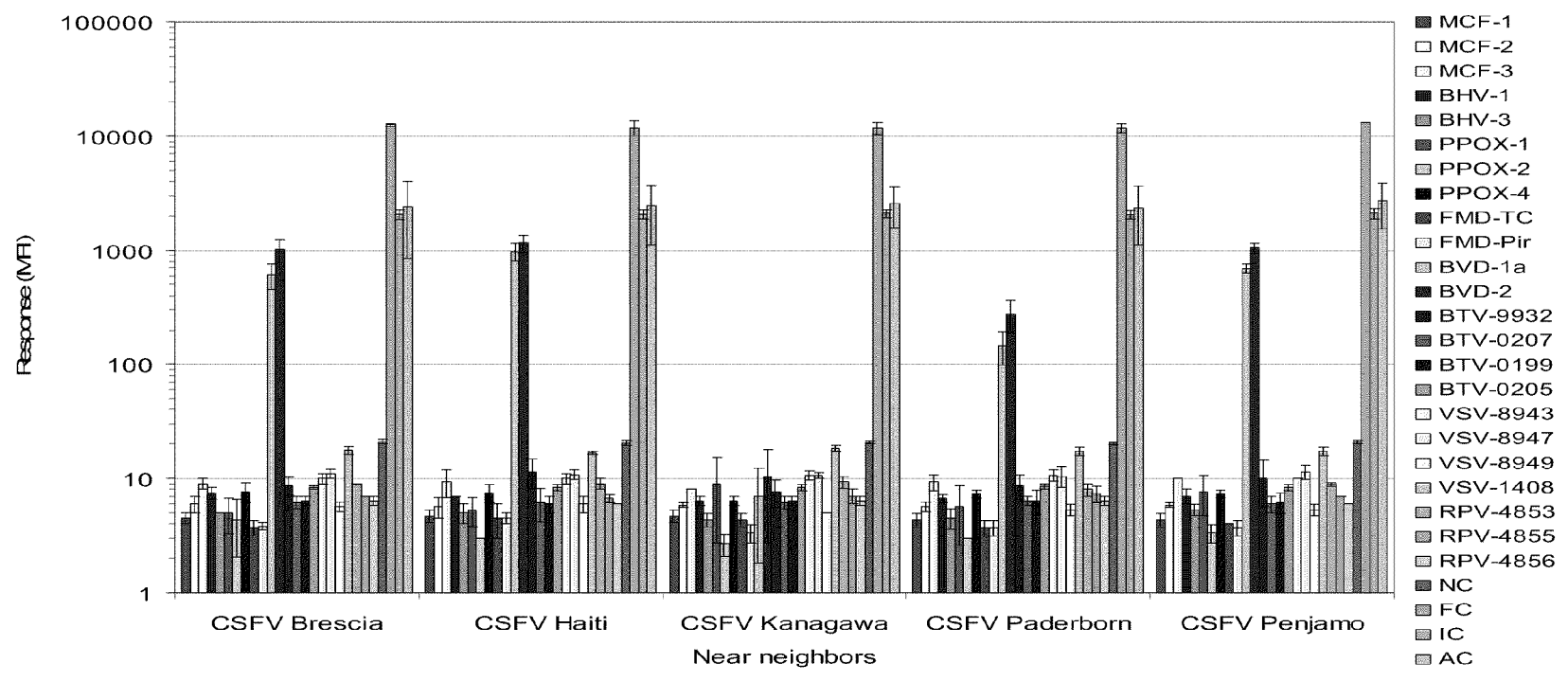
Figure 4:
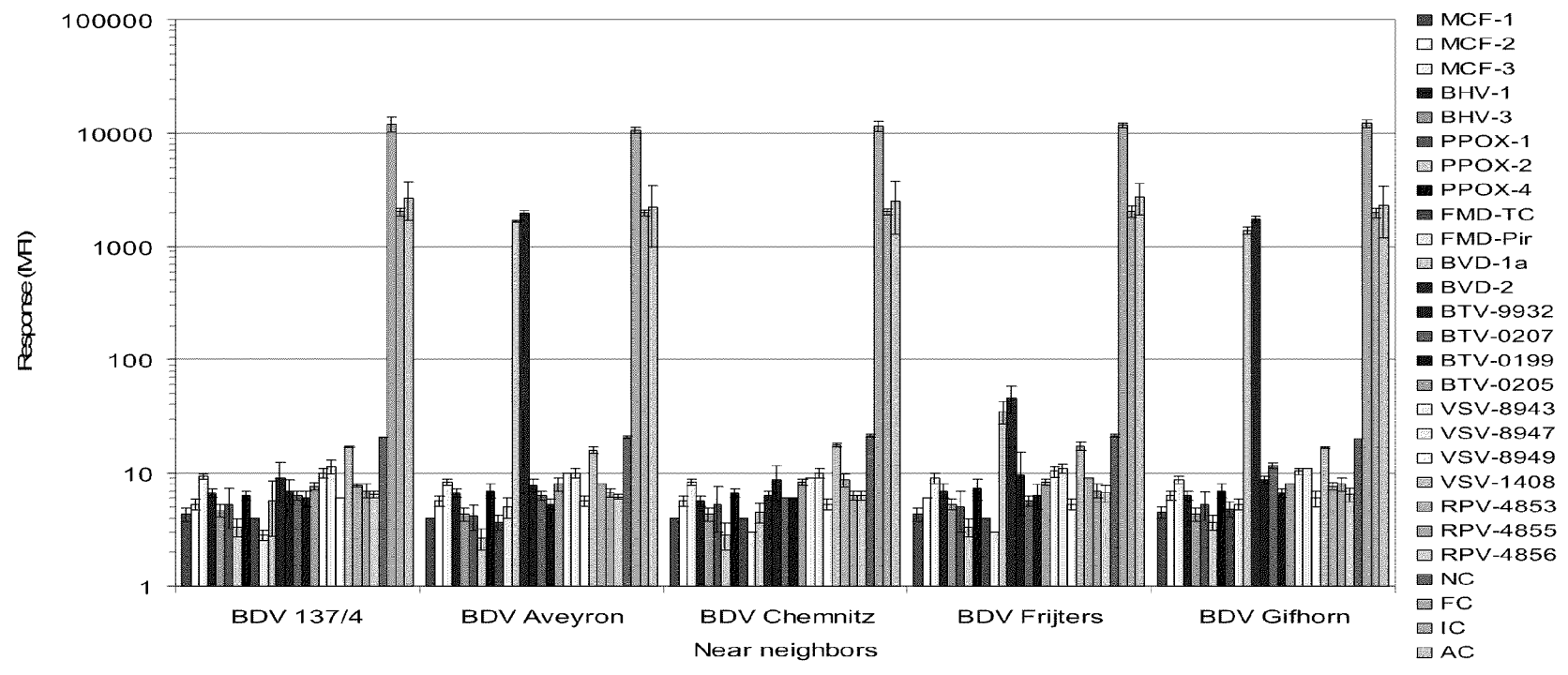

Results of the near-neighbor screening of the BVD-1a and BVD-2 signatures in the bovine panel against CSFV and BDV isolates are presented in FIG. 3 and FIG. 4, respectively.

Figure 5:
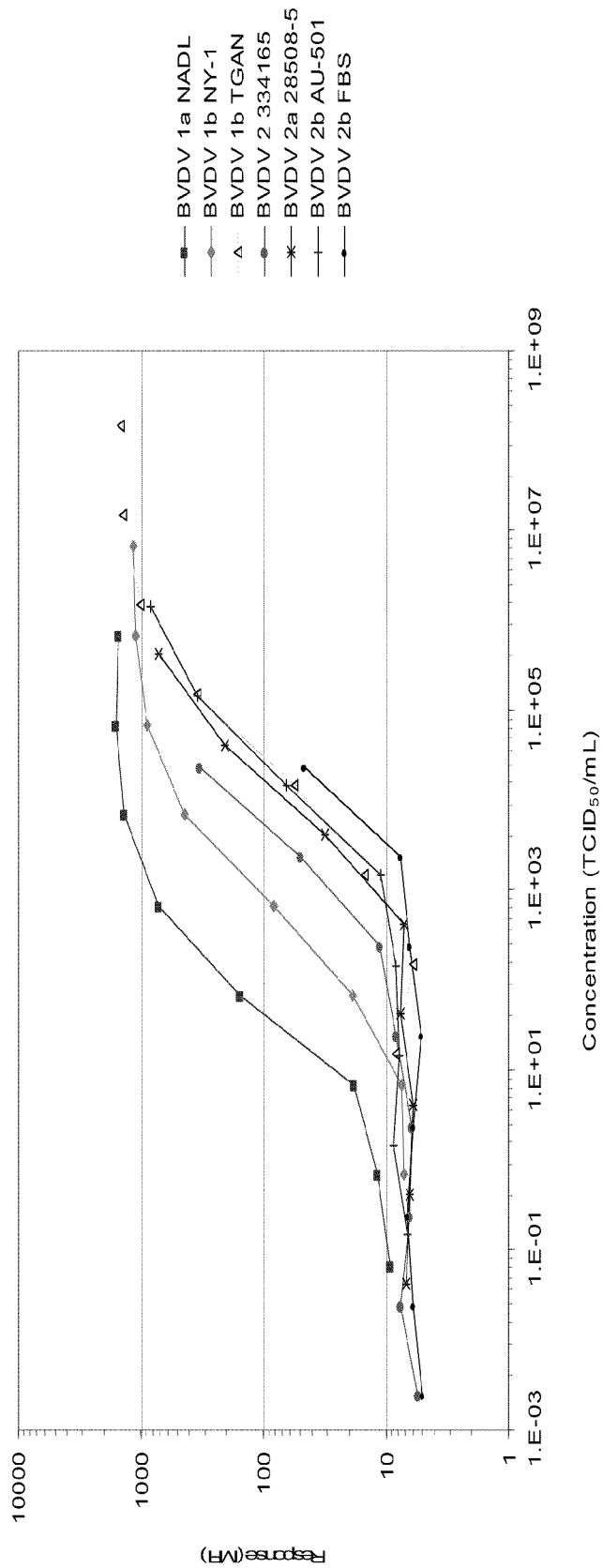
FIG. 5: BVD-1a signature response in the Version 1.0 panel to BVDV strains of both genotypes. Each titration series was constructed from stock solutions of titered virus-infected cell culture for both BVDV genotypes that was subsequently extracted (Ambion MagMax96). Each point represents the mean response (n=4) of four replicate analyses from extraction through detection.

Target screening: Titration curves were acquired for the BVD_1a signatures in the Version 1.0 panel and the results are shown in FIG. 5. Each titration series was constructed from serially diluted samples of titered virus-infected cell culture for both BVDV genotypes that were subsequently extracted (Ambion MagMax 96). In general, the BVD_1a signature response was stronger for lower concentrations of BVDV Type 1 compared to Type 2.

Figure 6:
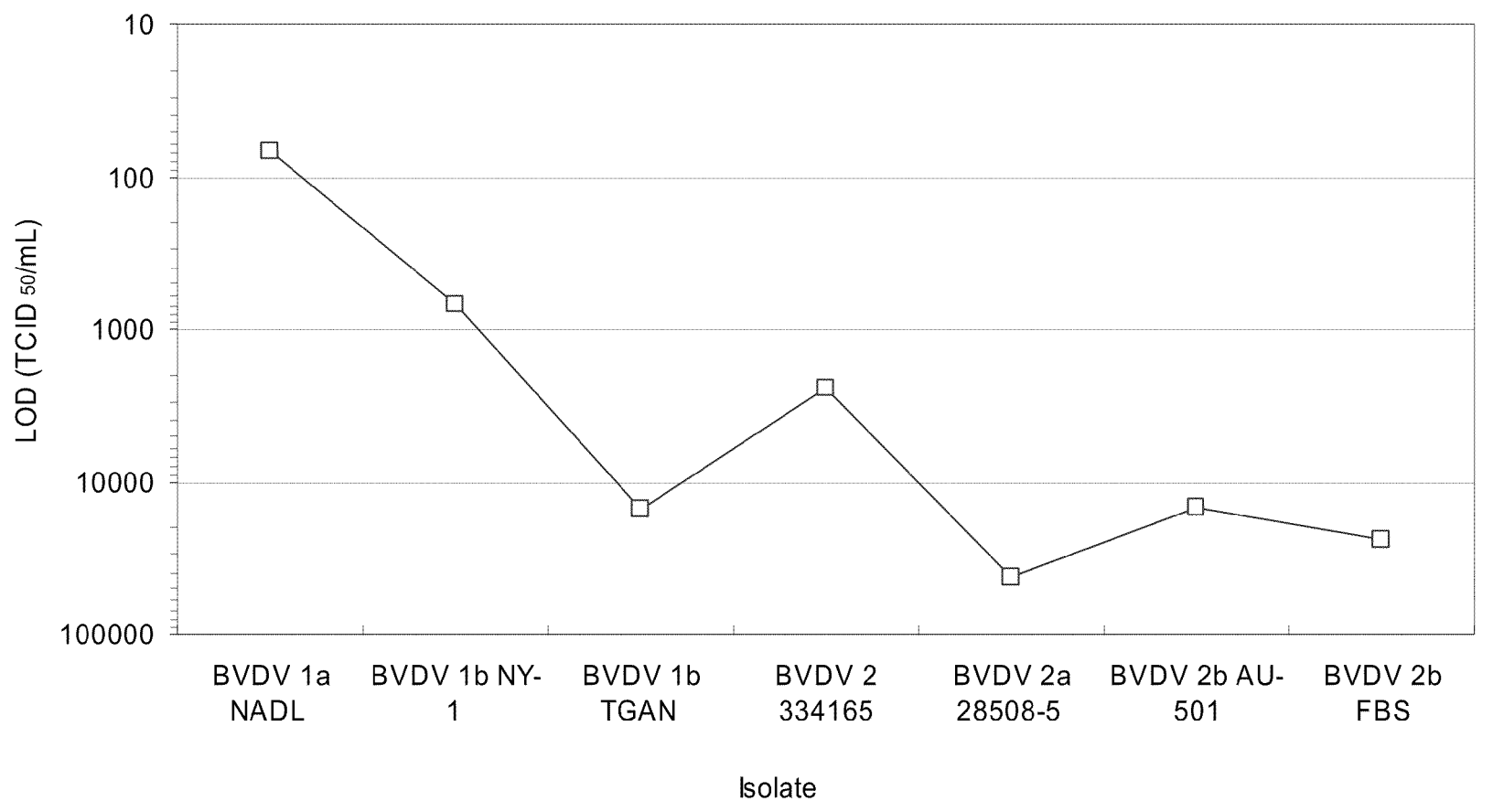

The results presented in FIG. 5 are summarized further in FIG. 6 where the qualitative limit of detection of the BVD_1a signature is shown for each strain.

Figure 7:
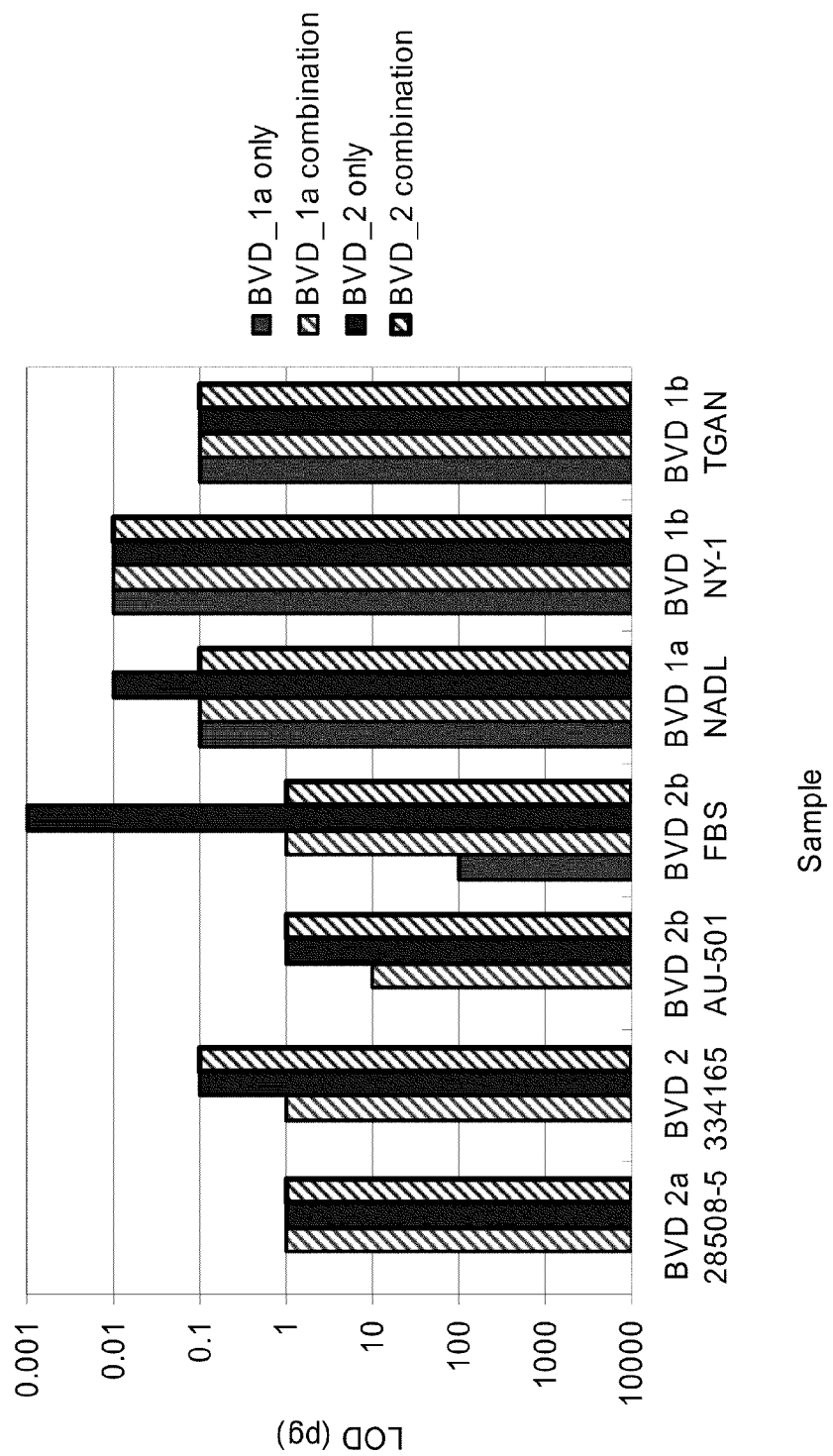
FIG. 7: Comparison of the response of BVD signatures (BVD_1a and BVD_2) when incorporated into a developmental Bovine multiplex panel showing that addition of the new BVD_2 only generated the best response for the seven strains tested. Multiplex titrations were performed using serial dilutions of total RNA extracted (Trizol) from live virus. The LOD (pg) represents the lowest amount of RNA tested that generated response above threshold. The threshold value of 40 MFI units was used for both BVD signatures. The means response (n=2) was determine from duplicate measurements for each mass of template in the calibration series.

To improve the response of a candidate Bovine multiplex panel to BVD Type 2 strains, the BVD_1a signature was modified leading to the generation of an additional signature BVD_2. Signature responses were compared using three developmental Bovine panels that included either BVD-1a only, BVD-2 only, or BVD_1a and BVD_2 in combination. FIG. 7 shows that the BVD-1a LOD for BVD Type 2 strains improved when BVD_2 was present in the multiplex. However, the new BVD_2 signature alone performed as well as, or better than the BVD_1a signature alone or in combination. No signature combination responded to the near-neighbor BDV (Coos Bay #4, 4-6-92).

The new BVD_2 signature alone or in combination with BVD_1a when added to the Bovine panel provides better coverage for BVDV Type 2.

2. Bluetongue Virus (BTV)—Bovine Panel

Signature candidates: One signature, BTV_1759932, was adopted from the Version 1.0 panel without change. The three new BTV signatures for consideration are BTV_1810199, BTV_1810205 and BTV_1810207.

Signature origin: BTV_1759932 was developed by LLNL was adopted without change from the Version 1.0 panel. BTV_1810199, BTV_1810205 and BTV_1810207 were developed in 2006 as part of a collaborative effort between LLNL and USDA ARS ABADRL using published (Genbank) and unpublished (ABADRL) sequence information for segments 5 and 10. Signature screening and characterization was also performed in partnership between LLNL and USDA ARS ABADRL.

Near-neighbor screening: Signatures were screened at USDA ABADRL against eleven EHDV isolates from all eight EHDV serotypes. Samples were dsRNA purified by LiCl precipitation of RNA extracted from virus-infected cell culture. No signature cross-reaction was observed at 200 pg of EHDV dsRNA.

Figure 8:
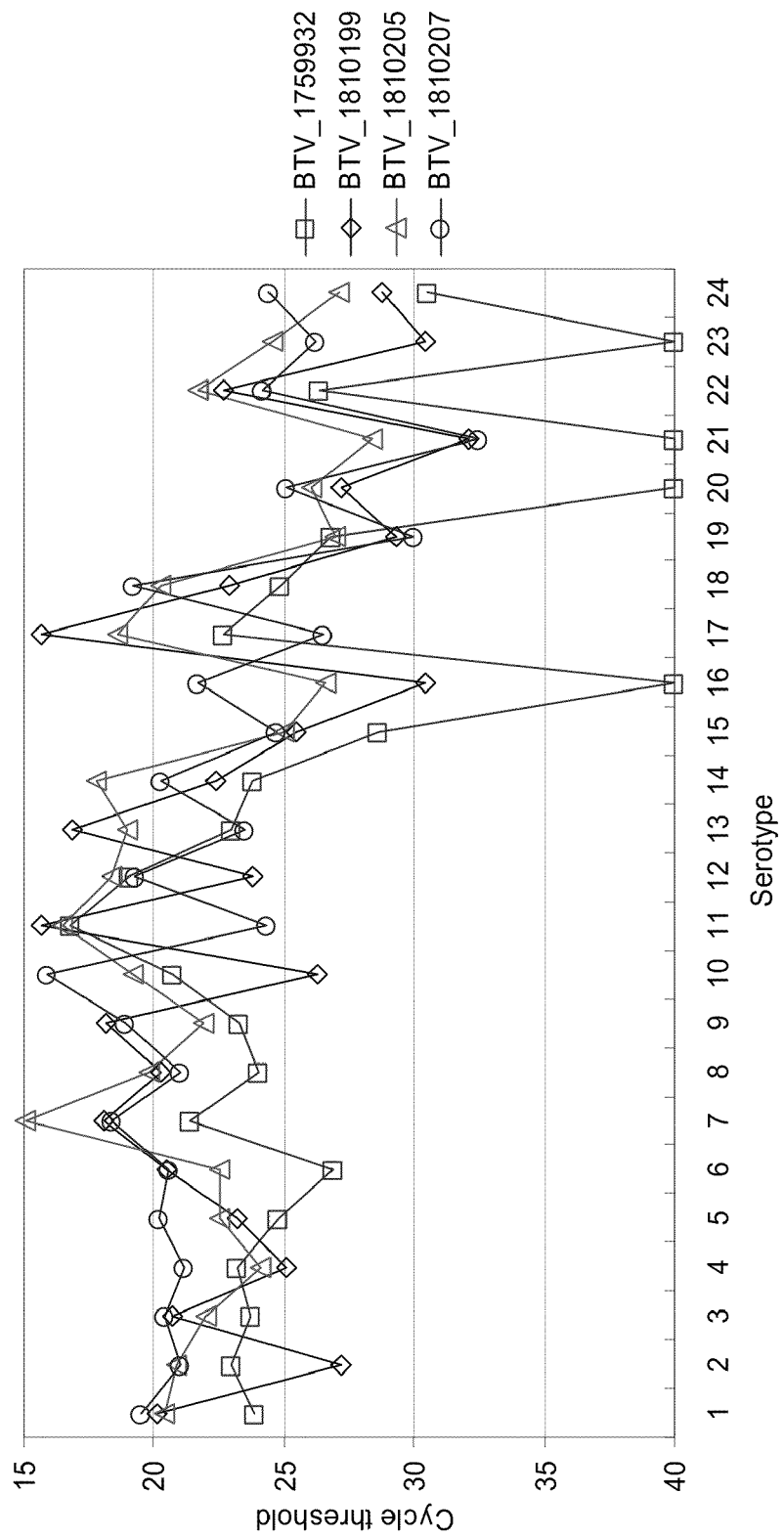
FIG. 8: Taqman screening of BTV signatures against isolates representing twenty-four BTV serotypes. Testing was conducted at UDSA ABARDL (University of Wyoming) Samples were dsRNA purified by LiCl precipitations of RNA extracted (Pure Script, Gentra Systems) from virus-infected cell culture. Each reaction was spiked with 200 pg of template. Each point represents the mean (n=3) cycle threshold. If no cycle threshold was reached (i.e. infinite cycle threshold), a cycle threshold of 40 was assigned in this plot.

Target screening: All signatures were screened against purified dsRNA from BTV strains representing twenty-four serotypes. Samples were dsRNA purified by LiCl precipitations of RNA extracted from virus-infected cell culture. The results summarized in FIG. 8 show that the new signatures BTV_1810199, BTV_1810205 and BTV_1810207 responded to 24/24 serotypes tested. BTV_1759932 responded to 20/24 serotypes tested; no response was observed for BTV_1759932 for serotypes 16, 20, 21 and 23. Additional Taqman screening was conducted at LLNL and USDA ABARDL to determine qualitative limits of detection for each signature.

Singleplex screening was conducted for BTV_1759932 using one strain of BTV (data not shown). These four signatures were incorporated into the Bovine multiplex panel.

Near-neighbor screening Version 1.0: In Version 1.0, BTV_1759932 did not respond to nucleic acid (200 pg) extracted from three EHD-1 serotypes (isolates Georgia, New Jersey, Santa Barbara) and EHD-2 serotype Alberta.

Figure 9:
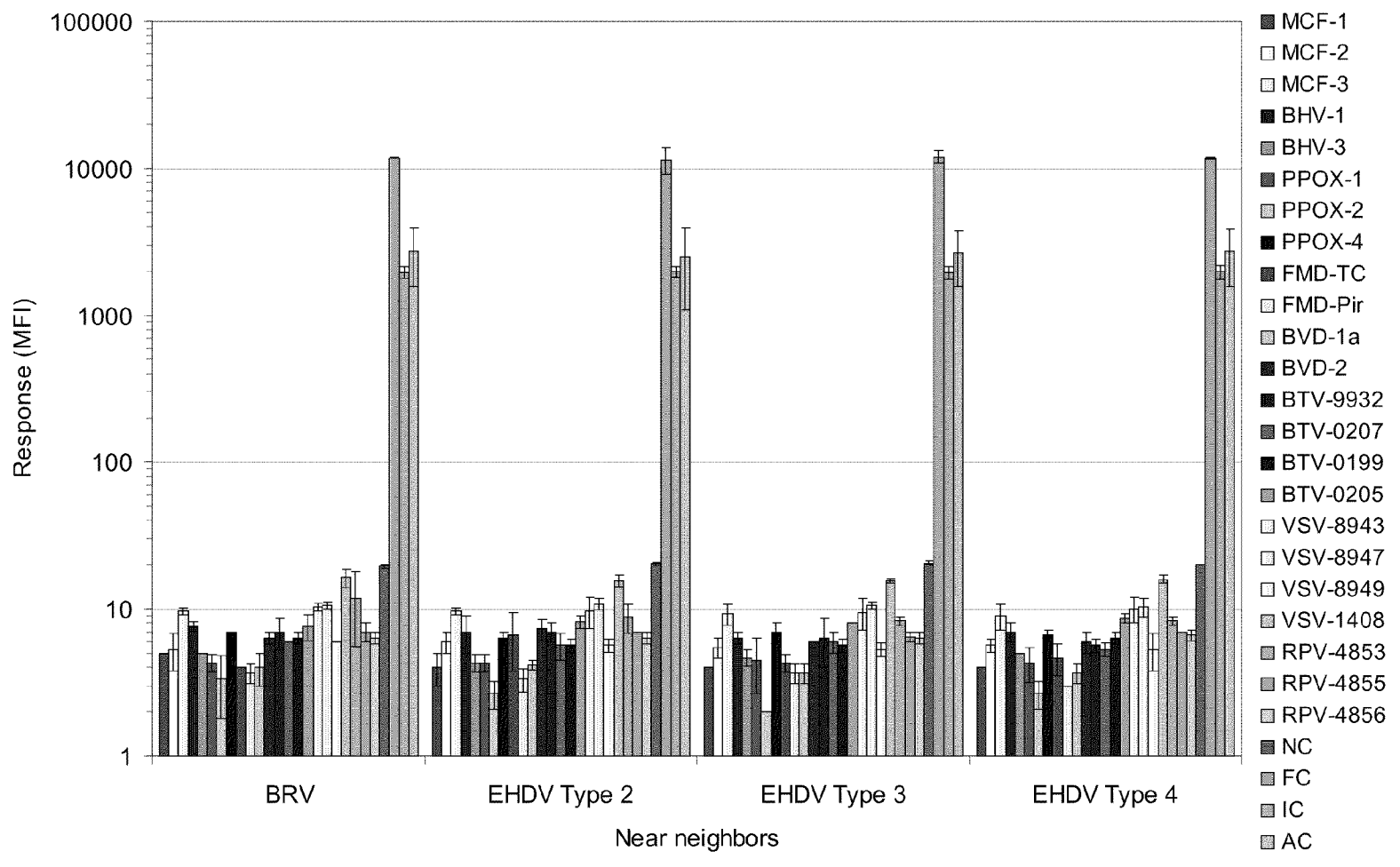
Figure 10:
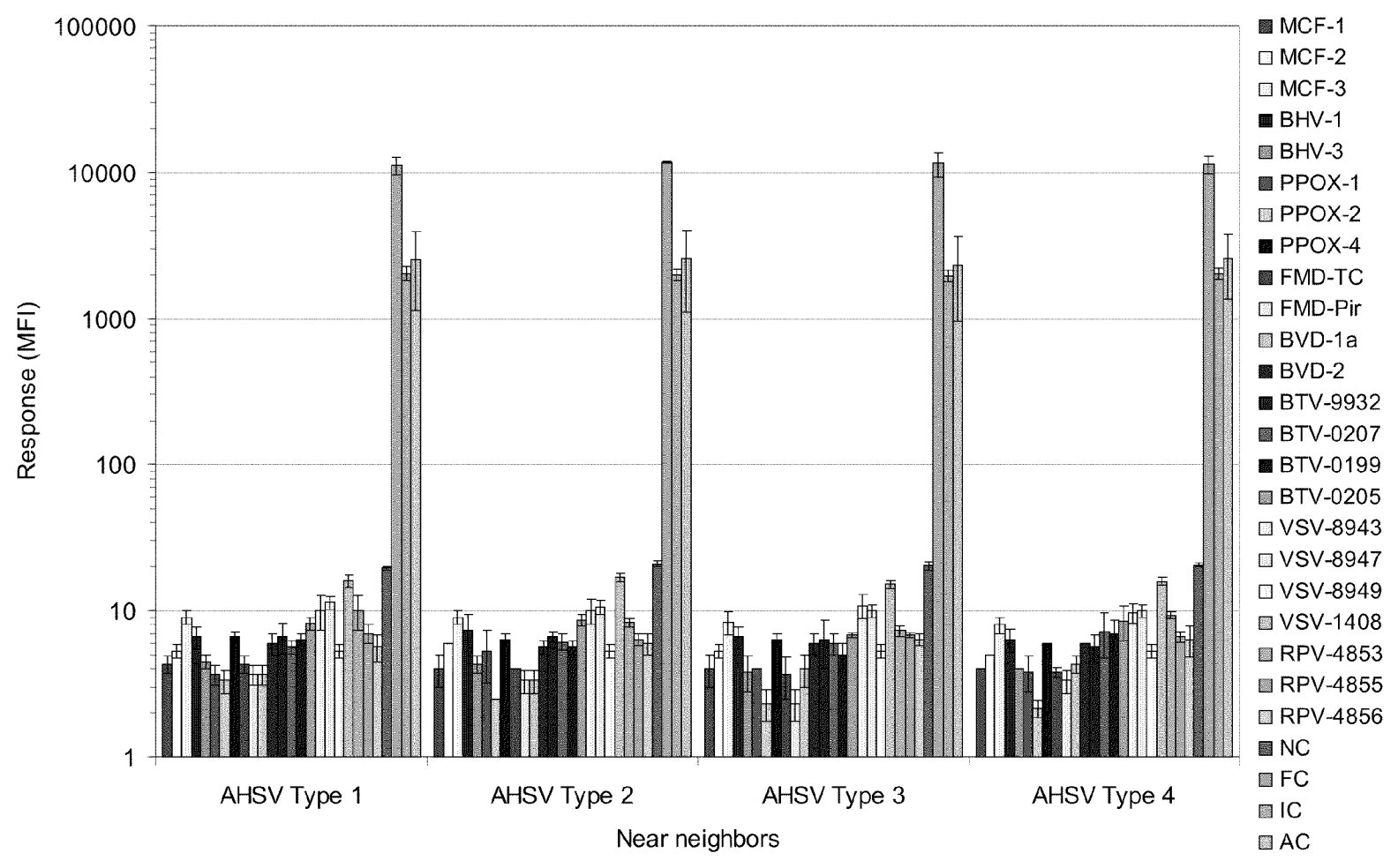

Near-neighbor screening (Bovine panel): The BTV signatures did not cross-react with BRV, EHDV Types 2, 3 or 4, or AHSV Types 1-4 as shown in FIG. 9 and FIG. 10. This testing was conducted at PIADC.

Figure 11A:
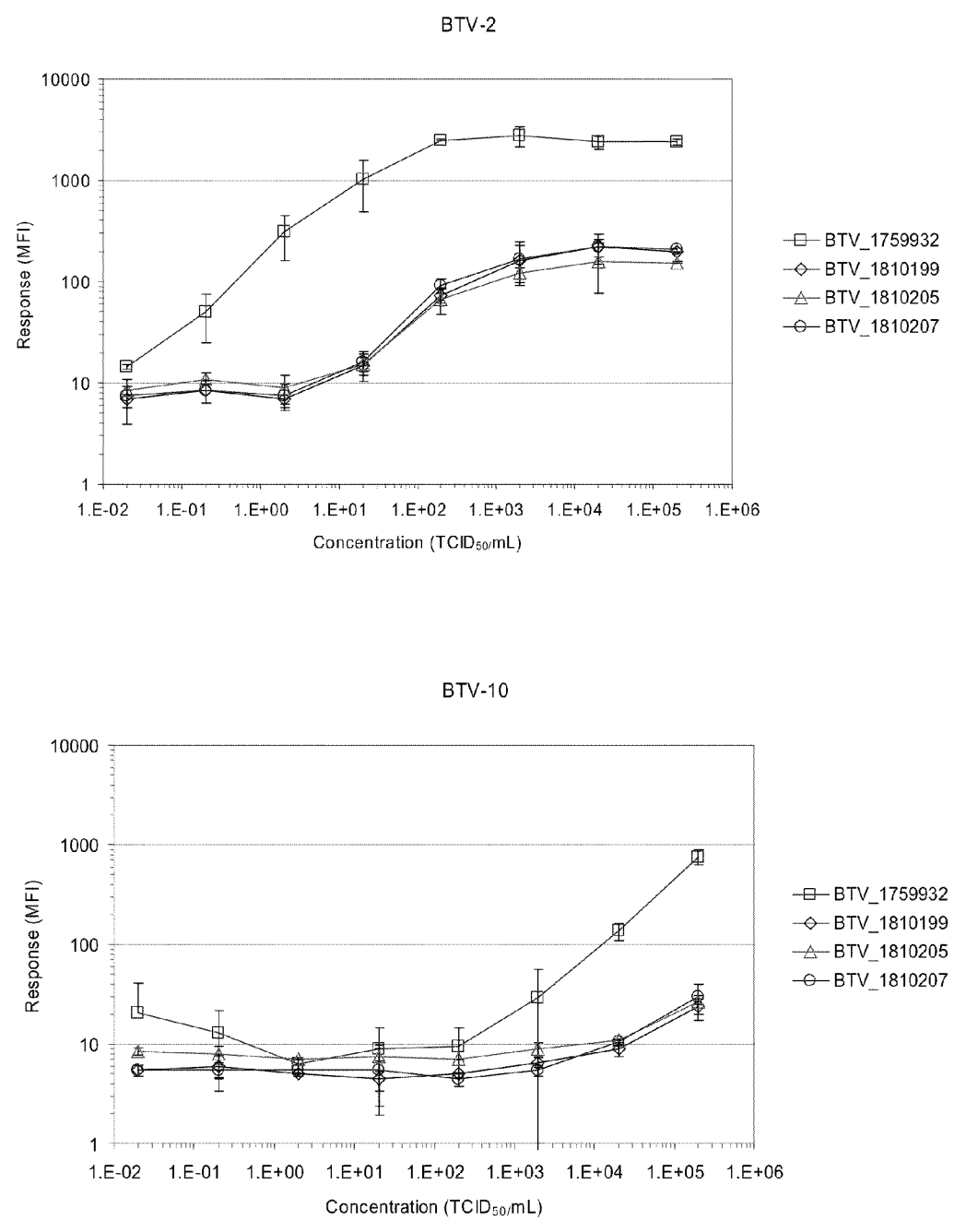
Figure 11B:
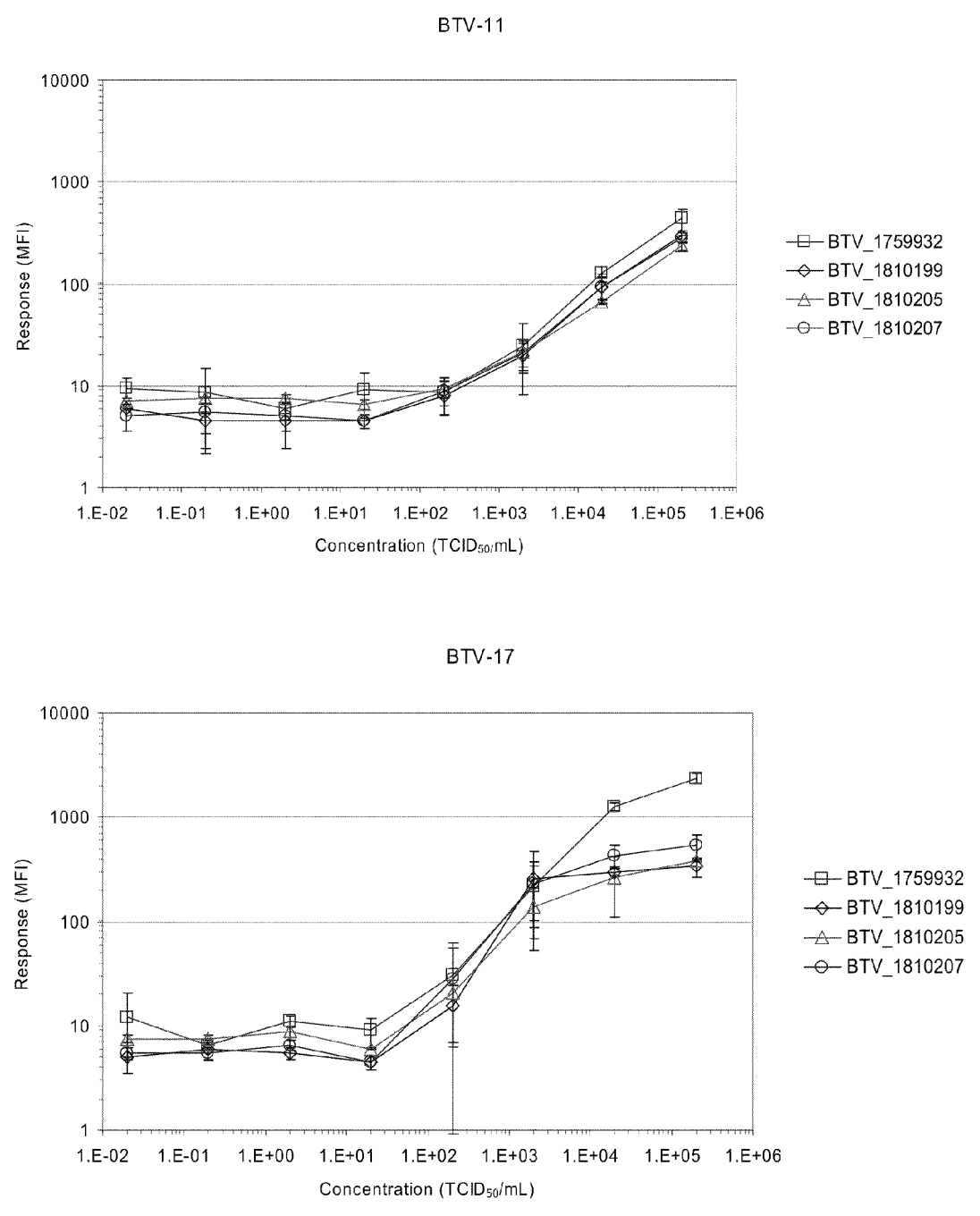

Target screening: The four signatures have consistently low background response in the absence of template in the current Bovine panel. The Bovine panel was screened against five US strains of BTV (2, 10, 11, 13 and 17). The signatures responded over a wide concentration range as shown in FIG. 11. BTV_1759932 generated a stronger response to BTV serotypes 2 and 10, compared to the three newly developed signatures. Testing conducted at USDA ABARDL was done using BTV strains different to those used for at LLNL.

The BTV signatures together demonstrated promising performance in both Taqman and multiplex formats. The four signatures may provide pan-serotype detection capability for BTV.

3. Foot-and-Mouth Disease Virus (FMDV)—Bovine and Porcine Panels

Signature candidates: FMDV-TC (USDA ARS/Tetracore) and FMDV-Pir (Institute for Animal Health, Pirbright). Both signatures were adopted from published assays and the Version 1.0 panel without change.

Signature origin: Two independent real-time reverse transcriptase polymerase chain reaction (rRT-PCR) assays targeting conserved regions of the internal ribosomal entry site of 5' untranslated region (5'UTR) and the viral RNA polymerase (3D) on the highly variable FMD genome. An in-depth comparative evaluation of diagnostic sensitivity (D-SN) was reported in which samples of epithelial suspension from tissue collected from suspect FMD cases were analyzed. In combination, these singleplex Taqman assays reported higher D-SN compare to virus isolation and antigen-ELISA. The 5'UTR (FMD_PIR) and 3D (FMD_TC) Taqman signatures were adapted directly to the multiplex format.

Figure 12:
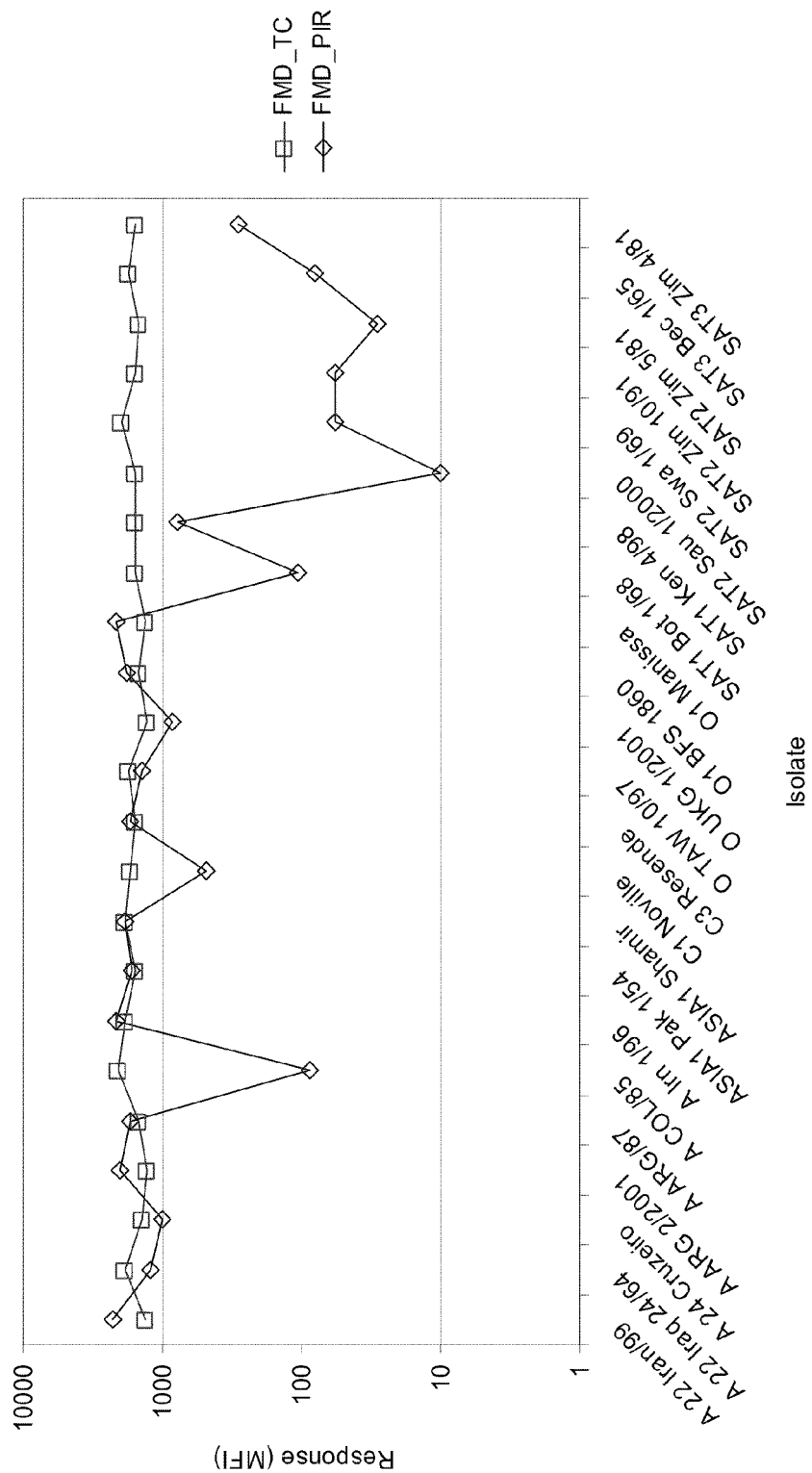
FIG. 12: FMDV signature screening in singleplex against multiple FMDV isolates. Samples were total nucleic acid extracted from untitered virus-infected cell culture. Each point represents the mean response (n=2). No template control response was <10 MFI units for both signatures.

Singleplex screening of the FMD signatures against twenty-three isolates representing all seven serotypes was conducted. The FMD¬_TC signature showed a high response to all serotypes tested (FIG. 12). The FMD_Pir signature had a weaker response to SAT 1, 2 and 3 samples, as well as A COL/85 and C1 Noville.

Figure 13:
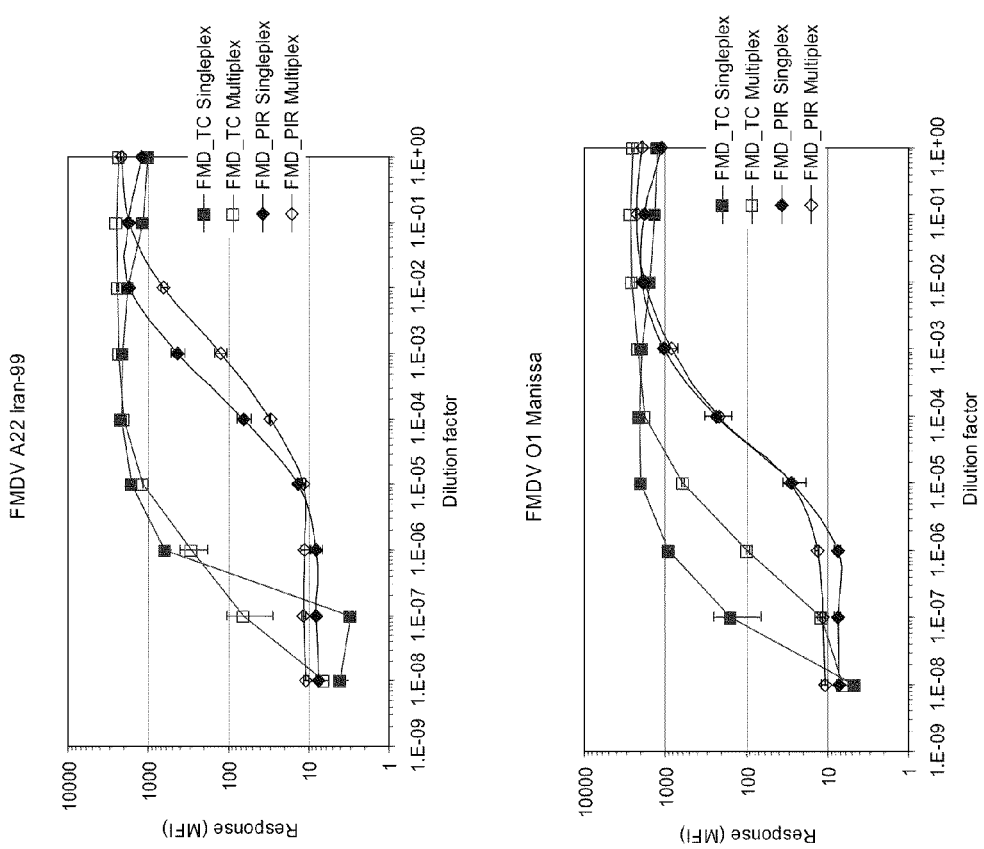
FIG. 13: FMDV signature screening in singleplex and multiplex Version 1.0 format against two FMD isolates A22 Iran-99 and O1 Manissa. The two samples were serially diluted from a stock sample of total RNA extracted from virus-infected cell culture. The original sample concentration is unknown so the results are plotted as response vs. dilution factor of the original sample. Each point represents the mean response (n=2). Error bars indicate ±1σ of the mean.

Both signatures were tested in singleplex format using a dilution series of FMDV A22 Iran-99 and O1 Manissa extracted RNA. The results in FIG. 13 are plotted together with data acquired with a developmental multiplex assay comprised of eight primer sets. The singleplex and multiplex responses were comparable over the entire dilution series that spanned eight orders of magnitude. The FMD_PIR signature had a higher qualitative limit of detection than FMD-TC in both singleplex and multiplex formats against these two samples.

Near-neighbor screening (Version 1.0): FMD signatures in the Version 1.0 multiplex was examined by assays by running titrations against SVD (UKG-72), VSV (NJ 95366), VESV (A48), Rinderpest (Nig Buffalo), BHV-1 and BVDV (NY 1). No response greater than the background was observed for either FMD signature.

Figure 14:
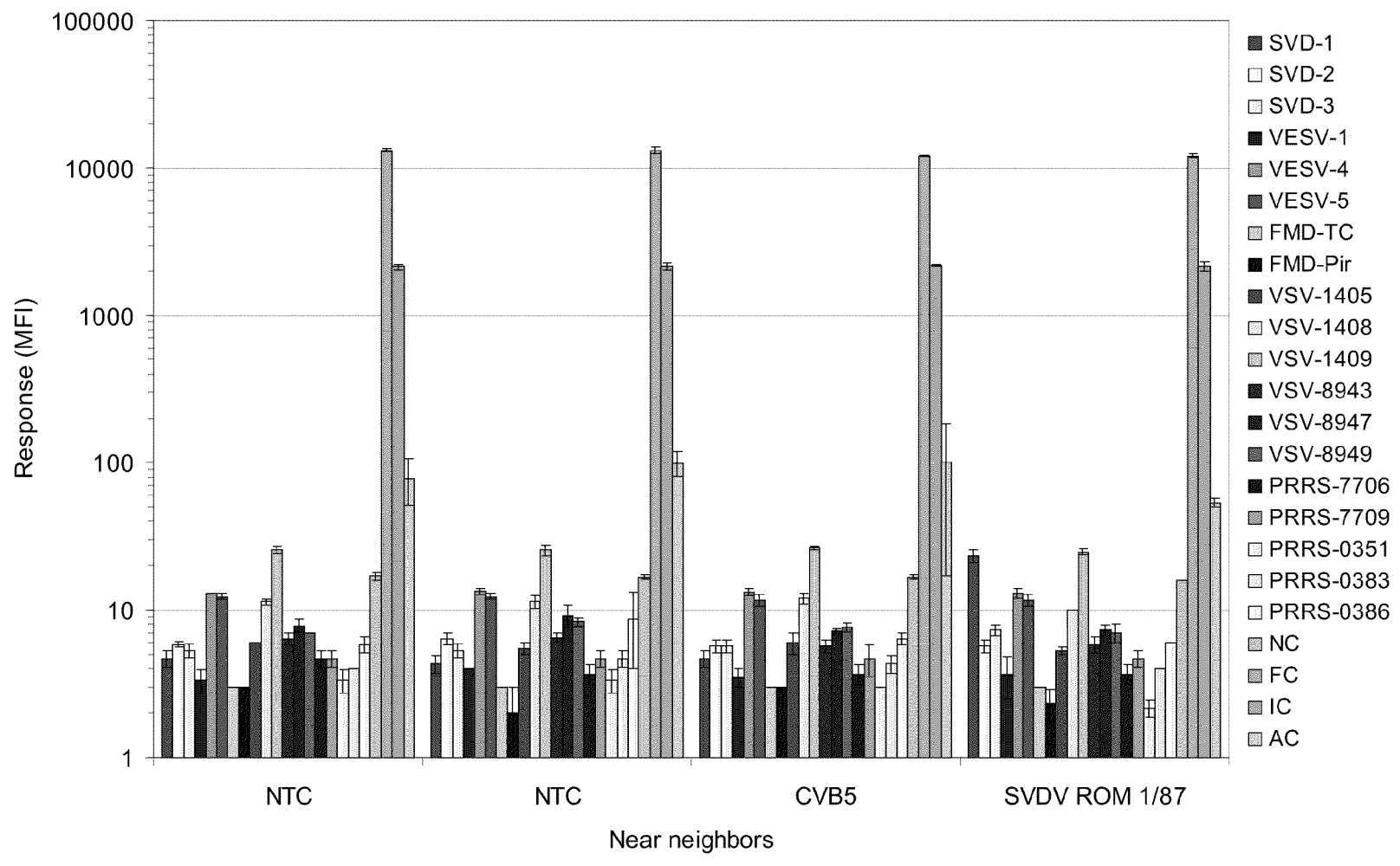
Figure 15:
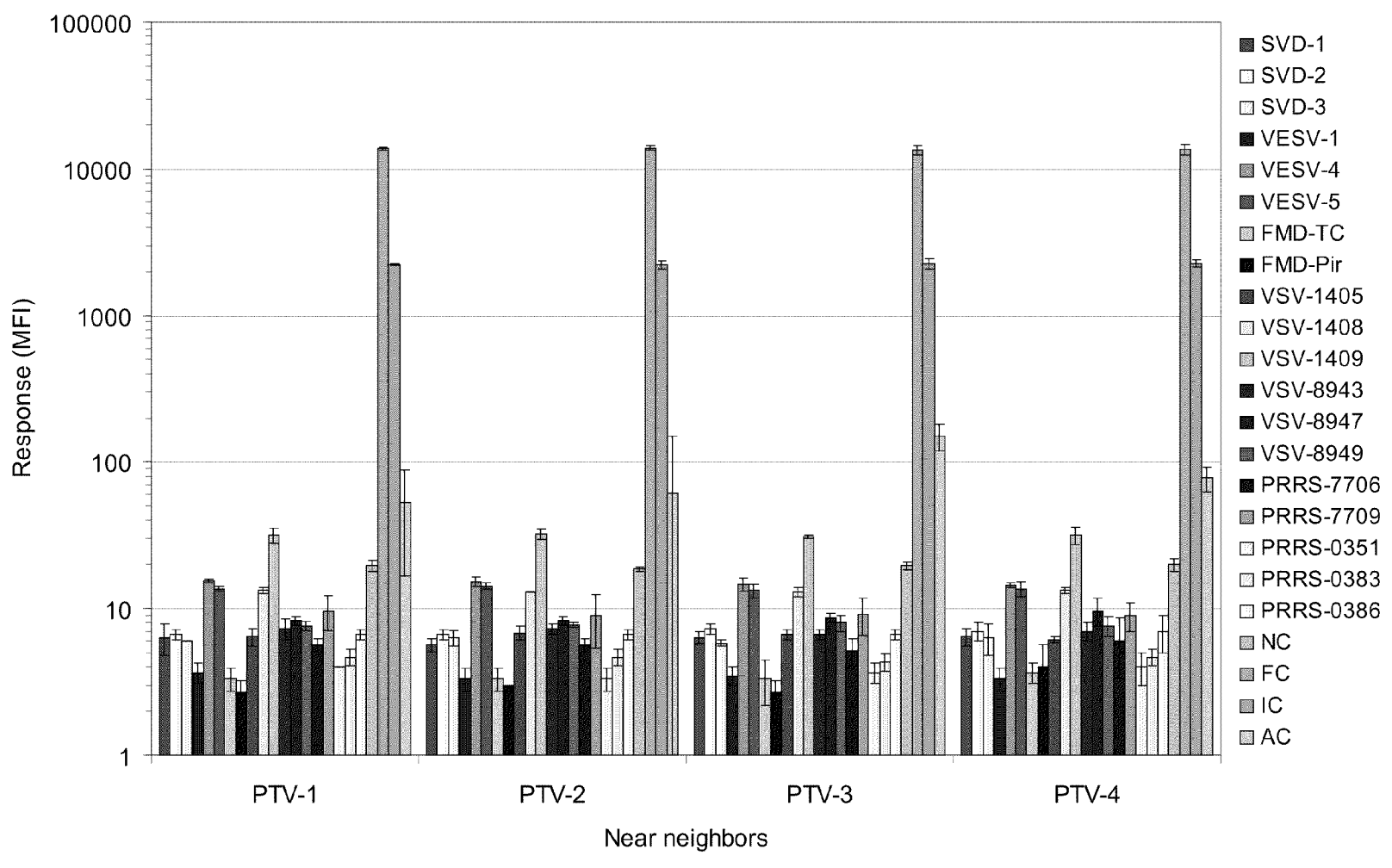
Figure 16:
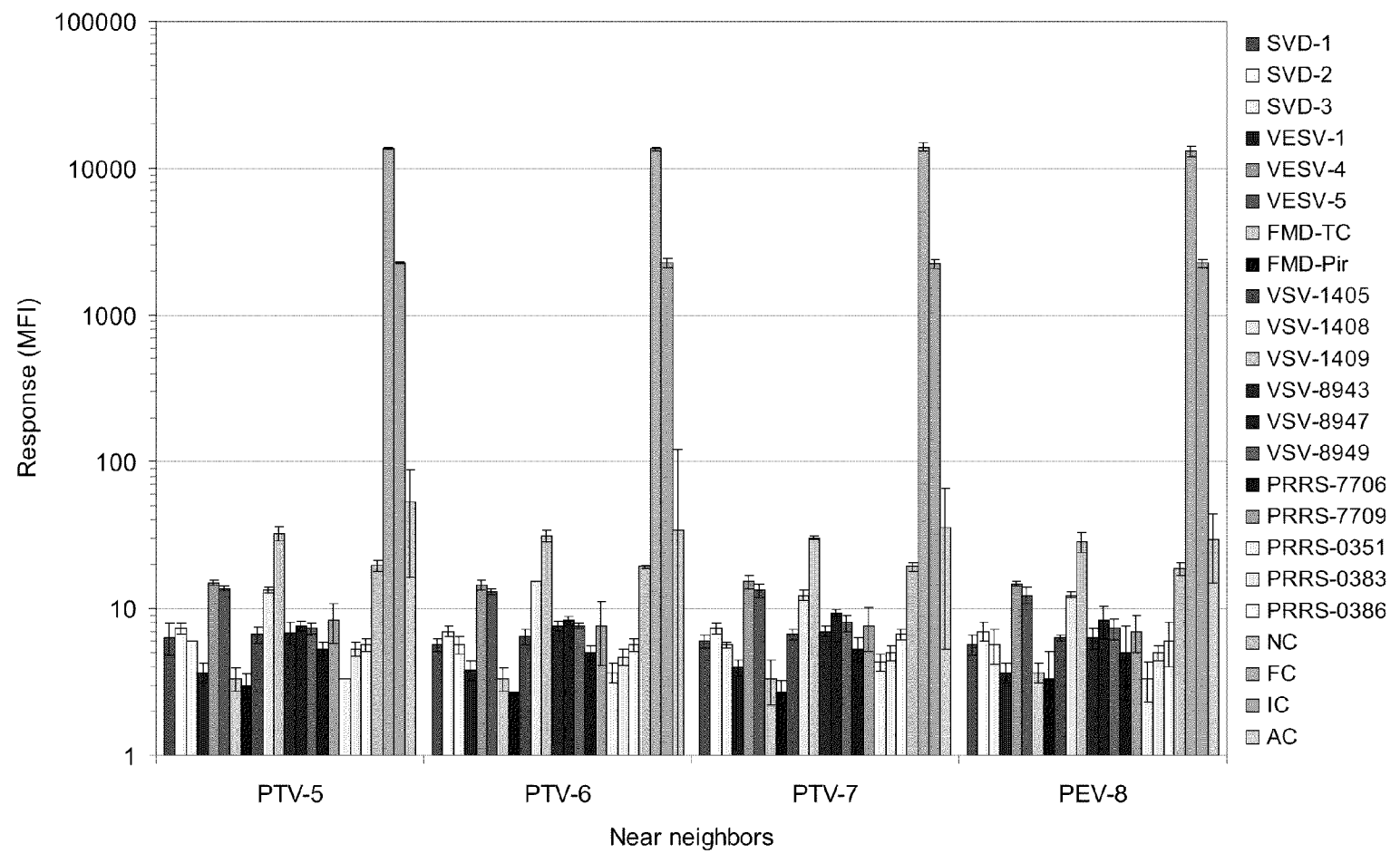

Near-neighbor screening (Porcine panel): FMD signatures in the Porcine panel were screened against C5B5 and an isolate of SVDV as shown in FIG. 14. PTV serotypes 1-7 and PEV-8 were also tested and did not elicit responses on either FMD signature as shown in FIG. 15 and FIG. 16.

Figure 17:
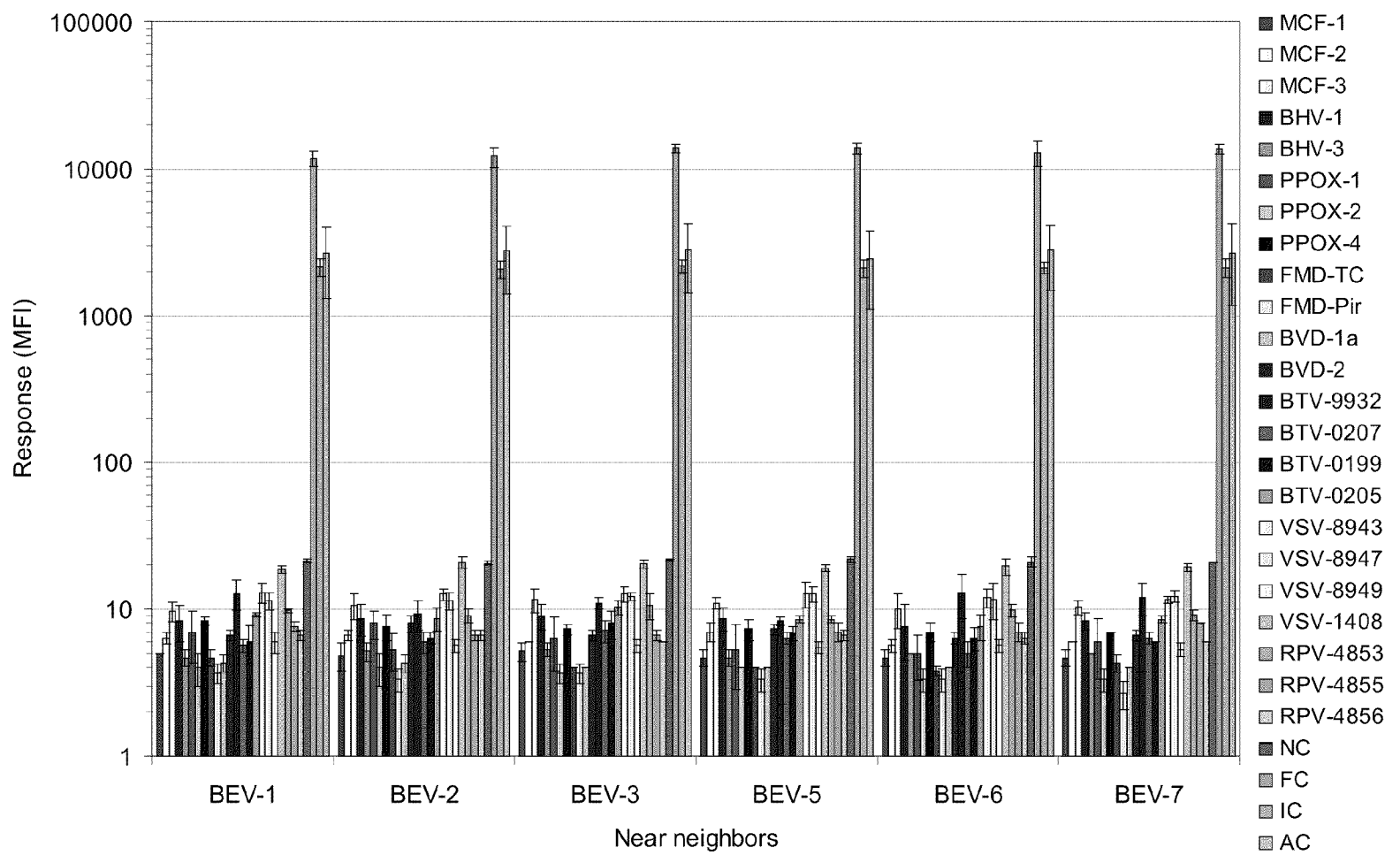
Figure 18:
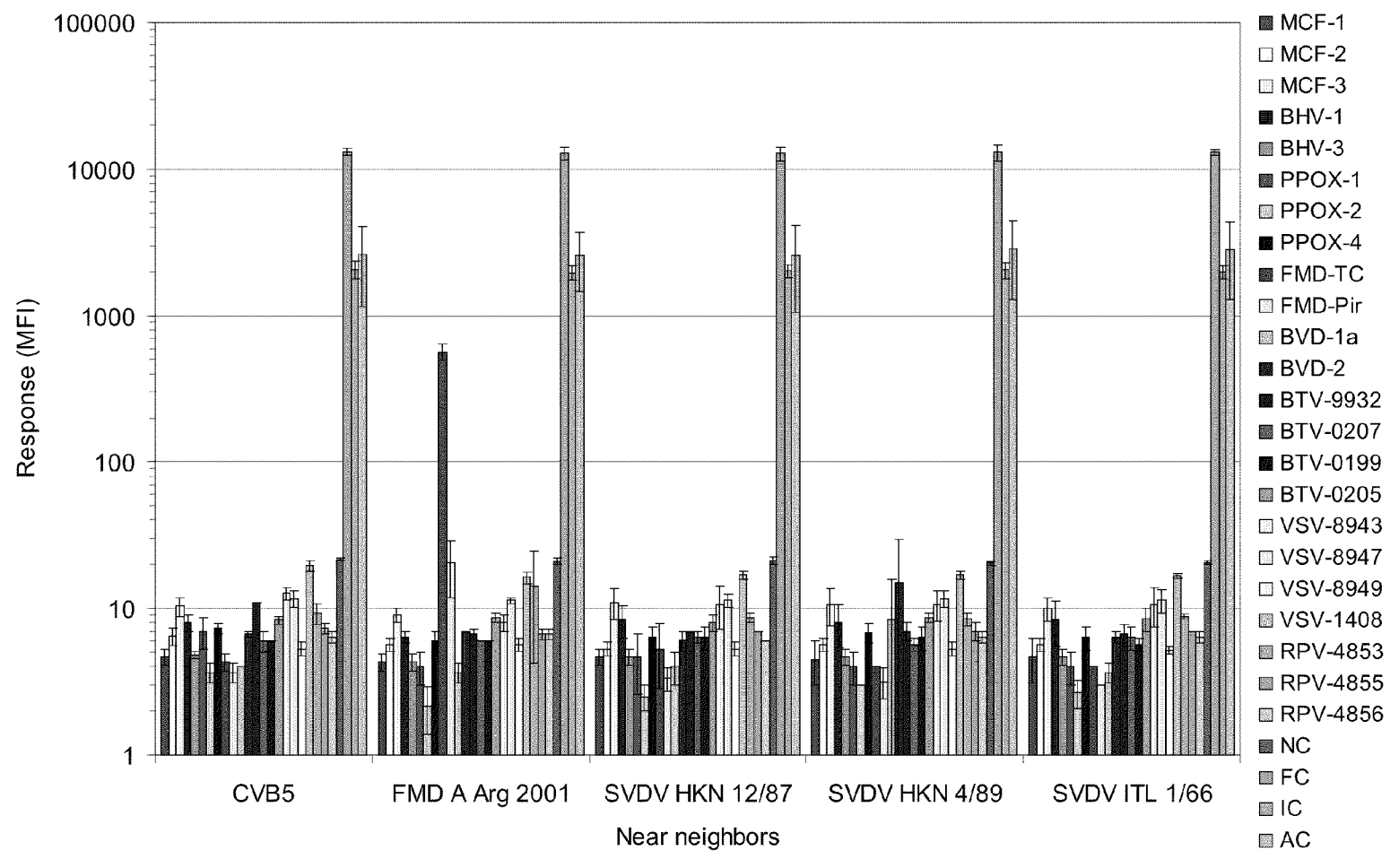
Figure 19:
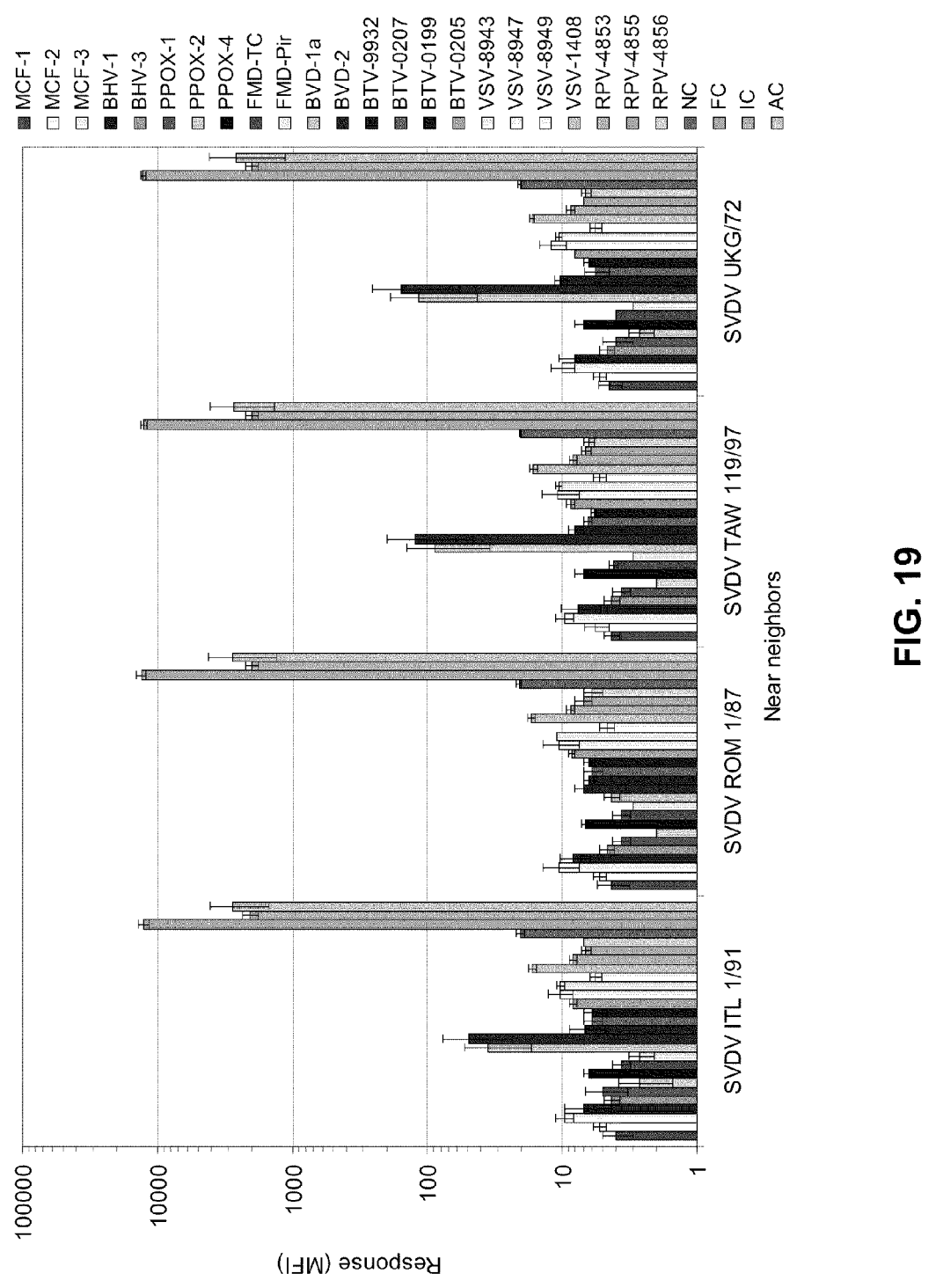

Near-neighbor screening (Bovine panel): FMD signatures in the Bovine panel were screened against BEV 1-7 with no cross reaction observed (FIG. 17). CVB5 did not cross-react with the FMD signatures, nor did the isolated of SVDV as shown in FIG. 18 and FIG. 19. The response of the BVD-1a and BVD-2 assays to SVD ITL 1/91, ROM 1/87, TAW 119/97 and UKG/72 are indicative of low-level BVDV contamination. BVD is a prevalent disease, and BVDV contamination is a common occurrence and often detectable in bovine-derived cell lines and proteins (e.g. BSA) used in media preparations. Evidence of low-level BVDV contamination is evident on several titration series.

Figure 20:
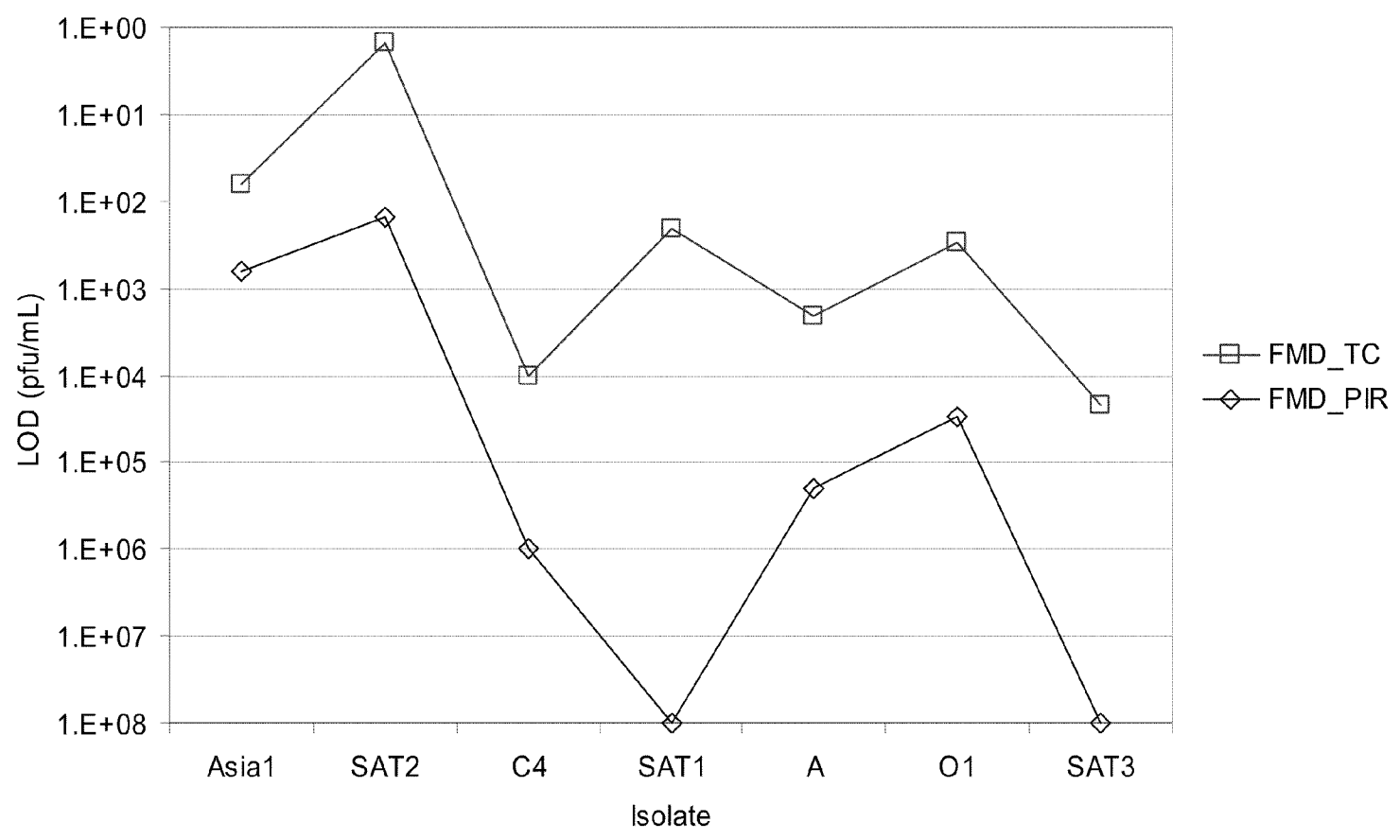

Target screening: Titration curves were acquired for the FMDV signatures in the Version 1.0 panel. The samples were a titration series constructed from titered virus-infected cell culture for each FMDV serotype. The FMD¬ _TC signature had a qualitative limit of detection typically 1-2 orders of magnitude better than FMD_PIR (FIG. 20). The FMD_PIR signature did not detect SAT1/6 SWA or SAT3/3 Bech 1Nov05 samples at any concentration tested.

Additional testing conducted at LLNL enabled the comparison of FMD signature response across three different versions of the multiplex assay panels. The results are presented in FIG. 21.

Figure 21A:
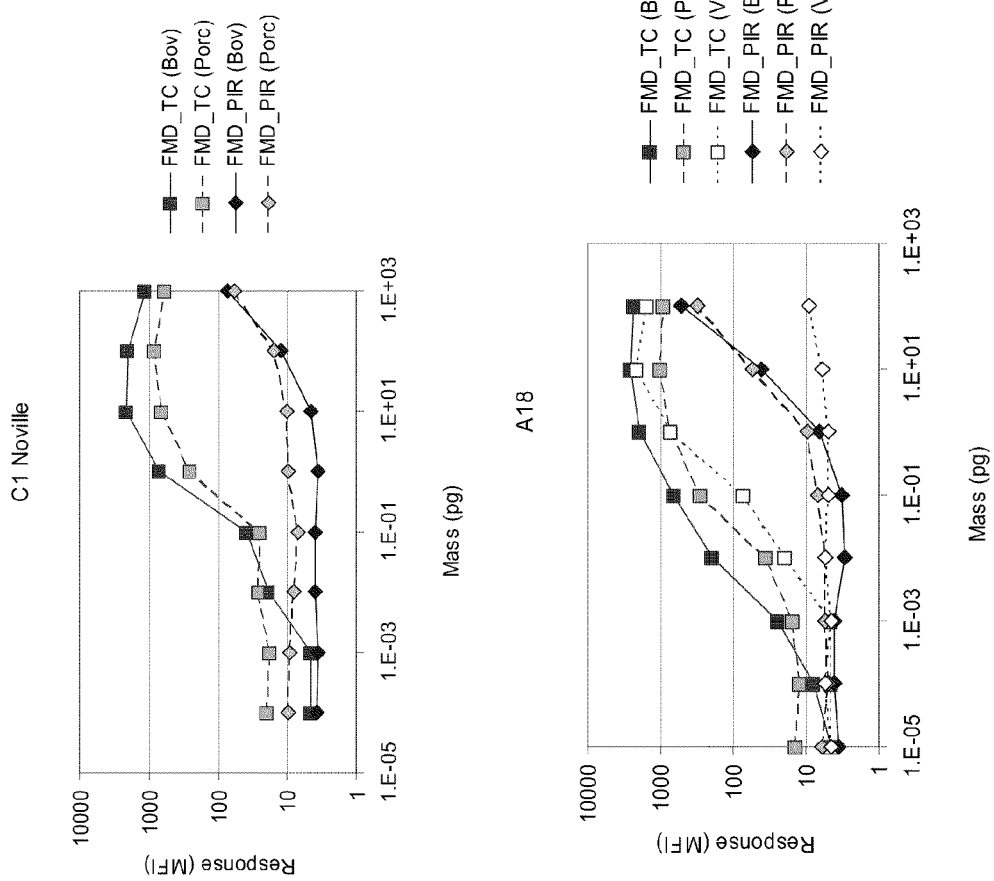
FIG. 21: Comparison of the response of two FMD signatures (FMD_TC and FMD_PIR) when incorporated into three different multiplex panels including the current Bovine (Bov), Porcine (Porc) and Version 1.0 (V1). Samples were serial dilution of extracted (Trizol) RNA from BEI inactivated FMDV virus representing five serotypes of FMDV. The Version 1.0 panel was not tested against C1 Noville.
Figure 21B:
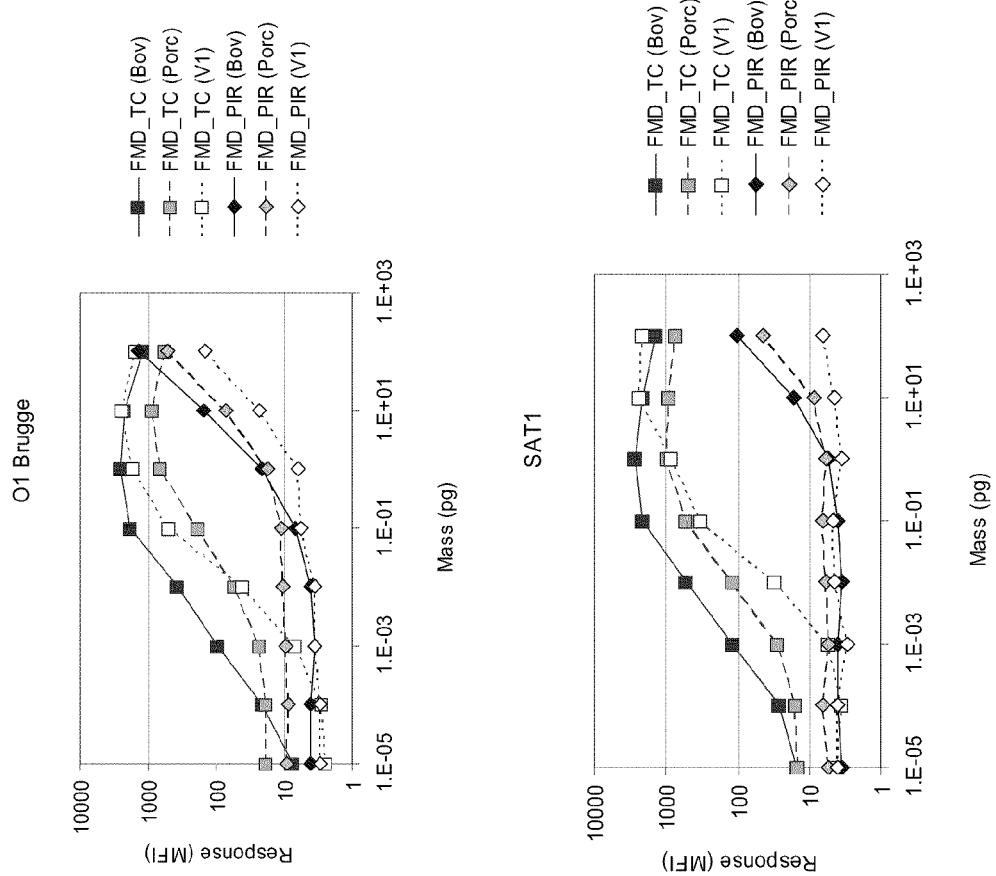
Figure 21C:
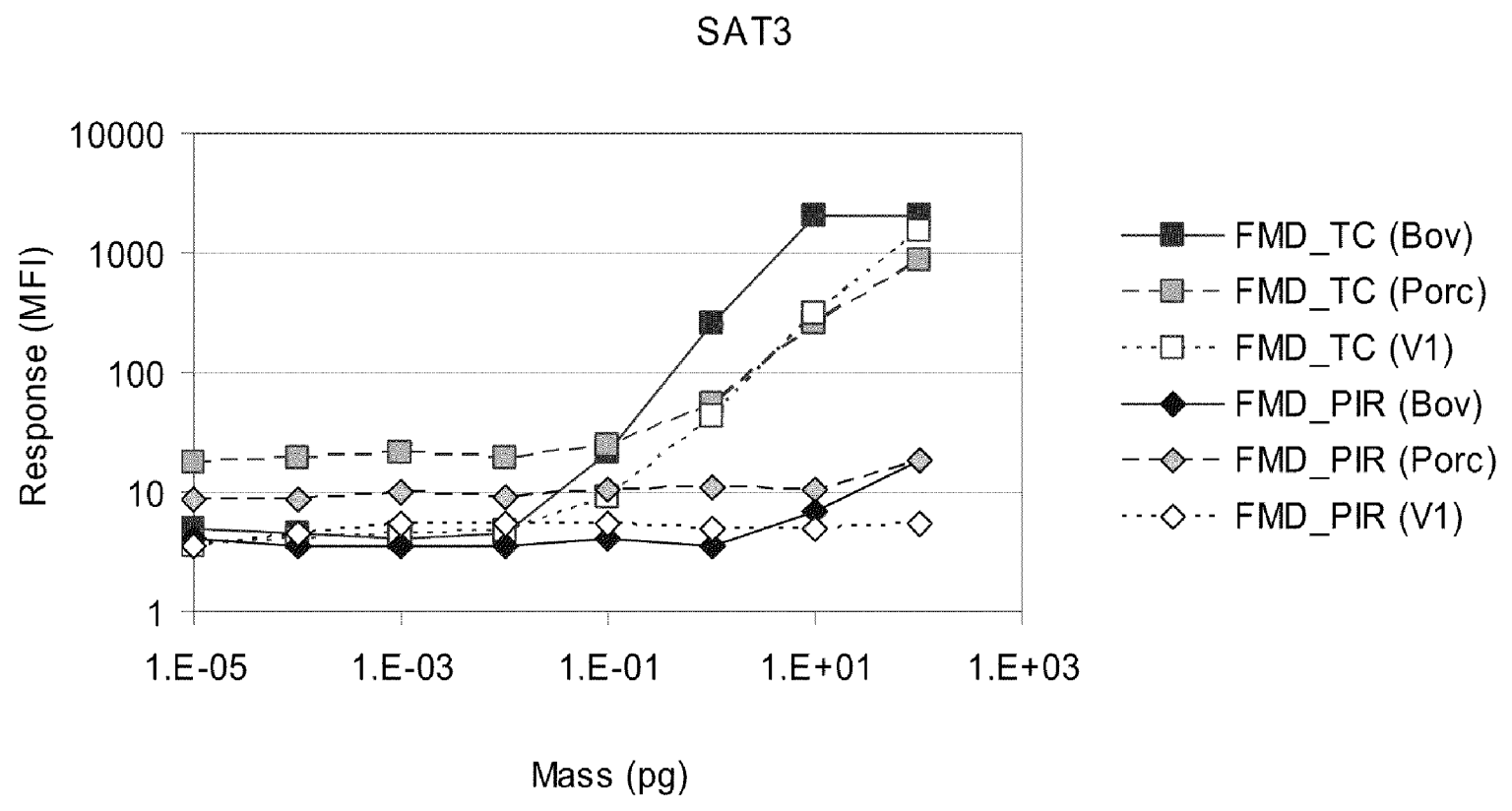
Figure 22:
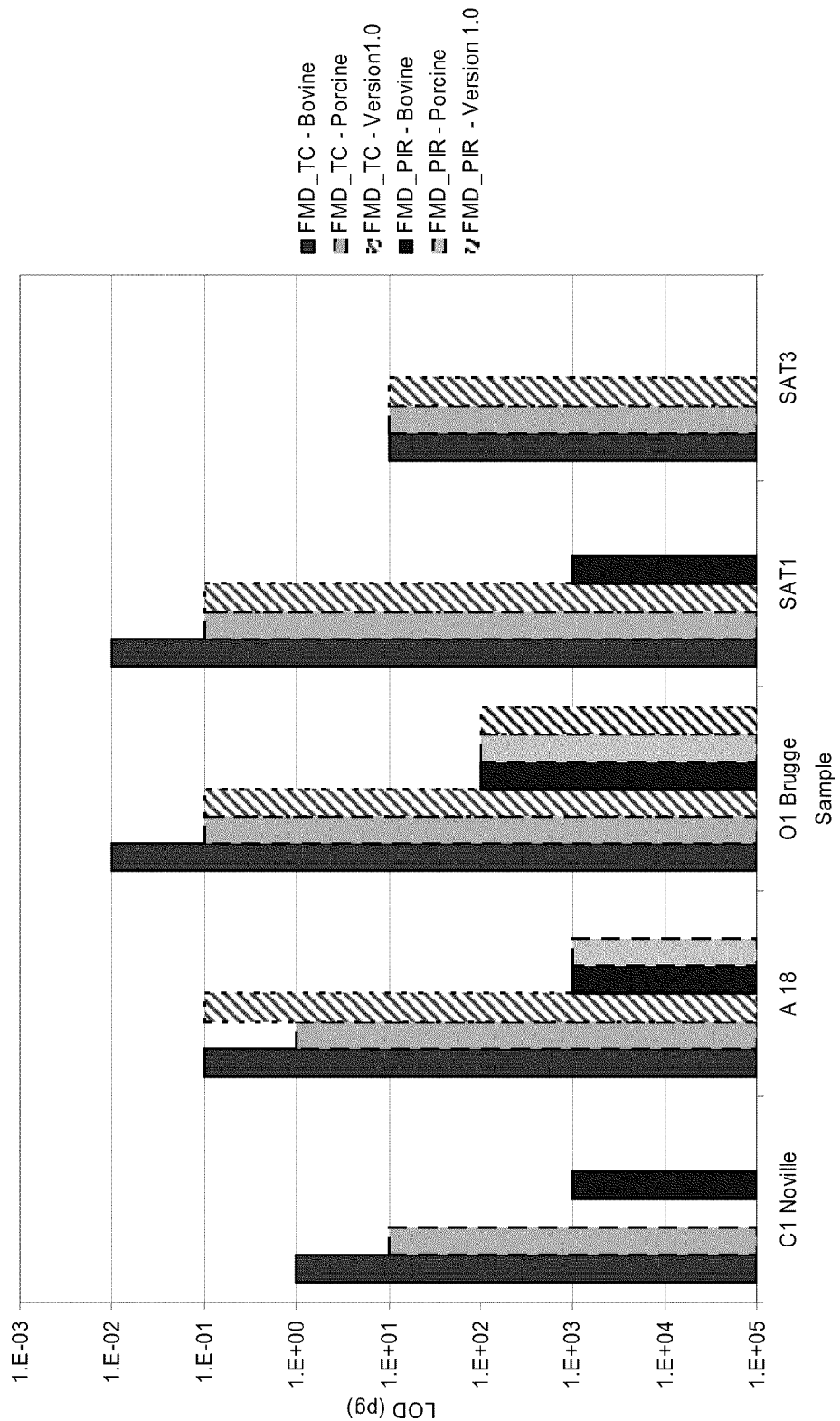
FIG. 22: Comparison of the response of two FMD signatures (FMD_TC and FMD_PIR) when incorporated into three different multiplex panels including the current Bovine (Bov), Porcine (Porc) and Version 1.0 (V1). Samples were serial dilution of purified RNA from BEI inactivated FMDV virus representing five serotypes of FMDV.

The results presented in FIG. 21 are summarized further in FIG. 22 where the qualitative limit of detection for each signature, in each panel, for each serotype of FMDV sample is presented. The qualitative LOD for FMD_TC has not changed more than one order of magnitude between panels. In some cases, the LOD of the FMD_TC signature in the Bovine panel improved over Version 1.0. Compared with Version 1.0, the FMD_PIR LOD improved for serotype A in the Bovine and Porcine panel. The between signature difference in LOD is also evident in the new Bovine and Porcine panels.

Target screening (Porcine panel): Titration data were obtained for the FMD signatures in the Porcine panel for strains representing each of the seven serotypes of FMDV. This testing was conducted at PIADC. The titration aimed to demonstrate that a given assay responds to the analyte of interest over a relevant concentration range. The titration series conducted were serial dilutions of nucleic acid purified from tittered virus-infected cell culture. The titration series enabled the estimation of the limit of detection for each assay for each strain of virus tested. The estimated limits of detection for the FMD signature in the porcine panel are shown in Table 26. The LOD of the FMD-Pir assay was superior to that of the FMD-Pir signature. To gauge fitness for purpose, this LOD data should be evaluated in context of the amount of FMDV likely to be present in the target sample matrix. For example, a loss of 3 orders of magnitude of analytical sensitivity may translate to a few percent loss of diagnostic sensitivity.

TABLE 26

Estimated LOD data for FMD signatures in the bovine
panel determined from target screening data acquired at PIADC.

| Serotype or strain | LOD, pfu/mL (MFI) | |
| --- | --- | --- |
| | FMD-TC | FMD-Pir |
| A Arg 2001 | 20000 (54.5) | 2000 (34.0) |
| O1 Korea | 2000 (41.5) | 11000 (32.5) |
| C4 Tierra | 200000 (60.5) | 200000 (10.5) |
| Asia 1 | 1100 (50.5) | 20 (10.5) |
| SAT 1 | 2000 (31.0) | 1100000 (14.0) |
| SAT 2 | 2 (17.5) | 20000 (9.5) |
| SAT 3 | 200000 (23.0) | 20000 (35.0) |
| Cutoff | (14.0) | (7.1) |

The concentration is represented as pfu/mL, division by 200 is required to concert to pfu/reaction. The signature response (MFI) at the estimated limit of detection is provided in parentheses, together with the cutoff.

Target screening (Bovine panel): Titration data were obtained for the FMD signatures in the Bovine panel for strains representing each of the seven serotypes of FMDV. This testing was conducted at PIADC. The estimated limits of detection for the FMD signatures in the porcine panel are shown in Table 27.

TABLE 27

Estimated LOD data for FMD signatures in the bovine
panel determined from target screening data acquired at PIADC.

| Serotype or strain | LOD, pfu/mL (MFI) | |
| --- | --- | --- |
| | FMD-TC | FMD-Pir |
| A Arg 2001 | 20 (31.5) | 2000 (6.0) |
| O1 Korea | 11 (87.0) | 1100 (14.5) |
| C4 Tierra | 1100 (77.0) | 20000 (7.0) |
| Asia 1 | 2 (20.5) | 11 (13.0) |
| SAT 1 | 11 (34.5) | 200000 (10.0) |
| SAT 2 | 0.11 (175.0) | 20000 (20.0) |
| SAT 3 | 1100 (20.5) | 2000 (11.0) |
| Cutoff | (7.6) | (4.8) |

The concentration is represented as pfu/mL, division by 200 is required to convert to pfu/reaction.

As described in a separate report, the LOD of both FMD signatures in the multiplex assay is higher than the singleplex Taqman assays, which in effect causes a reduction of diagnostic sensitivity. Using the signatures in combination does increase the overall diagnostic sensitivity of the multiplex assay. The combination of signatures in a finalized panel can cause LOD for any signature within the panel to change. Once a panel's composition has been finalized, further work could be conducted to determine the analytical sensitivity of all signatures including FMDV and undertake further optimization if required. Near-neighbor screening indicated that the specificity of the FMD signatures was preserved after their incorporation into the multiplex bovine and porcine panels.

4. Malignant Catarrhal Fever (MCF)—Bovine Panel

Signature candidates: Three new signatures are available for consideration, including MCF-1, MCF-2 and MCF-3. MCF can be caused by two viruses: ovine herpesvirus-2 (OvHV-2) and alcelaphine herpesvirus-1 (AHV1).

Signature origin: Signatures were designed at LLNL using one complete genome. All three signatures target different genes. MCF-1 targets the DNA polymerase gene ORF09. MCF-2 was not found to be associated with a known gene region. MCF-3 targets the putative major envelope glycoprotein gene ORF68.

Figure 23:
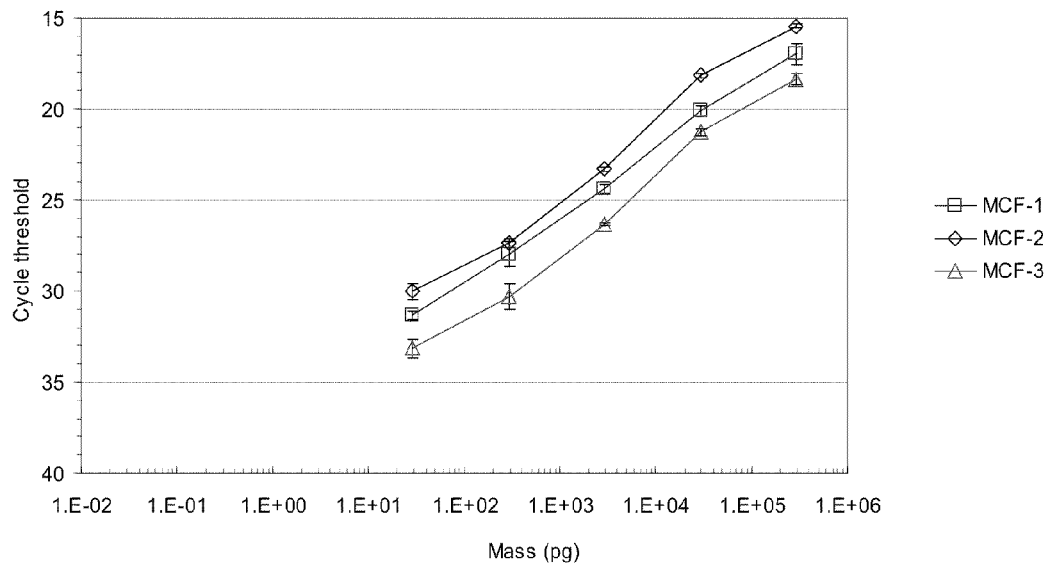
FIG. 23: Taqman screening of MCF signatures against A1HV-1 (MN, WC11). Total nucleic acid extracted (Ambion MagMax) from virus-infected cell culture media was used as template. Each point represents the mean response (n=3). Error bars indicate ±1σ of the mean. If no cycle threshold was reached (i.e. infinite cycle threshold), a cycle threshold of 40 was assigned in this plot.
Figure 23:
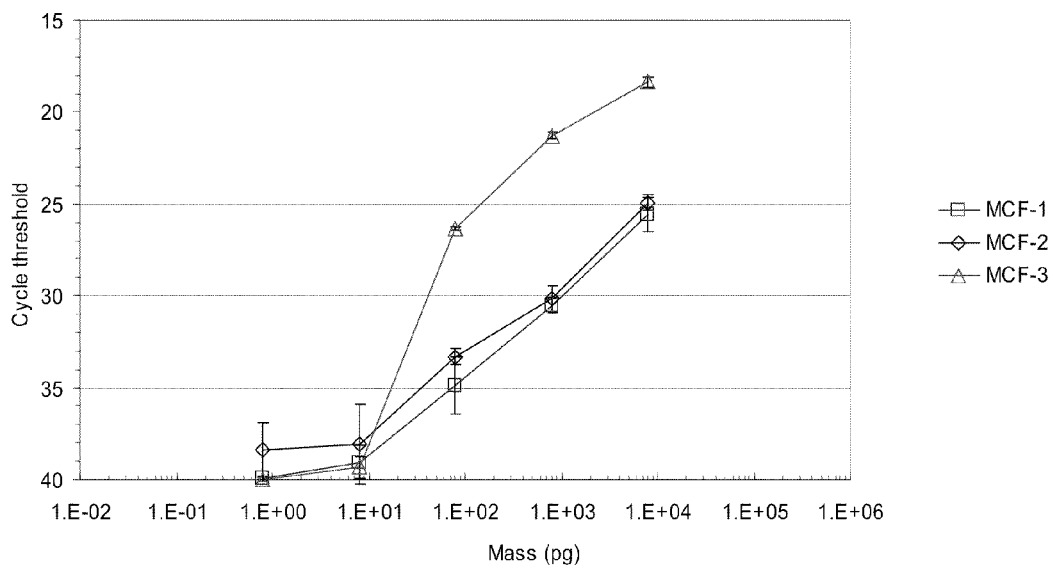

Target screening: The three signatures were screened against A1HV-1 (MN), A1HV-1 (WC11, an attenuated isolate) and OvHV-2 over a wide concentration range. All signatures responded well to A1HV-1 and the results are shown in FIG. 23. The signatures did not respond to the OvHV-2 strain. At the time the signatures were generated, no complete genome sequence information was available for OvHV-2.

Figure 24:
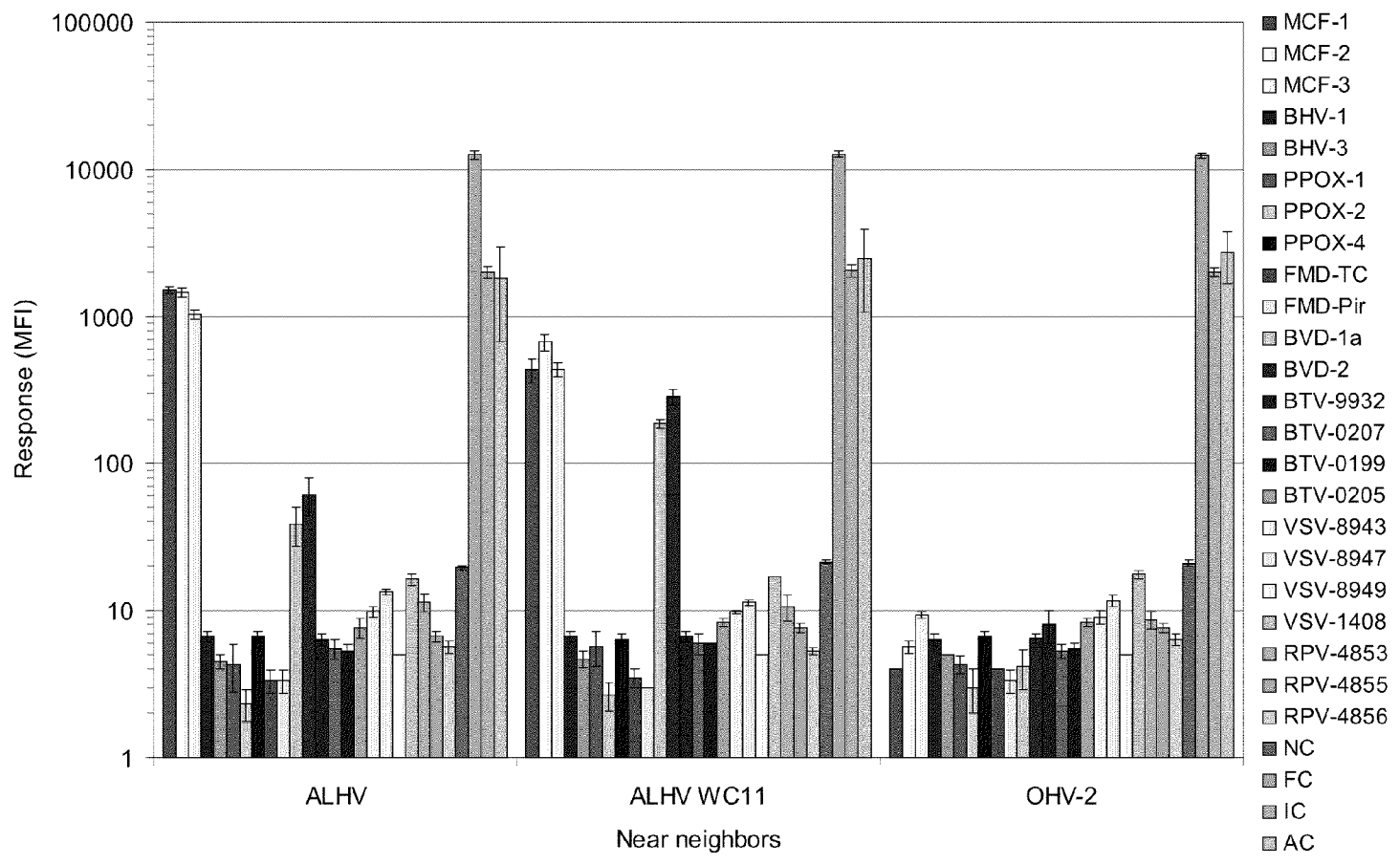

Near-neighbor screening: Near-neighbor testing conducted at PIADC shows that the MCF signatures detect AHV but not OVH-2 (FIG. 24). Other viruses considered near-neighbors include other common herpes viruses of cattle. The specificity or the MCF signatures is evident in screening at titration data presented for other viruses belonging to the Herpesviridae family presented in the bovine herpes virus-1 section.

Figure 25:
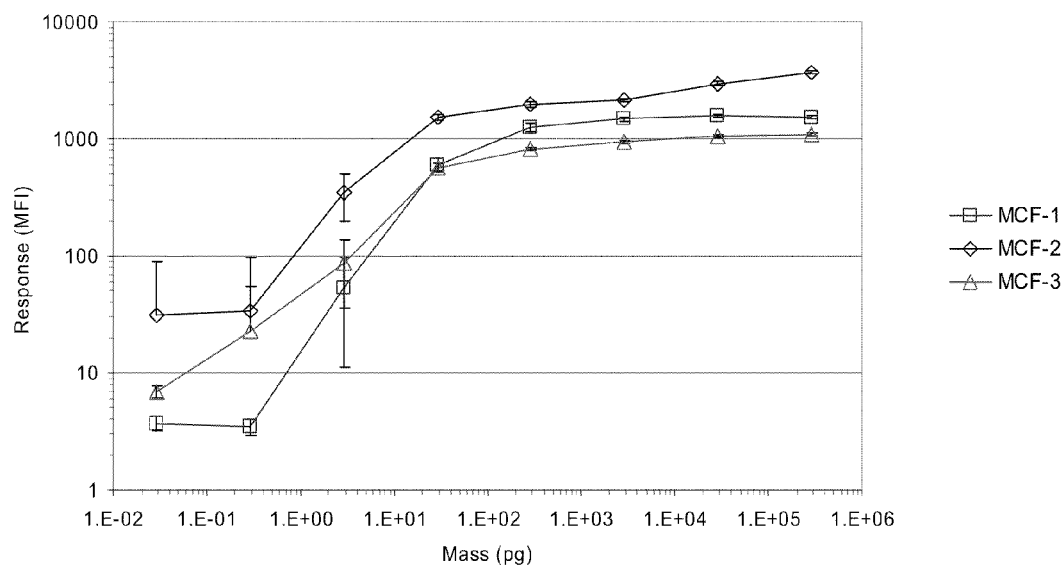
FIG. 25: Multiplex screening data for the three MCF signatures against AIHV-1 (MN, WC11) using a developmental version of the Bovine Panel. Serial dilution of nucleic acid extracted (Ambion MagMax 96) from virus-infected cell culture. Each point represents the mean response (n=4). Error bars indicate ±1σ of the mean.
Figure 25:
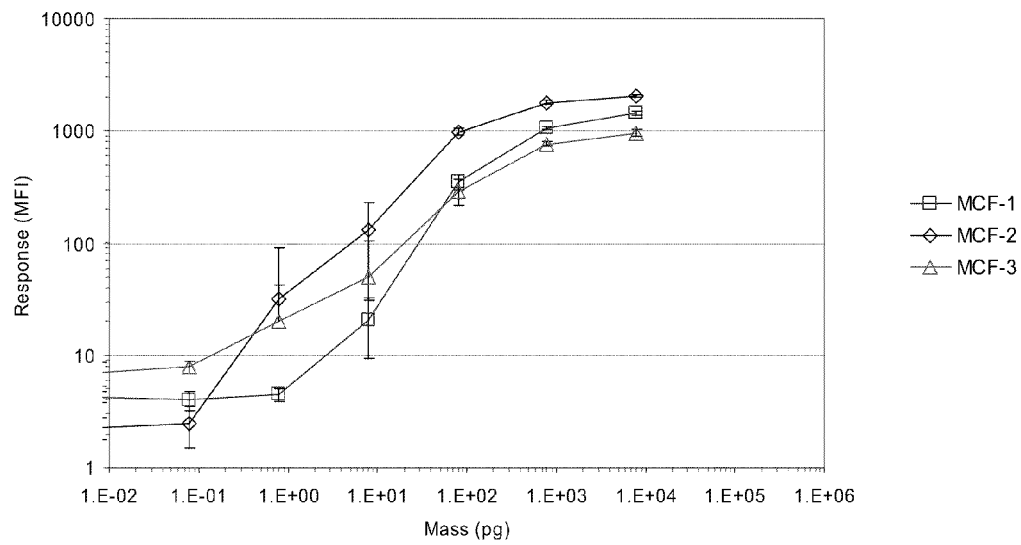

Target screening: All three signatures were added to current Bovine panel where they show low background response in the absence of template. The same samples used during the TaqMan screening phase were used to conduct multiplex screening using a developmental version of the Bovine panel. The multiplex titration results in FIG. 25 show that all three signatures responded similarly to both A1HV-1 strains. The results obtained in Taqman and multiplex formats agreed over the concentration ranges tested. Likewise, the three signatures did not respond to OvHV-2 DNA (6.4 ng) in multiplex format (data not shown).

Titration data were obtained for the MCF signatures in the Bovine panel. This testing was conducted at PIADC. The estimated limits of detection for the RPV signatures in the bovine panel are shown in Table 28.

TABLE 28

Estimated LOD data for MCF signatures in the bovine
panel determined from target screening data acquired at PIADC.

| Serotype or strain | LOD, copies/reaction (MFI) | | |
| --- | --- | --- | --- |
| | MCF-1 | MCF-2 | MCF-3 |
| A1Hv-1 MN | 55 (321.0) | 0.055 (9.0) | 1 (34.0) |
| WC11 | $10^a$ (100.0) | $5.5^a$ (95.5) | $10^a$ (166.0) |
| OvHv-2 | ND | ND | ND |
| Cutoff | (6.0) | (8.0) | (12.6) |

ND = not detected;
$^a$ = pg

All three signatures perform equivalently against the limited strains of material available during the development phase. The data indicates that all three MCF signatures could be incorporated into a Bovine panel. AHV-1 causes wildebeest-associated MCF and therefore warrants inclusion in a bovine multiplex FMDV rule-out assay. OHV-2 causes sheep-associated MCF, a prevalent disease of sheep. Cattle can become infected with OHV-2. If detection of OHV-2 is desired, LLNL has signatures for OHV-2 that could be considered for inclusion in a bovine multiplex assay panel.

5. Porcine Respiratory Reproductive Syndrome Virus (PRRSV)—Porcine Panel

Signature candidates: Five new signatures are available. Two signatures designed to detect North America (domestic) PRRSV include PRRS__1807706 and PRRS__1807709. Three signatures designed to detect European PPRSV include PRRS__1810351, PRRS__1810383 and PRRS__1810386.

Signature origin: Signatures were designed at LLNL in two main sets North American or domestic and European. For the domestic signatures PRRS genomes cluster into two sets identified by Dr. Kay Faaberg (our collaborator) as VR-2332/Minn and those identified as belonging to the RFLP 142 group. We used 8 complete genomes of the 142 group and 14 genomes for the VR-2332/Minn group which contained two unpublished complete genomic sequences of genomes from the latter group. For the European signatures we used a set of three complete genomes suggested by Dr. Faaberg that constitute that group. North American signatures PRRS_1807706 and PRRS_1807709 target the envelope protein GP2 and the nucleocapsid protein N genes, respectively. The European signatures PRRS_1810351, PRRS_1810383 and PRRS_1810386 target the replicase polyprotein 1A, GP2, and GP3-GP4 genes, respectively.

Figure 26:
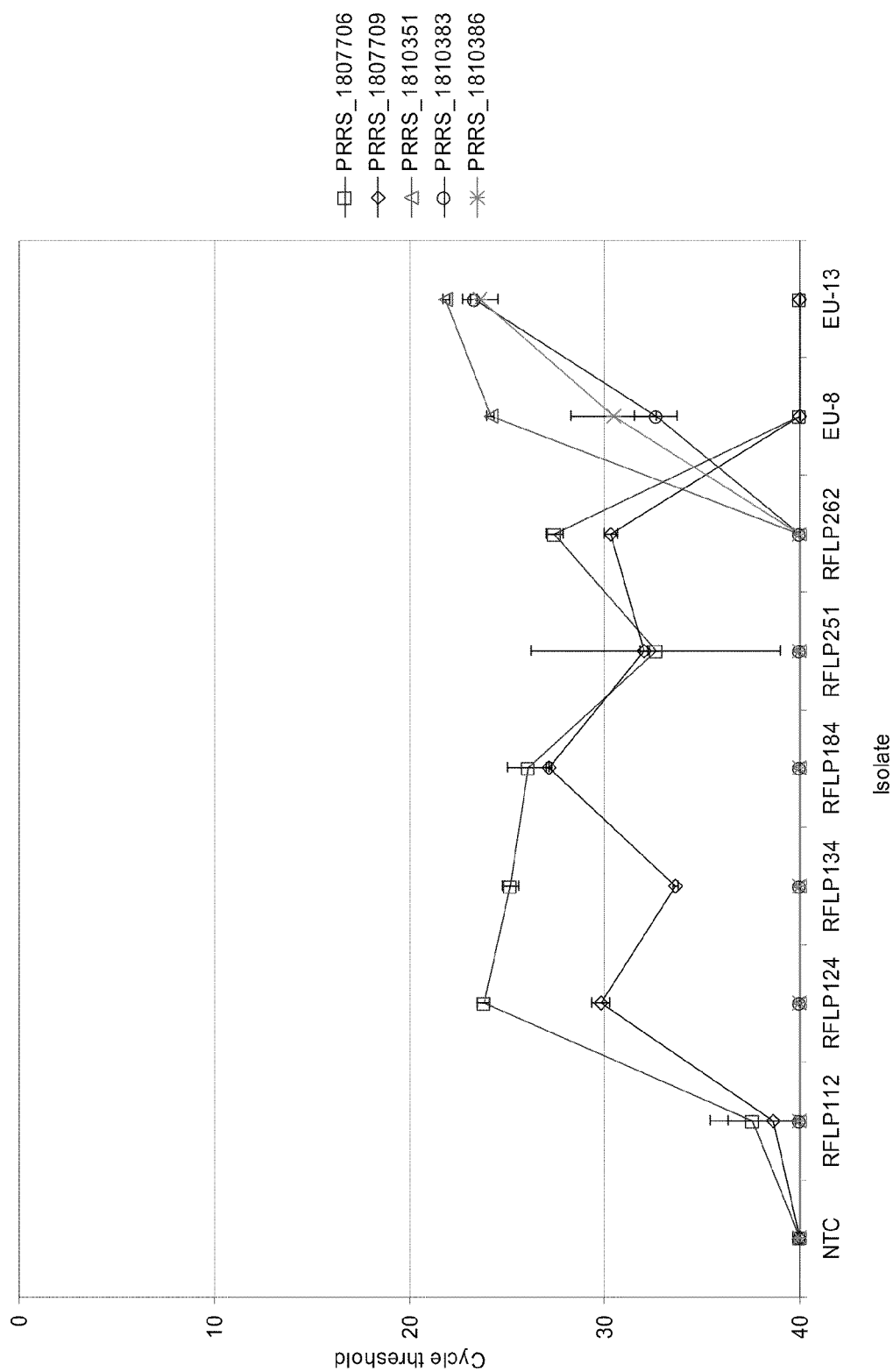
FIG. 26: Taqman screening of PRRS signatures against six North American and two European isolates. Total RNA (Trizol extracted) from non-infected (no template control, NTC) and virus-infected cell culture media wad used as a template. Each reaction was spiked with 200 pg. Each point represents the mean (n=3) cycle threshold. If no cycle threshold was reached (i.e. infinite cycle threshold), a cycle threshold of 40 was assigned in this plot. Error bars indicate ±1σ of the mean.

Target screening: Taqman screening of PRRS signatures was conducted at the University of Minnesota using seven North American (RFLP112, 124, 134, 184, 251 and 262) and two European (EU-8, EU-13) isolates shown in FIG. 26. As intended, PRRS_1807706 and PRRS_1807709 signatures responded to North American isolates, although the response to RFLP112 was weak for both signatures. The signatures PRRS_1810351, PRRS_1810383 and PRRS_1810386 only responded to European isolates.

Near-neighbor screening: The PRRS signatures in the current porcine panel were screened against two porcine coronaviruses. No cross-reaction was observed.

Target screening: All five signatures were added to the Porcine panel. The PRRS_1807709 exhibits an elevated background response (–50 to 200 MFI) in the Porcine panel. One possible cause of this behavior is a non-specific interaction between the PRRS_1807709 signature with another primer in the reaction mixture.

Figure 27:
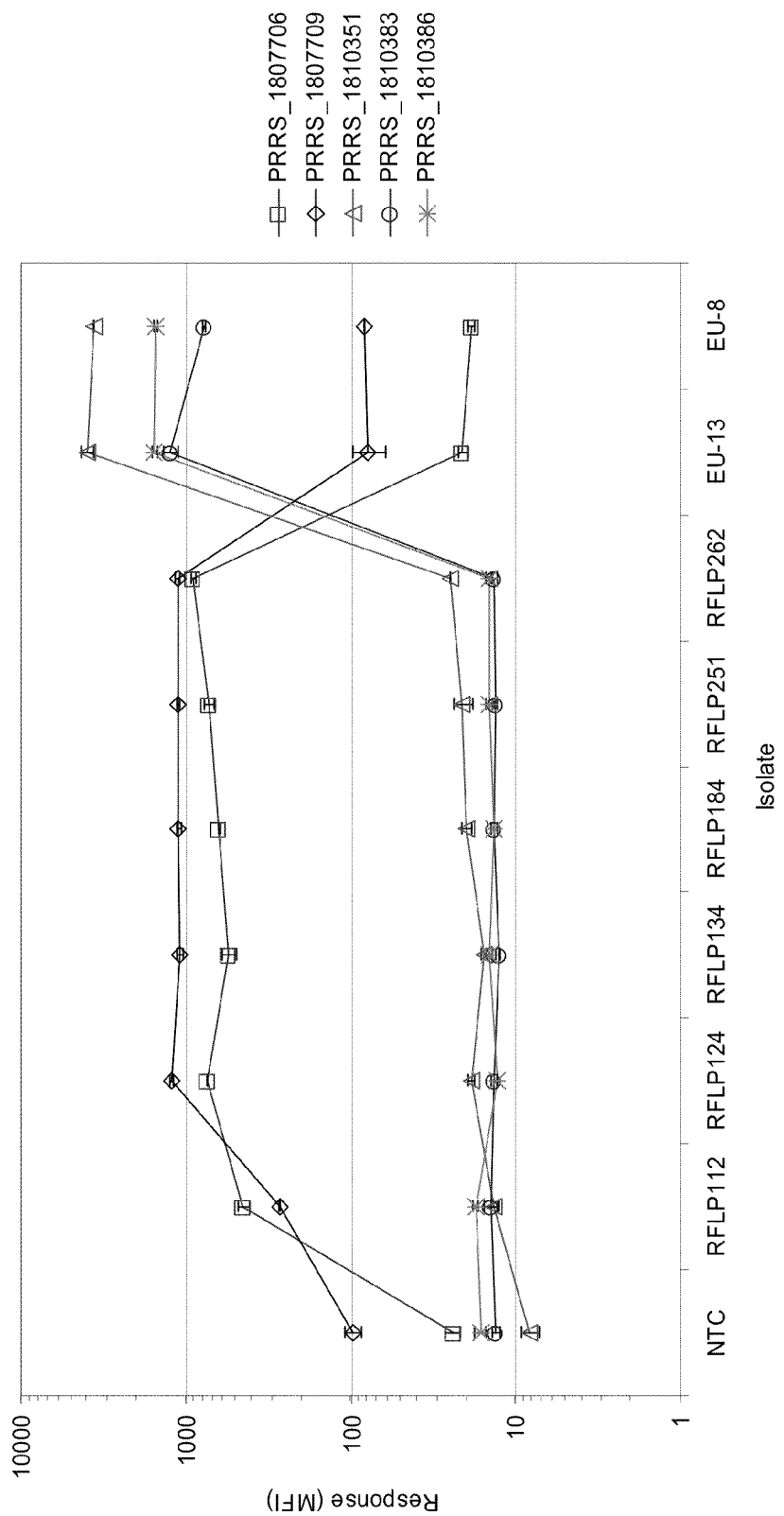
FIG. 27: Multiplex screening data for five PRRS signatures against six North American and two European isolates. Total nucleic acid was Trizol extracted from non-infected (no template control, NTC) and virus-infected cell culture media then used as a template. Each reaction was spiked with 200 pg. Each point represents the mean response (n=2). Error bars indicate ±1σ of the mean.

Different samples of the same isolates used during the Taqman screening phase (U. Minnesota) were used to conduct multiplex screening at LLNL. The multiplex spot-test results in FIG. 27 show that PRRS_1807706 and PRRS_1807709 signatures responded only to North American isolates, although their response to RFLP112 was weak. The signatures PRRS_1810351, PRRS_1810383 and PRRS_1810386 designed to respond to European PRRS strains only responded to European isolates. Taqman and multiplex target screening results agree.

Figure 28:
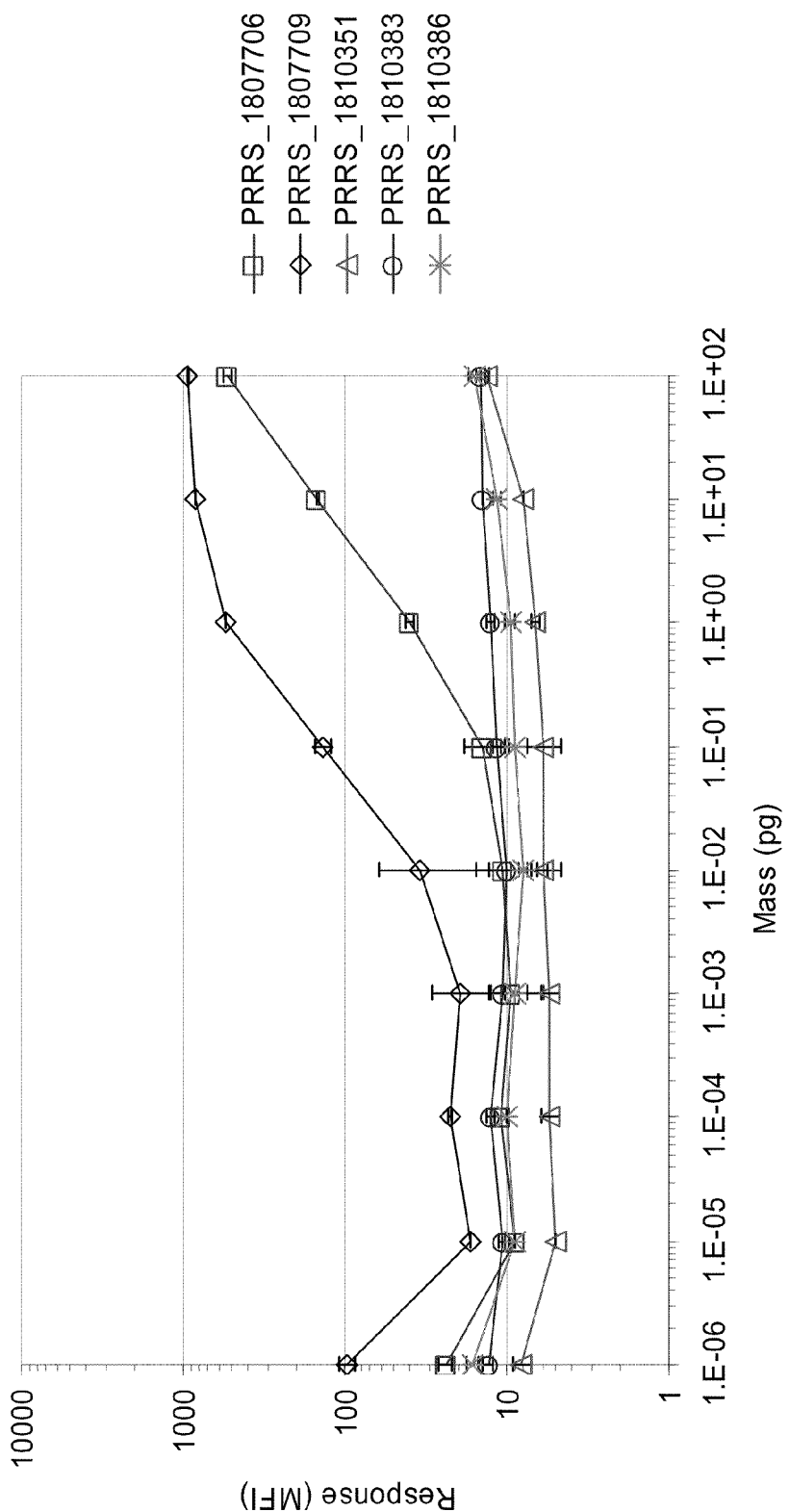
FIG. 28: Multiplex screening data for five PRRS signatures against the North American Strain (NVSL, 1989). Serial dilution of total nucleic acid Trizol extracted from virus-infected cell culture. Total nucleic acid was Trizol extracted from non-infected (no template control, NTC) and virus-infected cell culture media then used as template. Each point represents the mean response (n=2). Error bars indicate ±1σ of the mean.

Target screening using a North American strain (NVSL 89) was conducted at LLNL. FIG. 28 shows that both signatures PRRS_1807706 and PRRS_1807709 responded as expected to the North American strain over four orders of magnitude in concentration. The signatures PRRS_1810351, PRRS_1810383 and PRRS_1810386 designed to detect European strains did not respond to the North American strain.

Taman and multiplex target screening results are supportive of the advancement of these signatures to subsequent phases. Additional target screening may be required if further down-selection is required prior to addition in to the Porcine multiplex.

6. Rinderpest Virus (RPV)—Bovine Panel

Signature candidates: Three new RPV signature candidates are available for consideration. RPV signatures were not included in the Version 1.0 panel. The signatures are designated RPV_1814853, RPV_1814855 and RPV_1814856.

Signature origin: Signatures developed by LLNL using one published genome and five unpublished genomes. RPV_1814853 targets the nucleocapsid (N) protein RPV_1814855 and RPV_1814856 both target the polymerase (L protein) gene.

Near-neighbor screening: Signatures were screened at PIADC against five Peste de Petits Ruminants virus (PPRV) strains (RCA, Burkina Faso, Egypt 87, Dorcas and Ghana 76/1) at 200 pg (n=3) using extracted RNA template from virus-infected cell culture (Qiagen RNeasy Mini kit). No cross-reactivity was observed.

Figure 29:
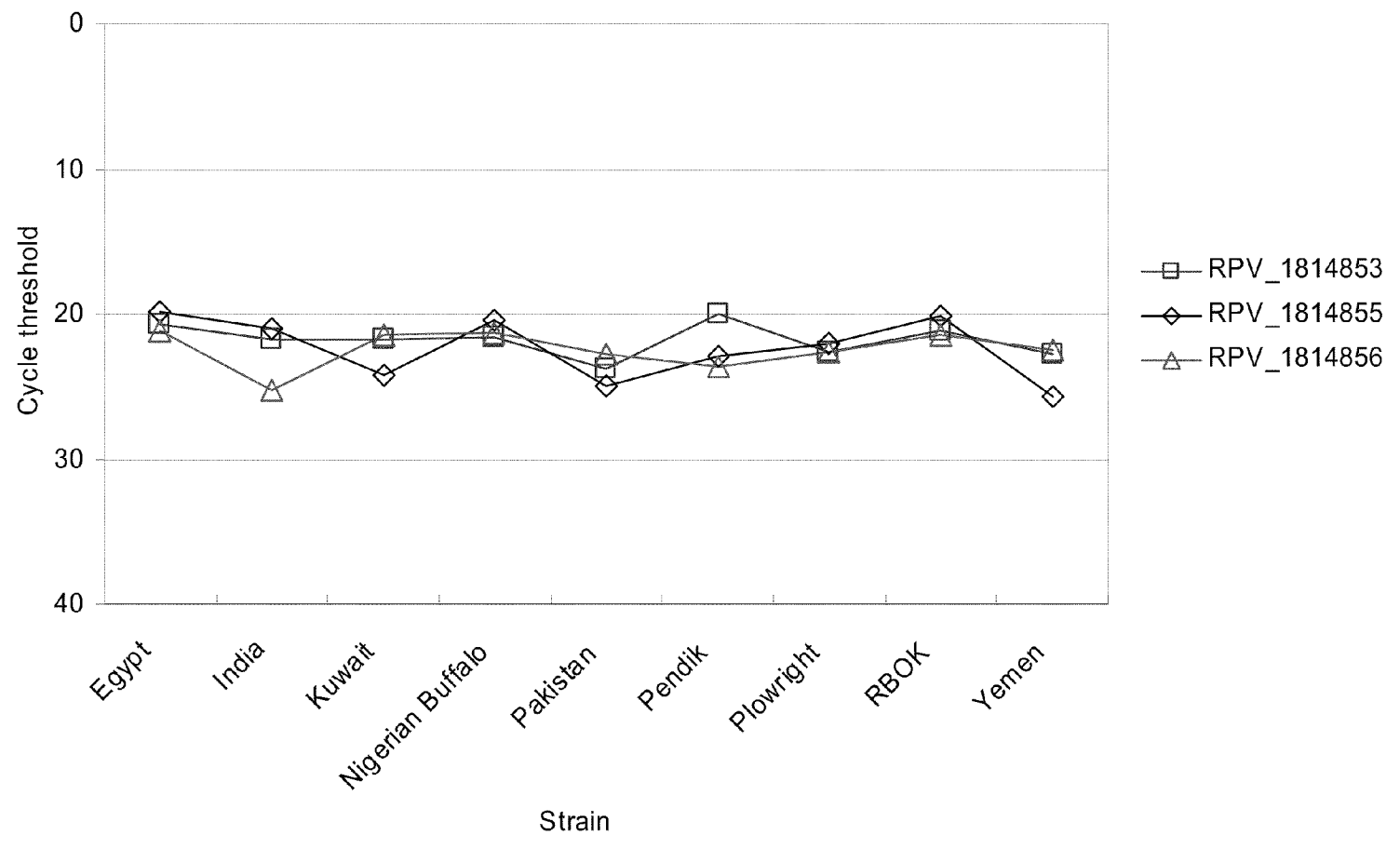

Target screening: All signatures were screened against nine RPV strains and the results are shown in FIG. 29. All three signatures responded well to 9/9 strains tested.

Figure 30A:
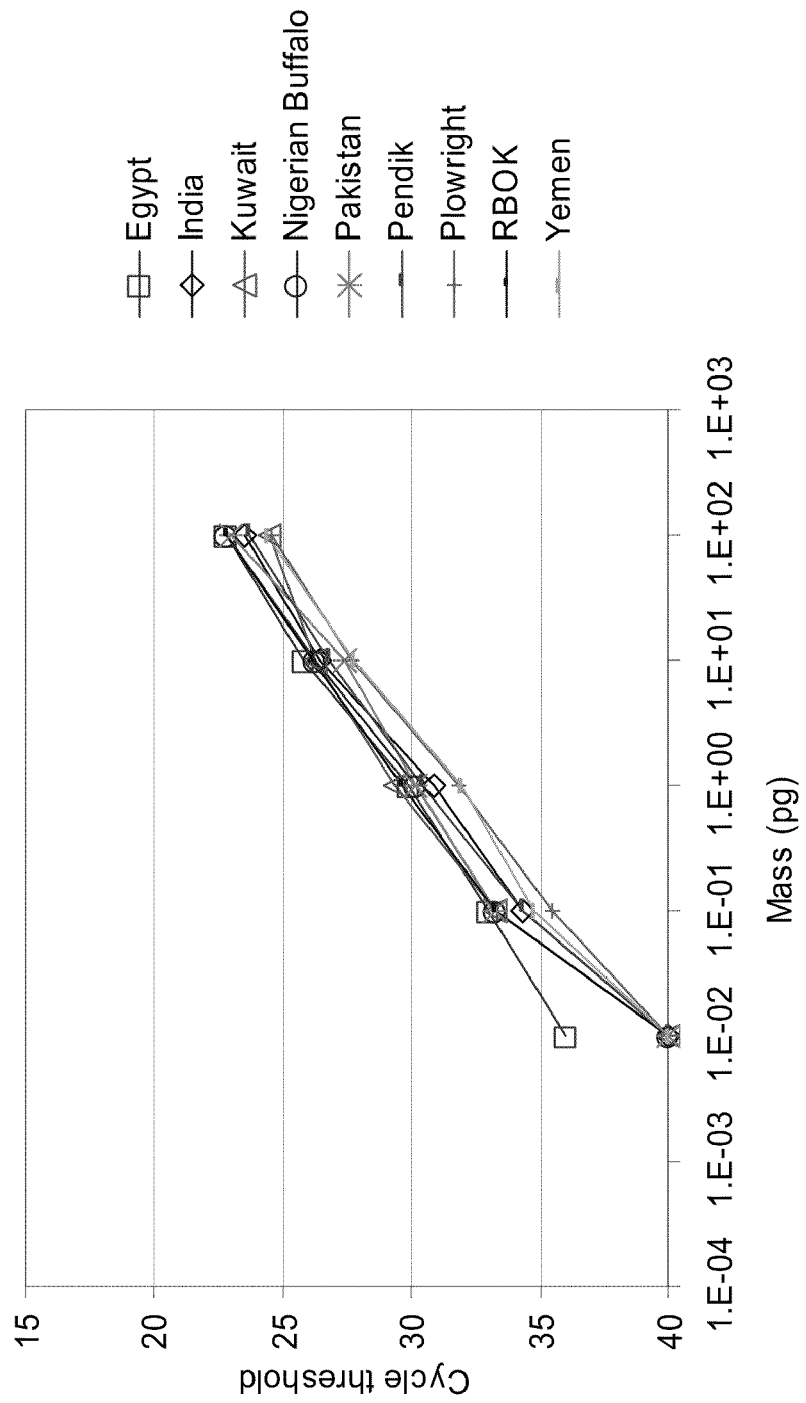
FIG. 30: Taqman response of RPV signatures (RPV_1814853, RPV_1814855 and RPV_1814856) against nine RPV strains over four orders of magnitude in template concentration. Samples were serial dilutions of total RNA extracted (Qiagen RNeasy Mini kit) from virus-infected cell culture (Qiagen RNeasy Mini kit). Each point represents the mean (n=3) cycle threshold. If no cycle threshold was reached (i.e. infinite cycle threshold), a cycle threshold of 40 was assigned in this plot.
Figure 30B:
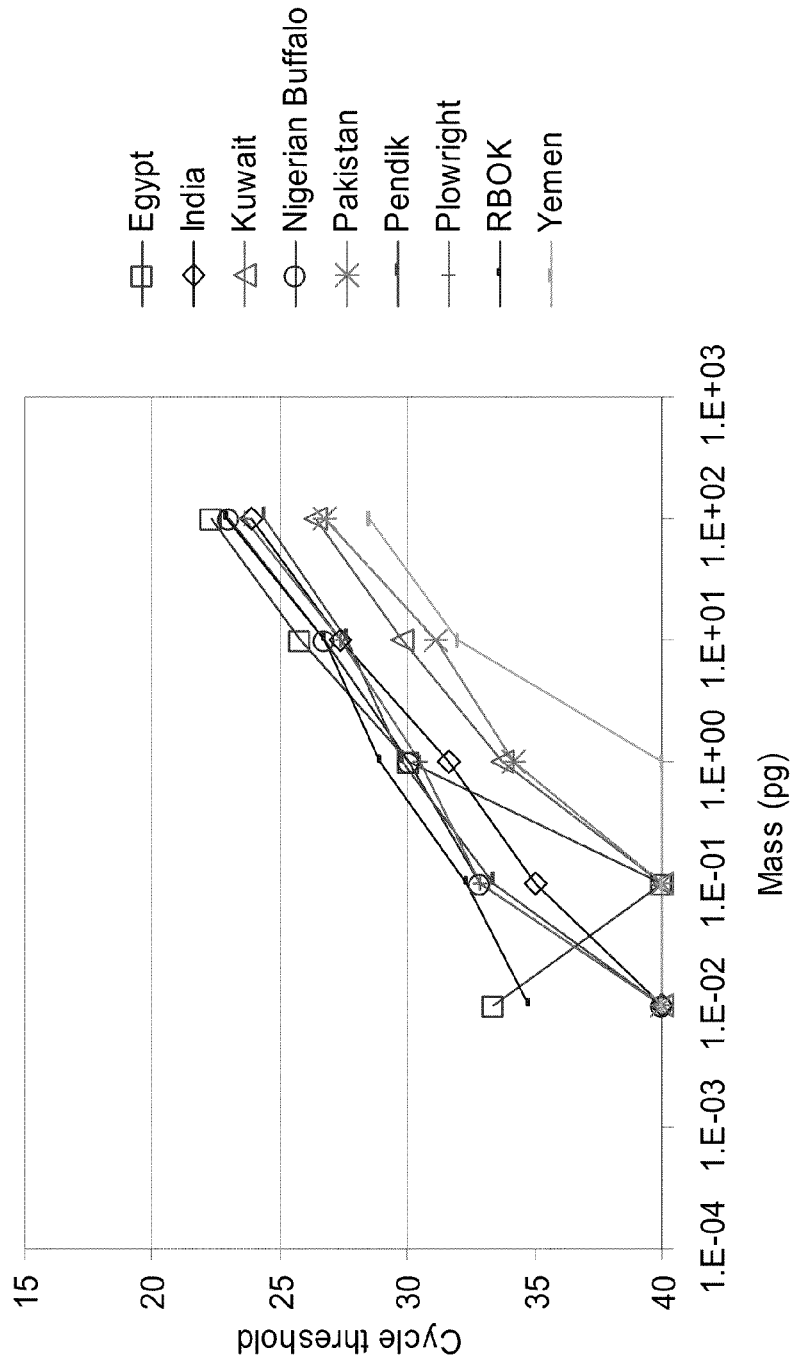
Figure 30C:
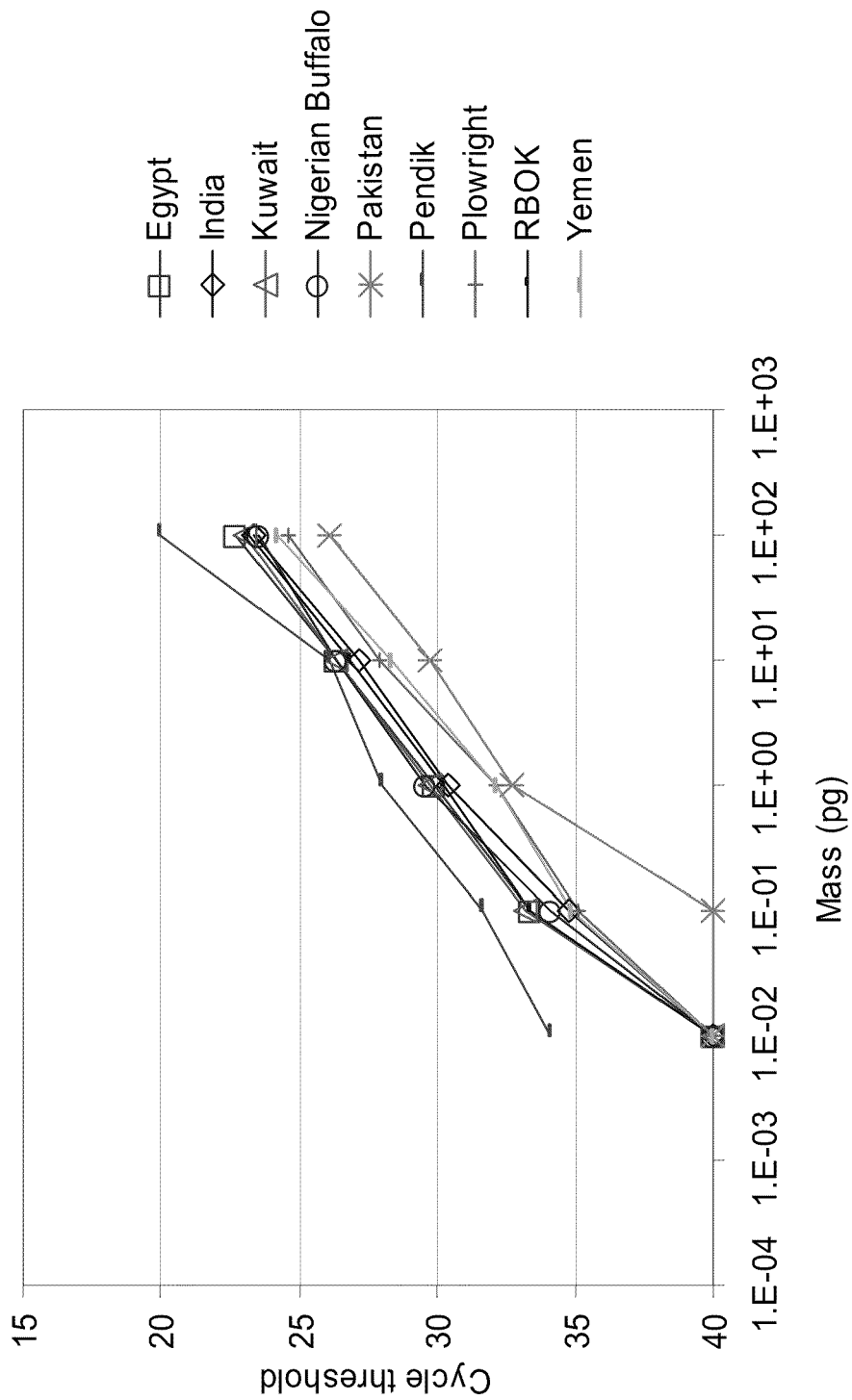

Additional Taqman screening was conducted at PIADC using serial dilutions of purified RNA of the same nine strains. The results summarized in FIG. 30 show that the cycle threshold decreased as the mass of template per reaction increased. RPV_1814853 signature showed the most consistent results over all concentrations for all strains.

Near-neighbor screening: Signatures were screened at PIADC against five PPRV strains (Burkina Faso, Dorcas, Egypt 87, Ghana 76/1 and RCA,) at 200 pg (n=3) using extracted RNA template from virus-infected cell culture (Qiagen RNeasy Mini kit). No cross-reactivity was observed.

Target screening: All three RPV signatures have been added to the current Bovine panel where they show consistently low background response in the absence of template. Target screening was conducted at PIADC against available strains of RPV. All three signatures responded to all strains of RPV tested. The estimated limits of detection for the RPV signatures in the bovine panel are shown in Table 29.

TABLE 29

Estimated LOD data for RPV signatures in the bovine panel determined from target screening data acquired at PIADC.

| Serotype or strain | LOD, TCID$_{50}$/mL (MFI) | | |
| --- | --- | --- | --- |
| | RPV-4853 | RPV-4855 | RPV-4856 |
| India | 20 (20.0) | 110 (43.0) | 2000 (6.0) |
| Pakistan | 2 (40.5) | 200 (38.5) | 1100 (14.5) |
| Egypt | 11 (261.0) | 2 (20.5) | 20000 (7.0) |
| Kuwait | 20 (47.5) | 2000 (30.5) | 11 (13.0) |
| Nigerian buffalo | 110 (127.0) | 110 (40.0) | 200000 (10.0) |
| Plowright | 101 (178.5) | 200 (87.5) | 20000 (20.0) |
| RBOK | 200 (51.0) | 200 (19.0) | 2000 (11.0) |
| Cutoff | (11.0) | (9.6) | (8.9) |

The RPV signatures together demonstrate promising performance in Taqman formats. Multiplex screening against target and near-neighbor material indicates that the three RPV signatures perform well in the prototype bovine panel.

7. Swine Vesicular Disease Virus (SVDV)—Porcine Panel

Signature candidates: SVD_1, SVD_2, SVD_3. These signatures were adopted from the Version 1.0 panel without change.

Signature origin: Signatures were designed at LLNL using five complete genomes. SVD_1, SVD_2 and SVD_3 signatures target ID protein (coat protein), membrane permeability enhancement and RdRp genes, respectively Near-neighbor screening: SVD-1 and SVD-2 did not cross-react with 10 human enterovirus B strains (Cox A9, B1, B4, B5, B6, Echo 11, Echo 9H11 and Echo24).

Figure 32:
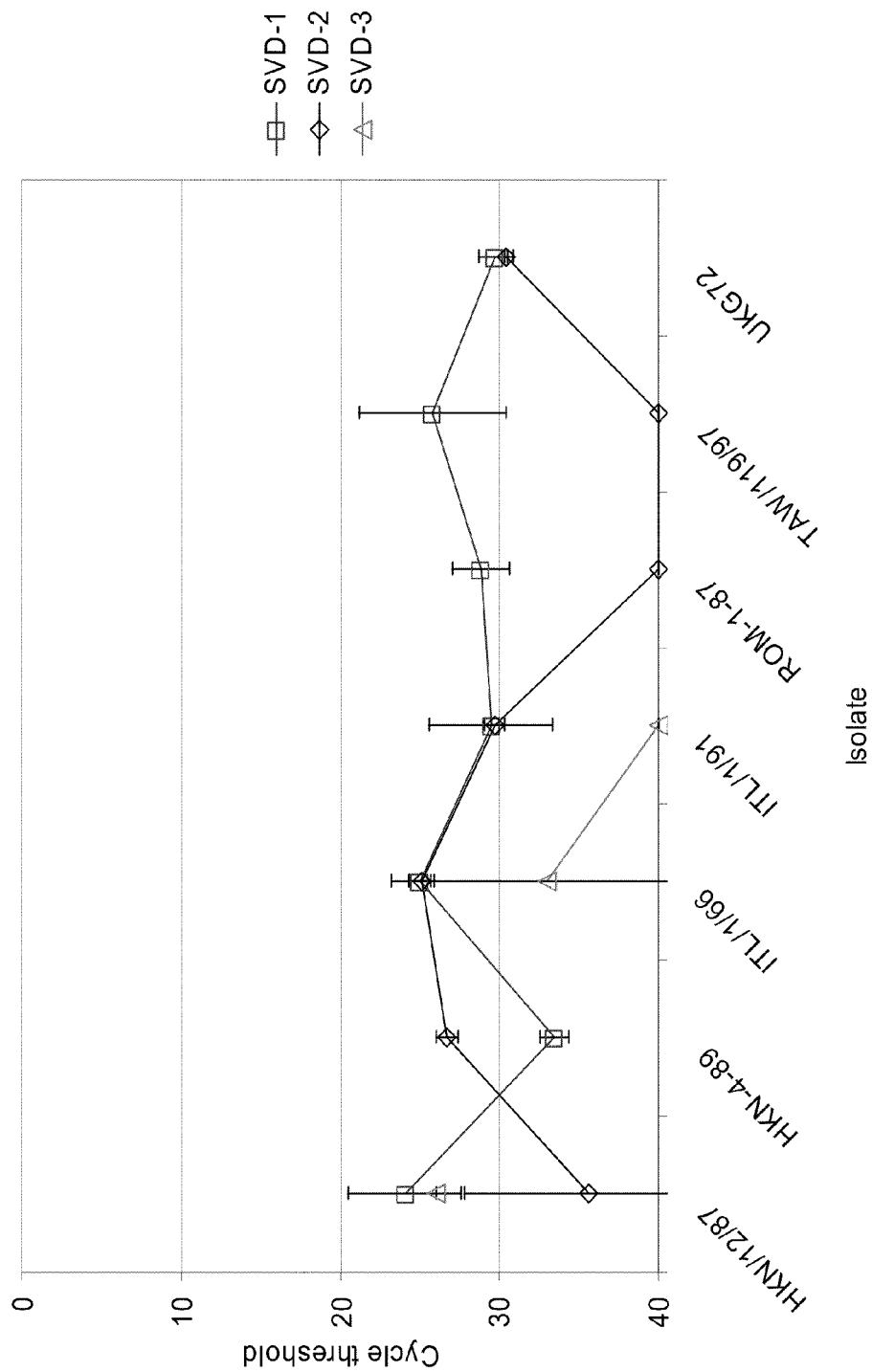
FIG. 32: Taqman screening of SVD signatures against seven isolates of SVDV (PIADC). Virus-infected cell culture media was used as template. Each point represents the mean (n=3) cycle threshold. If no cycle threshold was reached (i.e. infinite cycle threshold), a cycle threshold of 40 was assigned in this plot.

Target screening: The three SVD signatures were screened against eleven isolates of SVDV at PIADC (FIG. 32). SVD-1 detected 7/7 isolates. SVD-2 detected 4/7 isolates, missing HKN/12/8, RON-1-87, TAW/119/97. Taqman target screening for the SVD-3 signature is lacking data for five isolates and may need to be screened further. Of the two isolates screened to date, one generated a weak response (ITL/1/88) and the other no response (ITL/1/99).

Figure 33:
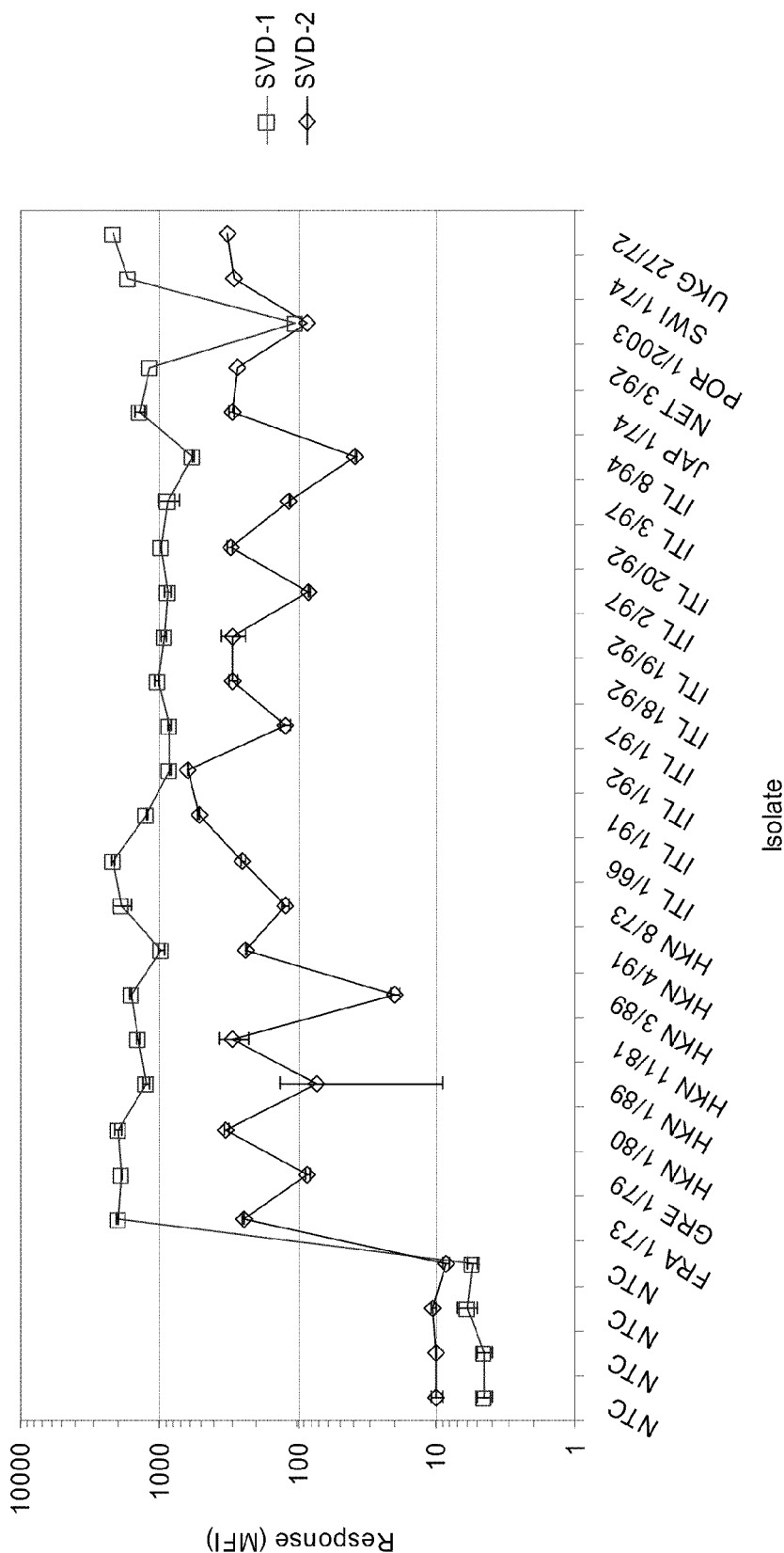
FIG. 33: SVDV signature screening in singleplex format against twenty-three isolates of SVDV (Canada). Samples comprised of a non-infected culture media (no template control, NTC) and virus-infected culture media spiked into each PCR reaction. Each point represents the mean response (n=2). Error bars indicate ±1σ of the mean.

Target screening: Spot-testing results using virus-infected cell culture as the template are shown in FIG. 33. SVD-1 showed a strong response to 23/23 isolates. SVD-2 response was up to 100 times weaker than SVD-1.

Figure 34:
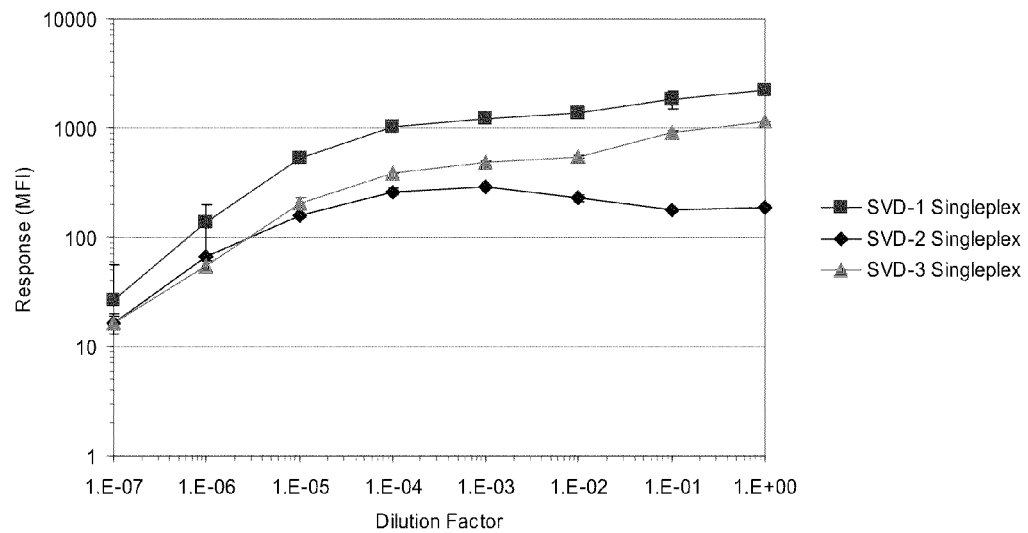
FIG. 34: SVDV signature screening in singleplex format showing signature response to two strains ITL1/66 and ITL 1/91. Samples were serial dilutions of total nucleic acid extracted from untitered virus-infected cell culture and are presented as dilution factor. Each point represents the mean response (n=2). Error bars indicate ±1σ of the mean.
Figure 34:
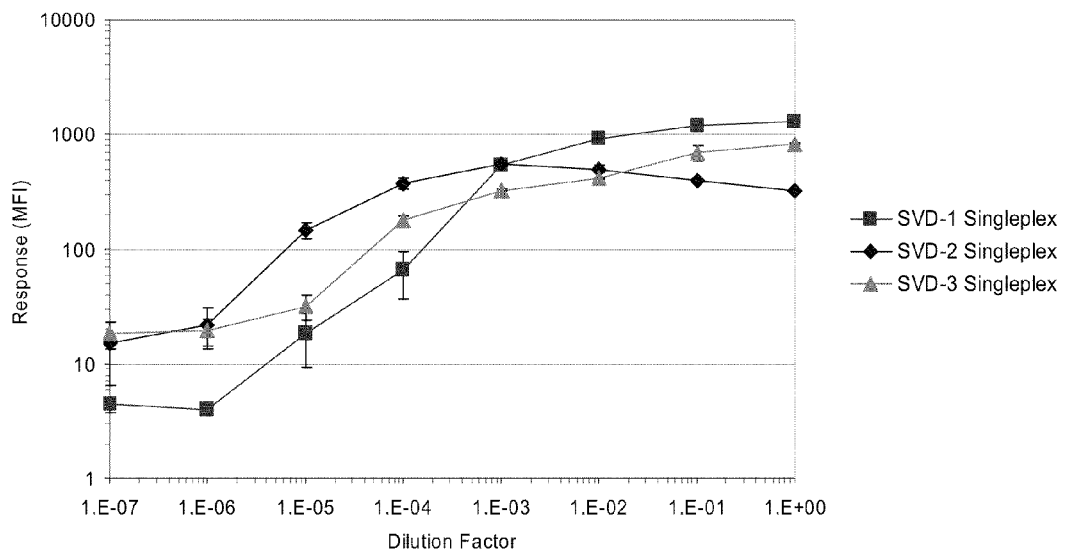

Further testing of the three signatures was undertaken in singleplex format during testing at NCFAD (Winnipeg, Canada). The results are shown in FIG. 34. These serial dilutions of untitered virus indicate that all three signatures responded over seven orders of magnitude of template concentration.

Near-neighbor screening: Near-neighbor testing of the SVD signatures was for the porcine panel. FMDV is considered a near-neighbor for SVDV. Specificity of the SVDV signatures is evident in data presented during FMDV target and near-neighbor screening. The SVDV signatures did not cross-react with FMDV, CVB5, PEV or PTV.

Figure 35:
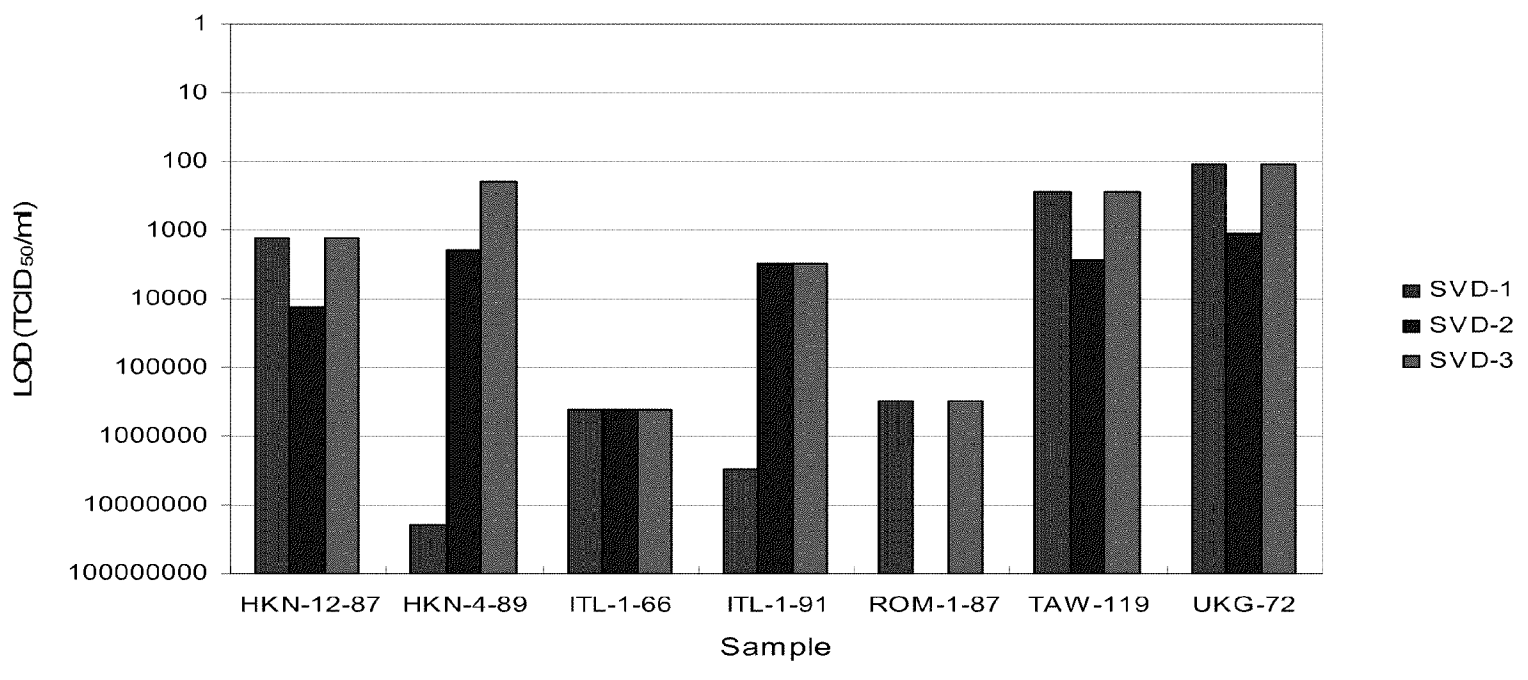

Target screening: Characterization data captured for these signatures in the Version 1.0 panel as supporting information. FIG. 35 indicates that three SVD signatures offer complementary coverage of SVD isolates.

The three signatures were added to the Porcine panel and were screened against targets at PIADC. The estimated limits of detection for the SVD signatures in the porcine panel are shown in Table 30.

TABLE 30

Estimated LOD data for SVD signatures in the porcine panel determined from target screening data acquired at PIADC.

| Strain | LOD, TCID$_{50}$/mL (MFI) | | |
|---|---|---|---|
| | SVD-1 | SVD-2 | SVD-3 |
| ITL 1/91 | 110000 (28.5) | 2000 (12.5) | 2000 (15.0) |
| HKN 12/87 | 1100 (27.0) | 20000 (27.5) | 2000 (29.5) |
| TAW 119/97 | 200 (14.0) | 20000 (13.0) | 200 (29.0) |
| ITL 1/66 | 110 (13.5) | 1100 (19.5) | 200 (11.0) |
| HKN 4/89 | 200000 (26.0) | 2000 (26.5) | 20 (8.0) |
| ROM 1/87 | 20000 (15.5) | ND | 20000 (8.3) |
| UKG 72 | 20 (9.5) | 200 (17.0) | 110 (22.0) |
| Cutoff | (8.6) | (9.4) | (7.8) |

ND = not detected

All three SVD signatures are suitable candidates for inclusion in the Porcine panel. Further screening of the SVD_3 signature against target and near-neighbors may need to be acquired to support signature selection.

8. Vesicular Exanthema of Swine Virus (VESV)—Porcine Panel

Signature candidates: VESV_1, VESV_4, VESV_5. These three signatures were adopted from the Version 1.0 panel without change.

Signature origin: Signatures were designed at LLNL using one complete genome. All three signatures target different regions of a large polyprotein gene that spans over 5000 base pairs.

Figure 36:
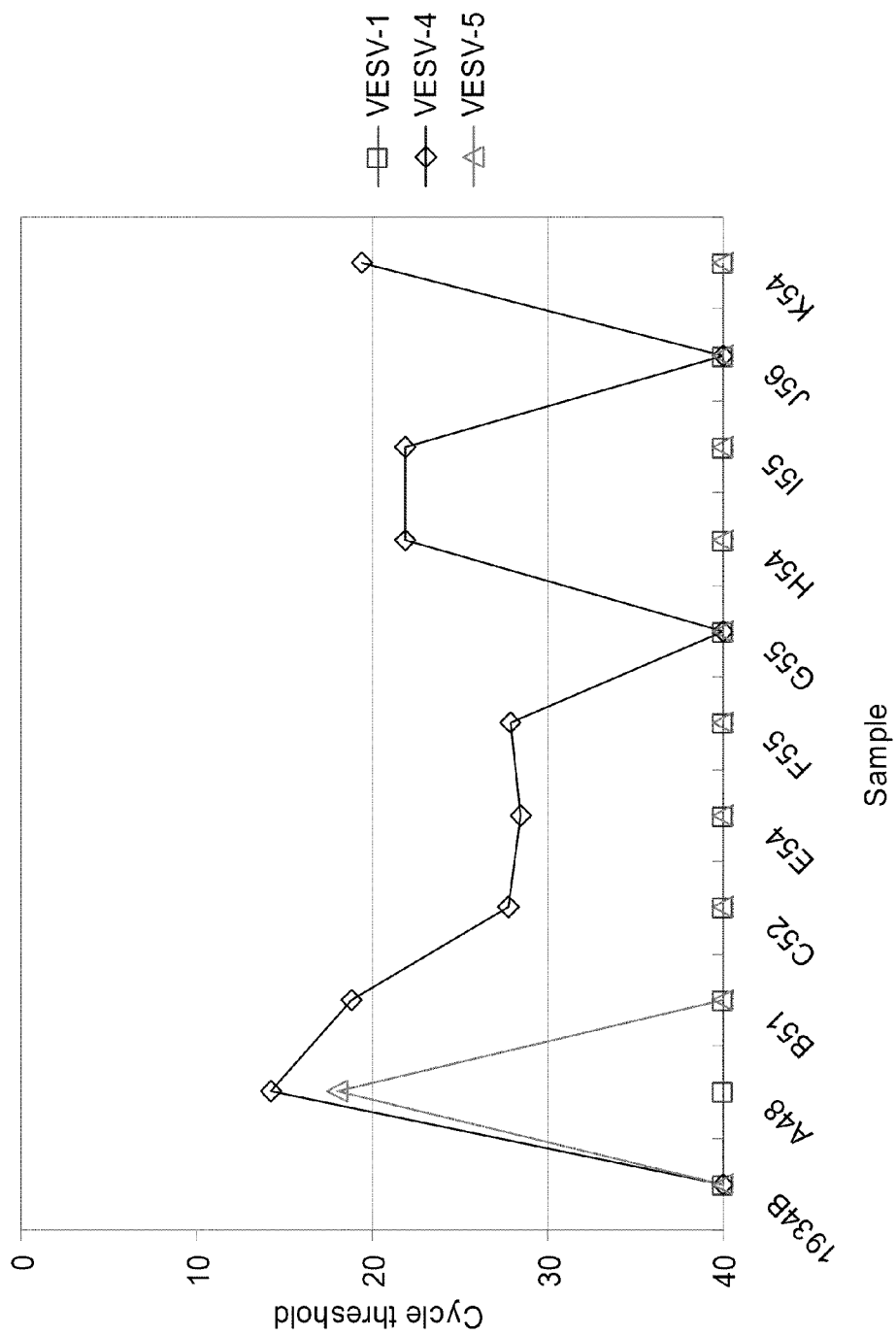
FIG. 36: Taqman screening of VESV signatures against eleven isolates of VESV. Virus-infected cell culture media was used as a template. Each point represent the mean (n=3) cycle threshold. If no cycle threshold was reached (i.e. infinite cycle threshold), a cycle threshold of 40 was assigned in this plot. Each point represents the mean response (n=3).

Target screening: VESV isolates 1934B, $A_{48}$, $B_{51}$, $C_{52}$, $D_{53}$, $E_{54}$, $F_{55}$, $G_{55}$, $H_{54}$, $I_{55}$, $J_{56}$ and $K_{54}$ were screened and the results are shown in FIG. 36. VESV_4 detected 8/11 strains tested. VESV_5 only detected 1/11 strains.

Figure 37:
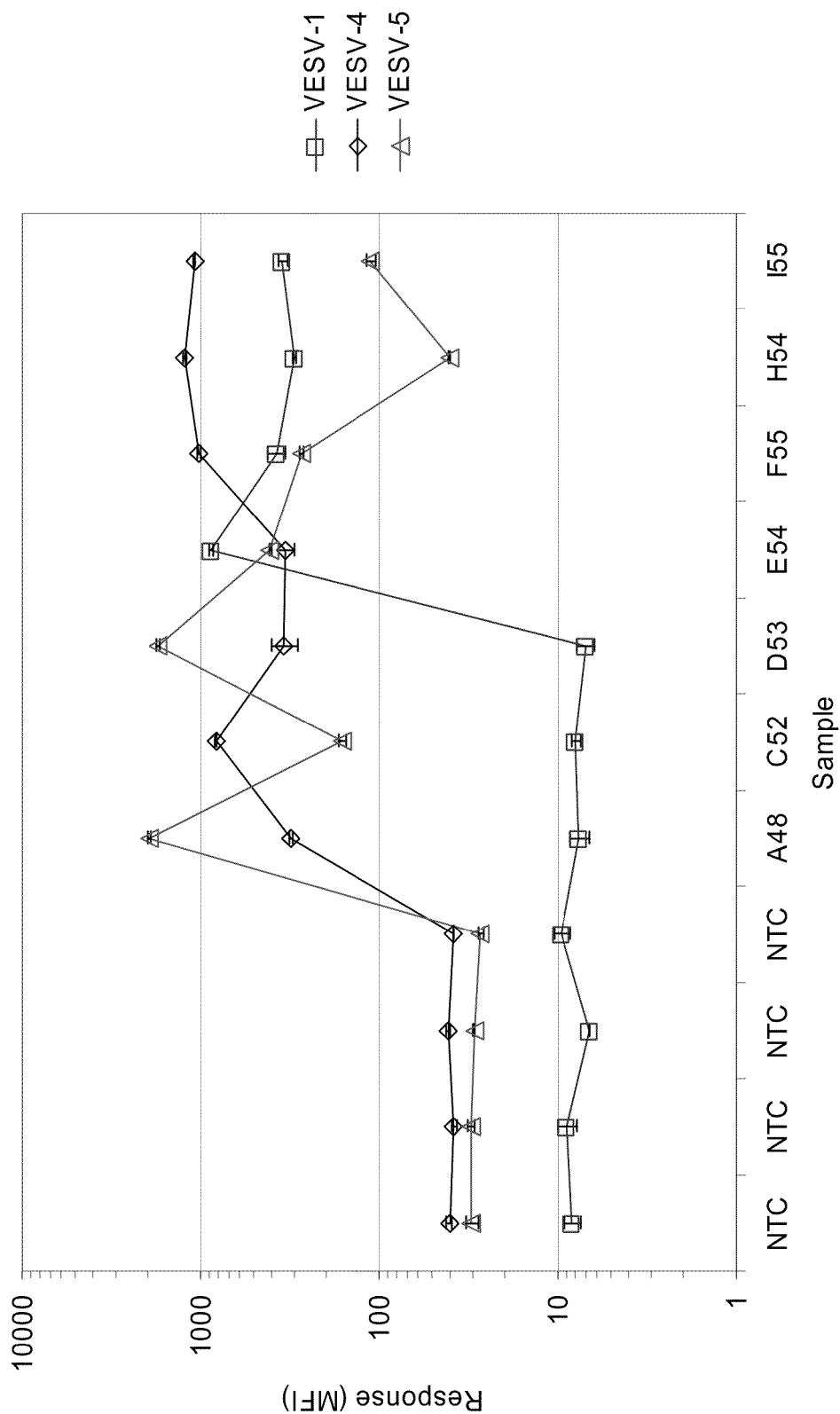
FIG. 37: VESV signature screening in singleplex format against seven strains of VESV. Samples comprised of a negative control (NTC, non-infected culture media) and virus-infected culture media. Each point represents the mean response (n=2). Error bars indicate ±1σ of the mean. VESV_1 response represents corrected data; raw data was on average 4.1 times higher for all channels during VESV_1 screening due to an operator error in instrument calibration.

Target screening: Spot-testing was conducted in singleplex format using virus-infected cell culture as the template shown in FIG. 37. VESV-4 detected 7/7 isolates which was consistent with Taqman target screening. VESV-5 detected 6/7 isolates (weak response on $H_{54}$) whereas VESV-1 detected 4/7 isolates.

Figure 38:
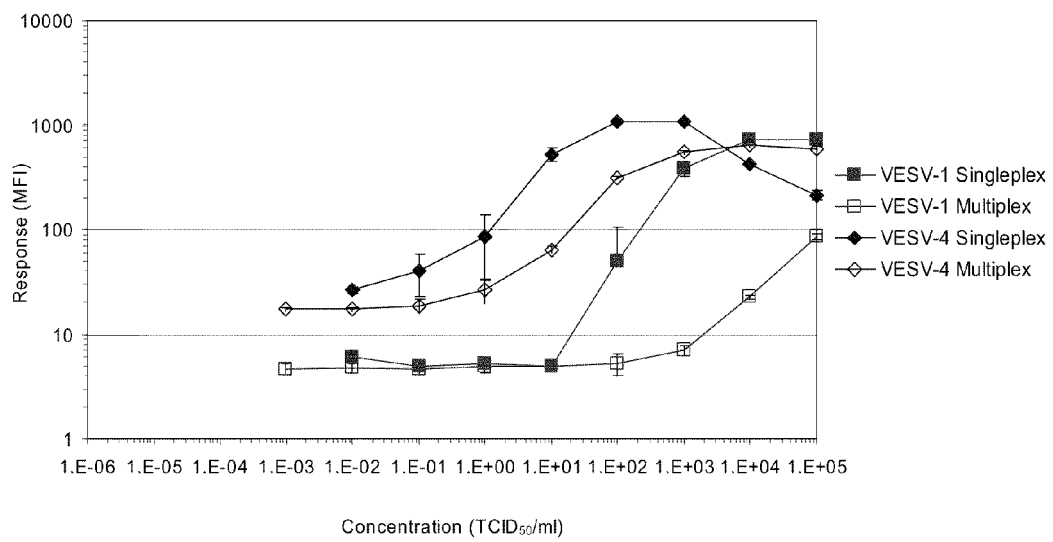
FIG. 38: VESV signature screening in singleplex format against two strains of VESV (E54 and H54) showing that the qualitative limit of detection increased approximately 10 to 100 times from Singleplex to Multiplex formats. Samples were serial dilutions of total nucleic acid extracted from titered virus-infected cell culture. Each point represents the mean response (n=4). Error bars indicate ±1σ of the mean.
Figure 38:
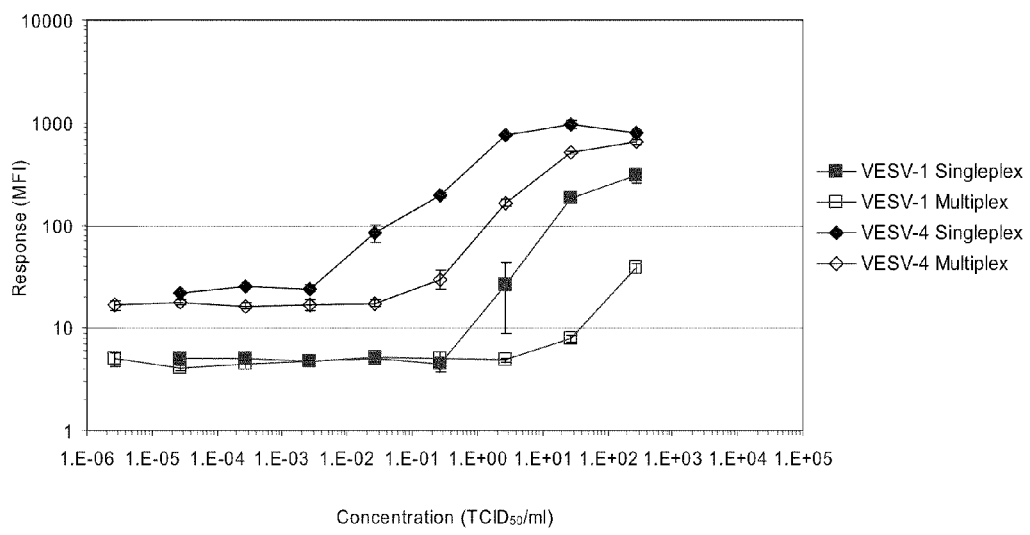

Further testing of the three signatures was undertaken in singleplex format. The results are shown in FIG. 38. The results are plotted together with the multiplex Version 1.0 results for comparison. These serial dilutions of titered virus indicate that VESV_1 and VESV_4 signatures have a higher qualitative limit of detection in multiplex than singleplex by approximately 10 to 100 times. The response of VESV_5 signature did not increase above the background for either strain in both singleplex and multiplex formats and was therefore omitted from FIG. 38 for clarity.

Near-neighbor and Target screening (Version 1.0): In Version 1.0, VESV_4 was the best performing signature against the samples available for testing. VESV_1 had a qualitative limit of detection approximately 100 to 1000 times higher than VESV_4. During characterization of the Version 1.0 panel at the Institute for Animal Health, Pirbright, target screening was conducted against the following nucleic acids extracted from virus-infected cell culture; VESV serotypes B1-34 (1934B), B51, and H54m; San Miguel Sea Lion Virus (SMSV) serotypes 6-13; bovine, cetacean, feline, primate, reptile and skunk caliciviruses. VESV_4 exhibited strong response to Cetacean calicivirus, SMSV serotypes 7, 10 and 13. VESV_4 generated weak responses to SMSV Serotypes 6 and 9, whilst 11 and 12 were not detected. VESV_4 generated strong responses to VESV serotypes B51 and H54 but did not response to B1-34 (1934B) which is consistent with Taqman target screening results. VESV_1 and VESV_5 signatures did not response to any of these isolates.

Figure 40:
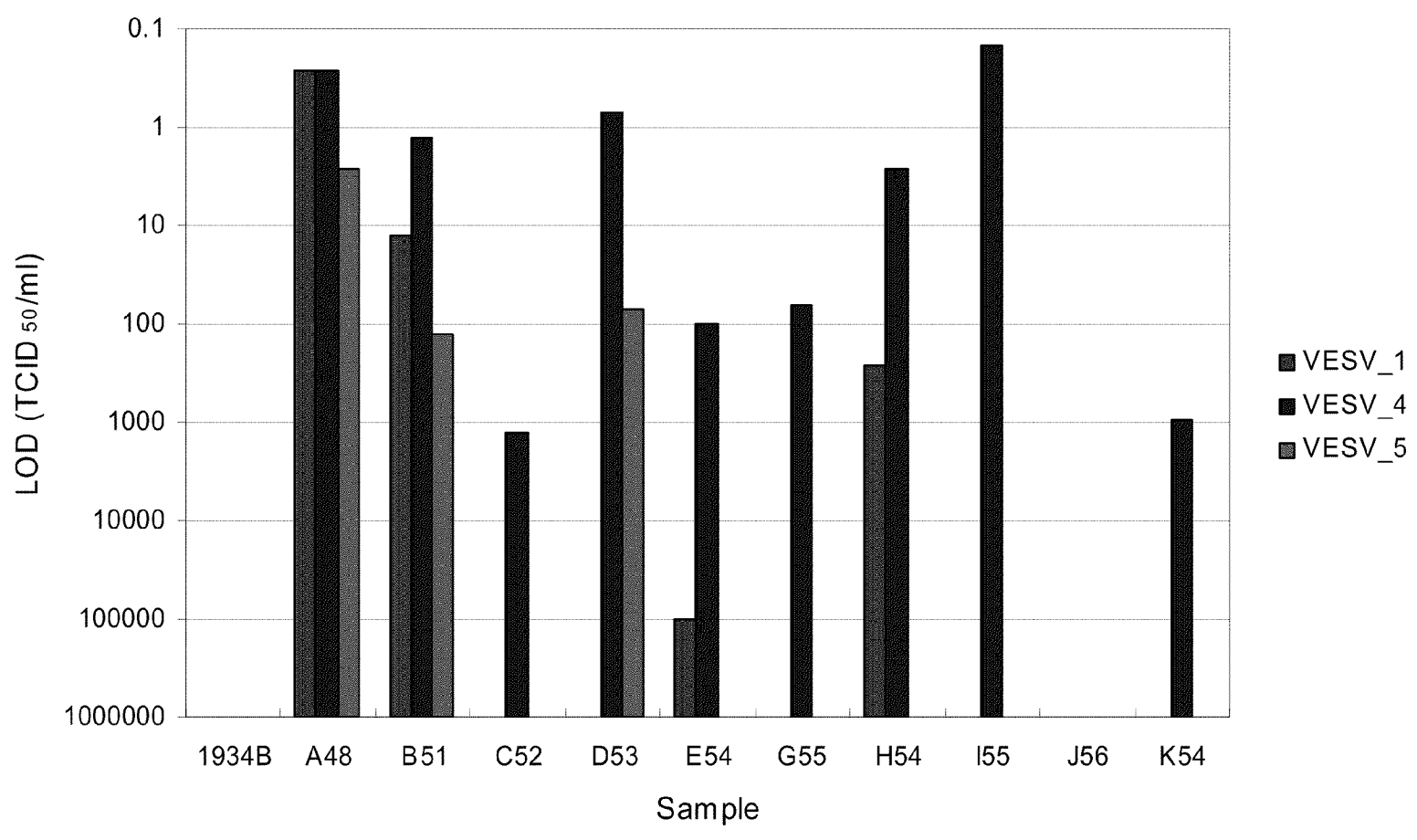

VESV_4 was the best performing signature in multiplex Version 1.0 as summarized in FIG. 40. VESV_1 and VESV_5 signatures were weak assays in Taqman, singleplex and multiplex assay formats against the sample set tested.

Near-neighbor and Target screening (Porcine panel): The three signatures were added the Porcine panel and screened against near-neighbors and targets at PIADC. The VESV-4 signature responded to SMSV Type 2. This is not surprising as SMSV and the vesicular exanthema of swine VESV cause vesicular disease in swine and other hosts, are very similar at the genetic level and constitute a single genotype.

The VESV signatures were screened against targets at PIADC. The estimated limits of detection for the VESV signatures in the porcine panel are shown in Table 31.

TABLE 31

Estimated LOD data for VESV signatures in the porcine panel determined from target screening data acquired at PIADC.

| Serotype or strain | LOD, TCID$_{50}$/mL (MFI) | | |
|---|---|---|---|
| | VESV-1 | VESV-4 | VESV-5 |
| E54 | 2000 (7.3) | 0.2 (22.3) | 2000 (29.0) |
| H54 | 110 (8.5) | 0.101 (37.0) | 110 (19.5) |
| K54 | ND | 20 (38.5) | 200 (22.0) |
| C52 | 2000 (10.0) | 1100 (41.5) | 2000 (22.5) |
| G55 | ND | 0.2 (21.0) | 200 (22.5) |
| D53 | ND | 0.11 (27.5) | 2 (19.0) |
| A48 | 0.11 (15.0) | 0.02 (167.5) | 0.02 (28.0) |
| Cutoff | (6.2) | (18.5) | (17.6) |

The data acquired on the samples tested thus far indicates that VESV_4 is the most promising signature to carry forward in the Porcine panel.

9. Vesicular Stomatitis Virus (VSV)—Bovine and Porcine Panel

Signature candidates: Six new VSV signature candidates are available for consideration for the Porcine panel. VSV signatures were not included in the Version 1.0 panel. Four signatures intended to detect VSV IND are designated VSV_1793943, VSV_1798947, VSV_1798949 and VSV_1811405. Two signatures intended to detect VSV NJ are designated VSV_1811408 and VSV_1811409. Four of these signatures including VSV signature candidates are candidates for the Bovine panel. VSV_1793943, VSV_1798947, VSV_1798949 and VSV_1811409.

Signature origin: Signatures developed by others were modified to match LLNL's assay design criteria to increase compatibility in the multiplex format. VSV_1811405 targets the polymerase (L protein) gene whilst VSV_1811408 and VSV_1811409 both target the nucleocapsid (N) protein gene. The three signatures VSV_1793943, VSV_1798947, VSV_1798949 were designed at LLNL using four complete VSV IND genomes. VSV_1793943 targets the nucleocapsid (N) protein gene whilst VSV_1798947, VSV_1798949 both target the polymerase (L protein) gene.

Near-neighbor screening: Signatures were screened at PIADC against eight vesiculovirus near-neighbors (as determined by serological analysis, not sequence) at 200 pg (n=3) of extracted RNA template from virus-infected cell culture (Qiagen RNeasy Mini kit). These included BeAr, Hilo CT AN, Calchaqui, Klamath, NM-85-488, Jurona, Piry, Chandipura isolates. No cross-reactivity was observed.

Figure 42:
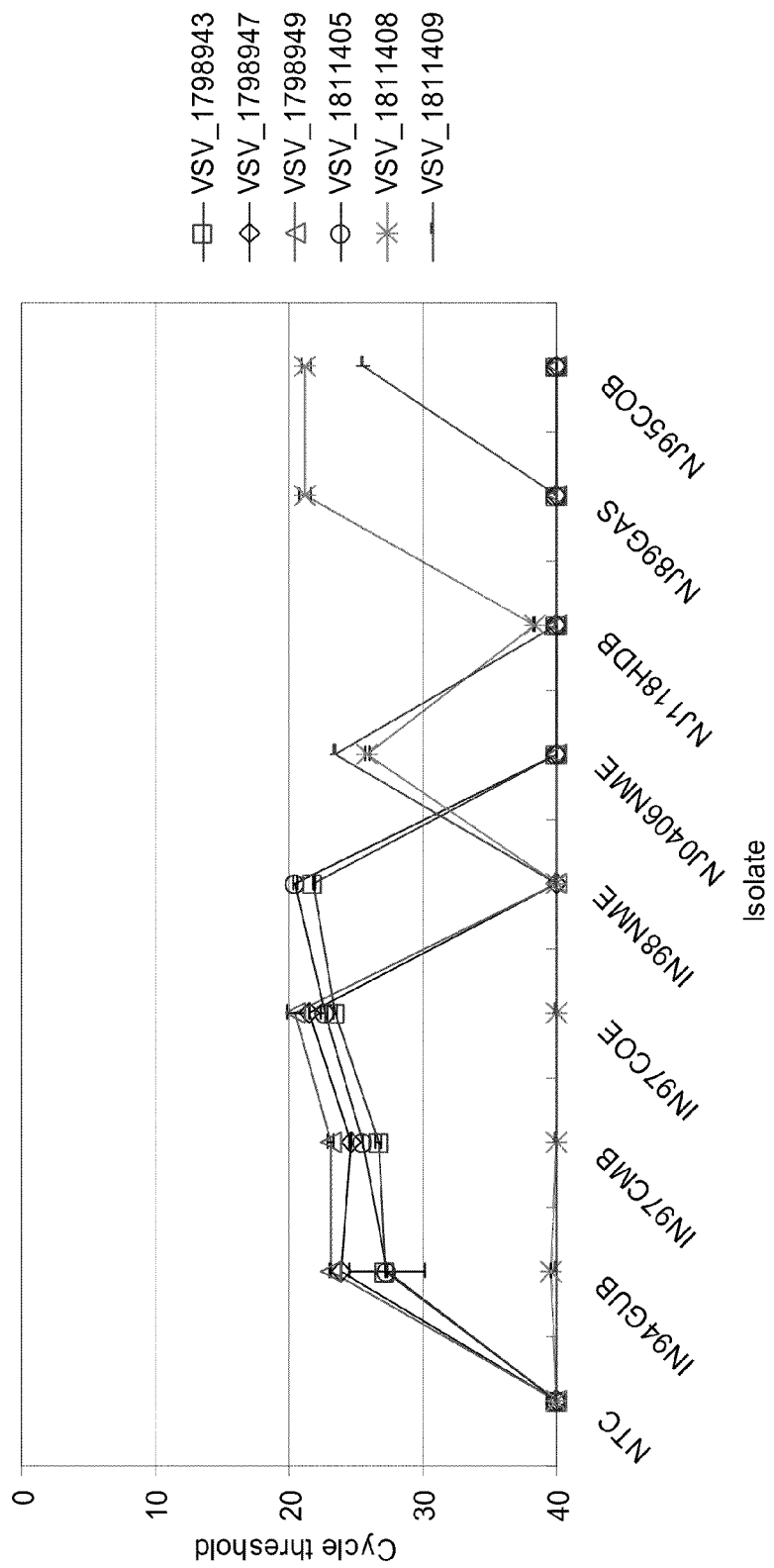
FIG. 42: Taqman screening of VSV signatures against eight VSV isolates conducted at PIADC. Samples were serial dilutions of total nucleic acid Trizol extracted from virus-infected cell culture. Each reaction was spiked with 200 pg of template. Each point represents the mean (n=3) cycle threshold. If no cycle threshold was reached (i.e. infinite cycle threshold), a cycle threshold of 40 was assigned in this plot.

Target screening: All signatures were screened against four IND-1 and four NJ strains and the results are shown in FIG. 42. These results indicate selectivity between signature sets in that IND signatures responded to IND-1 but not NJ strains, whereas NJ signatures responded to NJ but not IND-1 strains. NJ strain NJ118HDB generated a weak response on VSV_1811408 and VSV_1811409 signatures. In concert, the two signature sets responded to 7/8 strains tested and worked well to provide complementary coverage.

Figure 43:
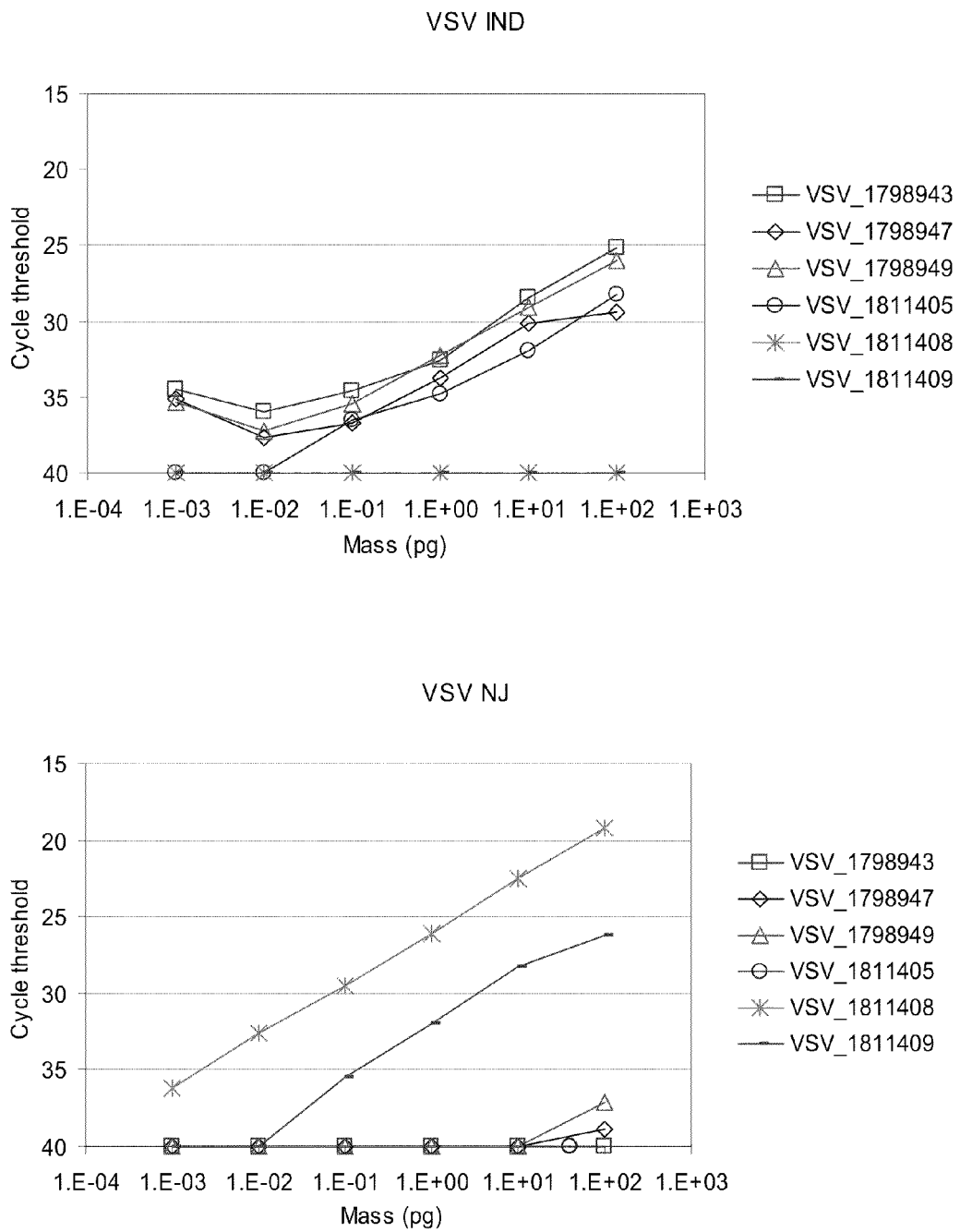
FIG. 43: Taqman screening of six VSV signatures against one VSV IND and one NJ strain showing response over a wide range of template concentrations. Samples were serial dilutions of total RNA Trizol extracted from virus-infected cell culture. Each reaction was spiked with 200 pg of template. Each point represents the mean (n=3) cycle threshold. If no cycle thresh sequences in the target and hybridization to probes covalently coupled to beads. Individual primer pairs (biotinylated forward and standard reverse) that bracket the target genomic sequence are included in an automated PCR master mix of buffers, Taq polymerase, dNTPs, etc. After target amplification by PCR, the amplicons are mixed with beads where target amplicons containing the forward biotinylated primer hybridize to the complementary probe on the appropriate beads. A fluorescent reporter molecule (strepavidin-phycoerythrin) then binds biotin functional groups. Therefore, the completed assay comprises a bead+probe+biotinylated (and fluorescently tagged) amplicon. The sample is then analyzed using a Luminex detector.

Additional Taqman screening was conducted at LLNL using one IND and one NJ strain acquired from the NVSL. The results summarized in FIG. 43 also show selectivity between signature sets. As expected, the cycle threshold decreased as the mass of template per reaction increased. VSV_1811408 showed a stronger response than VSV_1811409 against this single NJ strain.

Figure 44:
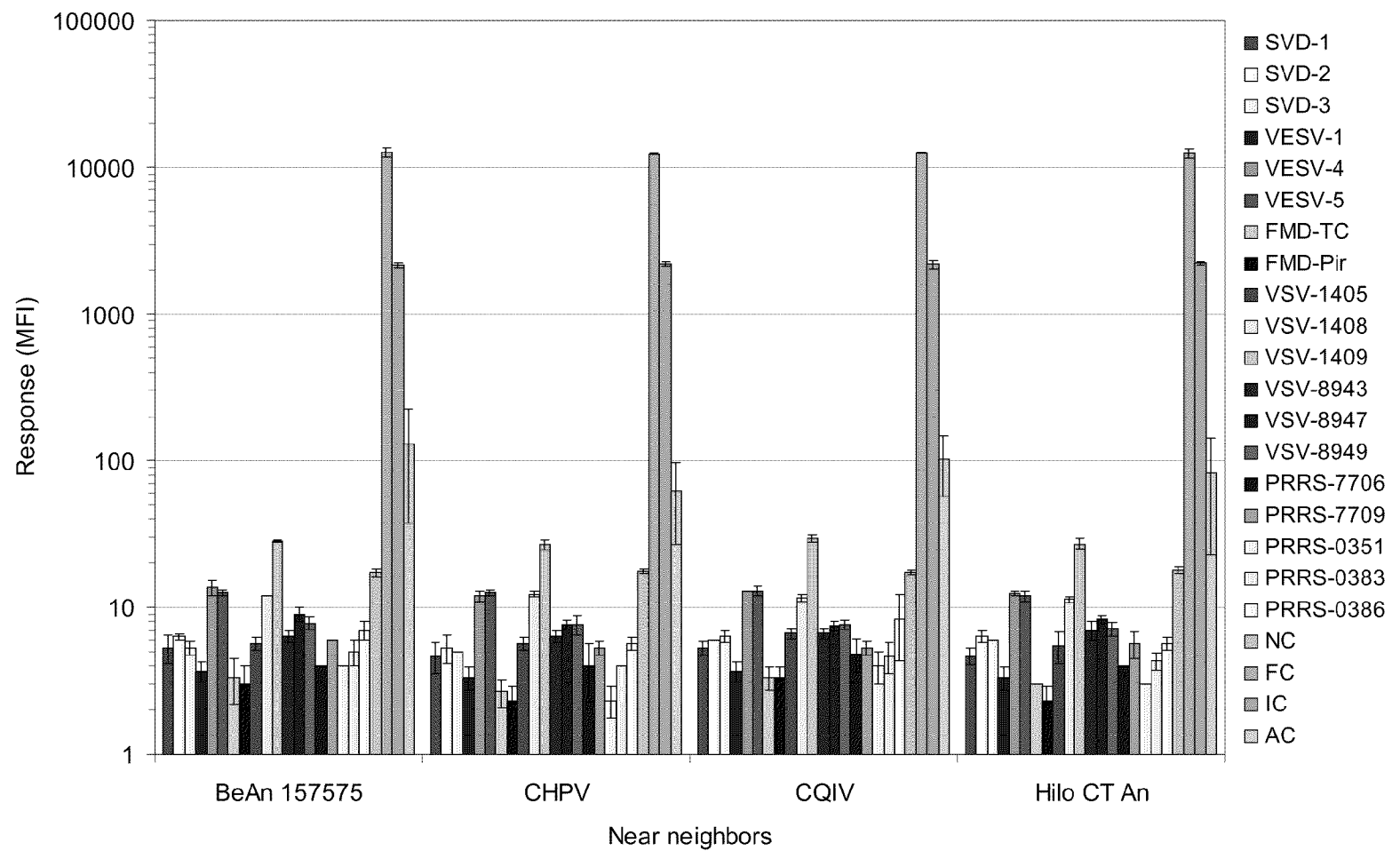
Figure 45:
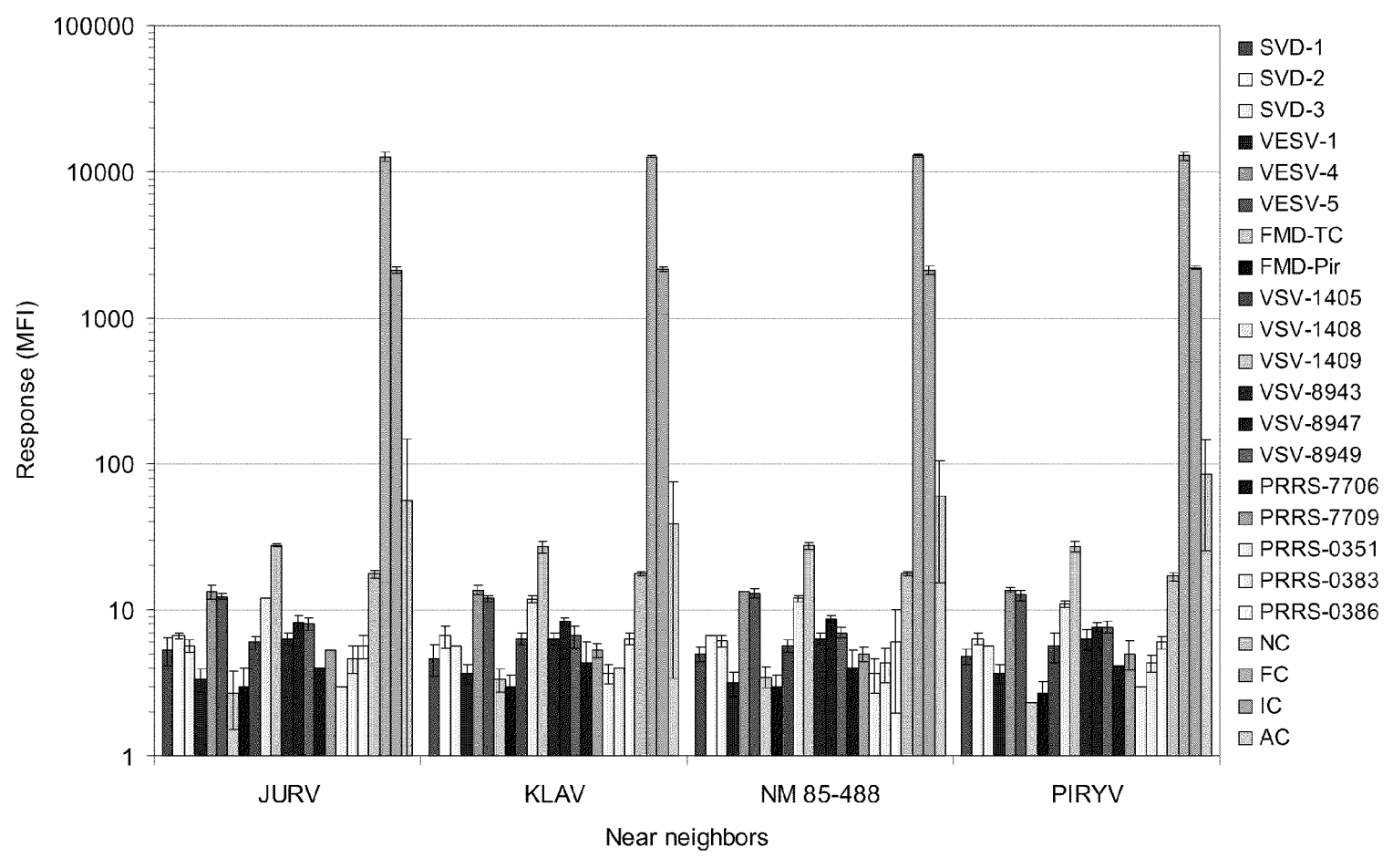

Near-neighbor screening (Porcine Panel): This work was conducted at PIADC. The VSV signatures did not cross react with vesiculoviruses as shown in FIG. 44 and FIG. 45.

Figure 46:
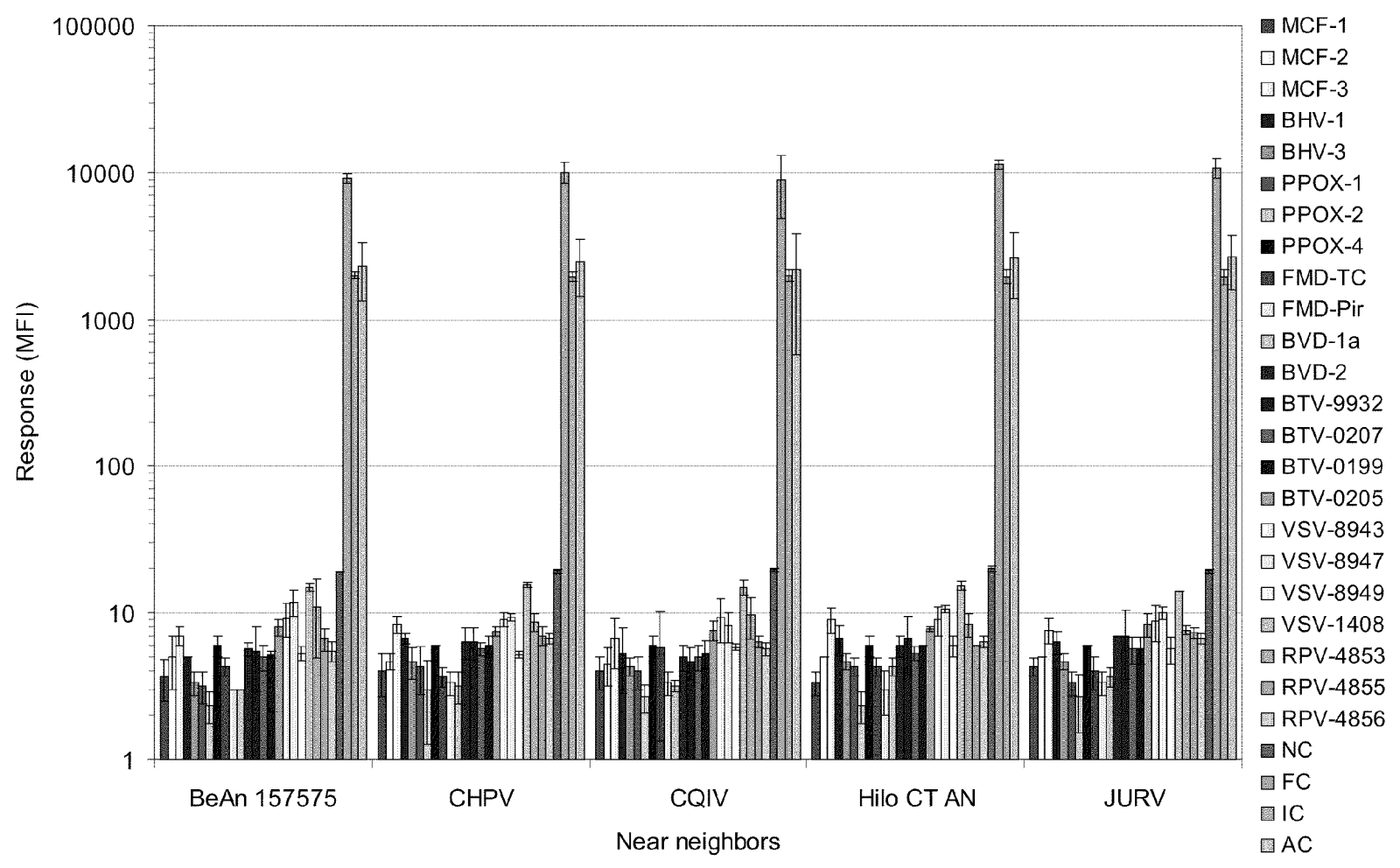
Figure 47:
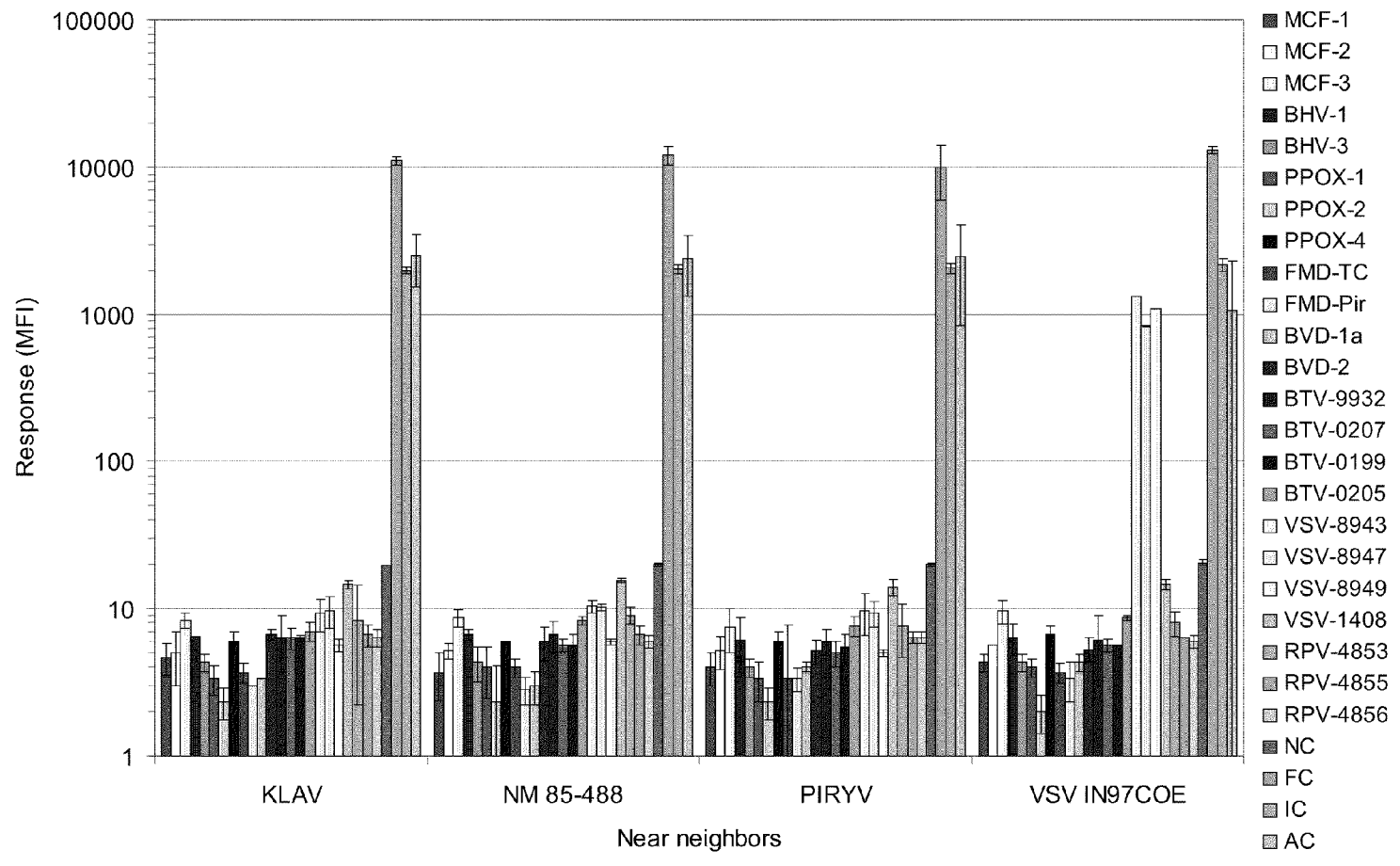

Near-neighbor screening (Bovine Panel): This work was conducted at PIADC. The VSV signatures did not cross react with vesiculoviruses as shown in FIG. 46 and FIG. 47.

Target screening (Porcine Panel): All six VSV signatures have been added to the current porcine multiplex. Five of the signatures show consistently low background response in the absence of template. VSV_1811409 in the current panel configuration exhibits an elevated background response (MFI values ranging from 50-200) which may be caused by a non-specific interaction with other primers in the reaction mixture.

Figure 48:
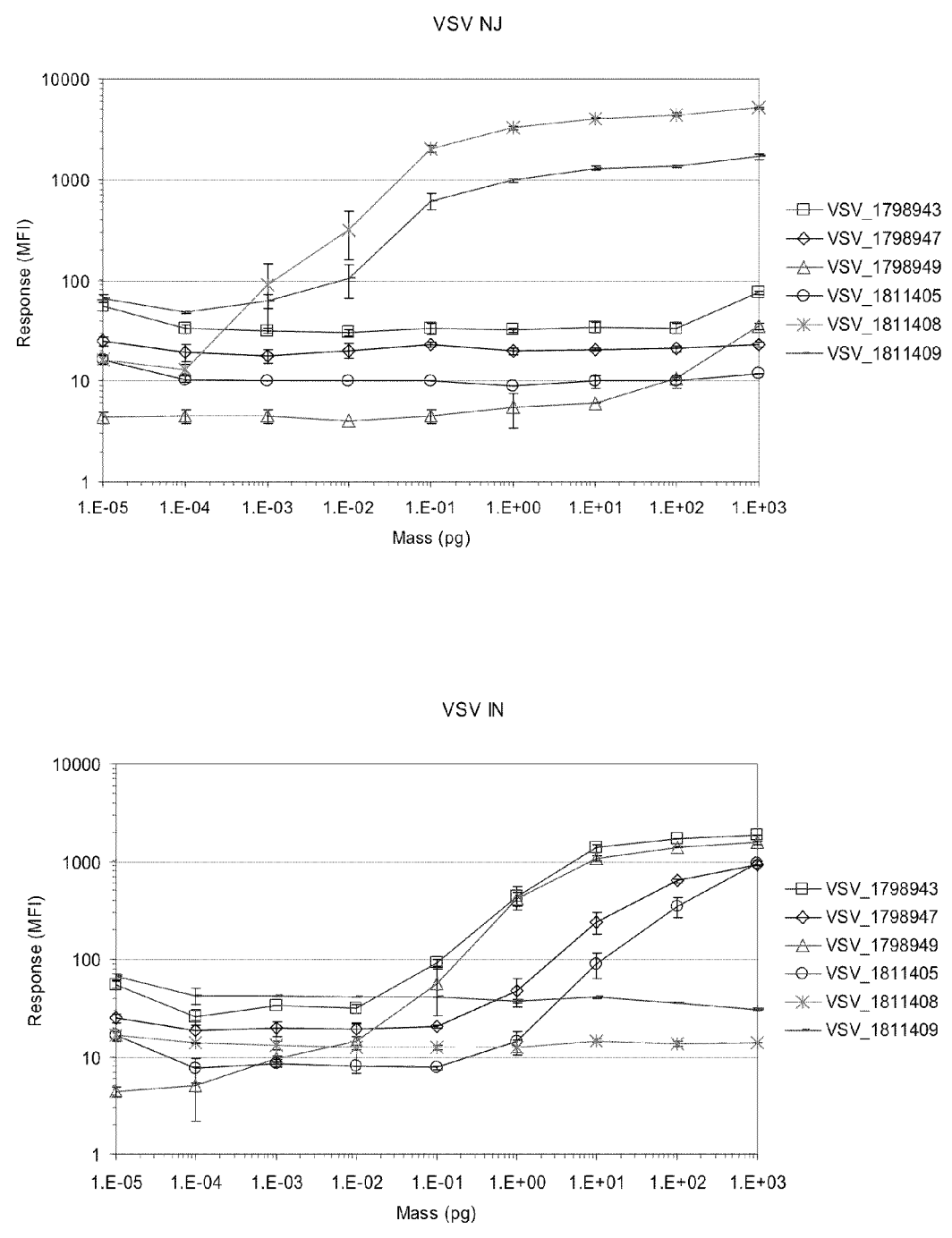

Multiplex screening results (FIG. 48) were in excellent agreement with the Taqman results. In multiplex, the VSV_1811408 also showed a stronger response than VSV_1811409 against the NJ species. Additional calibration data has been acquired at LLNL using titered material for the two NVSL isolates.

Multiplex screening results (FIG. 48) were also acquired using total RNA Trizol extracted from titered virus-infected cell culture.

The VSV signatures were screened against targets at PIADC. The estimated limits of detection for the VSV signatures in the porcine panel are shown in Table 32.

TABLE 32

Estimated LOD data for VSV signatures in the porcine panel determined from target screening data acquired at PIADC.

| Serotype or strain | LOD, TCID$_{50}$/mL (MFI) | | | | | |
| --- | --- | --- | --- | --- | --- | --- |
| | VSV-1405 | VSV-1408 | VSV-1409 | VSV-8943 | VSV-8947 | VSV-8949 |
| IN97COE | 2000 (14.0) | ND | ND | 200 (33.0) | 200 (22.5) | 110 (32.0) |
| IN97CMB | 110000 (40.5) | ND | ND | 1100 (10.0) | 20000 (63.0) | 2000 (17.0) |
| IN94GUB | 110000 (11.5) | ND | ND | 20000 (13.5) | 110000 (53.0) | 2000 (12.5) |
| IN98NME | 0.01$^a$ (10.5) | ND | ND | 5.5 × 10$^{-4a}$ (18.0) | 0.01$^a$ (62.0) | 5.5 × 10$^{-4a}$ (25.5) |
| NJ95COB | ND | 200 (60.0) | 2000 (105.0) | ND | ND | ND |
| NJ89GAS | ND | 1100 (80.5) | 110000 (96.0) | ND | ND | ND |
| NJ0604NME | ND | 110 (117.5) | 110 (213.0) | ND | ND | ND |
| NJ1184HDB | ND | ND | ND | ND | ND | ND |
| Cutoff | (8.5) | (21.0) | (76.0) | (9.6) | (21.0) | (21.0) |

ND = not detected;
$^a$ = fg

Target screening (Bovine Panel): Four VSV signatures have been added to the current Bovine multiplex. The Bovine panel has two less VSV signatures than the Porcine panel, as two signatures were found to be incompatible during attempts to add them to multiplex. All four signatures show consistently low background response in the absence of template. Multiplex screening results (FIG. 52) were also acquired using total RNA Trizol extracted from titered virus-infected cell culture. Good agreement was obtained between the performance of these signatures in the current Bovine and Porcine panels.

The VSV signatures were screened against targets at PIADC. The estimated limits of detection for the VSV signatures in the porcine panel are shown in Table 33.

TABLE 33

Estimated LOD data for VSV signatures in the porcine panel determined from target screening data acquired at PIADC.

| Serotype or strain | LOD, TCID$_{50}$/mL (MFI) | | | |
|---|---|---|---|---|
| | VSV-8943 | VSV-8947 | VSV-8949 | VSV-1408 |
| IN97COE | 20 (65.0) | 110 (132.0) | 200 (158.0) | ND |
| IN97CMB | 1100 (49.0) | 1100 (93.5) | 1100 (44.0) | ND |
| IN94GUB | 20000 (189.5) | 2000 (20.0) | 2000 (38.0) | ND |
| IN98NME | 0.55$^b$ (62.0) | 0.1$^b$ (31.5) | 0.55$^b$ (30.0) | ND |
| NJ95COB | ND | ND | ND | 110 (58.0) |
| NJ89GAS | ND | ND | ND | 110 (70.0) |
| NJ0604NME | ND | ND | ND | 20 (75.5) |
| NJ1184HDB | ND | ND | ND | ND |
| Cutoff | (13.6) | (14.0) | (7.9) | (27.5) |

ND = not detected;
$^b$ = fg

The VSV signatures together demonstrate promising performance in both Taqman and multiplex formats. Together, the signatures are capable of detecting VSV NJ and IND and with apparent serotype selectivity.

10. Bovine Herpesvirus-1 (BHV-1)—Bovine Panel

Signature candidates: The two signatures available for consideration are BHV__1 and BHV__3. These two signatures were adopted from the Version 1.0 panel without change.

Signature origin: Signatures were designed at LLNL using one complete genome for the BHV-1.1 subtype (respiratory subtype). The two signatures target two different genes for glycoproteins. The BHV__1 signature targets the glycoprotein C gene and the BHV__3 signature targets the glycoprotein B gene.

Near-neighbor screening: The signatures did not respond to twenty near-neighbors including Rhadinovirus Caprine Herpes-2, V. Pseudorabies, Psuedorabies Shope, Equine Herpesvirus-1, Equine Herpesvirus-2, Feline herpes and Bovine Herpesvirus-5.

Figure 51:
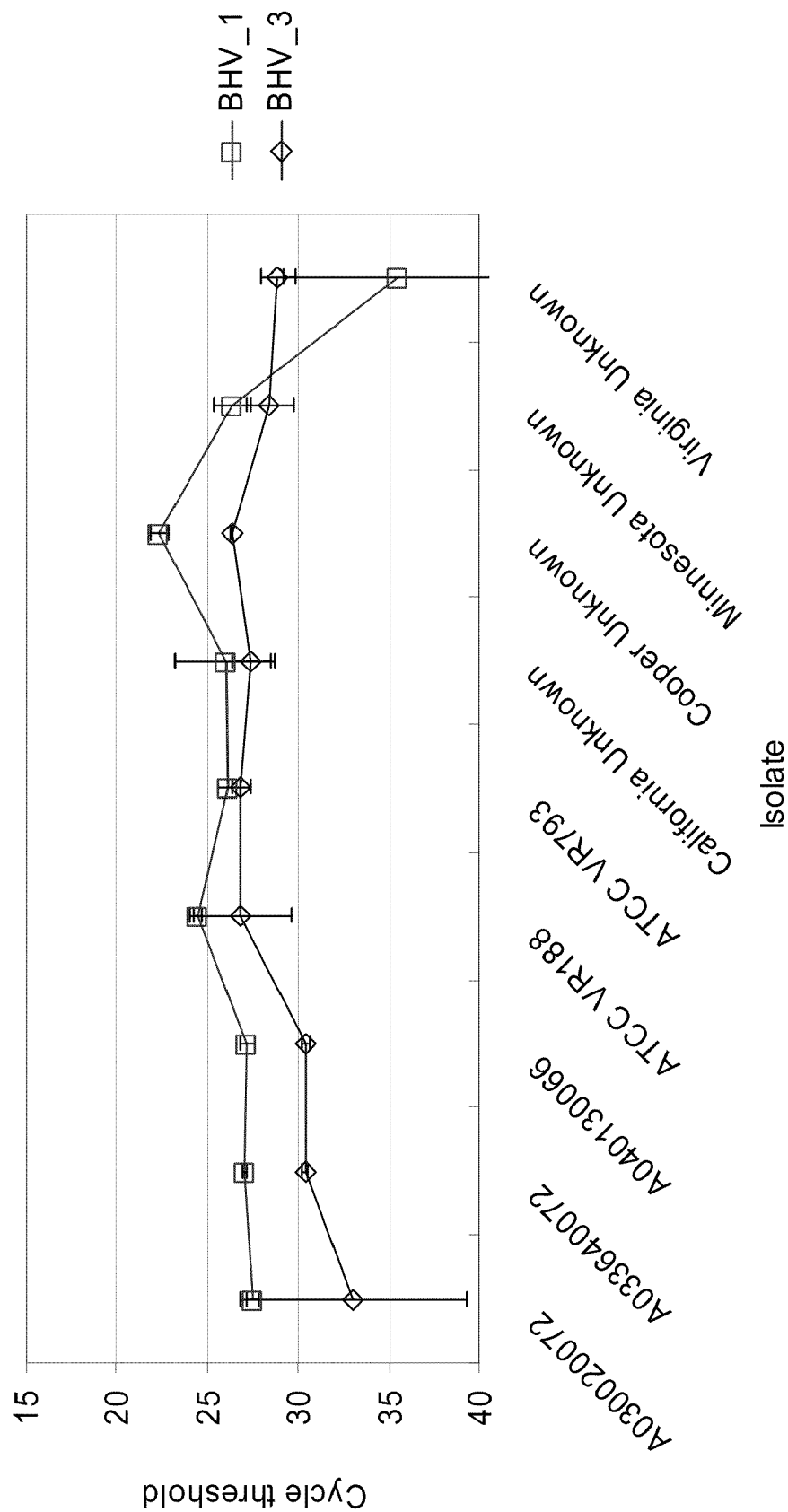

Target screening: Ten BHV-isolates were screened and the results are shown in FIG. 51. Both signatures responded to 10/10 isolates and did not cross-react with BHV-5.

Figure 52:
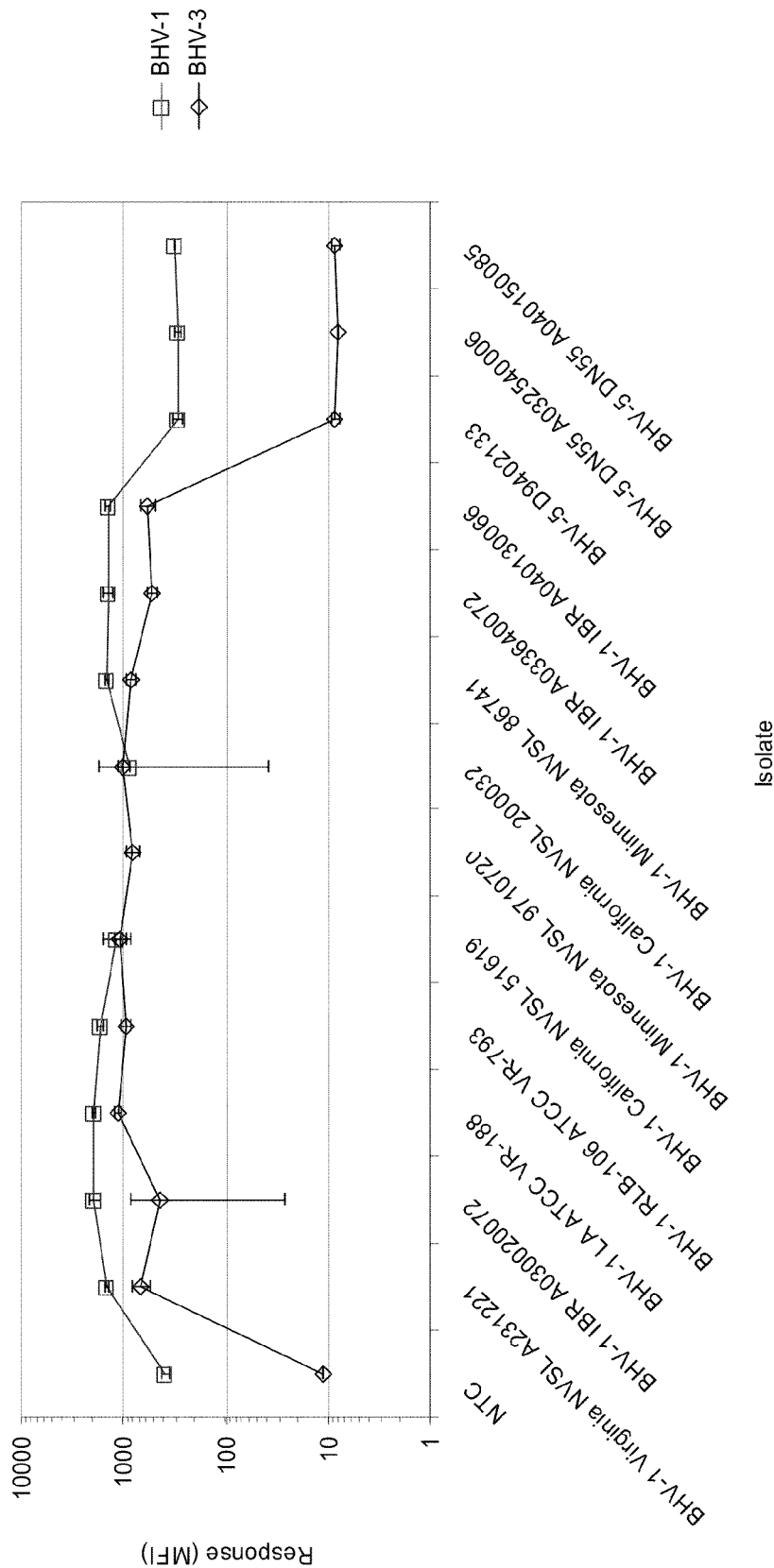

Target screening: FIG. 52 shows that both BHV__1 and BHV__3 signatures responded to 10/10 BHV-1 isolates but not to near-neighbor BHV-5.

Figure 53:
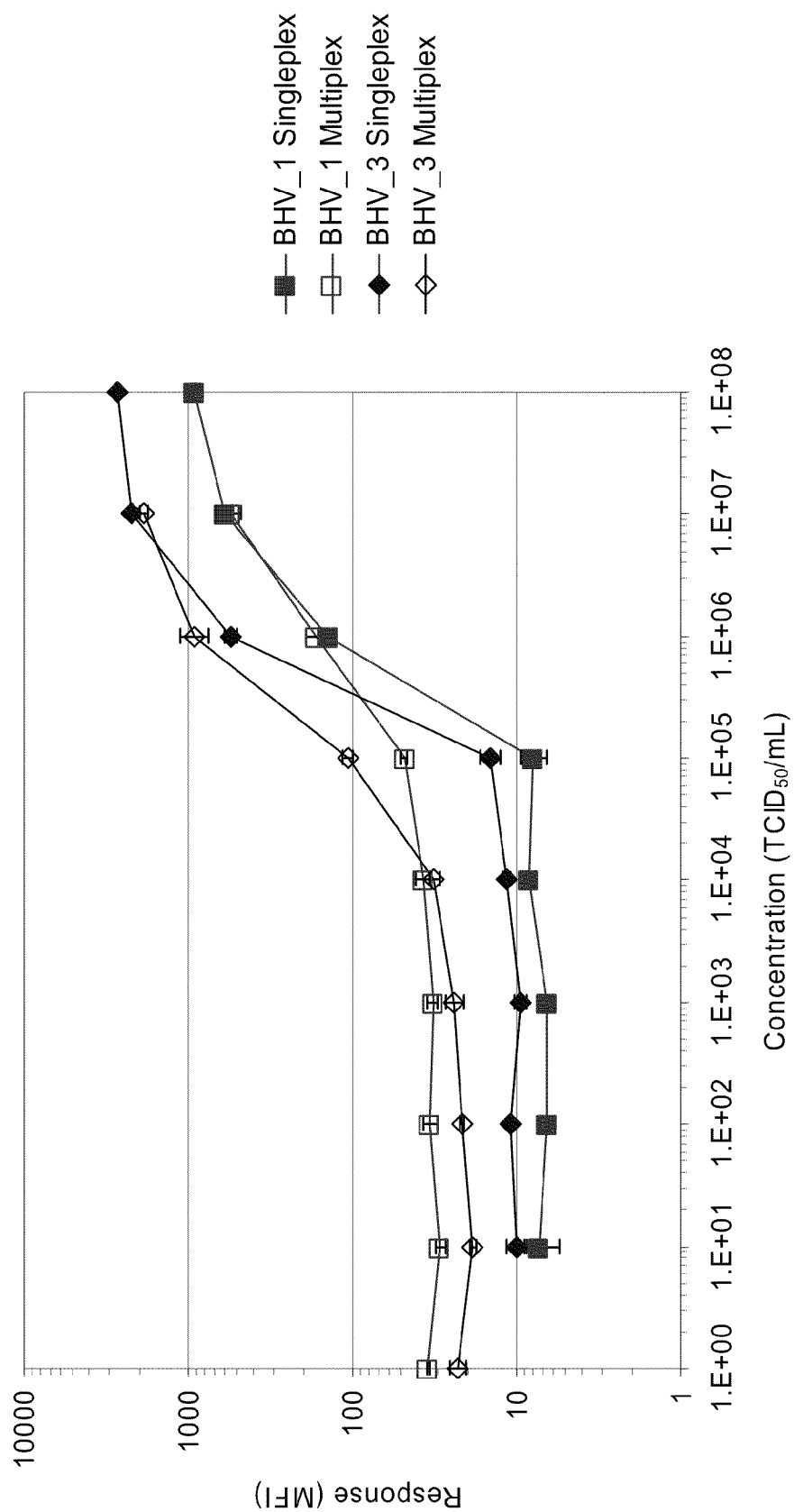

Both signatures were tested in singleplex format using a dilution series of a single BHV-1 strain (Colorado, NVSL). The singleplex results are plotted together with data acquired with the Version 1.0 panel (FIG. 53). Signature responses to template were comparable in singleplex and multiplex formats over the concentration range tested for this particular strain.

Near-neighbor screening: The signatures in multiplex did not generate responses above background when screened against near-neighbors including Rhadinovirus Caprine Herpes-2, V. Pseudorabies, Pseudorabies Shope, Equine Herpesvirus-1, Equine Herpesvirus-2, Feline herpes and Bovine Herpesvirus-5. These results agree with those obtained during Taqman screening.

Figure 54:
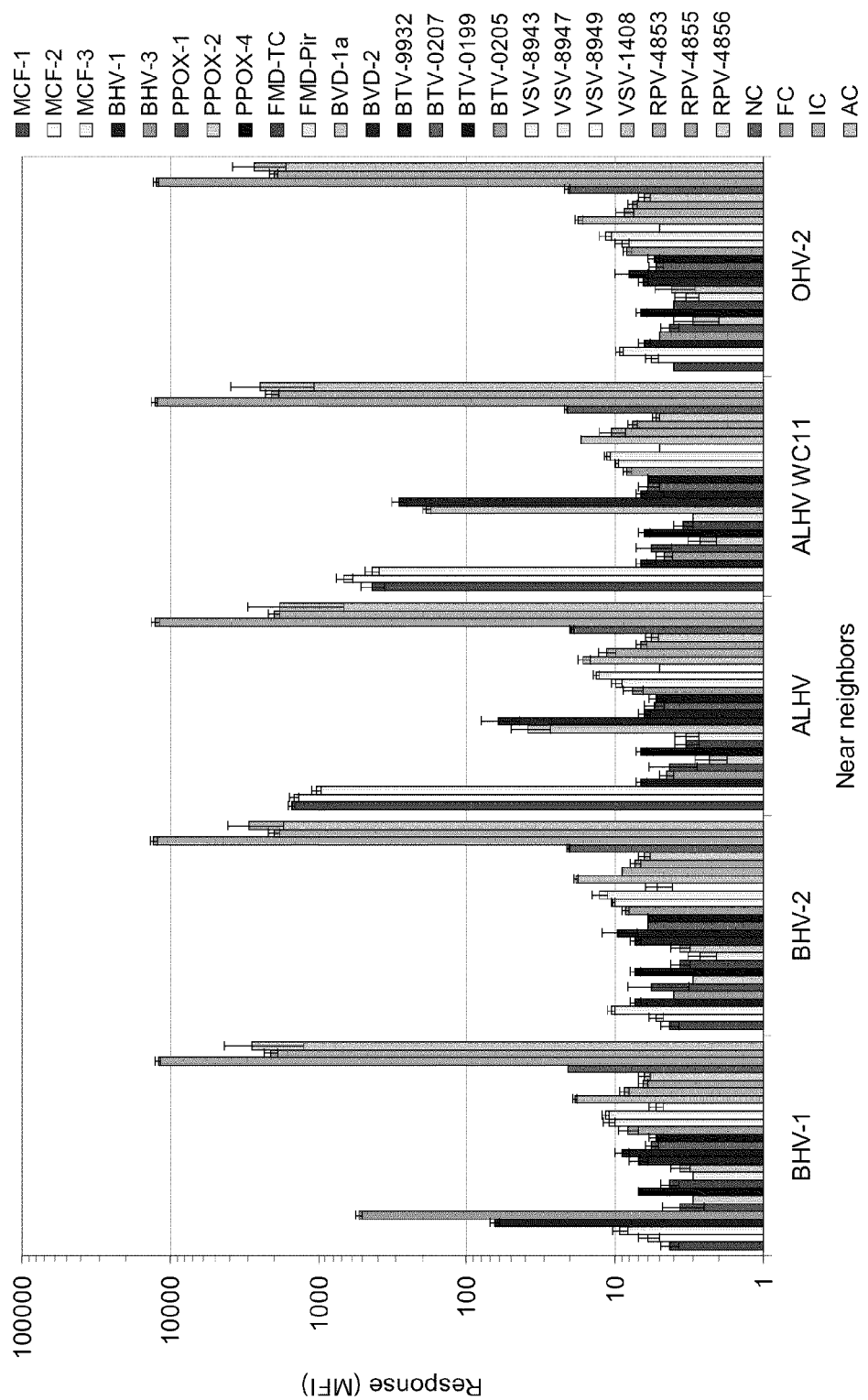

Additional screening at PIADC was conducted. FIG. 54 shows the results of screening of the BHV signatures against viruses belonging to the Herpesviridae family. Low-level BVDV contamination is noted on the ALHV samples. These data indicate specificity of the BHV signatures.

Figure 55:
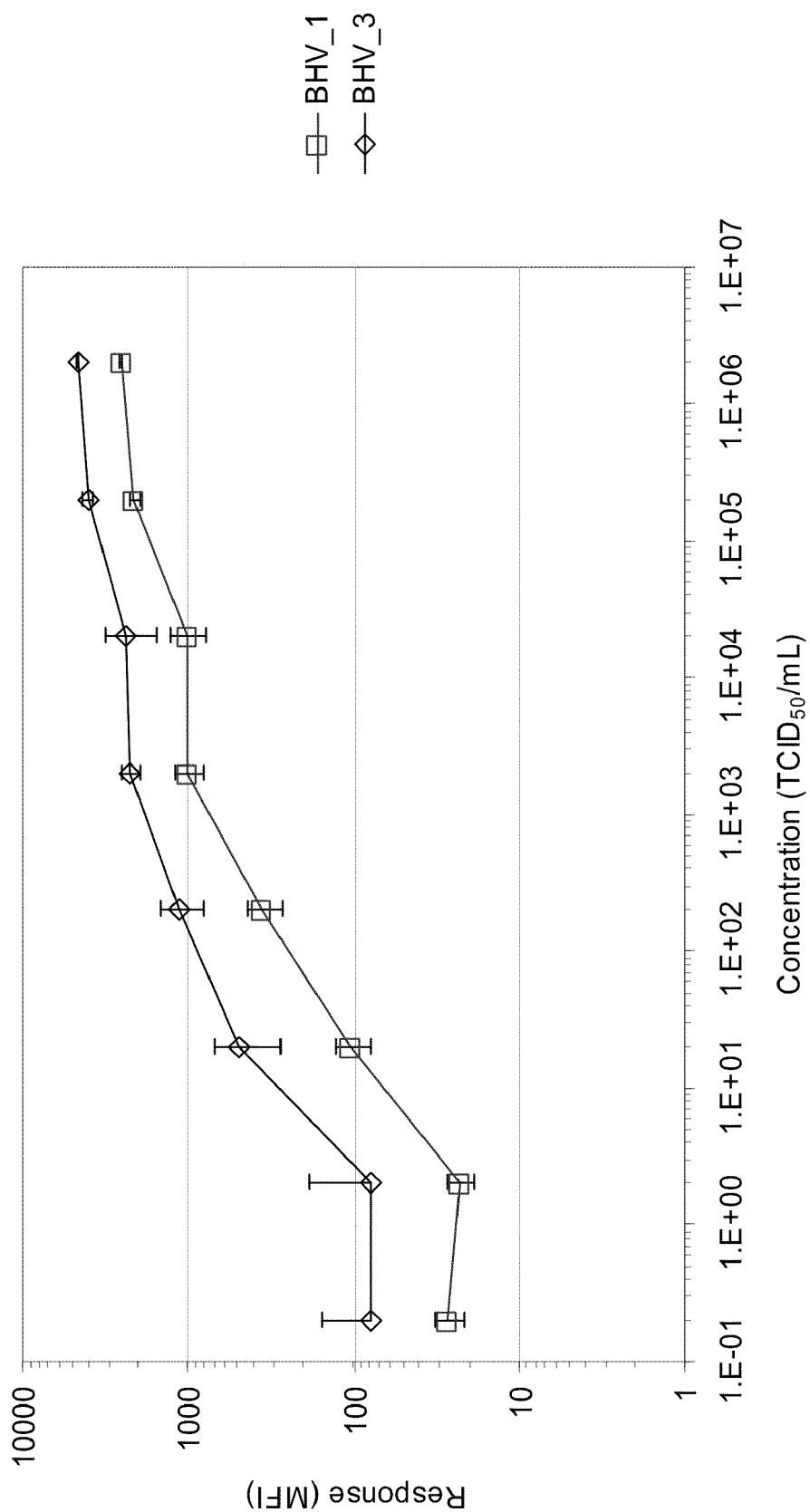

Target screening: Both signatures were added to the current Bovine panel where they generate consistently low background response in the absence of template. Both signatures responded as shown in FIG. 55. These results compare to results from the Version 1.0 panel.

The two BHV signatures BHV__1 and BHV__3 respond to the target when incorporated into the current Bovine panel. The near-neighbor testing conducted to date indicates that both signatures do not respond to genetic near-neighbors. The signature response indicates that the signatures could be capable of detecting BHV-1 virus at clinically relevant concentrations.

11. Parapox (PPox)—Bovine Panel

Signature candidates: Three signatures were adopted from the Version 1.0 panel without change, including PPOX__1, PPOX__2 and PPOX__4.

Signature origin: Signatures were designed at LLNL using a four genome alignment each varying in size from 134,000-137,000 bp. The PPOX__1 signature targets the ORF108 DNA packaging protein ATPase gene with similarities to Vaccinia strain Copenhagen A32L and Molluscum contagiosum virus MC140L. The PPOX__2 signature targets the ORF025 DNA polymerase. The PPOX__4 signature targets the ORF083 DNA early transcription factor VETFL gene.

Near-neighbor screening: Seven near-neighbor isolates of goatpox (V717 Pendik, Held LT5, Nigerian G165), sheeppox (Kenyan LT1, Vaccine 0-180 15LK V2164 and X783 6LT) were screened found to not cross react with any of the signatures.

Figure 56:
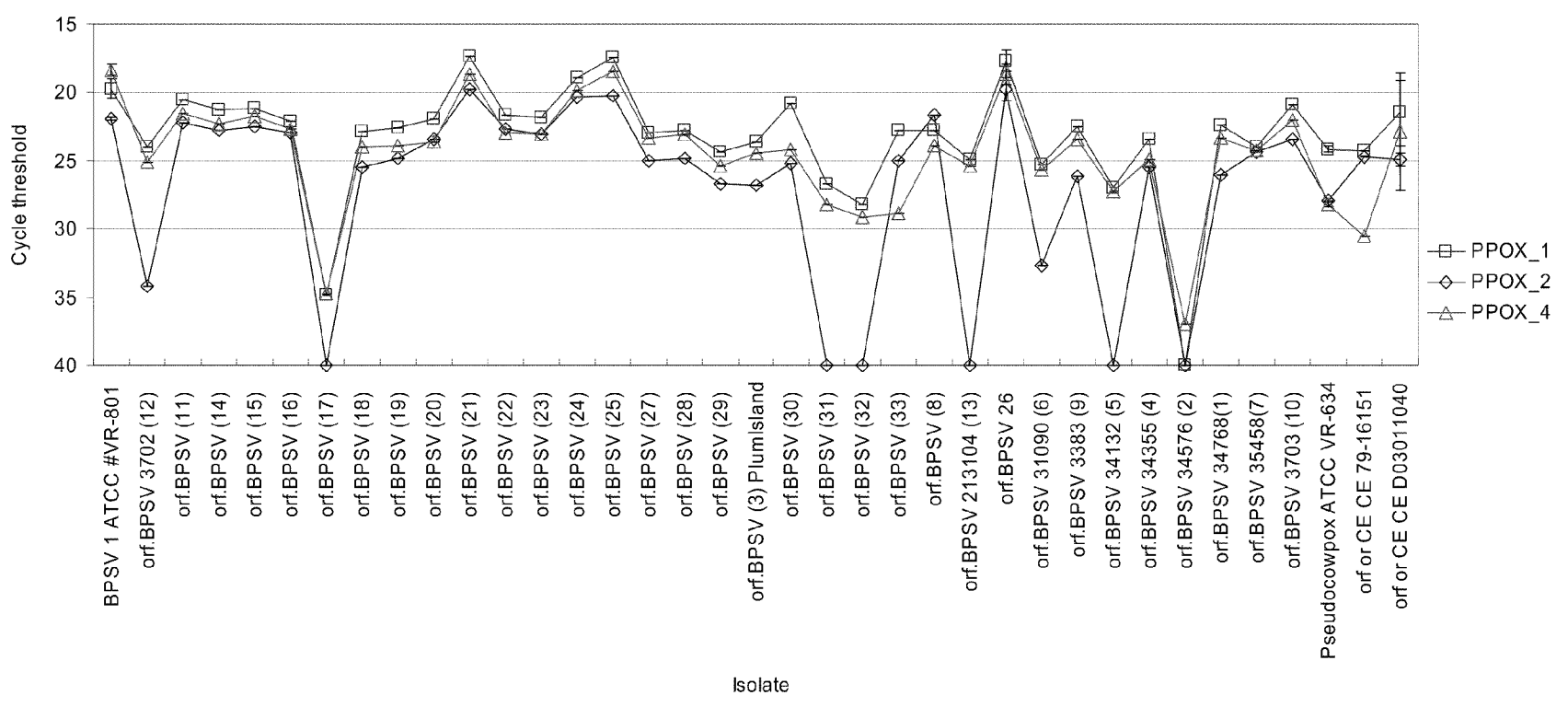

Target screening: Thirty-seven parapoxvirus isolates were screened and the results are shown in FIG. 56. Signatures PPOX-1 and PPOX-4 detected 36/37 isolates, while PPOX__2 detected 31/37.

Figure 57:
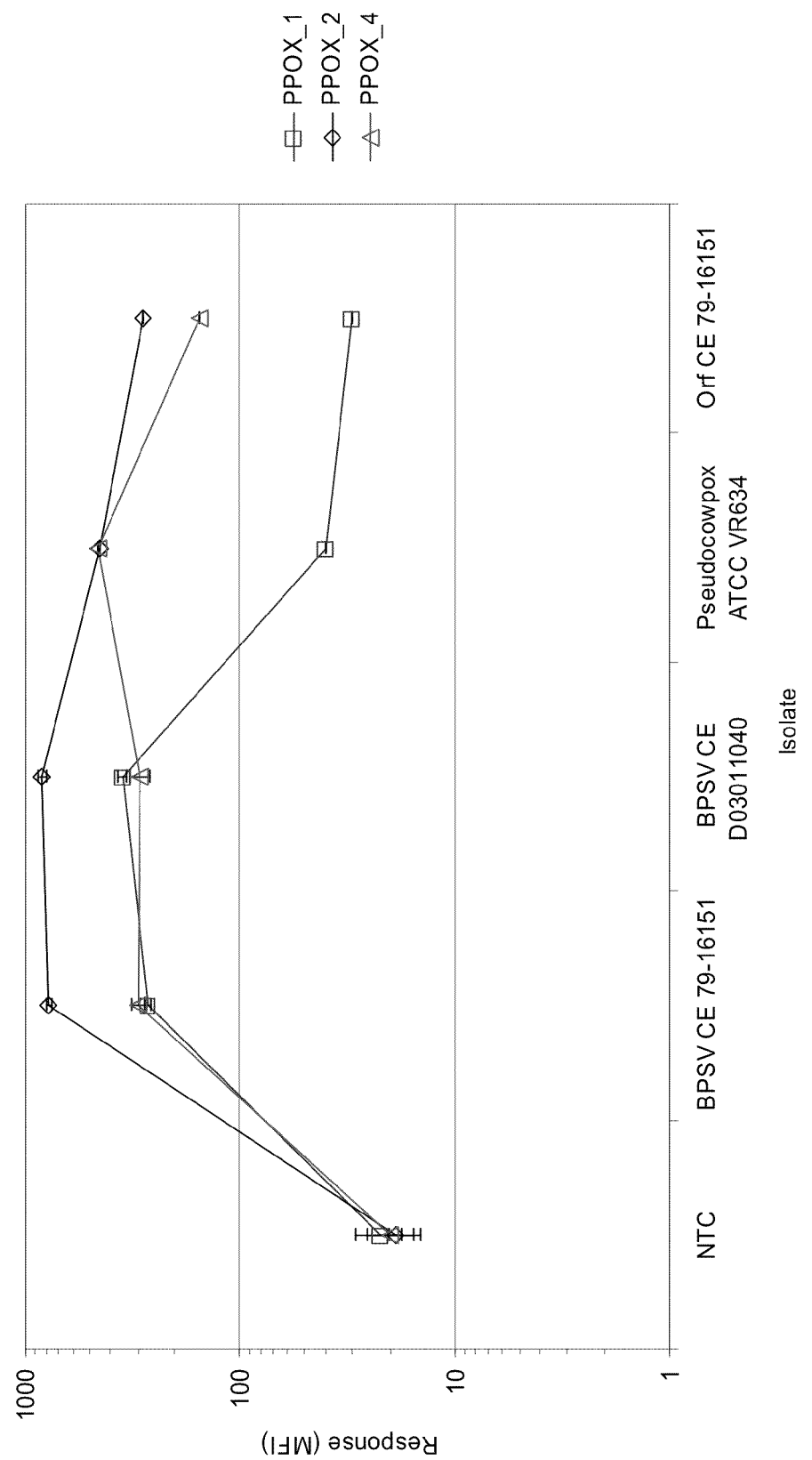

Target screening: Spot-testing was conducted in singleplex format using nucleic acid extracted virus-infected cell culture as the template (FIG. 57). PPOX__1 and PPOX__2 responded to all four strains tested. The PPOX__4 signature did not respond to 2/4 strains tested.

Figure 58:
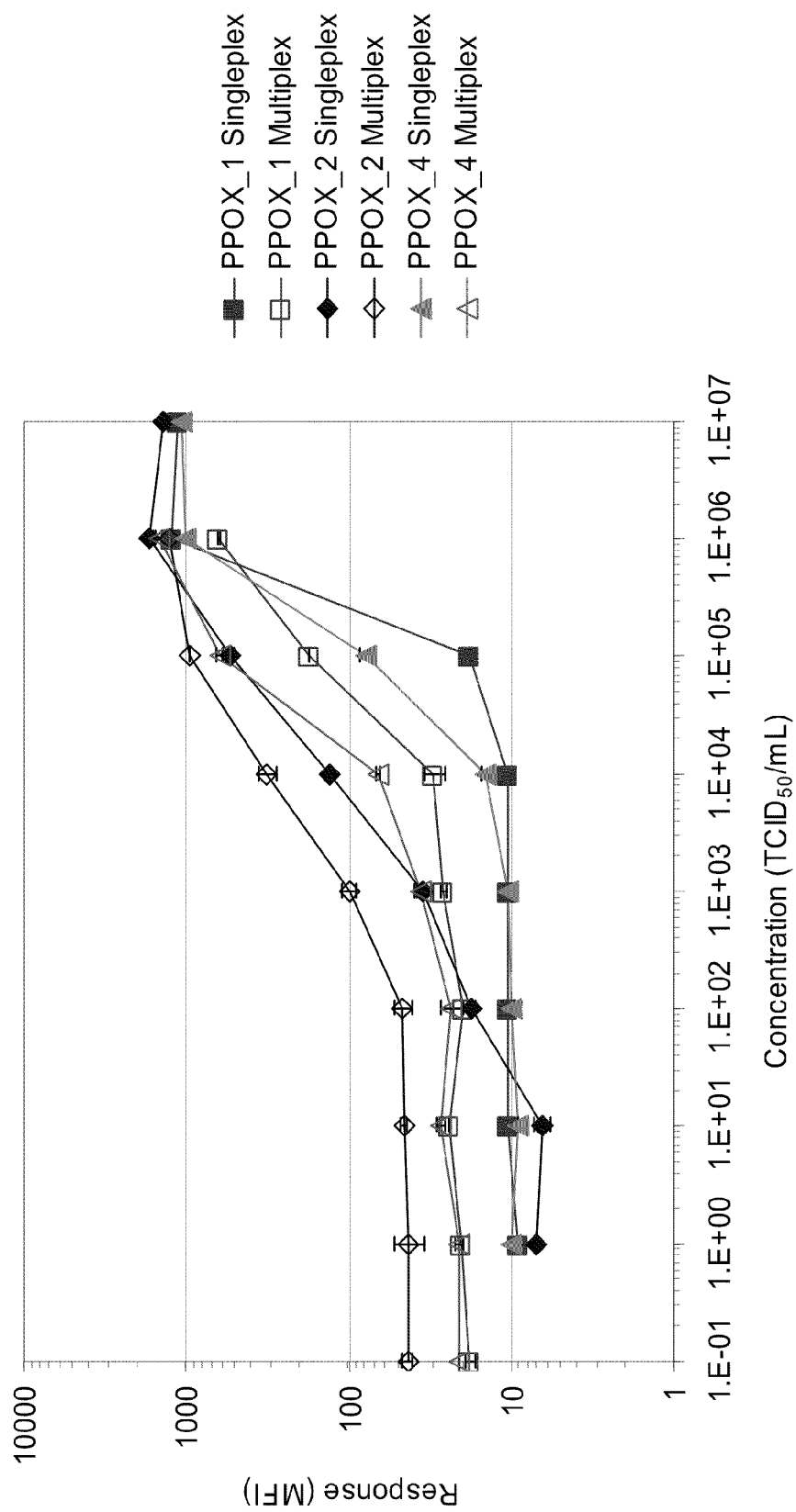
Figure 60:
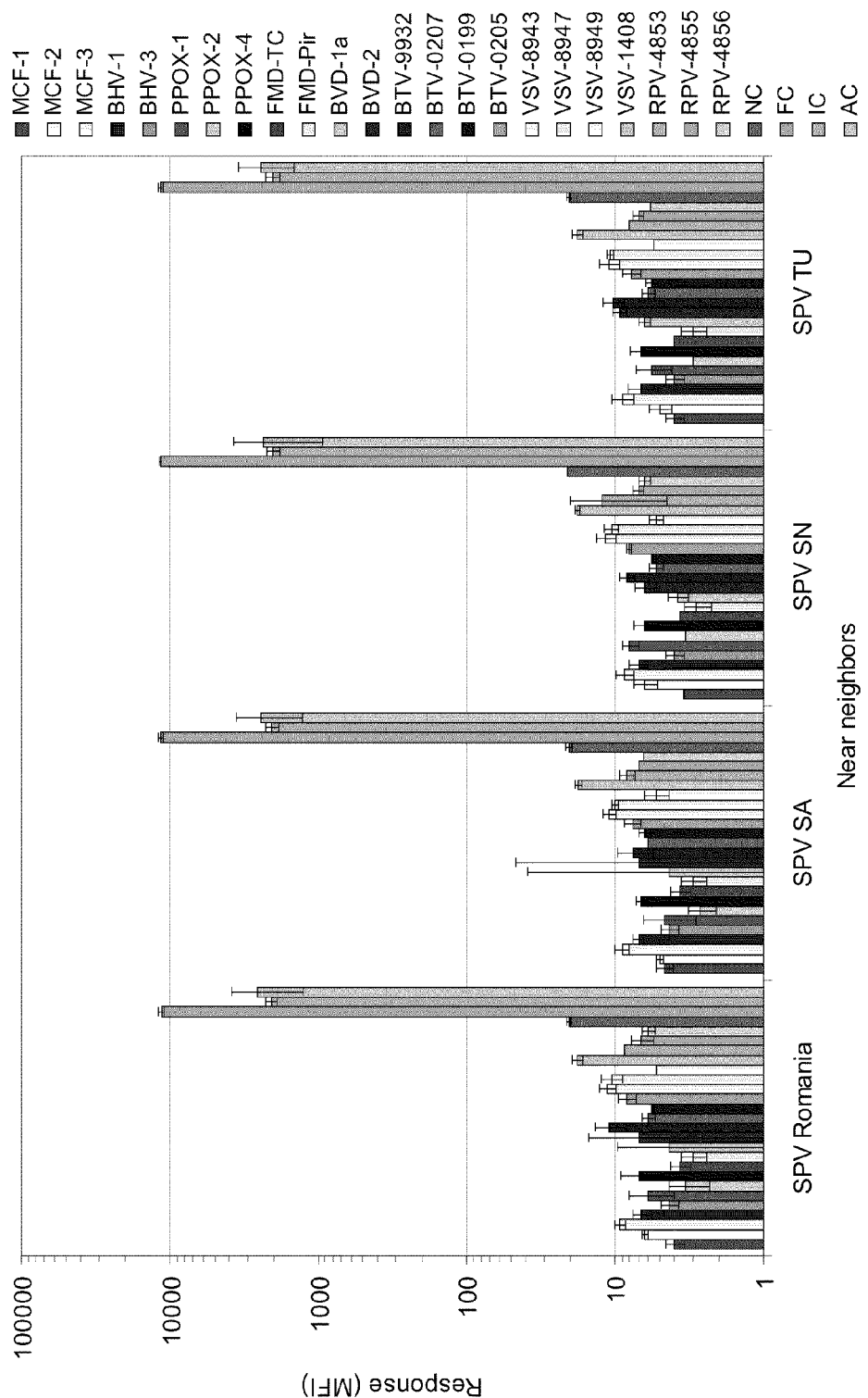

Further testing of the three signatures was undertaken in singleplex format. The singleplex results are compared directly to those acquired using the Version 1.0 panel (FIG. 58). The background response increased for all three signatures from singleplex to multiplex; however, similar responses were obtained over the concentration ranges tested.

Figure 61:
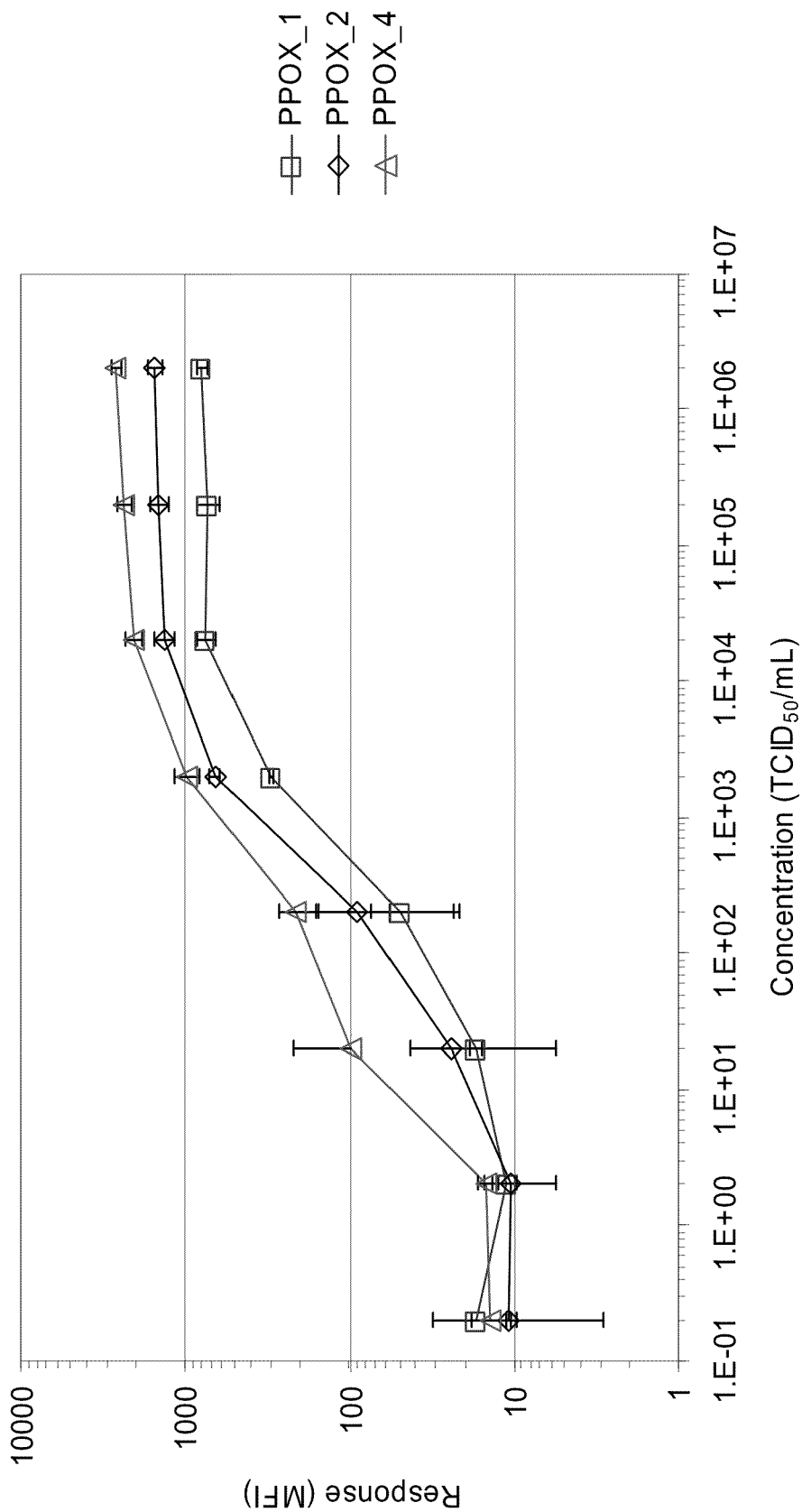

Target screening: The three Parapox signatures have been incorporated into the current Bovine panel where they showed consistently low background response. All three signatures responded equivalently to target material over a wide range of concentrations (FIG. 61).

Figure 62:
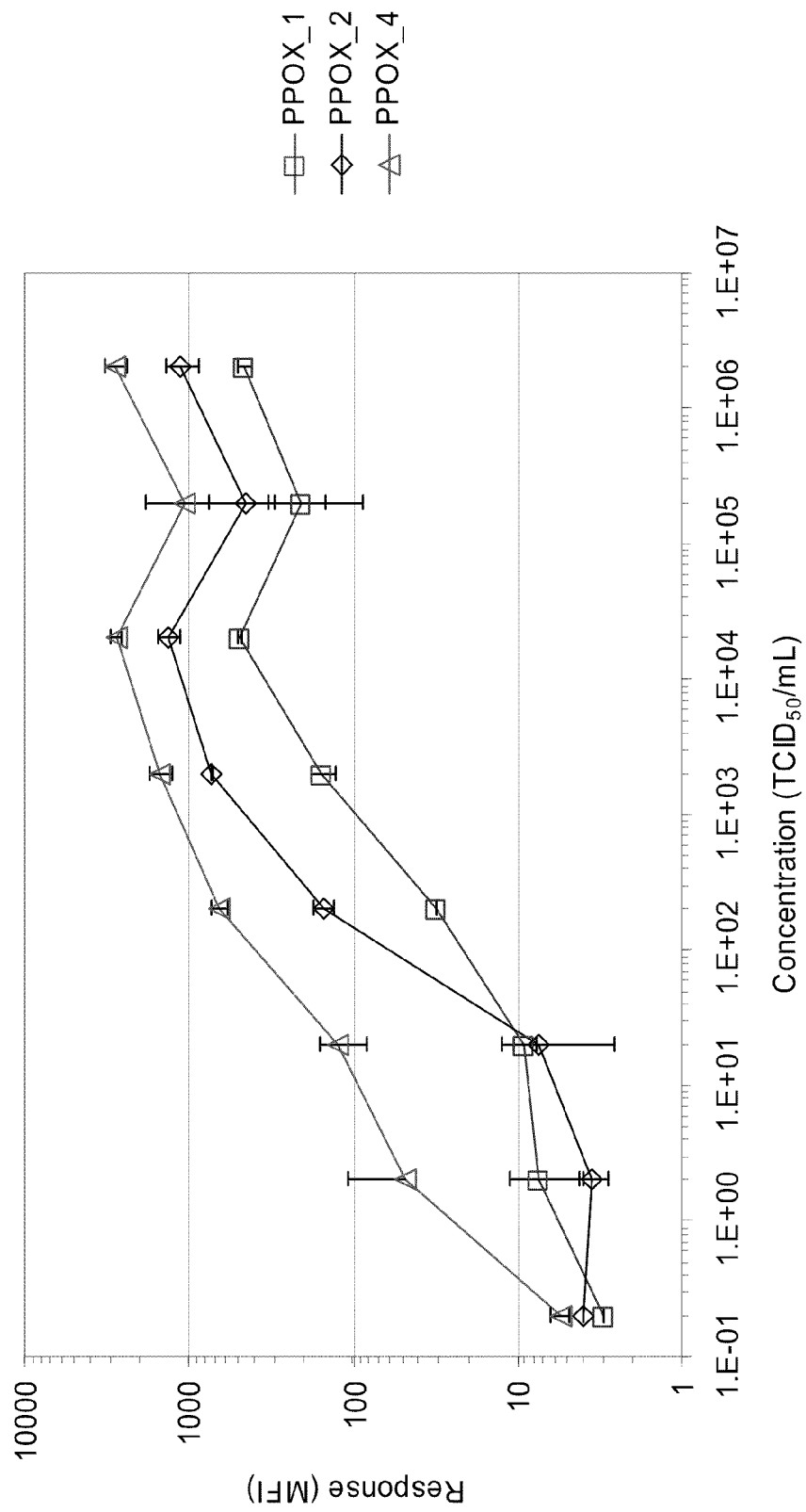
Figure 63:
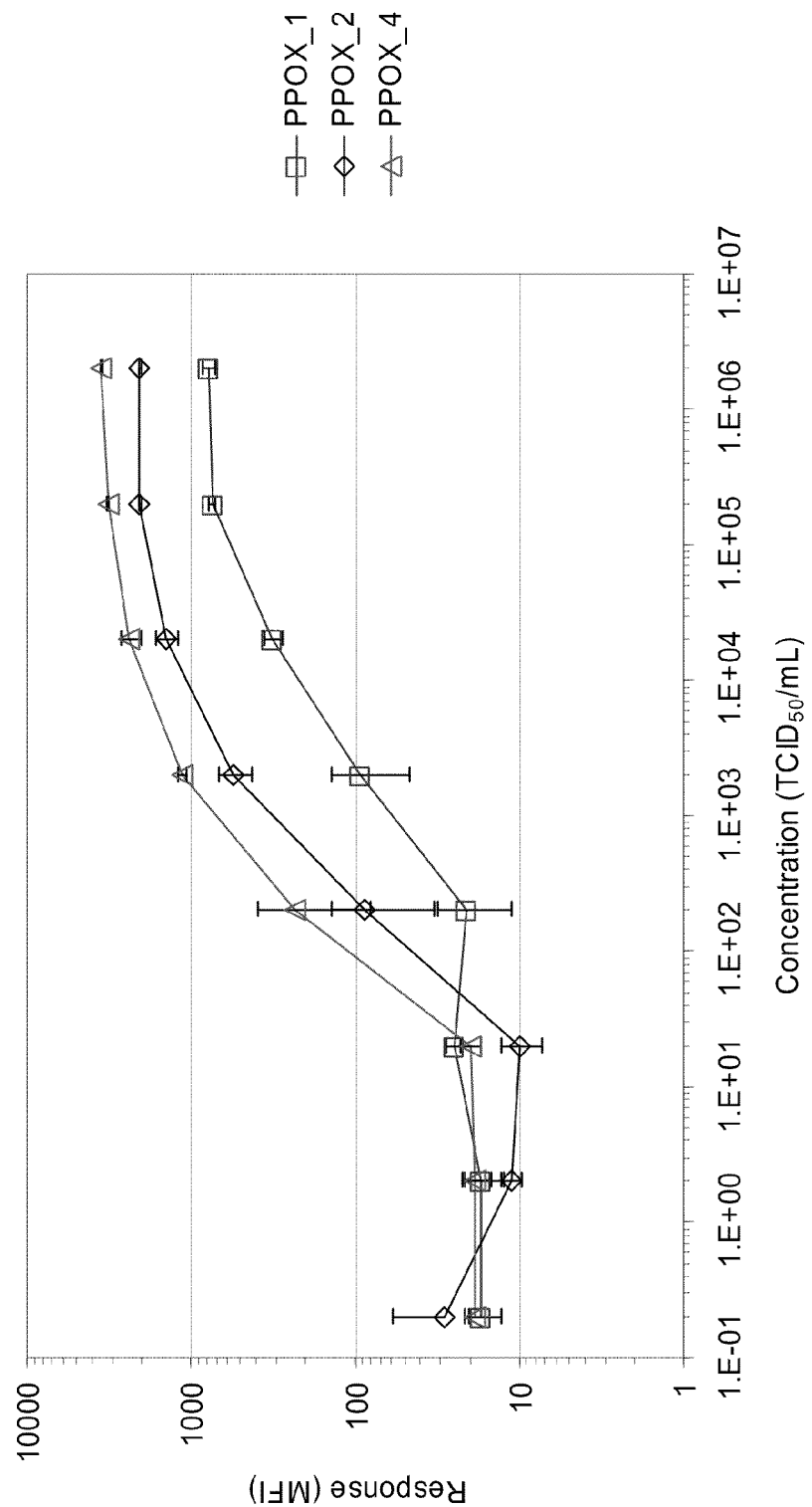

The three Parapox signatures in the current Bovine panel were also screened against Pseudocowpox (FIG. 62) and Orf (FIG. 63) strains and generated a positive response over a wide range of concentrations.

Figure 64:
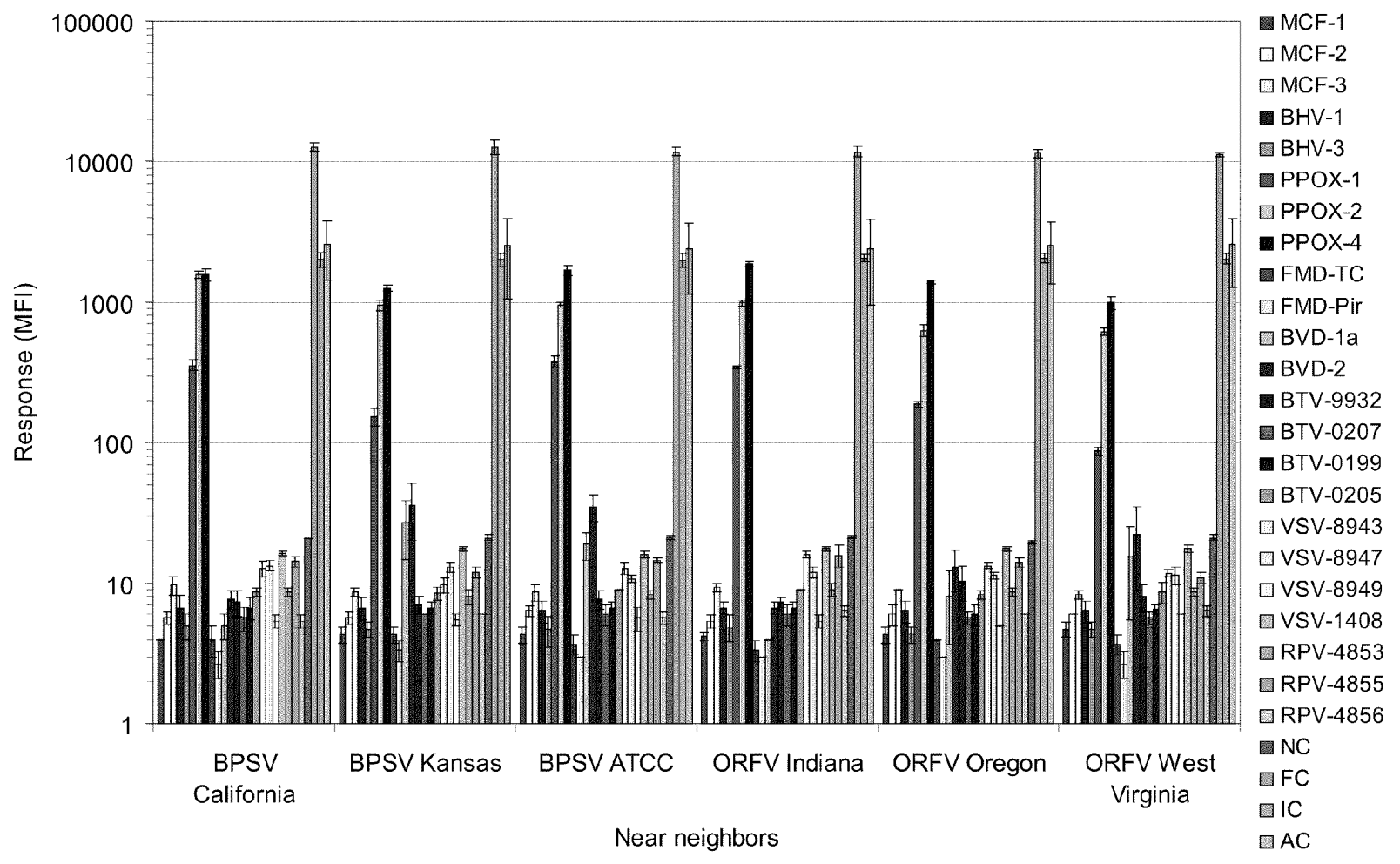

Additional target screening was conducted at PIADC. The results shown in FIG. 64 indicate specific detection of BPSV and ORFV.

The three Parapox signatures performed well when incorporated into the current Bovine multiplex panel. Together the signatures provide detection capability for Bovine Papular Stomatitis, Contagious Ecthyma and Pseudocowpox and potentially laboratory differentiation from foot-and-mouth disease within a multiplex panel.

Example 14

Multiplexed Detection of FMDV, PRRS, SVD, VESV, VSV, OvHV-2, AHV1, BHV, PPDX, BVD, BTV, and RPV Using a Microarray Approach In another embodiment, the signature sequences in Tables 11-12 are used for detection of FMDV, PRRS, SVD, VESV, VSV, OvHV-2, AHV1, BHV, PPDX, BVD, BTV, and RPV pathogens in a sample using a microarray coupled with the probes from Tables 11-12 as described in Example 10 above. To detect the pathogens, the pathogen nucleic acid sample can be amplified with fluorescently labeled random primers and the labeled DNA is hybridized to the chip. Alternatively, the pathogen nucleic acid sample can be fluorescently labeled, as described in, e.g., Example 16 below; and the labeled DNA is hybridized to the chip. The chip is washed to remove non-specifically bound samples and scanned using a laser scanner at high resolution. The raw data and images are analyzed using statistical tools and presence/absence calls are made for the signature sequences.

Example 15

Selection of Probes for Detection of Agricultural Pathogens on an Array

An initial genomic collection was obtained by downloading complete pathogen genomes, segments, and plasmid sequences from, e.g., NCBI Genbank, the Integrated Microbial Genomics (IMG) project at the Joint Genome Institute, the Comprehensive Microbial Resource (CMR) at the JC Venter Institute, and The Sanger Institute in the United Kingdom. The sequence data was then organized by family for all organisms or targets.

It has been shown that the length of longest perfect match (PM) is a strong predictor of hybridization intensity, and that for probes at least 50 nucleotide (nt) long, a PM≦20 base pairs (bp) have signal less than 20% of that with a PM over the entire length of the probe. Therefore, for each target family, regions with perfect matches to sequences outside the target family were eliminated. Using, e.g., the suffix array software vmatch (Giegerich, R., Kurtz, S, and Stoye, J. (2003) Efficient implementation of lazy suffix trees, Software-Practice and Experience, 33, 1035-1049.), perfect match subsequences of, e.g., at least 17 nt long present in non-target viral families or, e.g., 25 nt long present in the human genome or non-target bacterial families were eliminated from consideration as possible probe subsequences. Sequence similarity of probes to non-target sequences below this threshold was allowed. From these family-specific regions, probes 50-66 bases long were designed for one family at a time. Candidate probes were generated using, for example, MIT's Primer3 software. See, e.g., Steve Rozen, Helen J. Skaletsky (1998) Primer3.

The following Primer3 settings were modified from the default values:

PRIMER_TASK=pick_hyb_probe_only
PRIMER_PICK_ANYWAY=1
PRIMER_INTERNAL_OLIGO_OPT_SIZE=55
PRIMER_INTERNAL_OLIGO_MIN_SIZE=50
PRIMER_INTERNAL_OLIGO_MAX_SIZE=60
PRIMER_INTERNAL_OLIGO_OPT_TM=90
PRIMER_INTERNAL_OLIGO_MIN_TM=80
PRIMER_INTERNAL_OLIGO_MAX_TM=110
PRIMER_INTERNAL_OLIGO_MIN_GC=25
PRIMER_INTERNAL_OLIGO_MAX_GC=75
PRIMER_NUM_NS_ACCEPTED=0
PRIMER_EXPLAIN_FLAG=0
PRIMER_FILE_FLAG=1
PRIMER_INTERNAL_OLIGO_SALT_CONC=450
PRIMER_INTERNAL_OLIGO_DNA_CONC=100
PRIMER_INTERNAL_OLIGO_MAX_POLY_X=4

These settings identify candidate probes in the desired length range, melting temperature ($T_m$) range, GC % range, and without homopolymer repeats longer than 4 (i.e. regions with AAAAA, GGGGG, etc. are not selected as probe candidates).

The above step was followed by $T_m$ and homodimer, hairpin, and probe-target free energy (ΔG) prediction using, for example, Unafold (see, e.g., Markham, N. R. & Zuker, M. (2005) DINAMelt web server for nucleic acid melting prediction. Nucleic Acids Res., 33, W577-W581). Homodimers occur when an oligo hybridizes to another copy of the same sequence, and hairpining occurs when an oligo folds so that one part of the oligo hybridizes with another part of the same oligo. Candidate probes with unsuitable ΔG's, GC % or $T_m$'s were excluded as described in Jaing, C., Gardner, S., McLoughlin, K., Mulakken, N., Alegria-Hartman, M., Banda, P., Williams, P., Gu, P., Wagner, M., Manohar, C. and Slezak, T. (2008) A Functional Gene Array for Detection of Bacterial Virulence Elements, PLoS ONE, 3, e2163. Desirable range for these parameters was 50≦length≦66, $T_m$≧80° C., 25%≦GC %≦75%, trimer entropy>4.5, $\Delta G_{homodimer}=\Delta G$ of homodimer formation>15 kcal/mol, $\Delta G_{hairpin}=\Delta G$ of hairpin formation>−11 kcal/mol, and $\Delta G_{adjusted}=\Delta G_{complement}-1.45\ \Delta G_{hairpin}-0.33\ \Delta G_{homodimer}\leqq -52$ kcal/mol. In some cases, an additional minimum sequence complexity constraint was enforced, requiring a trimer frequency entropy of at least 4.5.

Probes with suitable annealing characteristics or preferred binding properties (e.g., polynucleotides from target specific regions with favored thermodynamic characteristics) were selected, in order to remove probes that are likely to bind to non-target sequences, whether the non-target sequence is the probe itself or a low complexity non-specific sequence. If fewer than a user-specified minimum number of candidate probes per target sequence (the specific value of which can depend upon the particular application needs and available number of probes on a particular array platform) passed all the criteria, then those criteria were relaxed to allow a sufficient number of probes per target. Candidates that passed the above mentioned first step but failed the above mentioned second step can be allowed. If no candidates passed the first step, then regions passing target-specificity (e.g. family specific) and minimum length constraints can be allowed.

From these candidates, probes were selected in decreasing order of the number of targets represented by that probe (i.e., probes detecting more targets in the family were chosen preferentially over those that detected fewer targets in the family), where a target was considered to be represented if, for example, a probe matched it with at least 85% sequence similarity over the total probe length, and a perfectly matching subsequence of at least 29 contiguous bases spanned the middle of the probe. It should be noted that the perfect-match stretch did not have to be centered, and data gathered by the applicants indicate, in some embodiments, higher probe sensitivity if the match falls toward the 5' end of the probe (for probes tethered to the solid support at the 3' end), so long as it extends over the middle of the probe.

For probes that tie in the number of targets represented, a secondary ranking was used to favor probes most dispersed across the target from those probes which had already been selected to represent that target. The probe with the same conservation rank that occurs at the farthest distance from any probe already selected from the target sequence is the next probe to be chosen to represent that target. The probes are shown in Tables 13-25.

Following probe selection, the probes are then arranged on a suitable substrate to form an array, as described in more detail below.

Example 16

Detection of Bovine Pathogens Using an Array

DNA microarrays are synthesized with probes from Tables 13-25 as described in, e.g., Jaing, C., Gardner, S., McLoughlin, K., Mulakken, N., Alegria-Hartman, M., Banda, P., Williams, P., Gu, P., Wagner, M., Manohar, C. and Slezak, T. (2008) A Functional Gene Array for Detection of Bacterial Virulence Elements, PLoS ONE, 3, e2163. The array probes can detect at least one or more of the following pathogens: OvHV-2, AHV1, BHV, PPDX, FMDV, BVD, BTV, VSV, and RPV. A bovine sample with cells that is possibly infected by one or more pathogens (e.g., OvHV-2, AHV1, BHV, PPDX, FMDV, BVD, BTV, VSV, and RPV) is obtained.

After treatment with Trizol reagent, RNA from cells is precipitated with isopropanol and washed with 70% ethanol. The RNA pellet is dried and reconstituted with RNase free water. 1 µg of RNA is transcribed into double-strand cDNA with random hexamers using Superscript™ double-stranded cDNA synthesis kit from Invitrogen (Carlsbad, Calif.). The DNA or cDNA is labeled using Cy-3 labeled nonamers from Trilink Biotechnologies and 4 µg of labeled sample is hybridized to the microarray for 16 hours as previously described (see Jaing, C., Gardner, S., McLoughlin, K., Mulakken, N., Alegria-Hartman, M., Banda, P., Williams, P., Gu, P., Wagner, M., Manohar, C. and Slezak, T. (2008) A Functional Gene Array for Detection of Bacterial Virulence Elements, PLoS ONE, 3, e2163).

Upon completion of hybridization and washing of the array, the array is scanned to determine the position on the array to which the target sequence(s) hybridize. The hybridization data obtained from the scan is typically in the form of fluorescence intensities (e.g., via Cy3) as a function of location on the array.

Example 17

Detection of Porcine Pathogens Using an Array

DNA microarrays are synthesized with probes from Tables 13-25 as described in, e.g., Jaing, C., Gardner, S., McLoughlin, K., Mulakken, N., Alegria-Hartman, M., Banda, P., Williams, P., Gu, P., Wagner, M., Manohar, C. and Slezak, T. (2008) A Functional Gene Array for Detection of Bacterial Virulence Elements, PLoS ONE, 3, e2163. The array probes can detect at least one or more of the following pathogens: FMDV, PRRS, SVD, VESV, and VSV. A porcine sample with cells that is possibly infected by one or more pathogens (e.g., FMDV, PRRS, SVD, VESV, and VSV) is obtained.

After treatment with Trizol reagent, RNA from cells is precipitated with isopropanol and washed with 70% ethanol. The RNA pellet is dried and reconstituted with RNase free water. 1 µg of RNA is transcribed into double-strand cDNA with random hexamers using Superscript™ double-stranded cDNA synthesis kit from Invitrogen (Carlsbad, Calif.). The DNA or cDNA is labeled using Cy-3 labeled nonamers from Trilink Biotechnologies and 4 µg of labeled sample is hybridized to the microarray for 16 hours as previously described (see Jaing, C., Gardner, S., McLoughlin, K., Mulakken, N., Alegria-Hartman, M., Banda, P., Williams, P., Gu, P., Wagner, M., Manohar, C. and Slezak, T. (2008) A Functional Gene Array for Detection of Bacterial Virulence Elements, PLoS ONE, 3, e2163).

Upon completion of hybridization and washing of the array, the array is scanned to determine the position on the array to which the target sequence(s) hybridize. The hybridization data obtained from the scan is typically in the form of fluorescence intensities (e.g., via Cy3) as a function of location on the array.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08354514B2). An electronic copy of the "Sequence Listing" will also be available from the USPTO upon request and payment of the fee set forth in 37 CFR 1.19(b)(3).

What is claimed is:

1. A kit for determining the presence or absence of at least two porcine pathogens in a sample, said pathogens selected from the group consisting of Foot-and-Mouth Disease Virus (FMDV), Porcine Respiratory Reproductive Syndrome Virus (PRRS), Swine Vesicular Disease Virus (SVD), Vesicular Exaanthema of Swine Virus (VESV), and Vesicular Stomatitis Virus (VSV), said kit comprising nucleic acid reagents for detection of at least one nucleic acid signature sequence from each of the at least two pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

2. The kit of claim 1, wherein the kit is for determining the presence or absence of FMDV, PRRS, SVD, VESV, and VSV in a sample, said kit comprising nucleic acid reagents for detection of SEQ ID NO:129, SEQ ID NO:133, SEQ ID NO:137, SEQ ID NO:141, SEQ ID NO:145, SEQ ID NO:149, SEQ ID NO:153, SEQ ID NO:157, SEQ ID NO:161, SEQ ID NO:165, SEQ ID NO:169, SEQ ID NO:173, SEQ ID NO:177, SEQ ID NO:181, SEQ ID NO:185, SEQ ID NO:189, SEQ ID NO: 193, SEQ ID NO: 197, and SEQ ID NO: 201.

3. The kit of claim 1, wherein said reagents comprise a set of oligonucleotides for each signature sequence to be detected, said set comprising PCR primers and hybridization probes for each signature sequence.

4. The kit of claim 1, wherein said reagents comprise at least two sets of oligonucleotides selected from the group consisting of set 1, set 2, set 3, set 4, set 5, set 6, set 7, set 8, set 9, set 10, set 11, set 12, set 13, set 14, set 15, set 16, set 17, set 18, and set 19, wherein set 1 comprises SEQ ID NOs: 126, 127, and 128, wherein set 2 comprises SEQ ID NOs: 130, 131, and 132, wherein set 3 comprises SEQ ID NOs: 134, 135, and 136, wherein set 4 comprises SEQ ID NOs: 138, 139, and 140, wherein set 5 comprises SEQ ID NOs: 142, 143, and 144, wherein set 6 comprises SEQ ID NOs: 146, 147, and 148, wherein set 7 comprises SEQ ID NOs: 150, 151, and 152, wherein set 8 comprises SEQ ID NOs: 154, 155, and 156, wherein set 9 comprises SEQ ID NOs: 158, 159, and 160, wherein set 10 comprises SEQ ID NOs: 162, 163, and 164, wherein set 11 comprises SEQ ID NOs: 166, 167, and 168, wherein set 12 comprises SEQ ID NOs: 170, 171, and 172, wherein set 13 comprises SEQ ID NOs: 174, 175, and 176, wherein set 14 comprises SEQ ID NOs: 178, 179, and 180, wherein set 15 comprises SEQ ID NOs: 182, 183, and 184, wherein set 16 comprises SEQ ID NOs: 186, 187, and 188, wherein set 17 comprises SEQ ID NOs: 190, 191, and 192, wherein set 18 comprises SEQ ID NOs: 194, 195, and 196, and wherein set 19 comprises SEQ ID NOs: 198, 199, and 200.

5. The kit of claim 2, wherein said reagents comprise set 1, set 2, set 3, set 4, set 5, set 6, set 7, set 8, set 9, set 10, set 11, set 12, set 13, set 14, set 15, set 16, set 17, set 18, and set 19, wherein set 1 comprises SEQ ID NOs: 126, 127, and 128, wherein set 2 comprises SEQ ID NOs: 130, 131, and 132, wherein set 3 comprises SEQ ID NOs: 134, 135, and 136, wherein set 4 comprises SEQ ID NOs: 138, 139, and 140, wherein set 5 comprises SEQ ID NOs: 142, 143, and 144, wherein set 6 comprises SEQ ID NOs: 146, 147, and 148, wherein set 7 comprises SEQ ID NOs: 150, 151, and 152, wherein set 8 comprises SEQ ID NOs: 154, 155, and 156, wherein set 9 comprises SEQ ID NOs: 158, 159, and 160, wherein set 10 comprises SEQ ID NOs: 162, 163, and 164, wherein set 11 comprises SEQ ID NOs: 166, 167, and 168, wherein set 12 comprises SEQ ID NOs: 170, 171, and 172, wherein set 13 comprises SEQ ID NOs: 174, 175, and 176, wherein set 14 comprises SEQ ID NOs: 178, 179, and 180, wherein set 15 comprises SEQ ID NOs: 182, 183, and 184, wherein set 16 comprises SEQ ID NOs: 186, 187, and 188, wherein set 17 comprises SEQ ID NOs: 190, 191, and 192, wherein set 18 comprises SEQ ID NOs: 194, 195, and 196, and wherein set 19 comprises SEQ ID NOs: 198, 199, and 200.

6. The kit of claim 5, further comprising reagents for detection of one or more control sequences.

7. A method for determining the presence or absence of at least two pathogens selected from the group consisting of FMDV, PRRS, SVD, VESV, and VSV in a sample, said method comprising the steps of using the kit of claim 1.

8. A method for determining the presence or absence of FMDV, PRRS, SVD, VESV, and VSV in a sample, said method comprising the steps of using the kit of claim 2.

9. The kit of claim 1, wherein the kit comprises nucleic acid reagents for detection of at least one nucleic acid signature sequence from each of at least three pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

10. The kit of claim 1, wherein the kit comprises nucleic acid reagents for detection of at least one nucleic acid signature sequence from each of at least four pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

11. The kit of claim 1, wherein the kit comprises nucleic acid reagents for detection of at least one nucleic acid signature sequence from each of the pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

12. The kit of claim 1, wherein the kit comprises nucleic acid reagents for detection of at least two nucleic acid signature sequences from each of at least two pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

13. The kit of claim 1, wherein the kit comprises nucleic acid reagents for detection of at least two nucleic acid signature sequences from each of at least three pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

14. The kit of claim 1, wherein the kit comprises nucleic acid reagents for detection of at least two nucleic acid signature sequences from each of at least four pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

15. The kit of claim 1, wherein the kit comprises nucleic acid reagents for detection of at least two nucleic acid signature sequences from each of the pathogens, wherein the following nucleic acid signature sequences are detected: for pathogen FMDV, signature sequences consisting of SEQ ID NO:129 or SEQ ID NO:133; for pathogen PRRS, signature sequences consisting of SEQ ID NO:137 or SEQ ID NO:141 or SEQ ID NO:145 or SEQ ID NO:149 or SEQ ID NO:153; for pathogen SVD, signature sequences consisting of SEQ ID NO:157 or SEQ ID NO:161 or SEQ ID NO:165; for pathogen VESV, signature sequences consisting of SEQ ID NO:169 or SEQ ID NO:173 or SEQ ID NO:177; and for pathogen VSV, signature sequences consisting of SEQ ID NO:181 or SEQ ID NO:185 or SEQ ID NO:189 or SEQ ID NO: 193 or SEQ ID NO:197 or SEQ ID NO:201.

16. The kit of claim 1, wherein said oligonucleotide probes are affixed to a solid support.

17. The method of claim 7, wherein said method comprises hybridization of each oligonucleotide to the sample.

18. The method of claim 7, wherein said method comprises amplification of at least one nucleic acid signature sequence from each of the at least two pathogens.

* * * * *